US008697650B2

(12) United States Patent
Gao et al.

(10) Patent No.: US 8,697,650 B2
(45) Date of Patent: Apr. 15, 2014

(54) HSA-RELATED COMPOSITIONS AND METHODS OF USE

(75) Inventors: Changshou Gao, Potomac, MD (US); Chaity Chaudhury, Germantown, MD (US); Xiaotao Yao, Germantown, MD (US)

(73) Assignee: Medimmune, LLC, Gaithersburg, MD (US)

( * ) Notice: Subject to any disclaimer, the term of this patent is extended or adjusted under 35 U.S.C. 154(b) by 0 days.

(21) Appl. No.: 13/578,688

(22) PCT Filed: Feb. 15, 2011

(86) PCT No.: PCT/US2011/024855
§ 371 (c)(1),
(2), (4) Date: Nov. 2, 2012

(87) PCT Pub. No.: WO2011/103076
PCT Pub. Date: Aug. 25, 2011

(65) Prior Publication Data
US 2013/0053322 A1    Feb. 28, 2013

Related U.S. Application Data

(60) Provisional application No. 61/304,954, filed on Feb. 16, 2010, provisional application No. 61/364,503, filed on Jul. 15, 2010.

(51) Int. Cl.
*A61K 38/38*    (2006.01)
*A61K 47/48*    (2006.01)
*C07K 14/76*    (2006.01)
*C07K 1/00*     (2006.01)
*C07K 14/00*    (2006.01)
*C07K 16/00*    (2006.01)
*C07K 17/00*    (2006.01)
*C07H 21/04*    (2006.01)

(52) U.S. Cl.
USPC .......................... 514/15.2; 530/363; 536/23.5

(58) Field of Classification Search
None
See application file for complete search history.

(56) References Cited

U.S. PATENT DOCUMENTS

| | | | |
|---|---|---|---|
| 7,189,690 B2 * | 3/2007 | Rosen et al. | 514/6.9 |
| 2006/0051859 A1 | 3/2006 | Fu et al. | |
| 2011/0002888 A1 | 1/2011 | Rosen et al. | |
| 2011/0015130 A1 | 1/2011 | Chuang et al. | |
| 2012/0322739 A1 * | 12/2012 | Andersen et al. | 514/15.2 |

FOREIGN PATENT DOCUMENTS

| WO | WO 95/23857 | 9/1995 |
|---|---|---|
| WO | WO 2009/126920 A2 | 10/2009 |
| WO | WO 2010/059315 A1 | 5/2010 |
| WO | WO 2010059315 A1 * | 5/2010 |
| WO | WO 2010/092135 A2 | 8/2010 |

(Continued)

OTHER PUBLICATIONS

Otagiri et al "Pharmaceutically Important Pre- and Posttranslational Modifications on Human Serum Albumin" Biol Pharm Bull 32:527-534. Published Apr. 2009.*

(Continued)

*Primary Examiner* — Cecilia J Tsang
*Assistant Examiner* — Zachary J Miknis
(74) *Attorney, Agent, or Firm* — Grant Anderson LLP

(57) ABSTRACT

Provided are human serum albumin (HSA) compositions with improved properties over native HSA.

30 Claims, 41 Drawing Sheets

(56) References Cited

FOREIGN PATENT DOCUMENTS

Figure 1A:
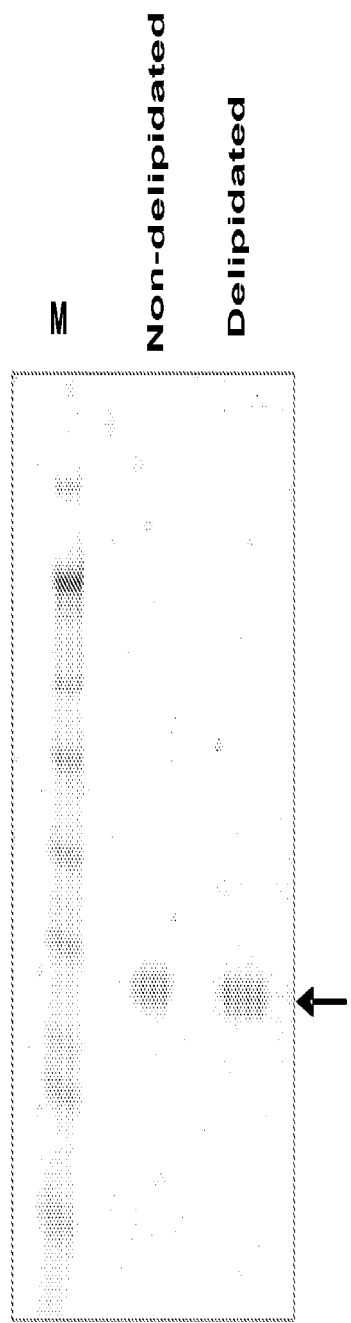

| WO | WO 2010/118169 A2 | 10/2010 |
|----|-------------------|---------|
| WO | WO 2011/051489 A2 | 5/2011 |
| WO | WO 2011/124718 A1 | 10/2011 |
| WO | WO 2011/146902 | 11/2011 |
| WO | WO 2012/059486 A1 | 5/2012 |
| WO | WO 2012/112188 | 8/2012 |
| WO | WO 2012/150319 A1 | 11/2012 |

OTHER PUBLICATIONS

Andersen, Jan Terje et al., 2010, "FcRn binding properties of an abnormal truncated analbuminemic albumin variant", Clinical Biochemistry, 43:367-372.

Andersen, Jan Terje et al., 2010, "Cross-species Binding Analyses of Mouse and Human Neonatal Fc Receptor Show Dramatic Differences in Immunoglobulin G and Albumin Binding", Journal of Biological Chemistry, 285(7):4826-4836.

Andersen, Jan Terje et al., 2011, "Extending Half-life by Indirect Targeting of the Neonatal Fc Receptor (FcRn) Using a Minimal Albumin Binding Domain", Journal of Biological Chemistry, 286(7):5234-5241.

Andersen, Jan Terje et al., 2011, "Structure-based mutagenesis reveals the albumin-binding site of the neonatal Fc Receptor", Nature Communications, 3:610:1-9.

Carlson, Joyce et al., 1992, "Alloalbuminemia in Sweden: Structural study and phenotypic distribution of nine albumin variants", Proc. Natl. Acad. Sci. USA, 89:8225-8229.

Galliano, Monica et al., 1993, "Protein and DNA sequence analysis of a 'private' genetic variant: albumin Ortonovo (Glu-505→Lys)", 1125:27-32.

Ishima, Yu et al., 2007, "S-Nitrosylation of Human Variant Albumin Liprizzi (R410C) Confers Potent Antibacterial and Cytoprotective Properties", The Journal of Pharmacology and Experimental Therapeutics, 320(3):969-977.

International Search Report corresponding to PCT/US11/24855 dated Apr. 11, 2011.

Iwao, Yasunori et al., 2007, "Changes of net charge and α-helical content affect the pharmacokinetic properties of human serum albumin", ScienceDirect, 1582-1590.

Kenanova, Vania et al. 2009, "HSA Domain III as a protein scaffold with defined serum pharmacokinetics", The Journal of Nuclear Medicine, Abstract #1582.

Kenanova, Vania et al. 2010, "Tuning the serum persistence of human serum albumin domain III: diabody fusion proteins", Protein Engineering, Design & Selection, 23(10):789-798.

Minchiotti, Lorenzo et al., 1987, "Structural characterization of two genetic variants of human serum albumin", Biochimica et Biophysica Acta 916:411-418.

Minchiotti, Lorenzo et al., 2008, "Mutations and Polymorphisms of the Gene of the Major Human Blood Protein, Serum Albumin", Human Mutation 29(8):1007-1016.

Otagiri, Masaki et al., 2009, "Pharmaceutically Important Pre- and Posttranslational Modifications on Human Serum Albumin", Bio, Pharm. Bull. 32(4): 527-534.

Peach, Robert J. et al., 1991, Structural characterization of a glycoprotein variant of human serum albumin: albumin Casebrook (494 Asp → Asn), Biochimica et Biophysica Acta, 1097:49-54.

Sandlie, Inger, 2012, "Tailoring the Lifespan of Biopharmaceuticals by Targeting the Neonatal Fc Receptor (FcRn)", 5th Annual Proteins Congress, London, Conference Presentation Slides 1-41.

Sheffield, William P. et al., 2000, "Modulation of Clearance of Recombinant Serum Albumin by Either Glycosylation or Truncation", Thrombosis Research, 99:613-621.

Takahashi, Nobuhiro et al., 1987, "Amino Acid substitutions in genetic variants of human serum albumin and in sequences inferred from molecular cloning", Proc. Natl. Acad. Sci. USA, 84:4413-4417.

International Search Report and Written Opinion dated Feb. 13, 2012 in International Application No. PCT/US2011/047040, filed: Aug. 9, 2011 and published as WO/2012/112188 on Aug. 23, 2012.

Supplementary European Search Report dated Jul. 17, 2013 in European Patent Application No. 11745103.9, filed on Feb. 15, 2011 and published as EP 2 536 756 on Dec. 26, 2012.

Chaudhury et al., "Albumin Binding to FcRn: Distinct from the FcRn-IgG Interaction" Biochemistry (2006) 45:4983-4990.

Sugio et al., "Crystal structure of human serum albumin at 2.5 angstroms resolution" protein Engineering (1999) 12:439-446.

* cited by examiner

EBNA-1 Protein

MSDEGPGTGPGNGLGEKGDTSGPEGSGGSGPQRRGGDNHGRGRGRGRGRGGGRPGAPGGSGSGPRHRDGVRRPQKRPSCIGCKGTHGG
TGAGAGAGGAGAGGAGAGGGAGAGGGAGGAGGAGGAGAGGGAGAGGGAGGAGGAGAGGCAGAGGGAGGAGAGGGAGGAGCAGAGGGAG
AGGGAGGAGAGGGAGGAGGAGAGGGAGAGGAGGAGGAGAGGAGAGGGAGGAGGAGAGGAGAGGAGAGGAGAGGAGGAGAGCAGGAGAG
GAGGAGAGGGAGGAGAGGAGGAGAGGAGGAGAGGAGGAGAGGAGGAGAGGGAGAGGACAGGGGRGRGGSGGRGRGGSGGRGRGGSGG
RRGRGRERARGGSRERARGRGRGRGEKRPRSPSSQSSSSGSPPRRPPPGRRPFFHPVGEADYFEYHQEGGPDGEPDVPPGAIEQGPAD
DPGEGPSTGPRGQGDGGRRKKGGWFGKHRGQGGSNPKFENIAEGLRALLARSHVERTTDEGTWVAGVFVYGGSKTSLYNLRRGTALAI
PQCRLTPLSRLPFGMAPGPGPQPGPLRESIVCYFMVFLQTHIFAEVLKDAIKDLVMTKPAPTCNIRVTVCSFDDGVDLPPWFPPMVEG
AAAEGDDGDDGDEGGDGDEGEEGQE    (SEQ ID NO: 15)

Figure 9A

EBNA-1 Gene sequence

```
ATGTCTGACGAGGGGCCAGGTACACGACCTGGAAATGGCCTAGGAGAGAAGGGAGACACATCTGGACCAGAAGGCTCCGGCGGCAGTG
GACCTCAAAGAAGAGGGGGTGATAACCATGGACGAGGACGGGGAAGAGGACGACGACGAGGAGGCGGAAGACCAGGAGCCCCGGCGG
CTCAGGATCAGGGCCAAGACATAGAGATGGTGTCCGGACACCCCAAAAACGTCCAAGTTGCATTGGCTGCAAAGGCACCCACCGTGGA
ACAGGAGCAGGAGCAGGAGCGGGACGGGCAGGAGCAGGACGGGCAGGAGCAGGAGGAGGGGCAGGAGCAGGAGGACGGGCAGGAGGGG
CAGGAGGGGCAGGACGGGCAGGAGCAGGAGGAGGGGCACCAGCAGGAGGAGGGCCAGGAGCCGCAGGAGGGGCAGCAGCAGGAGGAGG
GGCAGGAGCAGGAGGAGGGGCAGGAGGGGCAGGAGCAGGAGGAGGGGCAGGAGCGGCAGGACGGGCAGGAGCAGGAGGAGGGGCAGGA
GCAGGAGGAGGGGCAGGAGGGGCACGAGCAGGAGGAGGGCCAGGAGCGGCAGGAGGGGCACCAGCAGGAGGAGGGCCAGGAGCAGGAG
GGGCAGGAGGGGCAGGAGGGCAGCAGCAGGAGGGGCACCAGCAGGAGGAGGGCCAGGAGCCGCAGGAGGGGCAGCAGCAGGAGGGGC
AGGAGCAGGAGGGGCAGGAGCAGGAGGGGCAGGAGCAGCAGGGGCACGAGGGGCAGGAGCACGAGGGGCAGGAGGCGCAGGACCAGGA
GGGGCAGGAGGGGCAGGAGCAGGACGAGGGGCAGGAGGGCCAGGAGCAGGAGGAGGGGCACCAGGGGCAGGAGCACGAGGGGCAGGAG
GGGCAGGAGCAGGAGGGGCAGGAGCGGCAGGAGCAGGACCGGCAGGAGGGGCACGAGCAGCAGGAGGGGCAGGAGCAGGAGGCGCAGG
AGCAGGAGGTGGAGGCCGGGTCGAGGAGGCAGTGGAGCCGGGGTCGAGGAGCTAGTGGACGCCGGGGTCGAGGAGGTAGTCGAGGC
CGCCGGGGTAGAGGACGTGAAAGAGCCAGGGGGGAAGTCGTGAAAGAGCCAGCGGGAGACCTCGTGGACGTGGACAAAAGACGCCCA
GGAGTCCCAGTAGTCAGTCATCATCATCCGGGTCTCCACCGCGCAGGCCCCCTCCAGGTAGAAGGCCATTTTTCCACCCTGTAGGGGA
AGCCGATTATTTTGAATACCACCAAGAAGGTGGCCCAGATGGTGAGCCTGACGTGCCCCCGGGAGCGATAGAGCACGGCCCCGCAGAT
GACCCAGGAGAAGGCCCAAGCACTCGACCCCGGGGTCACCGTGATGGAGGCAGCCGCAAAAAAGGAGGGTGGTTTCGAAAGCATCGTG
GTCAAGGAGGTTCCAACCCGAAATTTGAGAACATTGCAGAAGGTTTAAGAGCTCTCCTGGCTAGGAGTCACGTAGAAAGGACTACCGA
CGAAGGAACTTGGGTCGCCGGTGTCTTCGTATATGGAGCTAGTAAGACCTCCCTTTACAACCTAAGGCGAGGAACTGCCCTTGCTATT
CCACAATGTCGTCTTACACCATTGAGTCGTCTCCCCTTTCGAATGGCCCCTGGACCCGGCCCACAACCTGGCCCGCTAAGGGAGTCCA
TTGTCTGTTATTTCATGGTCTTTTTACAAACTCATATATTTGCTGACGTTTTGAAGGATGCCATTAAGGACCTTGTTATGACAAAGCC
CGCTCCTACCTGCAATATCAGGGTCACTGTGTGCAGCTTTGACGATCGAGTAGATTTGCCTCCCTGGTTTCCACCTATGGTGGAAGGG
GCTGCCGCGGAGGGTGATGACGGACATGACGGAGATGAACGAGGTGATGGAGATGAGGGTCAGGAAGGGCAGGAGTGA
(SEQ ID NO: 16)
```

Figure 9B

OriP DNA sequence

CCTTTATGTGTAACTCTTGGCTGAAGCTCTTACACCAATGCTGGGGGACATGTACCTCCCAGGGGCCCAGGAACACTACGGGAGGCTA
CACCAACGTCAATCAGAGGGGCCTCTGTAGCTACCGATAAGCGGACCCTCAAGAGGGCATTAGCAATAGTGTTTATAAGGCCCCCTTG
TTAACCCTAAACGGGTAGCATATGCTTCCCGGGTAGTAGTATATACTATCCAGACTAACCCTAATTCAATAGCATATGTTACCCAACG
GGAAGCATATGCTATCGAATTAGGGTTAGTAAAAGGGTCCTAAGGAACAGCGATATCTCCCACCCCATGAGCTCTCACGGTTTTATTT
ACATGCGGTCAGGATTCCACGAGGCTAGTGAACCATTTTAGTCACAAGGGCAGTGGCTCAAGATCAAGGAGCGCGCAGTGAACTCTCC
TGAATCTTCGCCTGCTTCTTCATTCTCCTTCGTTTAGCTAATAGAATAACTGCTGAGTTGTGAACAGTAAGGTCTATGTGAGGTGCTC
GAAAACAAGGTTTCAGGTGACGCCCCAGAATAAAATTTGGACGGGGGGTTCAGTGGTCGCATTGTGCTATGACACCAATATAACCCT
CACAAACCCCTTGGGCAATAAATACTAGTGTAGGAATGAAACATTCTGAATATCTTTAACAATAGAAATCCATCGGGTGGGGACAAGC
CGTAAAGACTGGATGTCCATCTCACACGAATTTATGGCTATGGGCAACACATAATCCTAGTGCAATATGATACTGGGGTTATTAAGAT
GTGTCCCAGGCAGGGACCAAGACACGTGAACCATGTTGTTACACTCTATTTGTAACAAGGCGAAAGAGAGTGGACGCCGACAGCAGCG
GACTCCACTGGTTGTCTCTAACACCCCCGAAAATTAAACGGGCTCCACGCCAATGGGCCCCATAAACAAAGACAAGTGGCCACTCTT
TTTTTTGAAATTGTGGAGTGGGGGCACGCGTCAGCCCCCACACGCCGCCCTGCGGTTTTGCACTGTAAAATAACGGTGTAATAACTTG
GCTGATTGTAACCCCGCTAACCACTGCGGTCAAACCACTTGCCCACAAAACCACTAATGGCACCCCGGGGAATACCTGCATAAGTAGG
TGGGCGGGCCAAGATAGGGCGCGATTGCTGCGATCTGGAGGACAAATTACACACACTTGCGCCTGAGCGCCAAGCACAGGGTTGTTG
GTCCTCATATTCACGAGGTCGCTGAGAGCACGGTGGGCTAATGTTGCCATGGGTAGCATATACTACCCAAATATCTGGATAGCATATG
CTATCCTAATCTATATCTGGGTAGCATAGGCTATCCTAATCTATATCTGGGTAGCATATGCTATCCTAATCTATATCTGGGTAGTATA
TGCTATCCTAATTTATATCTGGGTAGCATAGGCTATCCTAATCTATATCTGGGTAGCATATGCTATCCTAATCTATATCTGGGTAGTA
TATGCTATCCTAATCTGTATCCGGCTAGCATATGCTATCCTAATAGAGATTAGGGTAGTATATGCTATCCTAATTTATATCTGGGTAG
CATATACTACCCAAATATCTGGATAGCATATGCTATCCTAATCTATATCTGGGTAGCATATGCTATCCTAATCTATATCTGGGTAGCA
TAGGCTATCCTAATCTATATCTGGGTAGCATATGCTATCCTAATCTATATCTGGGTAGTATATGCTATCCTAATTTATATCTGGGTAG
CATAGGCTATCCTAATCTATATCTGGGTAGCATATGCTATCCTAATCTATATCTGGGTAGTATATGCTATCCTAATCTGTATCGGGT
AGCATATGCTATCCTCATGCATATACAGTCAGCATATGATACCCAGTAGTAGAGTGGGAGTGCTATCCTTTGCATATGCCGCCACCTC
CCAAGGGGGCGTGAATTTTCGCTGCTTGTCCTTTTCCTGC    (SEQ ID NO: 17)

Figure 9C

US 8,697,650 B2

HSA-RELATED COMPOSITIONS AND METHODS OF USE

1 CROSS REFERENCE TO RELATED APPLICATIONS

This application is a National Stage Application of International Application No. PCT/US2011/024855 filed on Feb. 15, 2011, said International Application No. PCT/US2011/024855 claims benefit under 35 U.S.C. §119(e) of U.S. Provisional Application Nos. 61/304,954, filed on Feb. 16, 2010 and 60/364,503, filed on Jul. 15, 2010. Each of the above listed applications is incorporated by reference herein in its entirety for all purposes.

2 REFERENCE TO THE SEQUENCE LISTING

This application incorporates by reference a Sequence Listing submitted with this application as text file entitled MED0554_PCT_ST25.txt created on Jul. 25, 2012 and having a size of 38.5 kilobytes.

3 BACKGROUND OF THE INVENTION

The neonatal Fc receptor (FcRn) prolongs the lifespan of both IgG and human serum albumin (HSA), by a pH dependent mechanism, specifically binding both molecules at the acidic pH of the endosome and recycling them back to the cell surface, thus diverting both molecules away from the default lysosomal degradation pathway. It has been shown that FcRn binding capacity is intrinsic to domain-III of albumin.

4 SUMMARY OF THE INVENTION

The disclosure provides HSA-related compositions and methods of use. The present disclosure provides chimeric polypeptides comprising a human serum albumin (HSA) portion which comprises a neonatal FcRn binding fragment and a heterologous polypeptide or a bioactive fragment thereof, as well as compositions comprising the chimeric polypeptides in combination with a pharmaceutical carrier. Also disclosed are constructs useful for producing such chimeric polypeptides. Further, the present disclosure teaches methods of making the chimeric polypeptides and constructs that encode them. The disclosure further provides polypeptides comprising a human serum albumin (HSA) portion, which HSA portion comprises HSA domain III, or a neonatal Fc receptor (FcRn) binding fragment thereof wherein the HSA domain III comprises one to eighteen amino acid substitutions to increase one or both of affinity for FcRn and serum half-life of the polypeptide relative to a control polypeptide in which the HSA portion does not include said amino acid substitutions. The disclosure also provides chimeric polypeptides comprising a human serum albumin (HSA) portion, which HSA portion comprises HSA domain III, or a neonatal Fc receptor (FcRn) binding fragment thereof, and a heterologous protein, wherein the chimeric polypeptide retains a functional activity of the heterologous protein and can bind to an FcRn, and the HSA domain III comprises at least one amino acid substitution to increase one or both of affinity for FcRn and serum half-life of the chimeric polypeptide relative to a control chimeric polypeptide in which the HSA portion does not include said amino acid substitutions. Additionally, disclosed herein are methods of using the chimeric polypeptides, for example, to increase the serum half-life of a protein. Also disclosed are methods and vectors useful for the generation of adenovirus libraries useful for screening large diverse populations of polypeptides. Such methods are useful for the screening and identification of HSA domain III amino acid substitutions that increase one or both of affinity for FcRn and serum half-life.

In certain embodiments, the chimeric polypeptide has one or both of increased affinity for FcRn and increased serum half-life relative to a control polypeptide which does not comprise the HSA portion. In certain embodiments, the chimeric polypeptide has an increased serum half-life. In certain embodiments, the chimeric polypeptide has both increased affinity for FcRn and increased serum half-life. In certain embodiments, the chimeric polypeptide has increased affinity for FcRn at acidic pH (e.g., pH of approx 5.5). In other embodiments, the chimeric polypeptide has increased FcRn at acidic pH (e.g., pH of approx 5.5) the affinity of the chimeric polypeptide for FcRn at neutral pH (e.g., pH of approx 7.4) is not substantially altered.

The disclosure contemplates all combinations of any of the foregoing aspects and embodiments, as well as combinations with any of the embodiments set forth in the detailed description and examples.

5 BRIEF DESCRIPTION OF THE DRAWINGS

For the purpose of illustrating the invention, there are depicted in the drawings certain embodiments on the invention. However, the invention is not limited to the precise arrangements and instrumentalities of the embodiments depicted in the drawings.

Figure 1B:
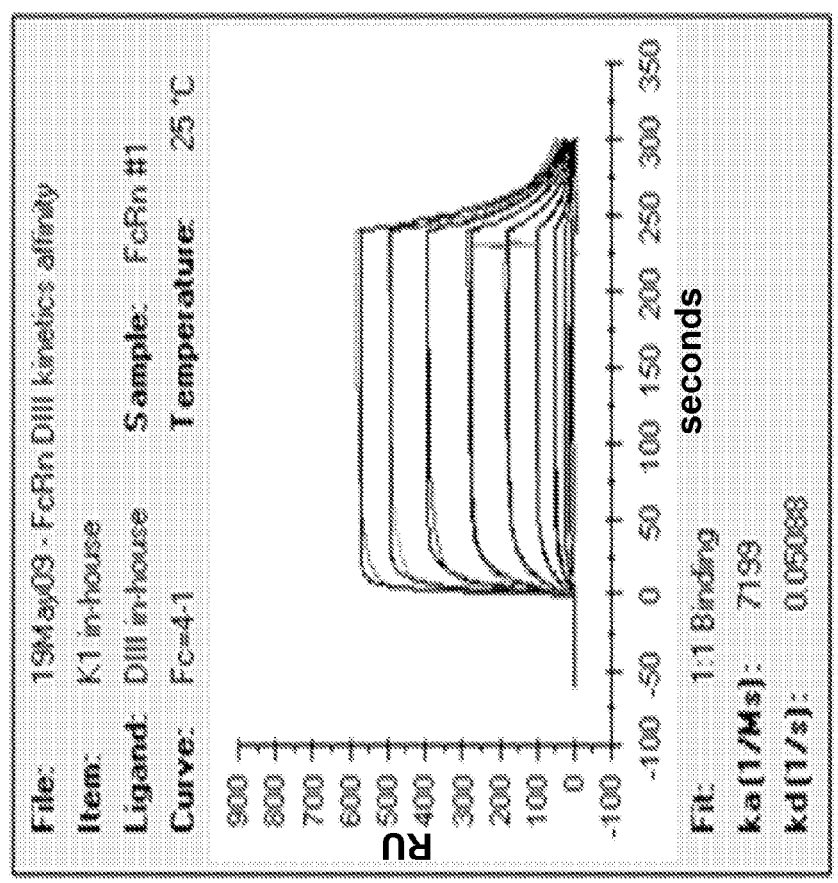
Figure 1C:
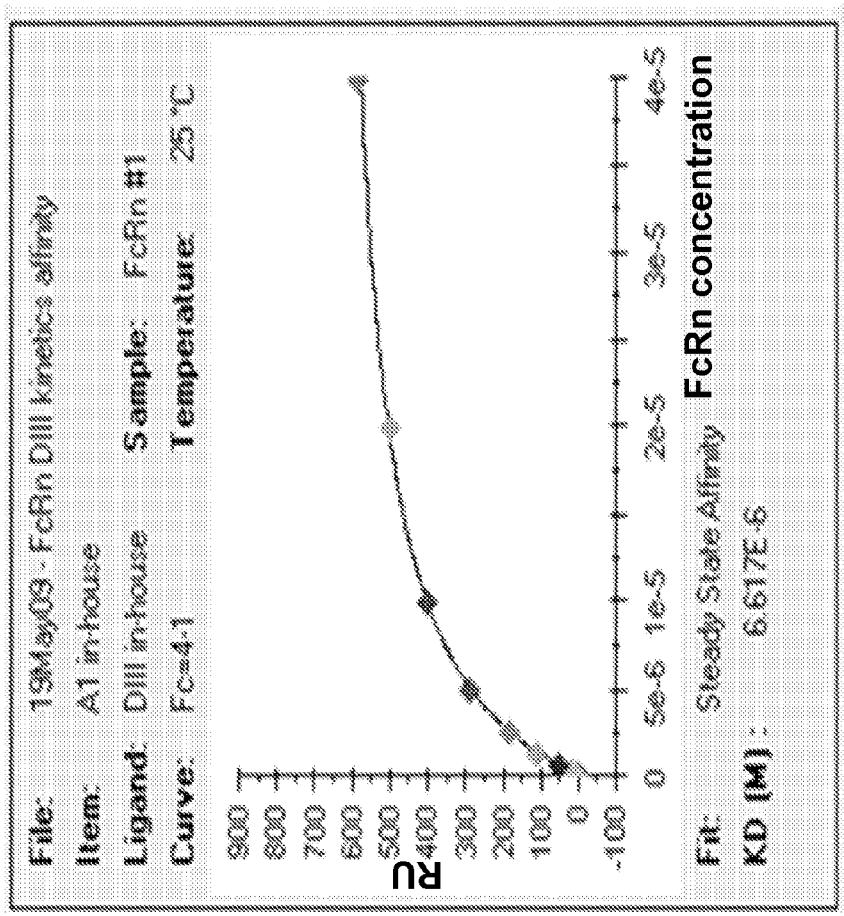

FIG. 1 provides kinetic and equilibrium analysis of human FcRn binding to domain III of human serum albumin (HSA). Presented here are the SPR-derived association, dissociation kinetics and equilibrium binding constant for human FcRn binding to immobilized domain III at pH 5.5. FIG. 1A represents a Coomassie stained PAGE gel documenting the successful expression and purification of domain III of HSA from *Pichia Pastoris* (indicated by arrow). FIG. 1B represents a binding sensorgram generated by injecting a range of FcRn concentrations over domain III immobilized on a CM5 chip. FIG. 1C represents a plot of binding response at equilibrium versus FcRn concentration fit to steady state affinity model.

Figure 2A:
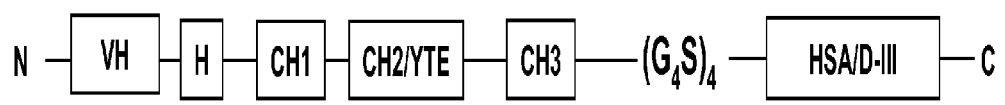
Figure 2B:
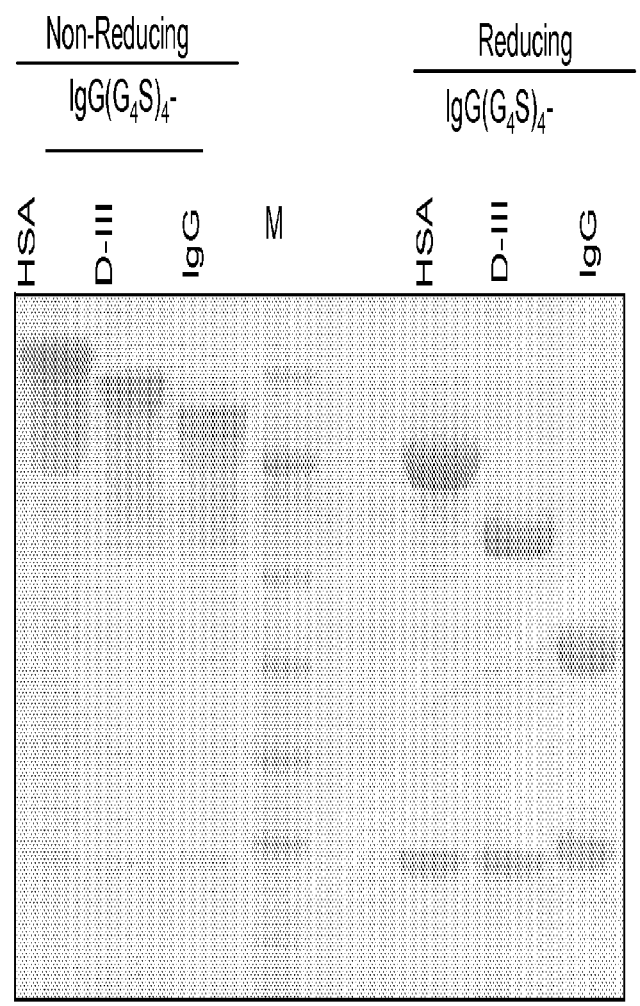
Figure 2C:
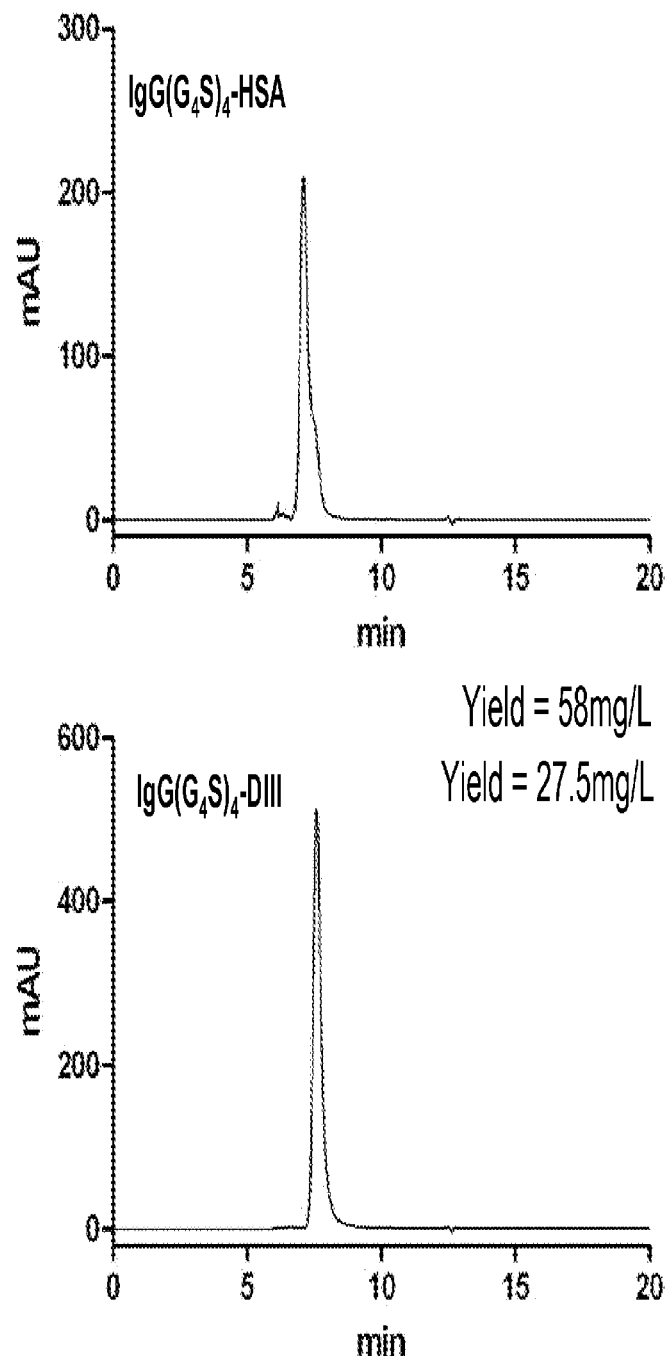

FIG. 2 provides a schematic representation of various construct designs, as well as information regarding purification and characterization of IgG fused to HSA and IgG fused to domain III. FIG. 2A represents the DNA construct of the heavy chain of the recombinant IgG-HSA or IgG-domain III fusion protein, as well as the YTE variant. FIG. 2B represents SDS PAGE analysis of purified fusion proteins (5 µg/lane) under reducing and non reducing conditions. FIG. 2C represents analytical size exclusion chromatography of purified IgG-fusion proteins.

Figure 3A:
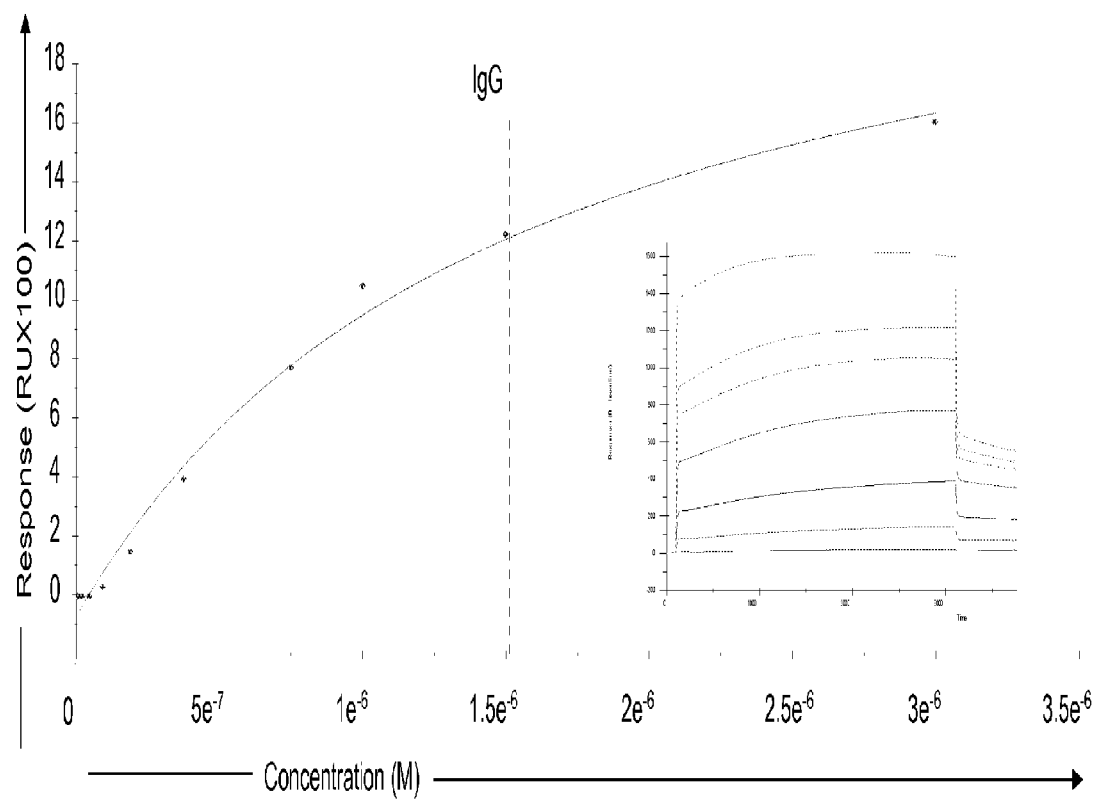
Figure 3B:
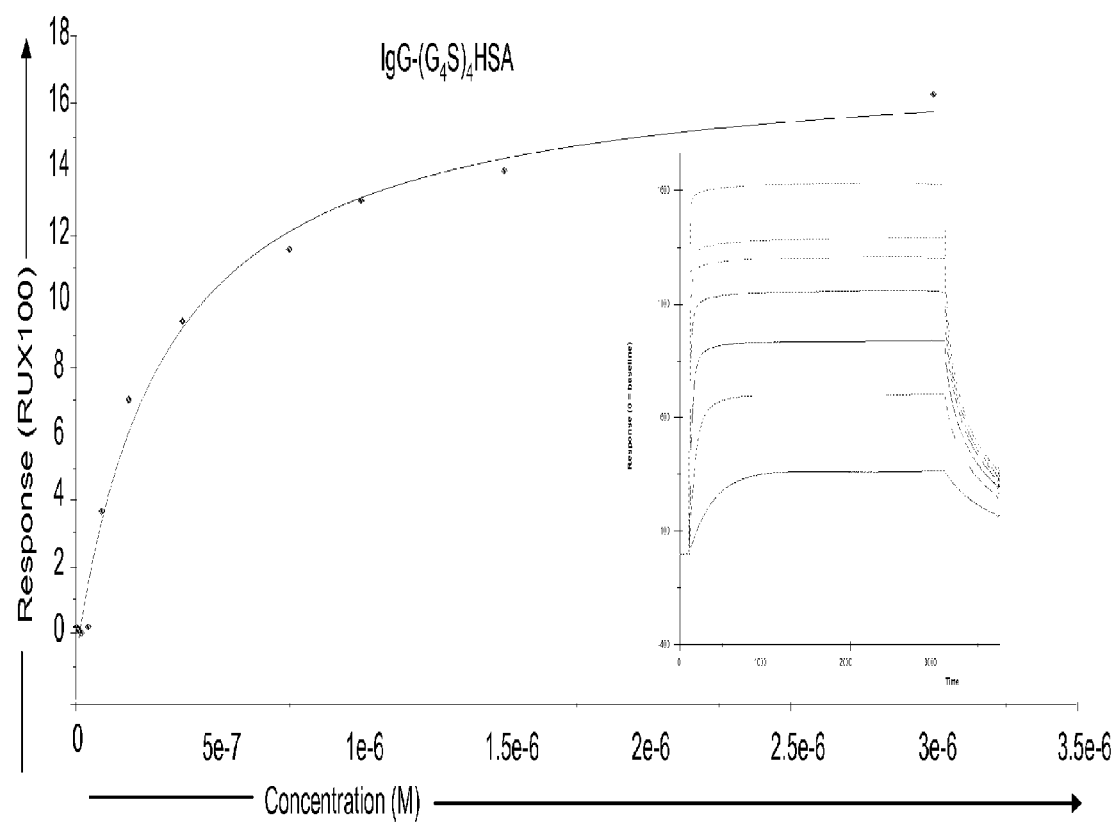
Figure 3C:
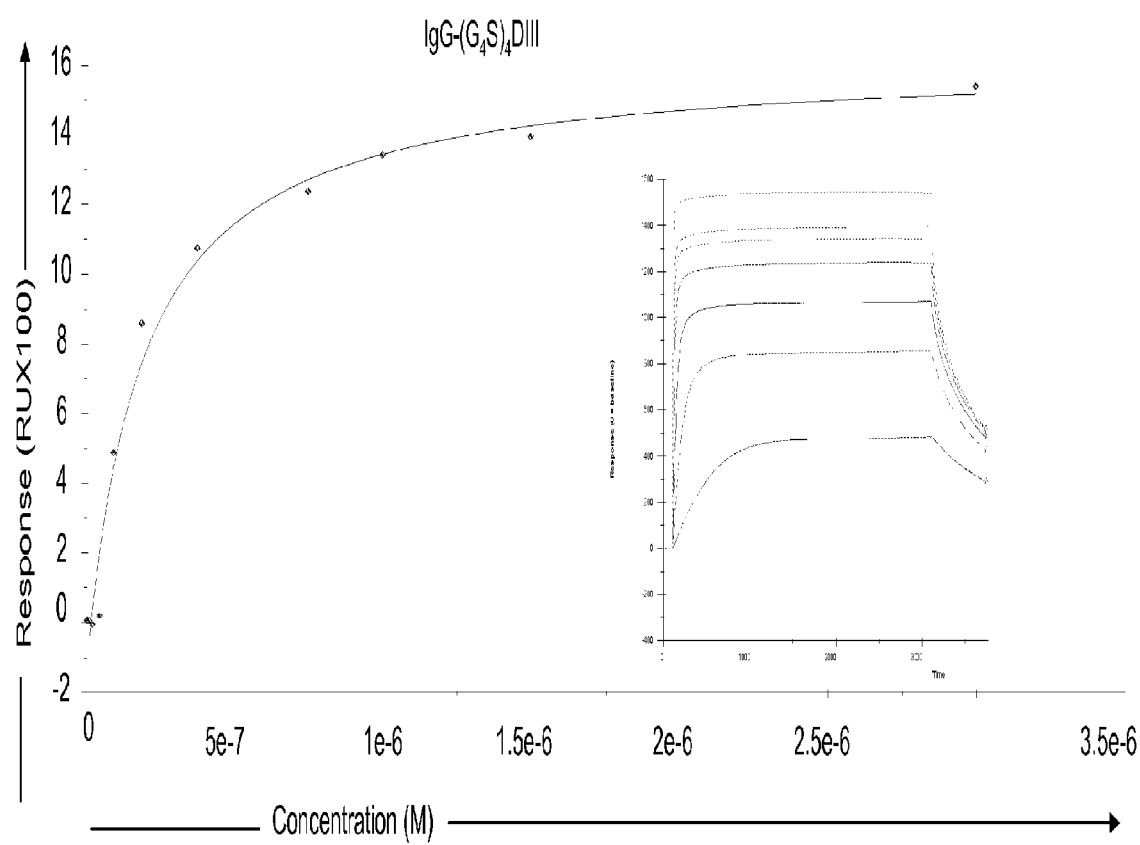

FIG. 3 provides SPR-derived equilibrium constants for human FcRn binding to IgG fused with HSA and IgG fused with domain III. The RU at equilibrium (Req) for each FcRn injection were plotted versus the human FcRn concentration, and the data were fit to a steady-state affinity model to calculate $K_D$ for immobilized IgG (panel A), IgG fused to HSA (panel B) and IgG fused to domain III (panel C). The sensorgrams in the insets show the mass (resonance units) of FcRn bound to immobilized ligand on the Y-axis after blank subtraction versus time on the X-axis.

Figure 4:
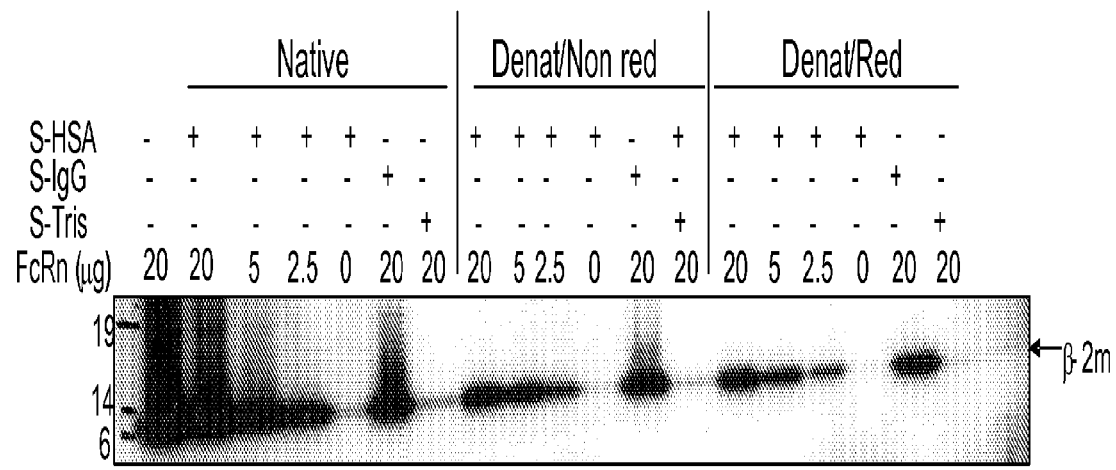

FIG. 4 provides evidence indicating that the epitope on HSA for FcRn is a conformational epitope. Sepharose (S)-HSA, S-IgG or S-Tris treated in three different ways was incubated with human FcRn at pH 5.5. Bound FcRn was eluted and quantified by immunoblotting with anti-132 microglobulin antibody. The positions of molecular weight markers (M, in kD) are shown. Lane 1 contains 20 µg human FcRn, the amount added to every adsorbent sample.

Figure 5A:
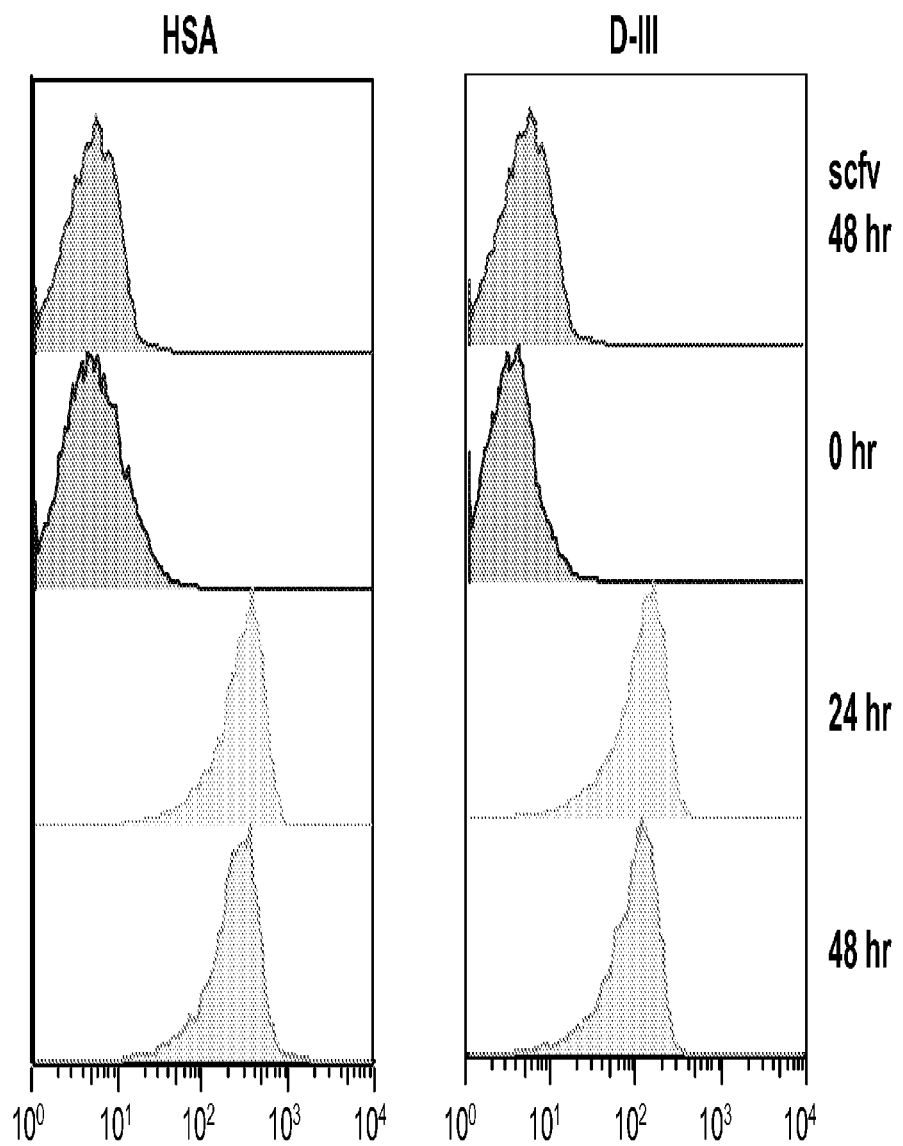
Figure 5B:
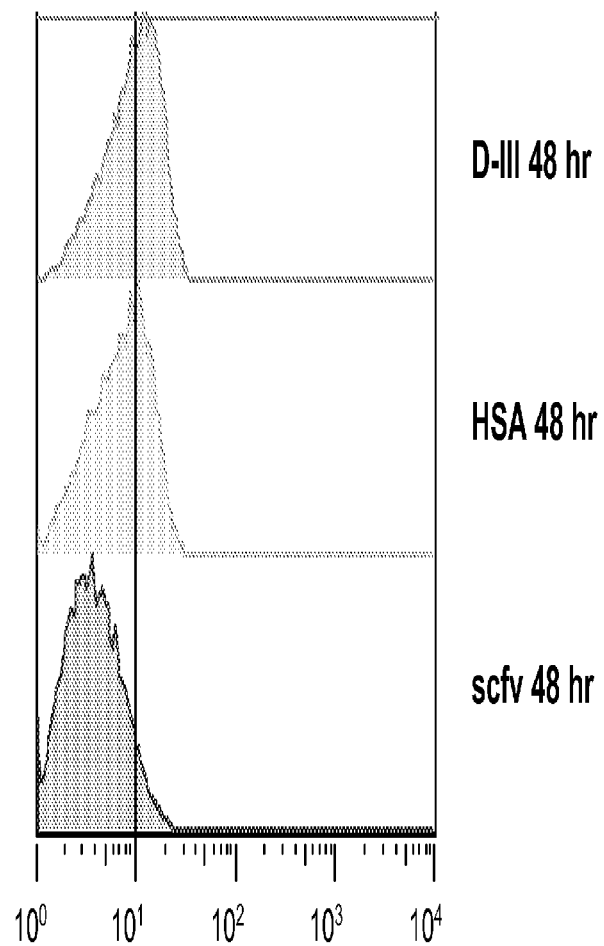
Figure 6A:
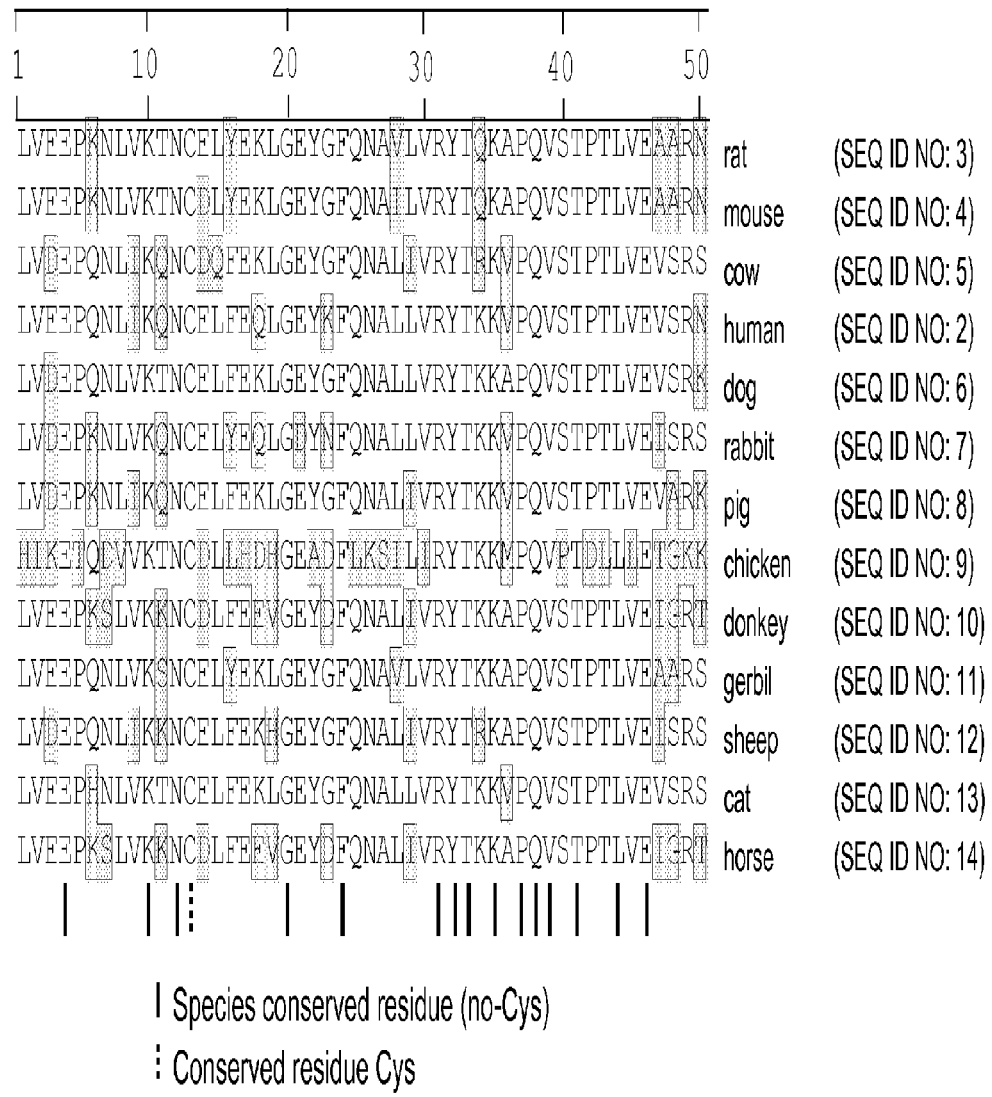
Figure 6B:
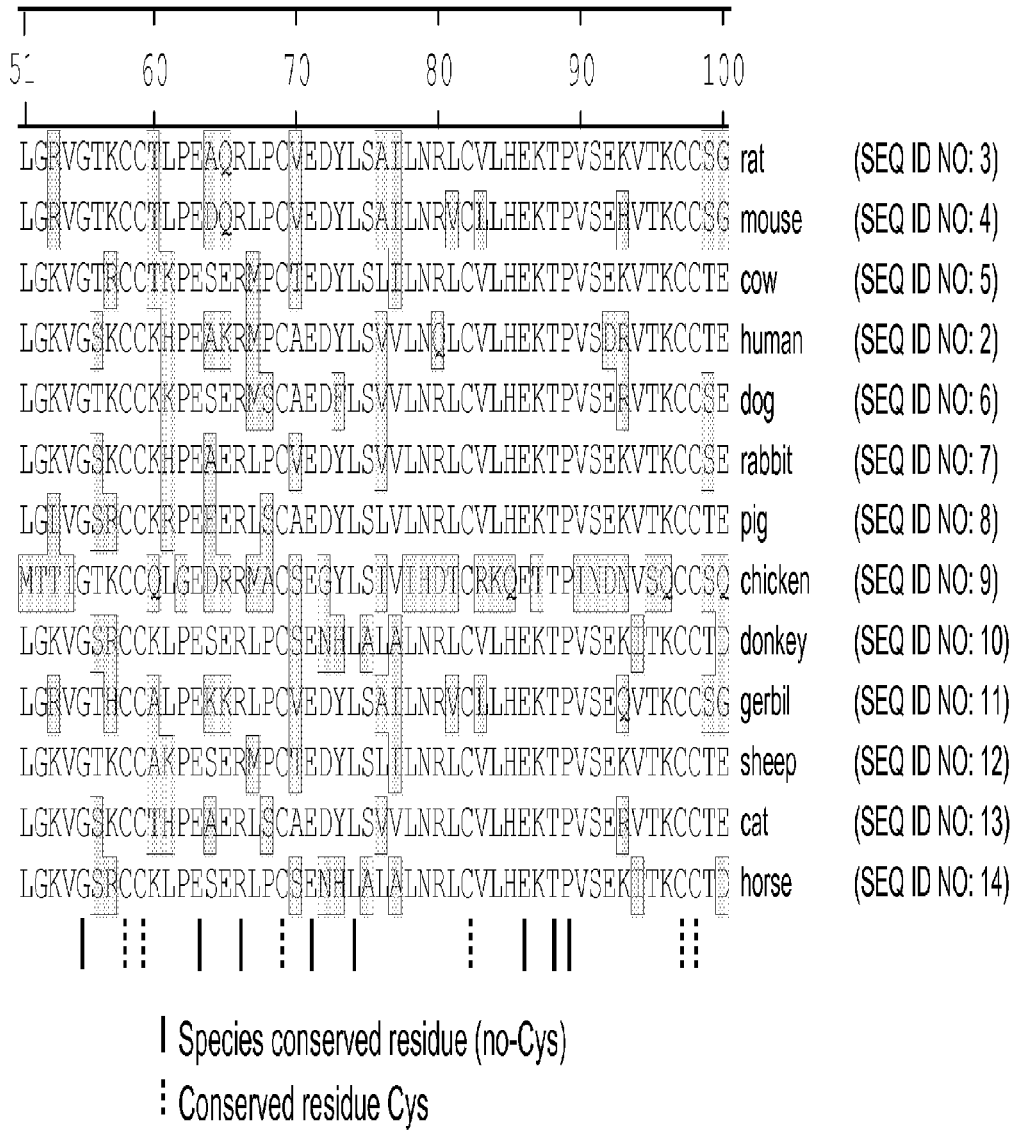
Figure 6C:
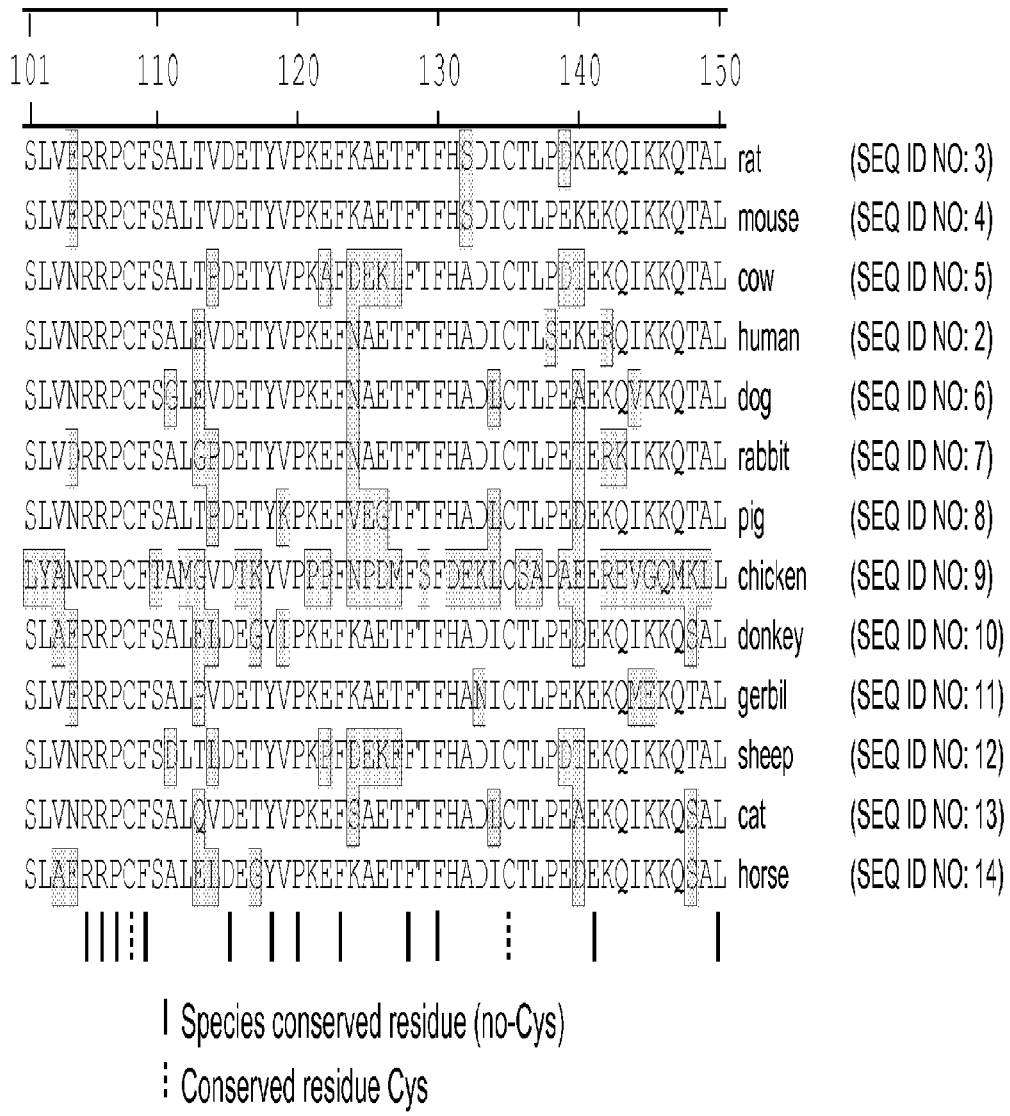
Figure 6D:
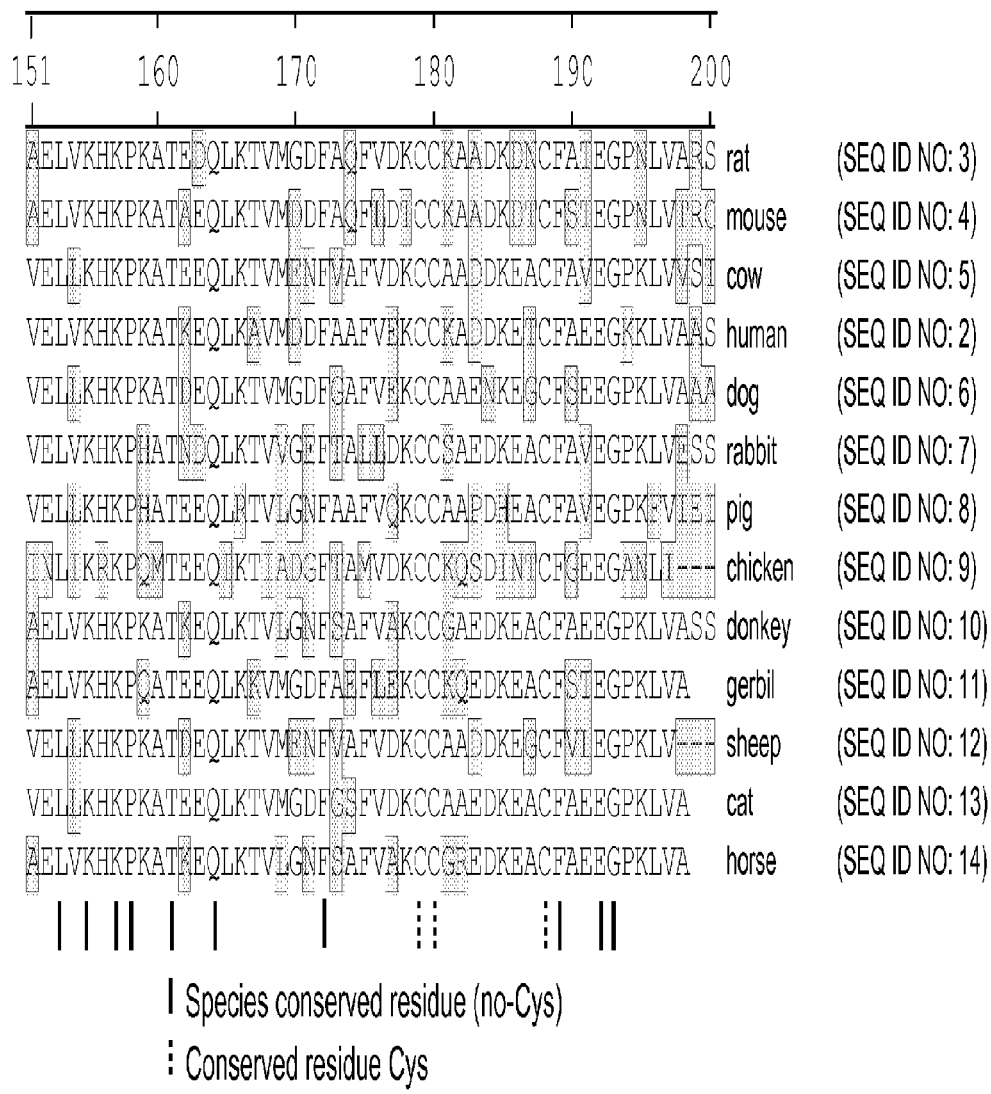
Figure 6E:
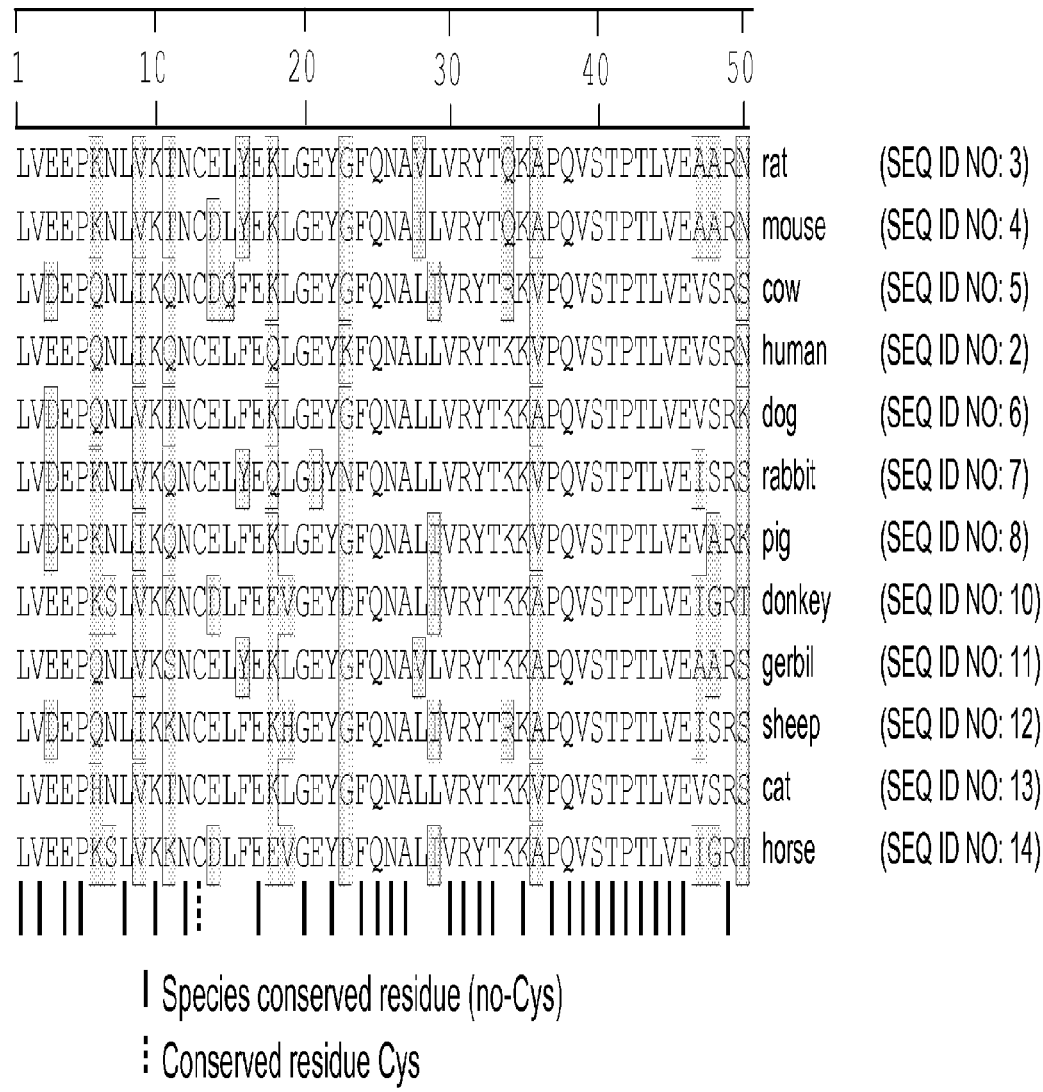
Figure 6F:
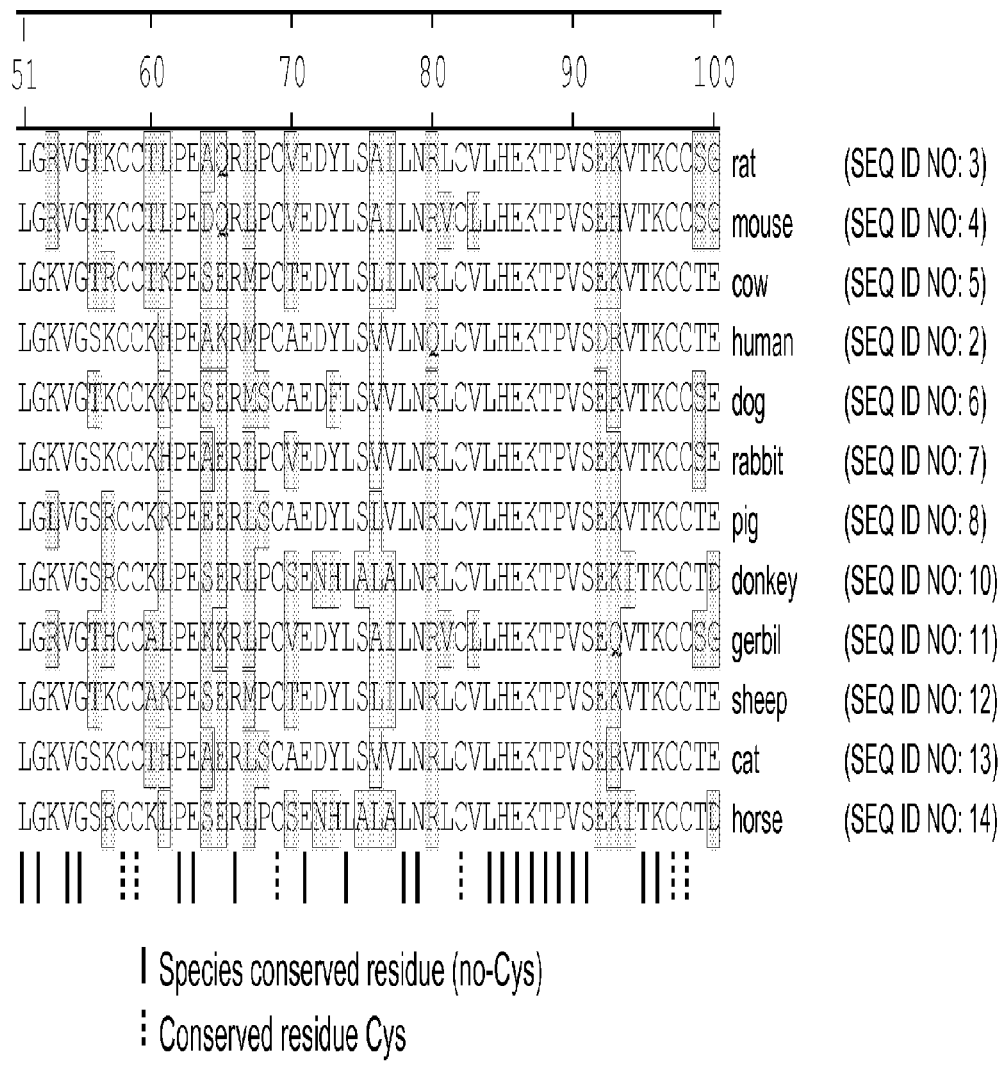
Figure 6G:
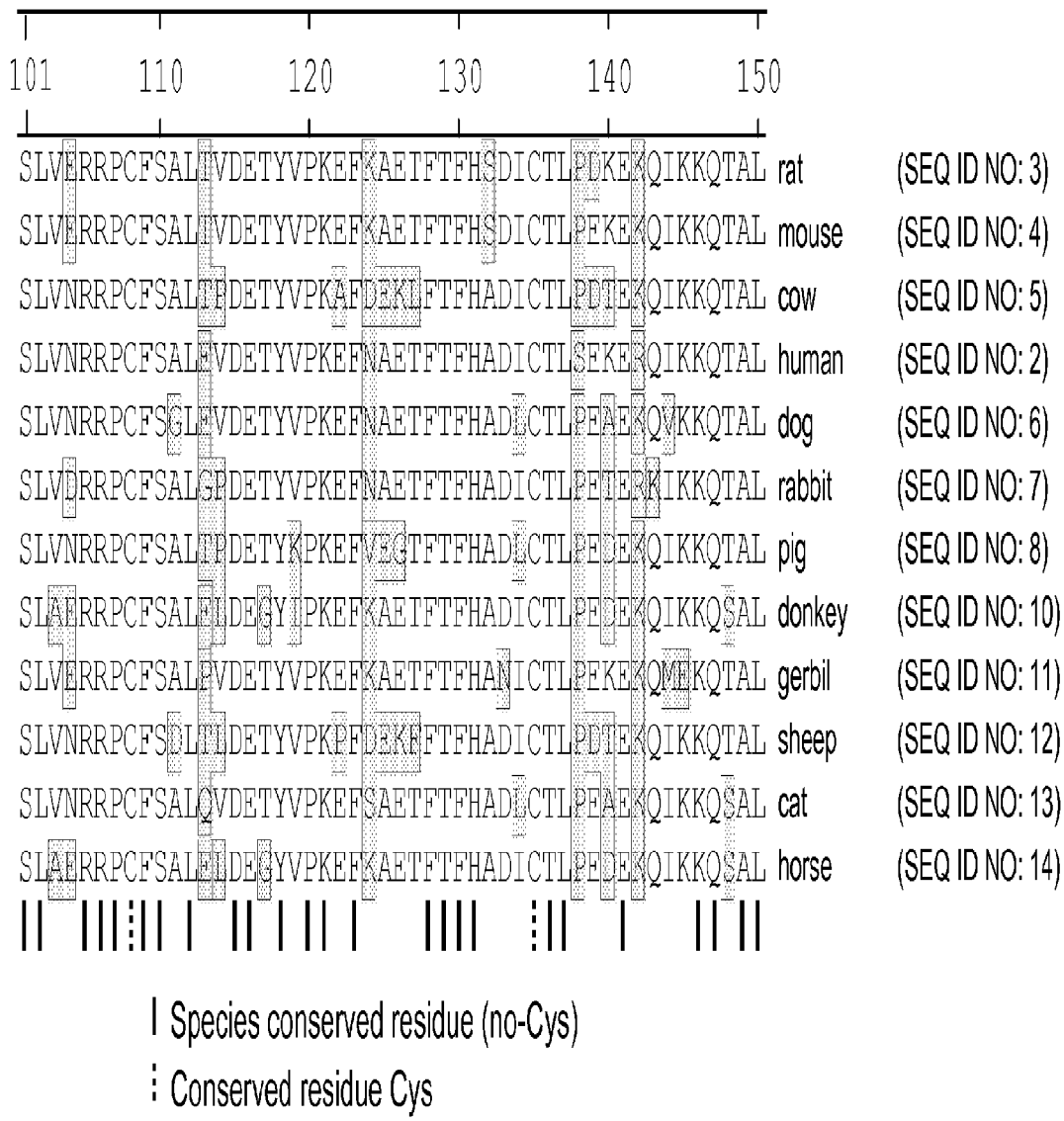
Figure 6H:
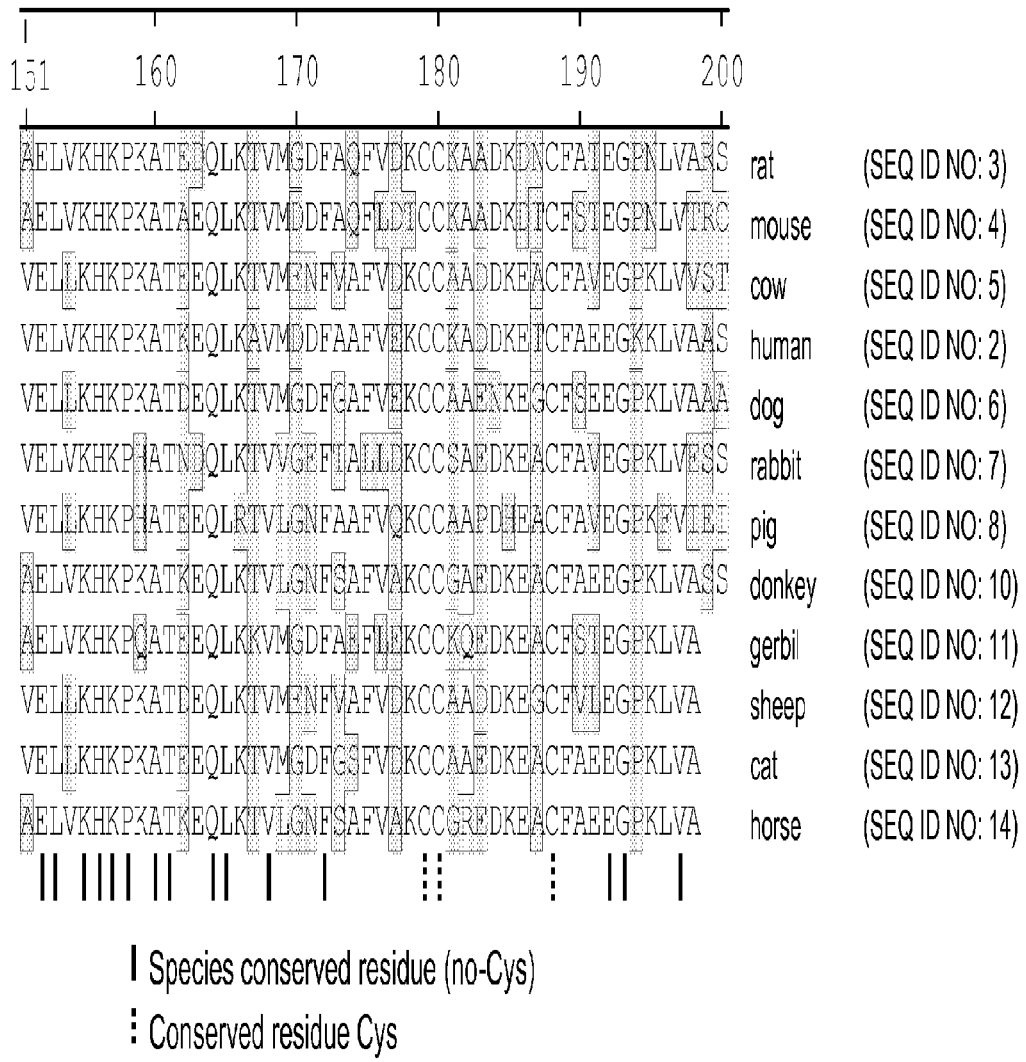

FIG. 5 shows that HSA and domain III displayed on the surface of yeast cells (*S. Cerevisiae*) retain FcRn binding capacity. FIG. 5A represents flow cytometry detection of HSA or domain III on *S. Cerevisiae* cells transformed with a galactose inducible pYD1 cell surface display plasmid using FITC conjugated anti-HSA antibody. The cells were induced with galactose for the indicated times. Panel B represents the binding of biotinylated human FcRn to HSA or domain III displayed on *S. Cerevisiae* cells induced for 48 hrs and visualized by anti-Streptavidin Phycoerythrin using flow cytometry. Yeast cells transformed with a scfv were used as a control for background fluorescence for FITC as well as phycoerythrin. Experiments are expressed as histograms of fluorescence intensity (log scale) versus the number of cells.

FIG. 6 provides an amino acid sequence alignment of domain III from different species (human, pig, rat, mouse, dog, rabbit, cow, chicken, donkey, Mongolian gerbil, sheep, cat, and horse). The alignment in panels A-D includes chicken while panels EH-excludes chicken. Amino acid residues conserved amongst different species are marked with a solid line and the conserved cysteine residues are marked with a dotted line. The shaded amino acid residues are not conserved amongst species. Note that the amino acid numbering in FIG. 6 is only with respect to human domain III, rather than shown with respect to the numbering of domain III relative to full length mature HSA.

Figure 7:
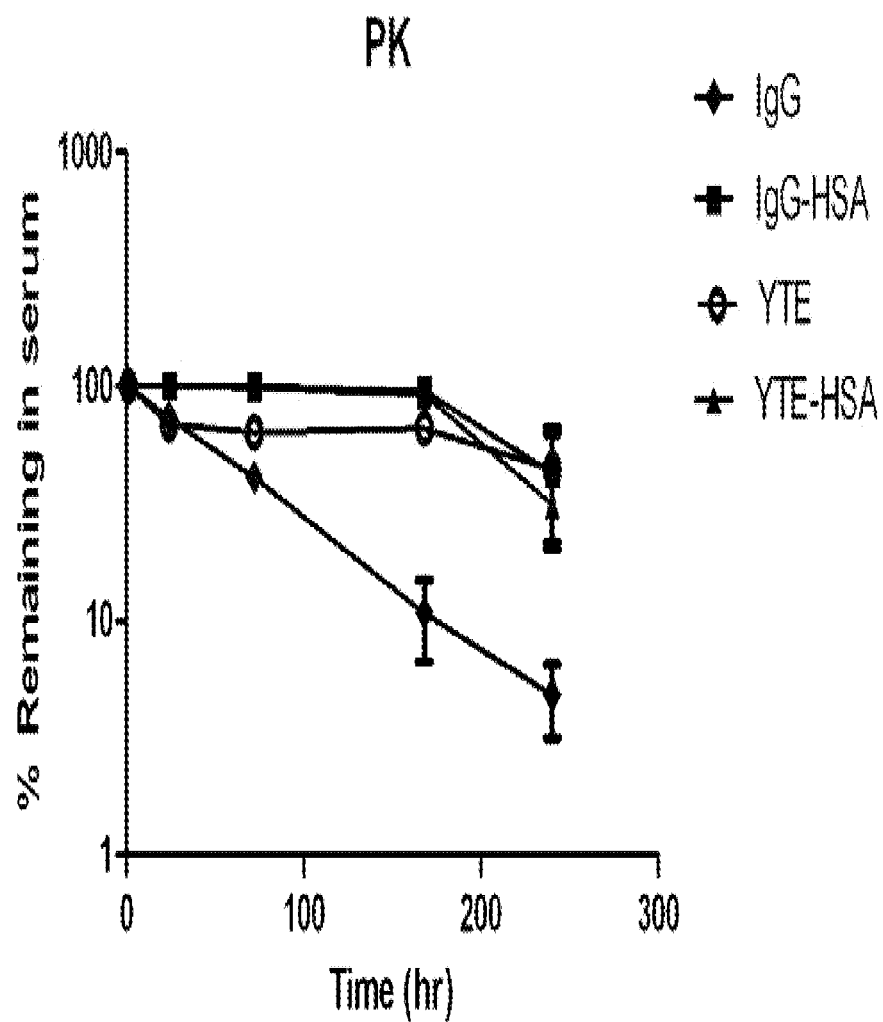

FIG. 7 shows that fusion of HSA to an IgG having a wild type increases serum persistence to a similar level as seen for the IgG-YTE variant. The % of the injected sample remaining in the serum is plotted over time (1 to 240 hours).

FIG. 8 depicts the plasmid maps of the scFv-Fc cell surface display library entry vectors. Panel A depicts the plasmid map of the pENDisplay vector containing an scFv-Fc-GPI-anchor cassette operably linked to a promoter (here a CMV promoter) and terminating with polyA sequence (here the BGH polyA sequence). The scFv portion is flanked by Sfi I and Not I restriction enzyme sites to facilitate cloning of diverse scFv sequences. The attL1 and attL2 sites flank the scFv-Fc-GPI-anchor expression cassette. Panel B depicts the plasmid map of the pENDisplay-OriP vector which is based on the vector shown in Panel A but incorporates the OriP sequence (see FIG. 9C) after the polyA tail of the scFv-Fc-GPI-anchor cassette.

FIG. 9 provides representative for EBNA-1 and OriP. The amino acid and nucleotide sequences for an EBNA-1 are provided in Panels A and B, respectively. The sequence of an OriP is provided in Panel C.

Figure 10:
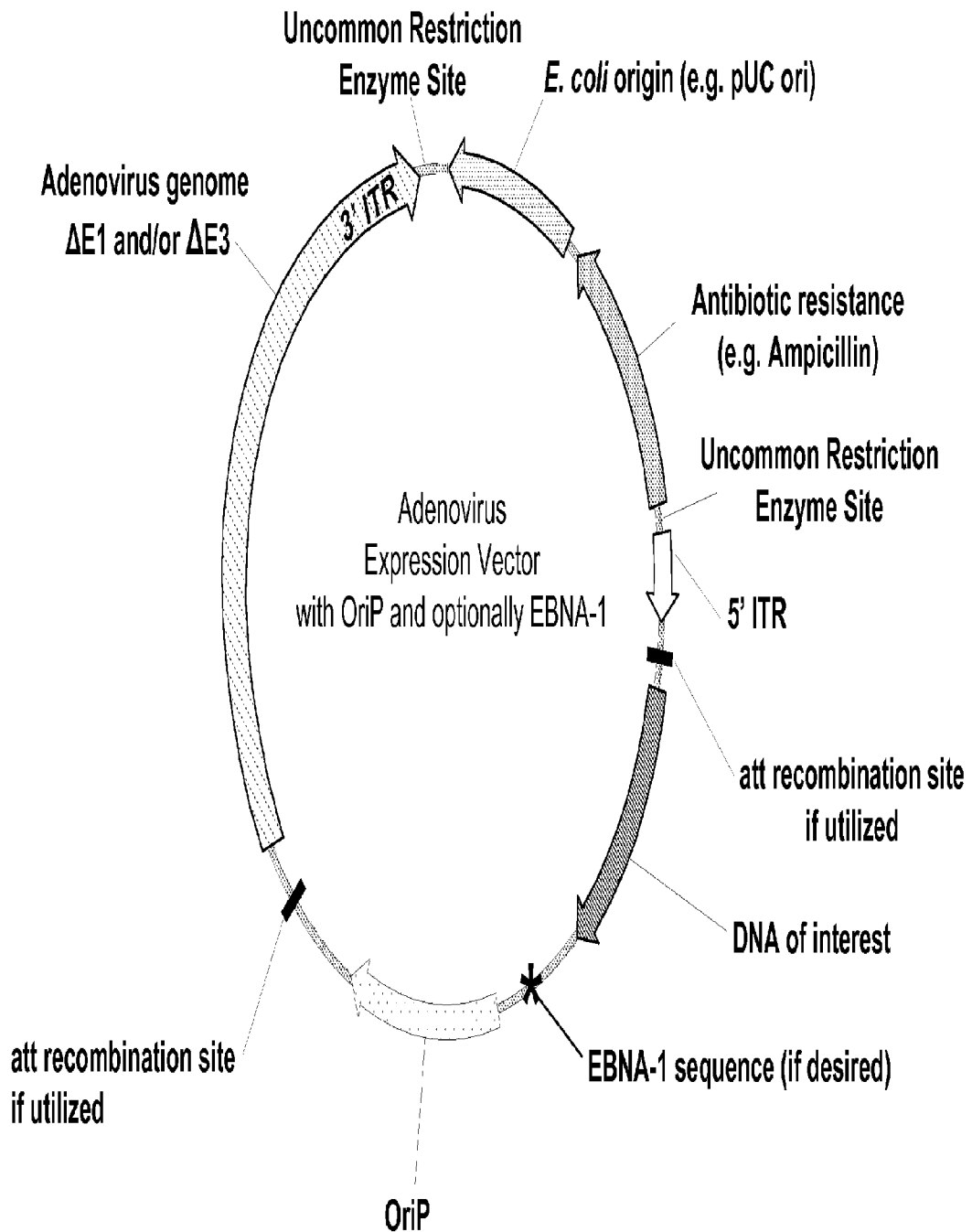

FIG. 10 provides a schematic of a representative generic adenovirus expression vector for expression of protein(s) of interest. The vector as depicted includes: a DNA sequence of interest which encodes for one or more proteins of interest; an OriP sequence and optionally an EBNA-1 coding region. These components are optionally flanked by att recombination sites which may have been used for construction of the vector. These components are flanked on one side by an adenovirus genome, in this case having a deletion of the E1 and/or E3 gene and by an ITR sequence. The 3' and 5' ITR sequences are indicated. The vector also provides sequences for replication (e.g. *E. coli* origin) and antibiotic selection (e.g. ampicillian resistance) in a bacterial cell for ease of construction, propagation and selection, these components are located such that they will not be incorporated into rescued adenovirus.

FIG. 11 shows that HSA displayed on the surface of mammalian cells (293F cells) retains FcRn binding capacity. Panel A depicts the mammalian expression construct designated pEN-HSA-GPI comprising a CMV promoter (thick line), a signal sequence (thick dotted line), an N-terminal Flag tag (thin dotted line), (G$_4$S)$_3$ linkers (thin solid line) flanking the HSA portion (hatched box) and the DAF-GPI sequence. Panel B represents flow cytometry detection of HSA on the surface 293-F cells infected with adenovirus generated from pEN-HSA-GPI after 16 and 24 hours, or a control plasmid encoding a control scFv-Fc fusion protein using FITC conjugated anti-HSA antibody (panel A). Panels C and D represent the binding of biotinylated human FcRn (25 µg/ml and 5 µg/ml, respectively) to HSA displayed on the 293F cells visualized by anti-Streptavidin Phycoerythrin using flow cytometry. Experiments are expressed as histograms of fluorescence intensity (log scale) versus the number of cells.

Figure 12:
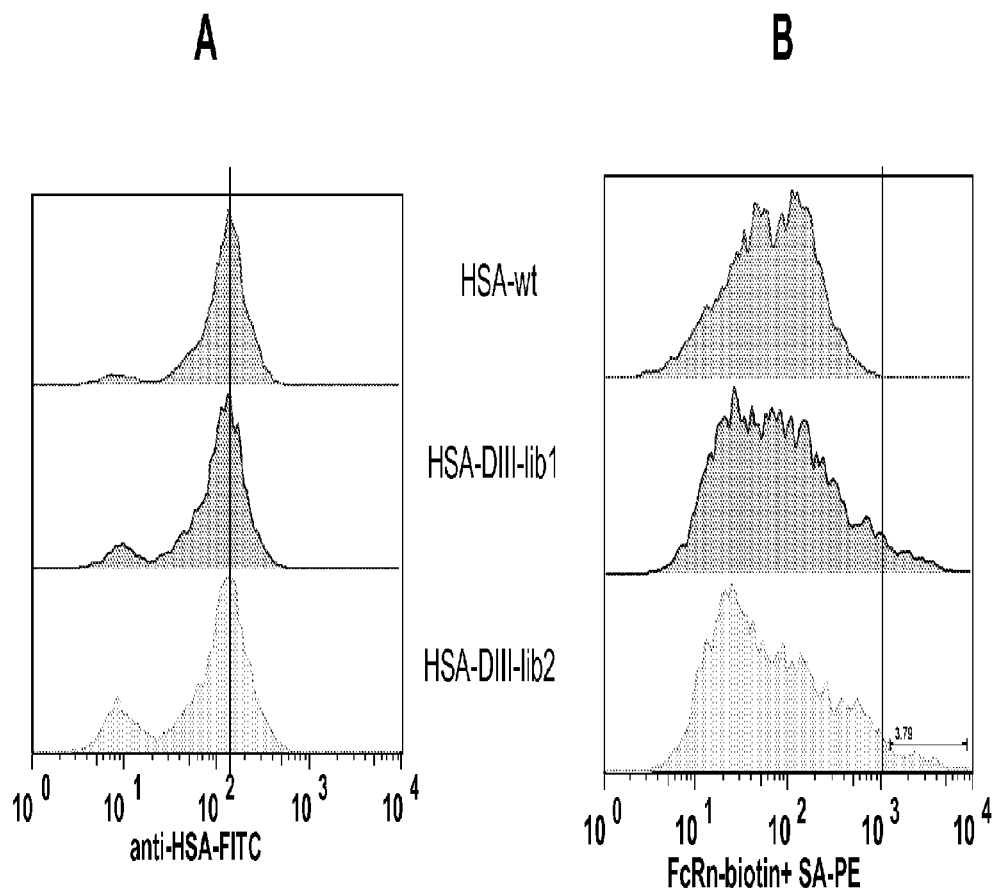

FIG. 12 shows changes in the binding profiles of biotinylated human FcRn to wildtype HSA (HSA-wt) and the two HSA mutant libraries (HSA-DIII-lib1 and HSA-DIII-lib2) displayed on 293F cells. Panel A represents flow cytometry detection of HSA on the surface of 293-F cells infected with wildtype and mutant HSA-DIII libraries. Panel B represents flow cytometry detection of biotinylated human FcRn bound HSA on the cell surface visualized by anti-Streptavidin Phycoerythrin. Experiments are expressed as histograms of fluorescence intensity (log scale) versus the number of cells.

Figure 13A:
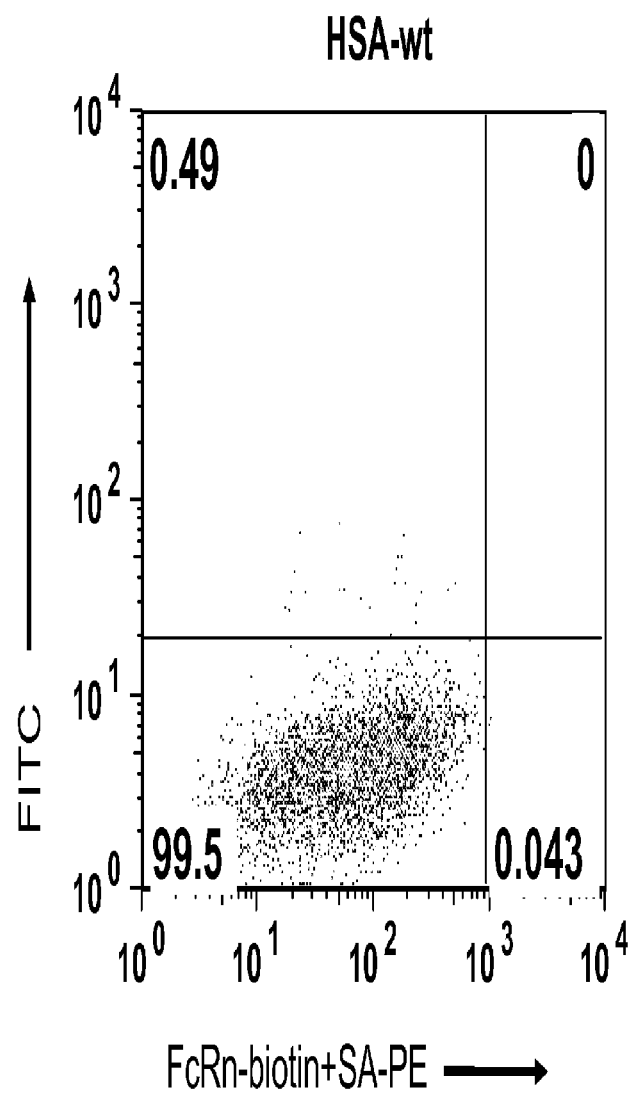
Figure 13B:
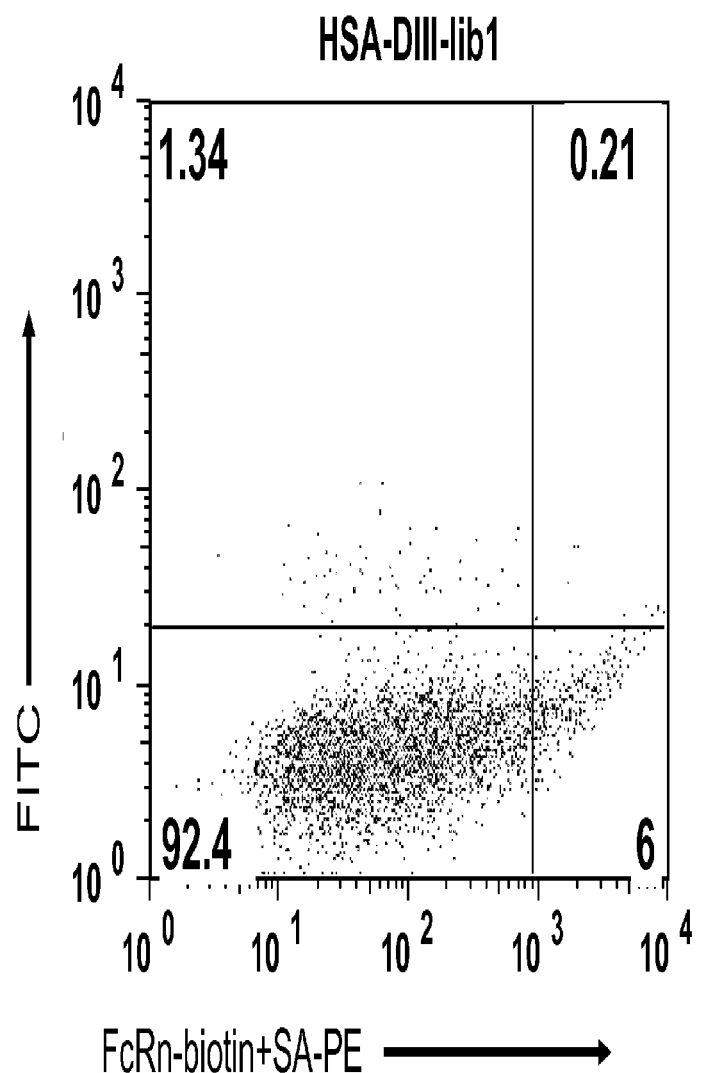
Figure 13C:
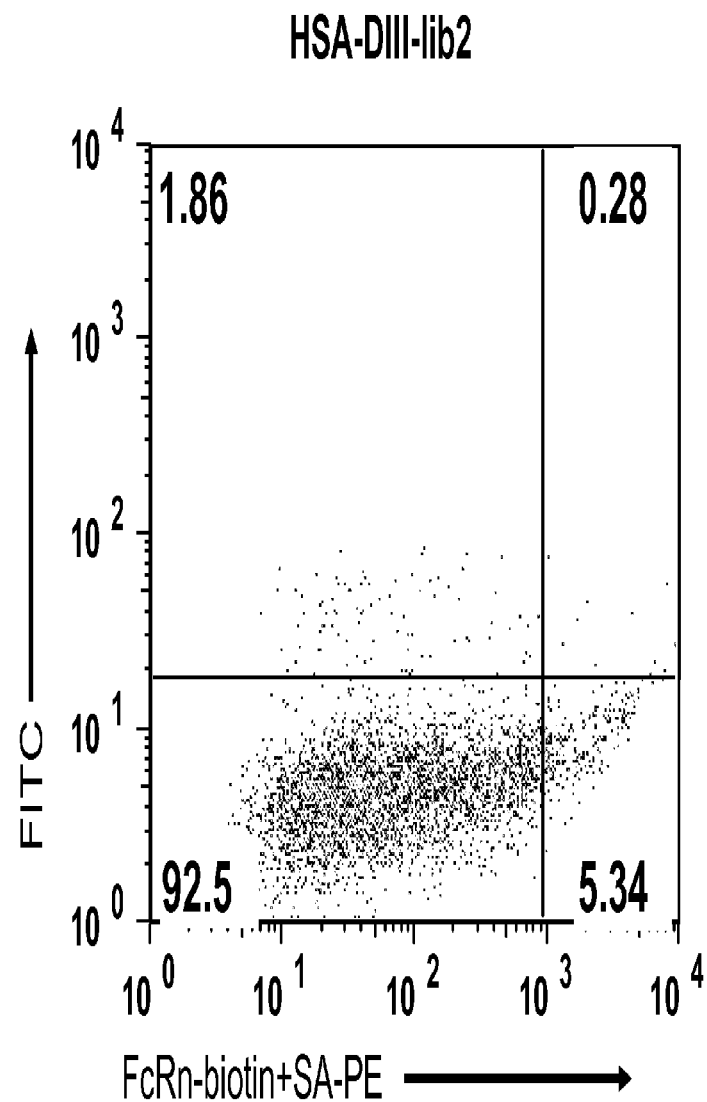

FIG. 13 shows the FACS sorting profiles of cells expressing wild type HSA (HSA-wt, Panel A) and the two HSA mutant libraries (HSA-DIII-lib1 and HSA-DIII-lib2, Panels B and C, respectively) stained biotinylated human FcRn (10 µg/ml) detected with anti-Streptavidin Phycoerythrin.

Figure 14A:
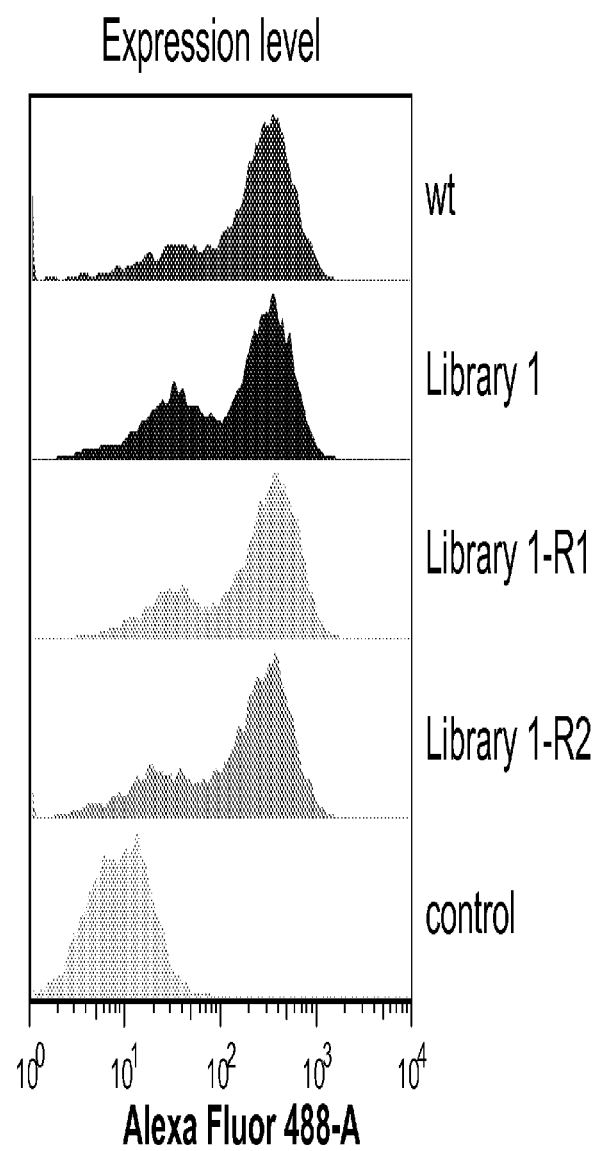
Figure 14B:
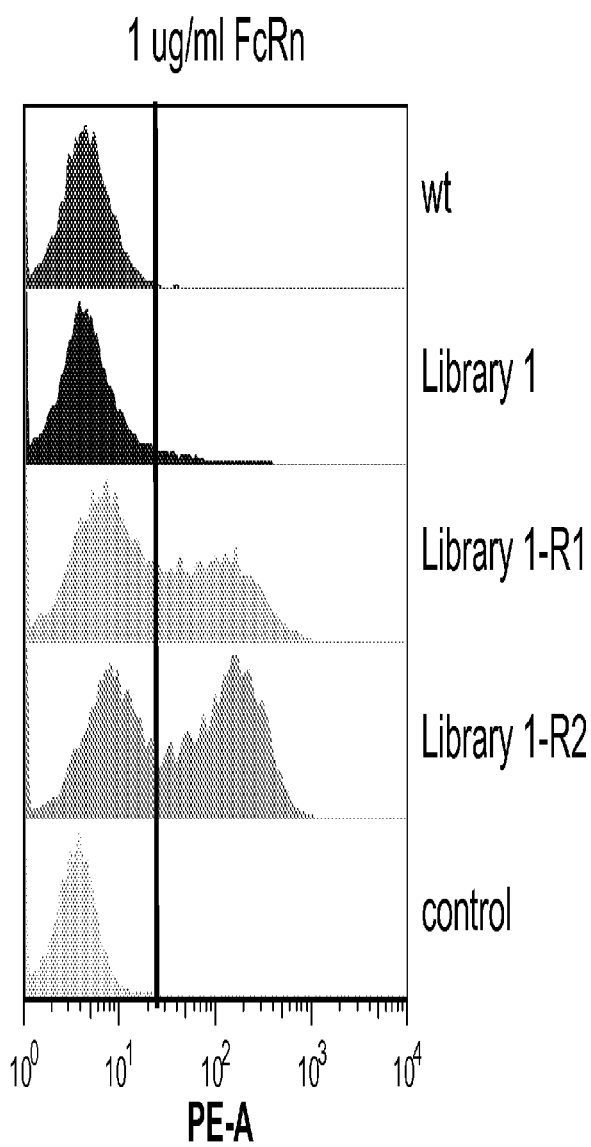
Figure 14C:
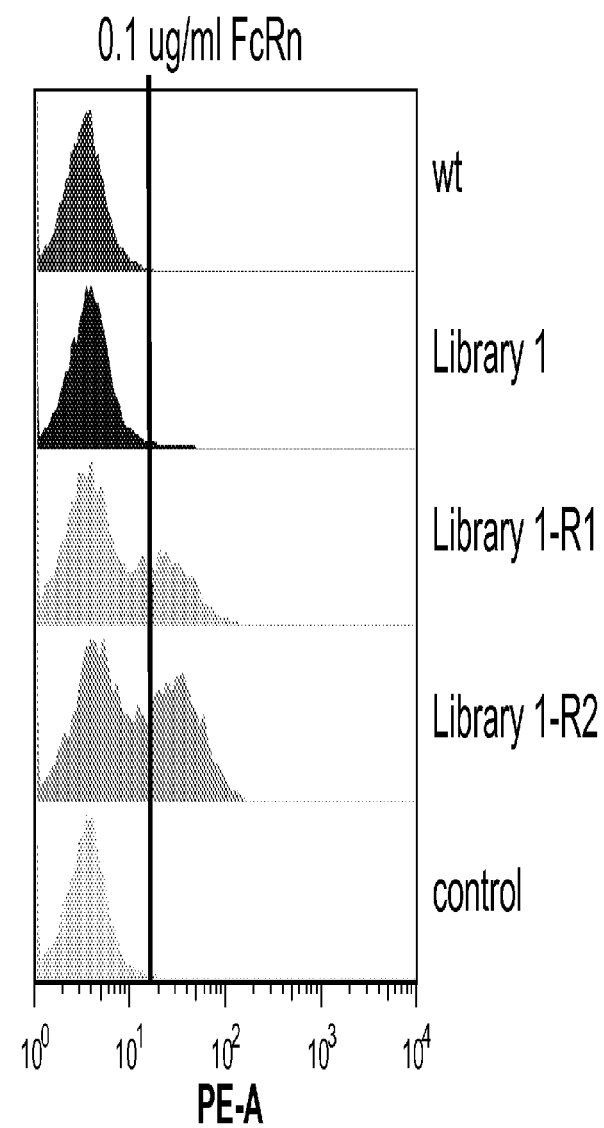

FIG. 14 shows changes in the binding profiles of biotinylated human FcRn to 293F cells expressing on their cell surface wildtype HSA (HSA-wt), the HSA-DIII-lib1 mutant library prior to sorting and after a first and second round of sorting. Panel A represents flow cytometry detection of HSA on the surface of 293F cells expressing wildtype, the HSA-DIII-lib1 prior to sorting and after a first and second round of sorting. Panels B and C represent the binding of biotinylated human FcRn (1 µg/ml and 0.1 µg/ml, respectively) to the same set of cells visualized by anti-Streptavidin Phycoerythrin using flow cytometry. Experiments are expressed as histograms of fluorescence intensity (log scale) versus the number of cells.

Figure 15:
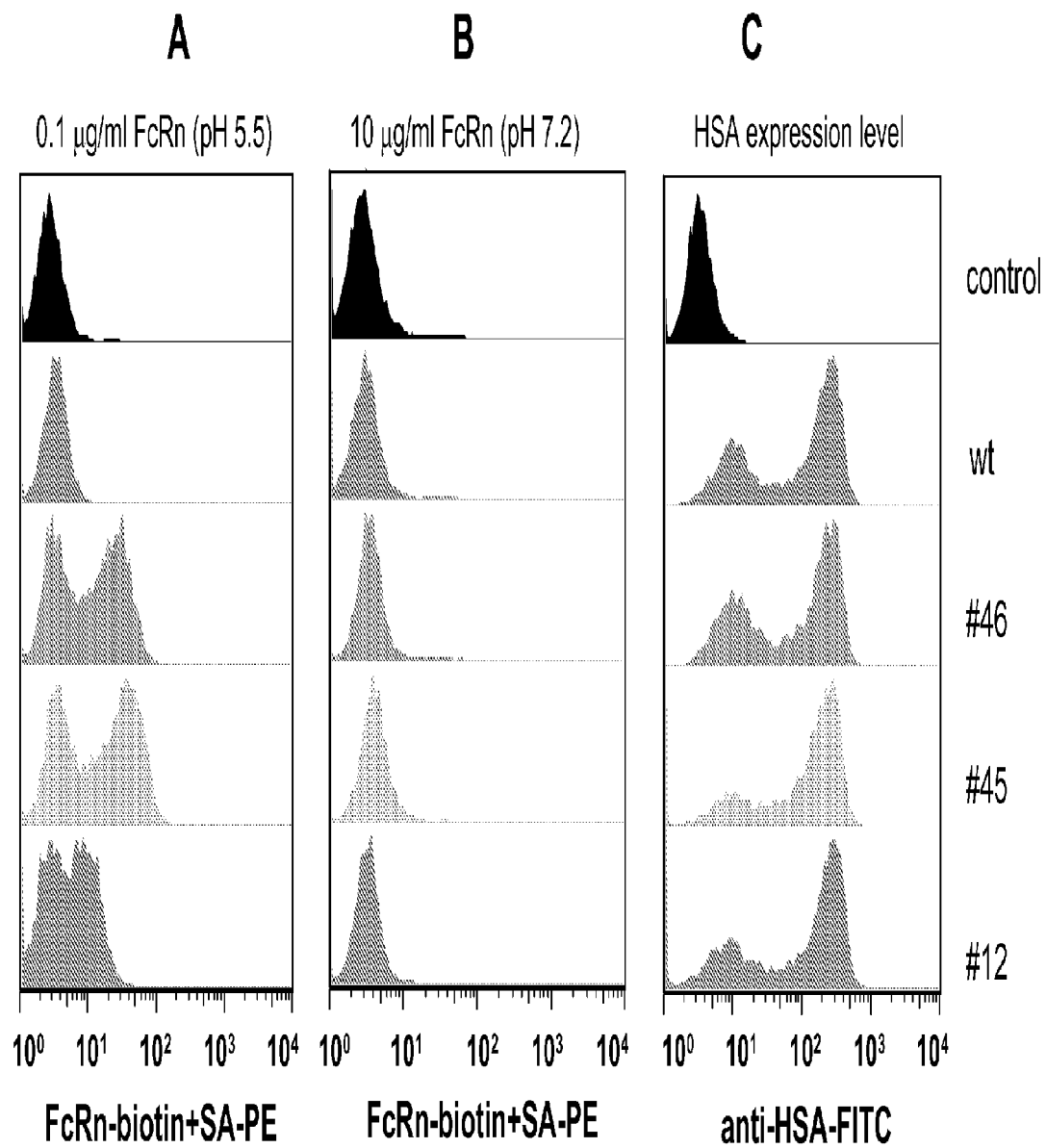

FIG. 15 shows that binding of FcRn to mutant HSA displayed on the cell surface is pH dependent. Panels A and B show flow cytometry detection of biotinylated human FcRn detected with anti-Streptavidin Phycoerythrin on the surface of 293F cells expressing a control scFv-Fc fusion protein, wildtype HSA, and three representative mutations (See Table 5) at pH 5.5 (0.1 µg/ml FcRn, panel A) and pH 7.2 (10 µg/ml, panel B). Panel C shows flow cytometry detection of HSA on the surface of these cells using FITC conjugated anti-HSA antibody.

Figure 16:
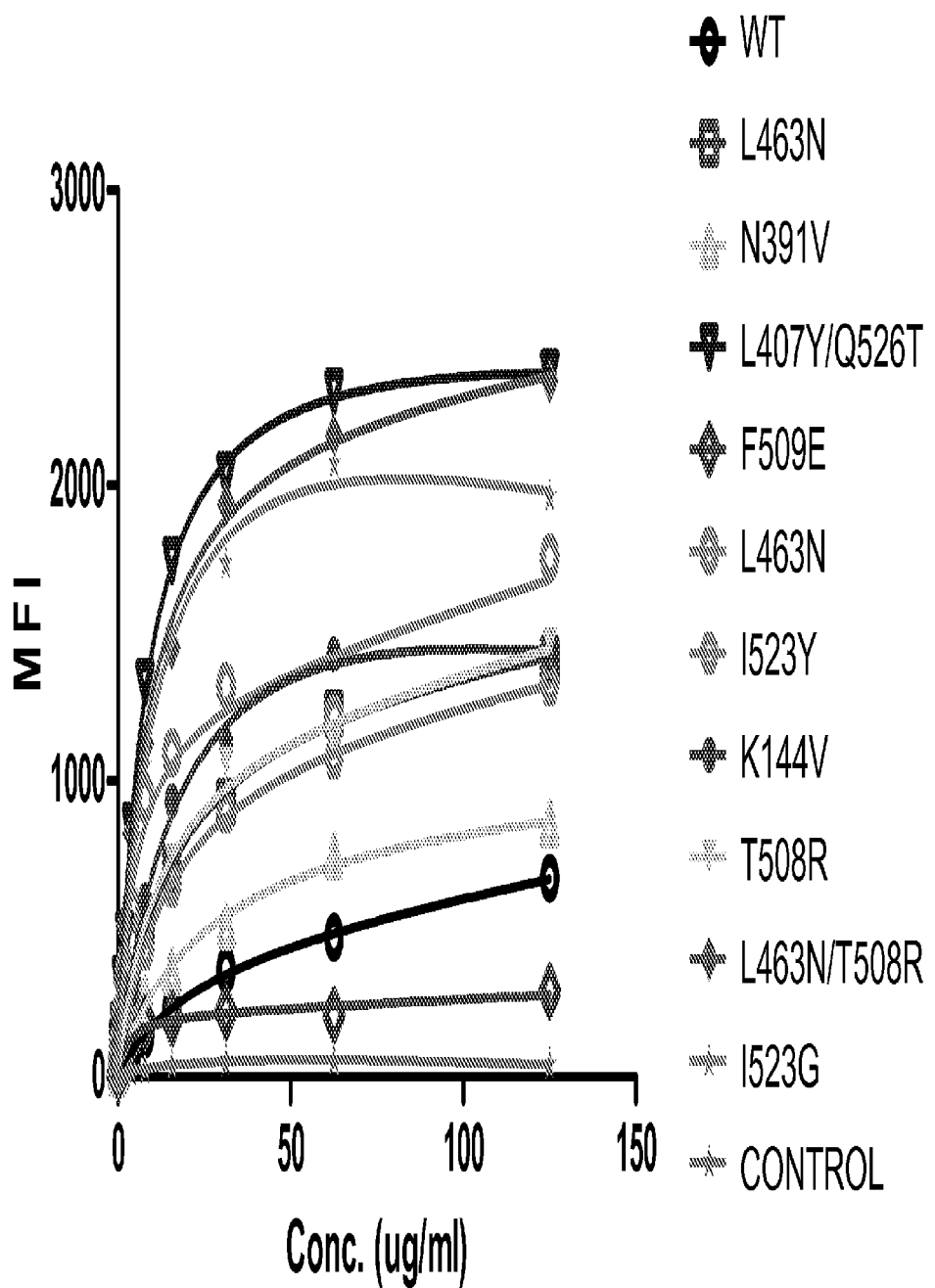

FIG. 16 shows that most isolated HSA mutations have higher affinity for FcRn as measured by flow cytometry. Wildtype HSA and a panel of selected mutants was analyzed for binding biotinylated human FcRn at different concentrations by flow cytometry. The data are plotted as MFI over FcRn concentration.

Figure 17:
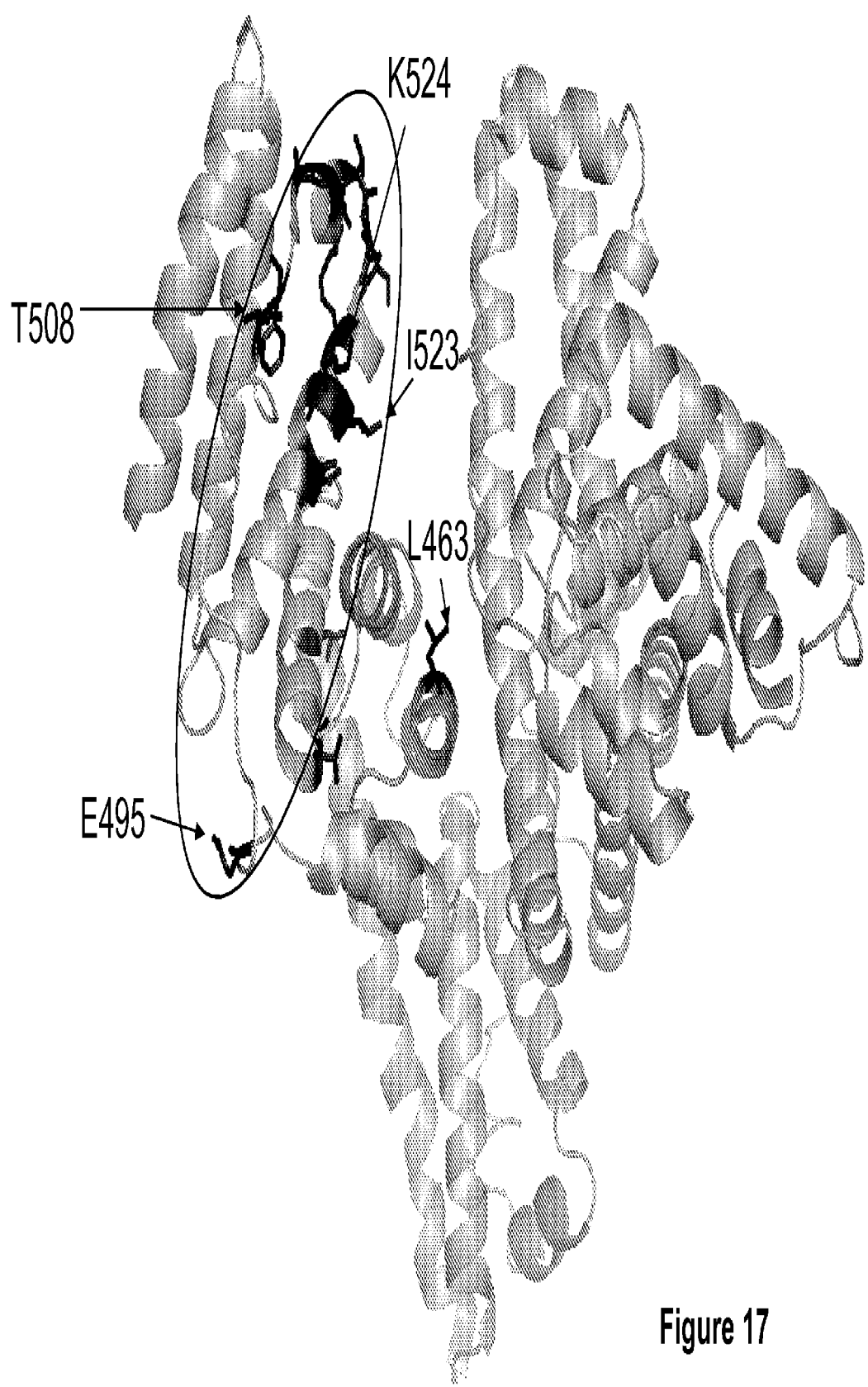

FIG. 17 depicts the location of a number of variants on solved structure of HSA (PDB Accession No. 1BM0). The bulk of the structure is represented as a ribbon diagram with residues L463, E495, T508, I523 and K534 represented by sticks and indicated with arrows. Loops 6 and 7 and helicies 7 and 8 encompassing residues 492-536 are circled. The majority of the hotspots and preferred spots are found in this region.

6 DETAILED DESCRIPTION OF THE INVENTION

6.1 Introduction

Neonatal Fc receptor (FcRn) prolongs the lifespan of both IgG and human serum albumin (HSA), by a pH dependent mechanism, specifically binding both molecules at the acidic pH of the endosome and recycling them back to the cell surface, thus diverting both molecules away from the default lysosomal degradation pathway. It has been shown that FcRn binding capacity is intrinsic to domain-III of albumin. As demonstrated herein, addition of the FcRn binding fragment of HSA can be used to increase the serum half-life of protein and/or the FcRn binding affinity of therapeutics such as antibodies, antibody alternatives, proteins, protein scaffolds, and peptides. In particular, as demonstrated herein the FcRn binding affinity at acidic pH (e.g. pH of approx 5.5) is increased while the affinity at neutral pH (e.g., pH of approx 7.4) is not substantially altered. Chimeric polypeptides comprising the FcRn binding domain variants of the disclosure may increase serum half-life or FcRn binding affinity of the protein even further than the wild type FcRn binding domain. HSA variant polypeptides of the invention may serve as scaffolds for binding to a therapeutic target or may be coupled to therapeutic agents.

The disclosure provides variants of domain III. Such variants of domain III can be used alone or can be used in the context of additional HSA sequence to increase serum half-life and/or FcRn binding affinity of a heterologous protein and/or a non-protein agent.

The chimeric polypeptides and HSA variants disclosed herein have numerous uses. It is appreciated that proteins and other molecules are sometimes cleared from a human or animal body relatively quickly. Rapid clearance can undermine the ability to study proteins and other molecules in animal models and can undermine the ability to use them effectively for therapeutic purposes. In some instances, a protein is cleared so quickly that it has no therapeutic effect. In other instances, a protein is cleared at a rate that necessitates frequent dosing. Frequent dosing adds to the costs associated with therapies, and also increases risk of non-compliance with a therapeutic regimen. In some instances, a protein is cleared at a rate that necessitates administering a larger dose. Larger doses of an active agent may increase the risk of side-effects, including immune reactions.

The chimeric polypeptides and variant HSA polypeptides of the instant disclosure help address the problems associated with rapid or relatively rapid protein clearance by increasing serum half-life and/or affinity for FcRn. Similarly, non-protein agent can be conjugated to variant HSA polypeptides of the instant disclosure to increase serum-half and/or affinity for FcRn.

6.2 Terminology

Before continuing to describe the present invention in further detail, it is to be understood that this invention is not limited to specific compositions or process steps, as such may vary. It must be noted that, as used in this specification and the appended claims, the singular form "a", "an" and "the" include plural referents unless the context clearly dictates otherwise.

Unless defined otherwise, all technical and scientific terms used herein have the same meaning as commonly understood by one of ordinary skill in the art to which this invention is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this invention.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. As used herein "amino acid substitution" is meant the replacement of an amino acid at a particular position in a parent polypeptide sequence with another amino acid. For example, the substitution L463N refers to a variant polypeptide in which Leucine at position 463 is replaced with Asparagine.

The numbering of amino acids in the variable domain, complementarity determining region (CDRs) and framework regions (FR), of an antibody follow, unless otherwise indicated, the Kabat definition as set forth in Kabat et al. Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insertion (residue 52a according to Kabat) after residue 52 of H2 and inserted residues (e.g. residues 82a, 82b, and 82c, etc according to Kabat) after heavy chain FR residue 82. The Kabat numbering of residues may be determined for a given antibody by alignment at regions of homology of the sequence of the antibody with a "standard" Kabat numbered sequence. Maximal alignment of framework residues frequently requires the insertion of "spacer" residues in the numbering system, to be used for the Fv region. In addition, the identity of certain individual residues at any given Kabat site number may vary from antibody chain to antibody chain due to interspecies or allelic divergence.

As used herein, the terms "antibody" and "antibodies", also known as immunoglobulins, encompass monoclonal antibodies (including full-length monoclonal antibodies), polyclonal antibodies, multispecific antibodies formed from at least two different epitope binding fragments (e.g., bispecific antibodies), human antibodies, humanized antibodies, camelised antibodies, chimeric antibodies, single-chain Fvs (scFv), single-chain antibodies, single domain antibodies, domain antibodies, Fab fragments, F(ab')2 fragments, antibody fragments that exhibit the desired biological activity (e.g. the antigen binding portion), disulfide-linked Fvs (dsFv), and anti-idiotypic (anti-Id) antibodies (including, e.g., anti-Id antibodies to antibodies of the invention), intrabodies, and epitope-binding fragments of any of the above. In particular, antibodies include immunoglobulin molecules and immunologically active fragments of immunoglobulin molecules, i.e., molecules that contain at least one antigen-binding site. Immunoglobulin molecules can be of any isotype (e.g., IgG, IgE, IgM, IgD, IgA and IgY), subisotype (e.g., IgG1, IgG2, IgG3, IgG4, IgA1 and IgA2) or allotype (e.g., Gm, e.g., G1m(f, z, a or x), G2m(n), G3m(g, b, or c), Am, Em, and Km(1, 2 or 3)). Antibodies may be derived from any mammal, including, but not limited to, humans, monkeys, pigs, horses, rabbits, dogs, cats, mice, etc., or other animals such as birds (e.g. chickens).

As used herein, the term "full length HSA" refers to the mature full length human serum albumin protein or to a nucleotide sequence that encodes such a protein. The full length HSA protein is approximately 585 amino acids (following removal of N-terminal pro- and prepro-sequence). Mature full length HSA (also referred to as full length mature HSA) protein is set forth in SEQ ID NO: 2. In certain embodiments, full length HSA refers to the mature full length form of HSA without pro-sequences. The sequence of prepro HSA (prior to removal of the N-terminal pro and prepro sequences) is 609 amino acids and is set forth in GenBank Accession number NP_000468. In addition, the identity of certain individual residues may vary from those presented in SEQ ID NO: 2 due to allelic divergence. Allelic variations which occur in domain III of HSA include: R→C at residue 410; K→E at residue 466; E→K at residue 479; D→N at residue 494; E→K at residue 501; E→K at residue 505; V→M at residue 533; K→E at residue 536; K→E at residue 541; D→A or D→G at residue 550; K→E at residue 560; D→N at residue 563; E→K at residue 565; E→K at residue 570; K→E at residue 573; K→E at residue 574; GKKLVAASQAALGL→PTMRIRERK at residues 572-585; and LVAASQAALGL→TCCCKSSCLRLITSHLKASQ PTMRIRERK 575-585, as numbered relative to the position in full length mature HSA.

As used herein, the term "domain III of HSA" refers to the conventional domain III of HSA spanning amino acids 381-585 of the full length mature HSA, approximately 205 amino acids, or a nucleotide sequence that encodes such a protein. Domain III of HSA is also abbreviated herein as domain III or simple DIII. The amino acid sequence for the domain III polypeptide is set forth in SEQ ID NO: 1. As noted above, the identity of certain individual residues may vary from those presented in SEQ ID NO: 1 due to allelic divergence.

As used herein, the term "chimeric polypeptide" refers to a polypeptide comprising at least two portions that are not heterologous with respect to each other. For example, a chimeric polypeptide, also referred to as a fusion polypeptide or fusion protein, comprises at least an HSA portion joined to a heterologous protein portion. The HSA portion and heterologous protein portion can themselves be fusions to, for example, Fc or other moieties. The HSA portion and heterologous protein portion may be joined via covalent or non-covalent interactions. By way of example, the HSA portion and heterologous protein portion may be chemically conjugated to each other or may be recombinantly fused (e.g., in-frame translational fusion).

As used herein, the term "heterologous protein" refers to all or a portion of a protein that is not HSA. Although the generic term "heterologous protein" is used herein, the term is intended to encompass bioactive peptides of varying lengths, as well as full or substantially full length proteins, including antibodies and antibody fragments. Preferred heterologous proteins can be used or studied for therapeutic purposes. Exemplary classes of heterologous proteins include, but are not limited to, enzymes, cytokines, and growth factors.

As used herein, HSA polypeptides include various bioactive fragments and variants, fusion proteins, and modified forms of the wildtype HSA polypeptide. Such bioactive fragments or variants, fusion proteins, and modified forms of the HSA polypeptides have at least a portion of the amino acid sequence of substantial sequence identity to the native HSA protein, and retain at least the FcRn binding activity of the native HSA protein. In certain embodiments, a bioactive fragment, variant, or fusion protein of an HSA polypeptide comprises an amino acid sequence that is at least 80%, 85%, 90%, 95%, 97%, 98%, 99% or 100% identical to an HSA polypeptide. As used herein, "fragments" are understood to include bioactive fragments or bioactive variants that exhibit FcRn binding activity. Suitable bioactive fragments can be used to make chimeric polypeptides, and such chimeric polypeptides can be used in any of the methods described herein.

As used herein, the terms "mutated", "mutant" and the like refer to a molecule, in particular an HSA polypeptide, which has undergone deletion, addition or substitution of one or more amino acids using well known techniques for site directed mutagenesis or any other conventional method.

6.3 HSA Domain III

In certain aspects, the disclosure provides a human serum albumin (HSA) variant polypeptide, comprising HSA domain III, or a neonatal Fc receptor (FcRn) binding fragment thereof, wherein said variant polypeptide can bind to an FcRn, and wherein said HSA domain III comprises one to eighteen amino acid substitutions to increase serum half-life or to increase affinity of said variant polypeptide for FcRn relative to a control HSA polypeptide lacking said amino acid substitutions.

In certain embodiments, the one to eighteen amino acid substitutions increases affinity of the HSA variant polypeptide for FcRn. In certain embodiments, the one to eighteen amino acid substitutions increases serum half-life of the HSA variant polypeptide. In certain embodiments, the one to eighteen amino acid substitutions increases both the affinity of the HSA variant polypeptide for FcRn and the serum half-life of the HSA variant polypeptide. In certain embodiments, the one to eighteen amino acid substitutions increases affinity of the HSA variant polypeptide for FcRn at acidic pH (e.g., pH of approx 5.5). In certain embodiments, the one to eighteen amino acid substitutions increases affinity of the HSA variant polypeptide for FcRn at acidic pH (e.g., pH of approx 5.5), but does not substantially alter the affinity of the HSA variant polypeptide for FcRn at neutral pH (e.g., pH of approx 7.4).

In certain embodiments, the HSA variant binds to FcRn and has an off rate or on rate that differs from that of said control HSA polypeptide. For example, in certain embodiments, the HSA variant binds to FcRn and has a faster on rate and/or a slower off rate. In other embodiments, the on rate is slower and/or the off rate is faster.

In certain embodiments, the disclosure provides chimeric polypeptides that include an HSA portion, which HSA portion comprises domain III, or an FcRn binding portion thereof, and a heterologous protein, wherein the chimeric polypeptide retains a functional activity of the heterologous protein. In certain embodiments the HSA portion comprises the entire HSA polypeptide or a bioactive fragment comprising HSA domain III, or a neonatal Fc receptor (FcRn) binding fragment thereof. In certain embodiments, the HSA portion comprises the HSA domain III, or a neonatal Fc receptor (FcRn) binding fragment thereof and at least a portion of another domain of HSA, for example at least a portion of HSA domain I, or at least a portion of HSA domain II, or at least a portion of HSA domains I and II. As used herein, HSA domain I comprises residues 1-197; HSA domain II comprises residues 189-385; HSA domain III comprises residues 381-585 as numbered relative to the position in full length mature HSA.

In certain embodiments, the chimeric polypeptide has one or both of increased affinity for FcRn and increased serum half-life relative to a control polypeptide which does not comprise the HSA portion. In certain embodiments, the chimeric polypeptide has increased affinity for FcRn. In certain embodiments, the chimeric polypeptide has an increased serum half-life. In certain embodiments, the chimeric polypeptide has both increased affinity for FcRn and increased serum half-life. In certain embodiments, the chimeric polypeptide has increased affinity for FcRn at acidic pH (e.g., pH of approx 5.5). In other embodiments, the chimeric polypeptide has increased FcRn at acidic pH (e.g., pH of approx 5.5) the affinity of the chimeric polypeptide for FcRn at neutral pH (e.g., pH of approx 7.4) is not substantially altered.

Further, as described herein, in certain embodiments, domain III of the HSA portion of a polypeptide (e.g., HSA variant or chimeric polypeptide) includes one to eighteen amino acid substitutions to increase one or both of affinity for FcRn and serum half-life of the chimeric polypeptide relative to a control chimeric polypeptide in which the HSA portion does not include said amino acid substitutions. In certain embodiments, the one to eighteen amino acid substitutions increases affinity of the chimeric polypeptide for FcRn. In certain embodiments, the one to eighteen amino acid substitutions increases serum half-life of the chimeric polypeptide. In certain embodiments, the one to eighteen amino acid substitutions increases both the affinity of the chimeric polypeptide for FcRn and the serum half-life of the chimeric polypeptide.

In certain embodiments, domain III of the HSA portion of a polypeptide (e.g. HSA variant polypeptide or chimeric polypeptide) includes 1, 2, 3, 4, 5, 6, 7, 8, 9, 10, 11, 12, 13, 14, 15, 16, 17, or 18 amino acid substitutions. Similarly, in the context of HSA variant polypeptides comprising domain III, or an FcRn binding portion thereof, domain III includes 1, 2, 3, 4, 5, 6, 7, 8, 9, 10, 11, 12, 13, 14, 15, 16, 17, or 18 amino acid substitutions. In certain embodiments, the amino acid substitution is not solely the substitution of a single amino acid to another residue present in an alleleic variant.

In certain embodiments, domain III of the HSA portion of a polypeptide (e.g., HSA variant polypeptide or chimeric polypeptide) includes at least one amino acid substitution at any of the following positions, numbered relative to the position in full length mature HSA: residue 381, residue 383, residue 391, residue 401, residue 402, residue 407, residue 411, residue 413, residue 414, residue 415, residue 416, residue 424, residue 426, residue 434, residue 442, residue 445, residue 447, residue 450, residue 454, residue 455, residue 456, residue 457, residue 459, residue 463, residue 495, residue 506, residue 508, residue 509, residue 511, residue 512, residue 515, residue 516, residue 517, residue 519, residue 521, residue 523, residue 524, residue 525, residue 526, residue 527, residue 531, residue 535, residue 538, residue 539, residue 541, residue 557, residue 561, residue 566, residue 569.

In certain embodiments, domain III of the HSA portion of a polypeptide (e.g., HSA variant polypeptide or chimeric polypeptide) comprises amino acid substitutions at any of the following positions, numbered relative to the position in full length mature HSA: (a) residues 383 and 413; (b) residues 401 and 523; (c) residues 407 and 447; (d) residues 407 and 447 and 539; (e) residues 407 and 509; (f) residues 407 and 526; (g) residues 411 and 535; (h) residues 414 and 456; (i) residues 415 and 569; (j) residues 426 and 526; (k) residues 442 and 450 and 459; (l) residues 463 and 508; (m) residues 508 and 519 and 525; (n) residues 509 and 527; (o) residues 523 and 538; (p) residues 526 and 557; and (q) residues 541 and 561.

In certain embodiments, increased affinity for FcRn and/or serum half-life is evaluated versus a different control. For example, the properties of the chimeric polypeptide can be evaluated versus that of the heterologous protein in the absence of an HSA portion or can be evaluated versus that of the same or a similar HSA portion, in the absence of the amino acid substitutions, and/or in the absence of the heterologous protein. Similarly, an HSA variant polypeptide can be evaluated versus that of an HSA molecule not have the amino acid substitutions.

In certain embodiments, the chimeric polypeptide/HSA variant polypeptide binds to FcRn with a higher affinity then said control polypeptide. In certain embodiments, the one to eighteen amino acid substitutions increases affinity of the chimeric polypeptide/HSA variant polypeptide for FcRn at acidic pH (e.g., pH of approx 5.5). In certain embodiments, the one to eighteen amino acid substitutions increases affinity of the chimeric polypeptide/HSA variant polypeptide for FcRn at acidic pH (e.g., pH of approx 5.5), but does not substantially alter the affinity of the chimeric polypeptide for FcRn at neutral pH (e.g., pH of approx 7.4). In certain embodiments, the chimeric polypeptide binds to FcRn with a higher affinity at acidic pH and has an increased serum half-life.

In certain embodiments, the chimeric polypeptide/HSA variant polypeptide binds to FcRn and has an off rate or on rate that differs from that of said control polypeptide. For example, in certain embodiments, the chimeric polypeptide/HSA variant polypeptide binds to FcRn and has a faster on rate and/or a slower off rate. In other embodiments, the on rate is slower and/or the off rate is faster.

In certain embodiments, the HSA domain III of a polypeptide (e.g., HSA variant or chimeric polypeptide with an HSA portion) comprises one to ten amino acid substitutions to increase the affinity of the polypeptide for FcRn and/or increase the serum half-life of the polypeptide relative to a control polypeptide in which the HSA portion does not include said amino acid substitutions. In certain embodiments, the HSA domain III comprises one amino acid substitution. In certain embodiments, the HSA domain III comprises 2, 3, 4, 5, 6, 7, 8, 9, or 10 amino acid substitutions. In certain embodiments, the HSA domain III comprises 11, 12, 13, 14, 15, 16, 17, or 18 amino acid substitutions. In certain embodiments, the HSA domain III comprises at least one amino acid substitution. In certain embodiments, the HSA domain III comprises at least ten amino acid substitutions.

Exemplary amino acid substitutions include: (i) replacement with alanine; (ii) conservative amino acid substitution; (iii) non-conservative amino acid substitution. The disclosure contemplates that all of the amino acid substitutions in domain III of a given polypeptide (may be a member of one of these categories of substitution, and also contemplates that each amino acid substitution in domain III of a given polypeptide (e.g., HSA variant and chimeric polypeptide with an HSA portion) may be individually and independently selected from these categories.

In certain embodiments, a substitution (at least 1, 2, 3, 4, 5, 6, etc. HSA domain III substitutions) is from a residue in HSA to alanine. In certain embodiments, a substitution (at least 1, 2, 3, 4, 5, 6, etc. HSA domain III substitutions) replaces a given neutral amino acid residue in HSA with another neutral amino acid residue. In certain embodiments, a substitution (at least 1, 2, 3, 4, 5, 6, etc. HSA domain III substitutions) replaces a given acidic amino acid residue in HSA with another acidic amino acid residue. In certain embodiments, a substitution (at least 1, 2, 3, 4, 5, 6, etc. HSA domain III substitutions) replaces a given basic amino acid residue in HSA with another basic amino acid residue. The disclosure contemplates embodiments wherein each substitution is independently chosen from among the foregoing classes of substitutions. Polypeptides (e.g., HSA variants and chimeric polypeptides with an HSA portion) comprising any combination of the forgoing categories of substitutions are specifically contemplated.

In certain embodiments, a substitution (at least 1, 2, 3, 4, 5, 6, etc. HSA domain III substitutions) replaces one amino acid with another within the following group: lysine (K; Lys), arginine (R; Arg); histidine (H; His). In certain embodiments, a substitution (at least 1, 2, 3, 4, 5, 6, etc. HSA domain III substitutions) replaces one amino acid with another within the following group: aspartate (D; Asp; aspartic acid) and glutamate (E; Glu; glutamic acid). In certain embodiments, a substitution (at least 1, 2, 3, 4, 5, 6, etc. HSA domain III substitutions) replaces one amino acid with another within the following group: asparagine (N; Asn), glutamine (Q; Gln), serine (S; Ser), threonine (T; Thr), and tyrosine (Y; Tyr). In certain embodiments, a substitution (at least 1, 2, 3, 4, 5, 6, etc. HSA domain III substitutions) replaces one amino acid with another within the following group: alanine (A; Ala), valine (V; Val), isoleucine (I; Ile), leucine (L; Leu), proline (P; Pro), phenylalanine (F; Phe), tryptophan (W; Trp), methionine (M; Met), cysteine (C; Cys) and glycine (G; Gly). In certain embodiments, a substitution (at least 1, 2, 3, 4, 5, 6, etc. HSA domain III substitutions) replaces one amino acid with another within the following group: phenylalanine, tryptophan and tyrosine. In certain embodiments, a substitution (at least 1, 2, 3, 4, 5, 6, etc. HSA domain III substitutions) replaces one amino acid with another within the following group: cysteine, serine, and threonine. In certain embodiments, a substitution (at least 1, 2, 3, 4, 5, 6, etc. HSA domain III substitutions) replaces one amino acid with another within the following group: asparagine, glutamine, serine, threonine, tyrosine, lysine, arginine, histidine, aspartate, glutamate. In certain embodiments, a substitution (at least 1, 2, 3, 4, 5, 6, etc. HSA domain III substitutions) replaces one amino acid with another within the following group: glycine, serine, threonine, alanine, valine, leucine, and isoleucine. The disclosure contemplates embodiments wherein each substitution is independently chosen from among the foregoing categories of substitutions. Polypeptides (e.g., HSA variants and chimeric polypeptides with an HSA portion) comprising any combination of the forgoing classes of substitutions are specifically contemplated.

In specific embodiments, domain III of the HSA portion of a polypeptide (e.g. HSA variant polypeptide or chimeric polypeptide) having increased affinity for FcRn and/or increase serum half life includes at least one amino acid substitution selected from the group consisting of: V381N, V381Q, E383A, E383G, E383I, E383L, E383V, N391A, N391G, N391I, N391L, N391V, Y401D, Y401E, K402A, K402G, K402I, K402L, K402V, L407F, L407N, L407Q, L407W, L407Y, Y411Q, Y411N, K413C, K413S, K413T, K414S, K414T, V415C, V415S, V415T, Q416H, Q416P, V424A, V424G, V424I, V424L, V424N, V424Q, V426D, V426E, V426H, V426P, G434C, G434S, G434T, E442K, E442R, R445F, R445W, R445Y, P447S, P447T, E450D, E450E, S454C, S454M, S454T, V455N, V455Q, V456N, V456Q, L457F, L457W, L457Y, Q459K, Q459R, L463N, L463Q, E495D, T506F, T506W, T506Y, T508K, T508R, T508S, F509C, F509I, F509L, F509M, F509V, F509W, F509Y, A511F, A511W, A511Y, D512F, D512W, D512Y, T515C, T515H, T515N, T515P, T515Q, T515S, L516F, L516S, L516T, L516W, L516Y, S517C, S517F, S517M, S517T, S517W, S517Y, K519A, K519G, K519I, K519L, K519V, R521F, R521W, R521Y, I523A, I523D, I523E, I523F, I523G, I523I, I523K, I523L, I523N, I523Q, I523R, I523V, I523W, I523Y, K524A, K524G, K524I, K524L, K524V, K525A, K525G, K525I, K525L, K525V, Q526C, Q526M, Q526S, Q526T, Q526Y, T527F, T527W, T527Y, E531A, E531G, E531I, E531L, E531V, H535D, H535E, H535P, K538F, K538W, K538Y, A539I, A539L, A539V, K541F, K541W, K541Y, K557A, K557G, K557I, K557L, K557V, A561F, A561W, A561Y, T566F, T566W, T566Y, A569H, and A569P. In certain embodiments, more than one amino acid substitution (e.g., 2, 3, 4, 5 . . . ) or even all of the amino acid substitutions in domain III are selected from the foregoing substitutions.

In other specific embodiments, domain III of the HSA portion of a polypeptide (e.g., HSA variant polypeptide or chimeric polypeptide) includes at least one amino acid substitution selected from the group consisting of: V381N, E383G, N391V, Y401E, K402A, L407N, L407Y, Y411Q, K414S, K413S, V415T, V415C, Q416P, V424I, V424Q, V426E, V426H, G434E, E442K, R445W, P447S, E450D, S454C, V455N, V456N, L457F, Q459R, L463N, E495D, T506Y, T508R, T508S, F509I, F509M, F509W, A511F, D512Y, T515P, T515Q, T515S, L516T, L516W, S517C, S517W, K519I, R521W, I523D, I523E, I523Q, I523K, I523G, I523R, I523Y, K524L, K524V, K525V, Q526T, Q526M, Q526Y, T527Y, E531I, H535N, H535P, K538Y, A539I, K541F, K557G, A561F, T566W, and A569P. In certain embodiments, more than one amino acid substitution (e.g., 2, 3, 4, 5 . . . ) or even all of the amino acid substitutions in domain III are selected from the foregoing substitutions.

In other specific embodiments, domain III of the HSA portion of a polypeptide (e.g., HSA variant polypeptide or chimeric polypeptide) includes at least one amino acid substitution selected from the group consisting of: L407N, L407Y, V415T, V424I, V424Q, V426E, V426H, P447S, V455N, V456N, L463N, E495D, T506Y, T508R, F509M, F509W, A511F, D512Y, T515Q, L516T, L516W, S517W, R521W, I523D, I523E, I523G, I523K, I523R, K524L, Q526M, T527Y, H535P and K557G. In certain embodiments, more than one amino acid substitution (e.g., 2, 3, 4, 5 . . . ) or even all of the amino acid substitutions in domain III are selected from the foregoing substitutions.

In other specific embodiments, domain III of the HSA portion of a polypeptide (e.g., HSA variant polypeptide or chimeric polypeptide) includes at least one amino acid substitution selected from the group consisting of: L407Y, V415T, V424I, V424Q, P447S, V455N, V456N, L463N, E495D, T506Y, T508R, S517W, I523D, I523E, I523G, I523K, I523R, K524L, Q526M, T527Y, H535P and K557G. In certain embodiments, more than one amino acid substitution (e.g., 2, 3, 4, 5 . . . ) or even all of the amino acid substitutions in domain III are selected from the foregoing substitutions.

In certain embodiments, domain III of the HSA portion of a polypeptide (e.g., HSA variant polypeptide or chimeric polypeptide) includes amino acid substitutions in HSA domain III selected from the group consisting of: (a) E383G/K413S; (b) Y401E/I523G; (c) L407N/P447S; (d) L407N/P447S/A539I; (e) L407N/F509M; (f) L407Y/Q526T; (g) Y411Q/H535N; (h) K414S/V456N; (i) V415T/A569P; (j) V426H/Q526Y; (k) E442K/E450D/Q459R; (l) L463N/T508R; (m) T508R/K519I/K525V; (n) F509I/T527Y; (o) I523Q/K538Y; (p) Q526M/K557G; and (q) K541F/A561F. In certain embodiments, more than one amino acid substitution (e.g., 2, 3, 4, 5 . . . ) or even all of the amino acid substitutions in domain III are selected from the foregoing substitutions.

In certain embodiments, domain III of the HSA portion of a polypeptide (e.g., HSA variant polypeptide or chimeric polypeptide) includes amino acid substitutions in HSA domain III selected from the group consisting of: (a) L407N/

P447S; (b) L407N/P447S/A539I; (c) L407N/F509M; (d) Y411Q/H535N; (e) K414S/V456N; (f) V426H/Q526Y; (g) L463N/T508R; (h) F509I/T527Y; (i) I523Q/K538Y; (j) Q526M/K557G; and (k) K541F/A561F.

In addition, fragments or variants can be chemically synthesized using techniques known in the art such as conventional Merrifield solid phase f-Moc or t-Boc chemistry. The fragments or variants can be produced (recombinantly or by chemical synthesis) and tested to identify those fragments or variants that can function as well as or substantially similarly to a native HSA protein, for example.

In certain embodiments, the present invention contemplates modifying the structure of an HSA polypeptide for such purposes as enhancing therapeutic or prophylactic efficacy, or stability (e.g., serum half-life, ex vivo shelf life and resistance to proteolytic degradation in vivo). Such modified HSA polypeptides have the same or substantially the same bioactivity as naturally-occurring (i.e., native or wild-type) HSA polypeptide. Modified HSA polypeptides may be conjugated to other therapeutic moieties (e.g., proteins and non-protein agents) as described herein. Modified polypeptides can be produced, for instance, by amino acid substitution, deletion, or addition. For instance, it is reasonable to expect, for example, that an isolated replacement of a leucine with an isoleucine or valine, an aspartate with a glutamate, a threonine with a serine, or a similar replacement of an amino acid with a structurally related amino acid (e.g., conservative amino acid substitutions) will not have a major effect on the biological activity of the resulting molecule. Conservative replacements are those that take place within a family of amino acids that are related in their side chains.

In certain embodiments, at least one of said amino acid substitutions in HSA domain III is of a residue that is conserved across multiple species. In certain embodiments, all of said amino acid substitutions in HSA domain III are of residues that are conserved across multiple species. In certain embodiments, at least one of said amino acid substitutions in HSA domain III is of a residue that is conserved among serum albumin proteins from human, pig, rat, mouse, dog, rabbit, cow, chicken, donkey, Mongolian gerbil, sheep, cat, and horse. In certain embodiments, all of said amino acid substitutions in HSA domain III are of residues that are conserved among serum albumin proteins from human, pig, rat, mouse, dog, rabbit, cow, chicken, donkey, Mongolian gerbil, sheep, cat, and horse. In certain embodiments, at least one of said amino acid substitutions in HSA domain III is of a residue that is conserved among serum albumin proteins from species highly conserved to humans, such as apes and monkeys. In certain embodiments, at least one of said amino acid substitutions in HSA domain III is of a residue that is conserved among serum albumin proteins from non-mammalian animals. In certain embodiments, all of said amino acid substitutions in HSA domain III are of a residue that is conserved among serum albumin proteins from species highly conserved to humans, such as apes and monkeys. In certain embodiments, all of said amino acid substitutions in HSA domain III are of a residue that is conserved among serum albumin proteins from non-mammalian animals. In certain embodiments, at least one of said amino acid substitutions in HSA domain III is of a residue that is conserved among serum albumin proteins from a majority of human, pig, rat, mouse, dog, rabbit, cow, chicken, donkey, Mongolian gerbil, sheep, cat, and horse. In certain embodiments, at least one of said amino acid substitutions in HSA domain III is of a residue that is conserved among serum albumin proteins from at least two species selected from the group consisting of human, pig, rat, mouse, dog, rabbit, cow, chicken, donkey, Mongolian gerbil, sheep, cat, and horse. In certain embodiments, at least one of said amino acid substitutions in HSA domain III is of a residue that is conserved among serum albumin proteins from at least three species selected from the group consisting of human, pig, rat, mouse, dog, rabbit, cow, chicken, donkey, Mongolian gerbil, sheep, cat, and horse. In certain embodiments, at least one of said amino acid substitutions in HSA domain III is of a residue that is conserved among serum albumin proteins from at least four species selected from the group consisting of human, pig, rat, mouse, dog, rabbit, cow, chicken, donkey, Mongolian gerbil, sheep, cat, and horse. In certain embodiments, at least one of said amino acid substitutions in HSA domain III is of a residue that is conserved among serum albumin proteins from at least five species selected from the group consisting of human, pig, rat, mouse, dog, rabbit, cow, chicken, donkey, Mongolian gerbil, sheep, cat, and horse. In certain embodiments, at least one of said amino acid substitutions in HSA domain III is of a residue that is conserved among serum albumin proteins from between two and five species selected from the group consisting of human, pig, rat, mouse, dog, rabbit, cow, chicken, donkey, Mongolian gerbil, sheep, cat, and horse. In certain embodiments, all of said amino acid substitutions in HSA domain III are of a residue that is conserved among serum albumin proteins from a majority of human, pig, rat, mouse, dog, rabbit, cow, chicken, donkey, Mongolian gerbil, sheep, cat, and horse. In certain embodiments, all of said amino acid substitutions in HSA domain III are of a residue that is conserved among serum albumin proteins from at least two species selected from the group consisting of human, pig, rat, mouse, dog, rabbit, cow, chicken, donkey, Mongolian gerbil, sheep, cat, and horse. In certain embodiments, all of said amino acid substitutions in HSA domain III are of a residue that is conserved among serum albumin proteins from at least three species selected from the group consisting of human, pig, rat, mouse, dog, rabbit, cow, chicken, donkey, Mongolian gerbil, sheep, cat, and horse. In certain embodiments, all of said amino acid substitutions in HSA domain III are of a residue that is conserved among serum albumin proteins from at least four species selected from the group consisting of human, pig, rat, mouse, dog, rabbit, cow, chicken, donkey, Mongolian gerbil, sheep, cat, and horse. In certain embodiments, all of said amino acid substitutions in HSA domain III are of a residue that is conserved among serum albumin proteins from at least five species selected from the group consisting of human, pig, rat, mouse, dog, rabbit, cow, chicken, donkey, Mongolian gerbil, sheep, cat, and horse. In certain embodiments, all of said amino acid substitutions in HSA domain III are of a residue that is conserved among serum albumin proteins from between two and five species selected from the group consisting of human, pig, rat, mouse, dog, rabbit, cow, chicken, donkey, Mongolian gerbil, sheep, cat, and horse. Polypeptides (e.g., HSA variants and chimeric polypeptides) comprising any combination of the foregoing categories of amino acid substitutions are also contemplated.

In certain embodiments, at least one amino acid substitutions in HSA domain III are at any of the following positions, numbered relative to the position in full length mature HSA: residue 383, residue 389, residue 391, residue 410, residue 417, residue 425, residue 442, residue 465, residue 467, residue 468, residue 486, residue 499, residue 502, residue 520, residue 532, residue 536, residue 543, and residue 571. In certain embodiments, at least one amino acid substitutions in HSA domain III are at any of the following positions, numbered relative to the position in full mature length HSA: residue 417, residue 442, residue 499, and residue 502. In certain embodiments, at least one amino acid substitutions in HSA domain III are at any of the following positions, numbered relative to the position in full length mature HSA: residue 392, residue 399, residue 403, residue 411, residue 412, residue 414, residue 416, residue 418, residue 420, residue 423, residue 434, residue 437, residue 438, residue 445, residue 448, residue 450, residue 453, residue 461, residue 476, residue 477, residue 484, residue 485, residue 487, residue 488, residue 494, residue 497, residue 507, residue 509, residue 514, residue 529, residue 534, residue 537, residue 540, residue 551, residue 558, residue 559, residue 567, residue 568, residue 572. In certain embodiments, more than one amino acid substitution (e.g., 2, 3, 4, 5, 6, 7, 8, 9, 10, 11, 12, 13, 14, 15, 16, 17, 18) or even all of the amino acid substitutions in domain III are in the foregoing residues. Polypeptides (e.g., HSA variants and chimeric polypeptides) comprising all combinations of amino acid substitutions in any one or more of the foregoing residues are specifically contemplated.

In certain embodiments, at least one of the amino acid substitutions in HSA domain III are at any of the following positions, numbered related to the position in full length mature HSA domain III: residue 383, residue 391, residue 411, residue 414, residue 416, residue 434, residue 442, residue 445, residue 450 and residue 509.

In certain embodiments, at least one of the amino acid substitutions in HSA domain III are selected from the group consisting of: E383A, E383G, E383I, E383L, E383V, N391A, N391G, N391I, N391L, N391V, Y411Q, Y411N, K414S, K414T, Q416H, Q416P, G434C, G434S, G434T, E442K, E442R, R445F, R445W, R445Y, E450D, E450E, F509C, F509I, F509L, F509M, F509V, F509W and F509Y. In certain embodiments, more than one amino acid substitution (e.g., 2, 3, 4, 5 . . . ) or even all of the amino acid substitutions in domain III are selected from the foregoing substitutions.

In certain embodiments, at least one of the amino acid substitutions in HSA domain III are at any of the following positions, numbered related to the position in full length mature HSA domain III: residue 380, residue 381, residue 384, residue 387, residue 396, residue 401, residue 404, residue 405, residue 406, residue 409, residue 419, residue 421, residue 422, residue 424, residue 428, residue 430, residue 431, residue 433, residue 441, residue 457, residue 458, residue 463, residue 464, residue 466, residue 469, residue 470, residue 474, residue 475, residue 480, residue 481, residue 489, residue 491, residue 495, residue 500, residue 508, residue 510, residue 515, residue 516, residue 524, residue 525, residue 526, residue 528, residue 531, residue 535, residue 539, residue 544, residue 547, residue 576. In certain embodiments, more than one amino acid substitution (e.g., 2, 3, 4, 5, 6, 7, 8, 9, 10, 11, 12, 13, 14, 15, 16, 17, 18) or even all of the amino acid substitutions in domain III are in the foregoing residues. Polypeptides (e.g., HSA variants and chimeric polypeptides) comprising all combinations of amino acid substitutions in any one or more of the foregoing residues are specifically contemplated.

In certain embodiments, at least one of the amino acid substitutions in HSA domain III are at any of the following positions, numbered related to the position in full length mature HSA domain III: residue 381, residue 401, residue 424, residue 457, residue 463, residue 495, residue 508, residue 515, residue 516, residue 524, residue 525, residue 526, residue 531, residue 535 and residue 539.

In certain embodiments, at least one of the amino acid substitutions in HSA domain III are selected from the group consisting of: V381N, V381Q, Y401D, Y401E, V242A, V242G, V424I, V424L, V424N, V424Q, V424V, L457F, L457W, L457Y, L463N, L463Q, E495D, T508K, T508R, T508S, T515C, T515H, T515N, T515P, T515Q, T515S, L516F, L516S, L516T, L516W, L516Y, K524A, K524G, K524I, K524L, K524V, K525A, K525G, K525I, K525L, K525V, Q526C, Q526M, Q526S, Q526T, Q526Y, E531A, E531G, E531I, E531L, E531V, H535D, H535E, H535P, A539I, A539L and A539V. In certain embodiments, more than one amino acid substitution (e.g., 2, 3, 4, 5 . . . ) or even all of the amino acid substitutions in domain III are selected from the foregoing substitutions.

In certain embodiments, at least one of said amino acid substitutions in HSA domain III is of a residue that is not conserved across multiple species. In certain embodiments, all of said amino acid substitutions in HSA domain III are of residues that are not conserved across multiple species. In certain embodiments, at least one of said amino acid substitutions in HSA domain III is of a residue that is not conserved among serum albumin proteins from human, rat, dog, rabbit, and cow. In certain embodiments, all of said amino acid substitutions in HSA domain III are of residues that are not conserved among serum albumin proteins human, rat, dog, rabbit and cow. In certain embodiments, at least one of said amino acid substitutions in HSA domain III is of a residue that is not conserved among serum albumin proteins from human, rat, dog, rabbit, and cow. In certain embodiments, all of said amino acid substitutions in HSA domain III are of residues that are not conserved among serum albumin proteins from human, rat, dog, rabbit, and cow. Polypeptides (e.g., HSA variants and chimeric polypeptides with an HSA portion) comprising any combination of the foregoing category of amino acid substitutions are also contemplated.

In certain embodiments, at least one amino acid substitution in HSA domain III are at any of the following positions, numbered relative to the position in full length mature HSA: residue 382, residue 385, residue 390, residue 397, residue 400, residue 402, residue 415, residue 429, residue 432, residue 435, residue 439, residue 440, residue 443, residue 444, residue 446, residue 447, residue 459, residue 471, residue 472, residue 478, residue 479, residue 483, residue 490, residue 492, residue 493, residue 503, residue 511, residue 517, residue 518, residue 519, residue 521, residue 538, residue 541, residue 542, residue 546, residue 549, residue 550, residue 552, residue 554, residue 556, residue 560, residue 562, residue 563, residue 565, and residue 566. In certain embodiments, more than one amino acid substitution (e.g., 2, 3, 4, 5, 6, 7, 8, 9, 10, 11, 12, 13, 14, 15, 16, 17, 18) or even all of the amino acid substitutions in domain III are in the foregoing residues. Polypeptides (e.g., HSA variants and chimeric polypeptides with an HSA portion) comprising any combinations of amino acid substitutions in any one or more of the foregoing residues are specifically contemplated.

In certain embodiments, at least one amino acid substitution in HSA domain III are at any of the following positions, numbered relative to the position in full length mature HSA: residue 402, residue 415, reside 447, residue 459, residue 511, residue 517, residue 519, residue 521, residue 538, residue 541, and residue 566.

In certain embodiments, at least one of the amino acid substitutions in HSA domain III are selected from the group consisting of: K402A, K402G, K402I, K402L, K402V, V415C, V415S, V415T, P447S, P447T, Q459K, Q459R, L463N, L463Q, A511F, A511W, A511Y, S517C, S517F, S517M, S517T, S517W, S517Y, K519A, K519G, K519I, K519L, K519V, R521F, R521W, R521Y, K538F, K538W, K538Y, K541F, K541W, K541Y, T566F, T566W, and T566Y. In certain embodiments, more than one amino acid substitution (e.g., 2, 3, 4, 5 . . . ) or even all of the amino acid substitutions in domain III are selected from the foregoing substitutions.

In certain embodiments, at least one of said amino acid substitutions in HSA domain III is of a surface accessible residue. In certain embodiments, all of said amino acid substitutions in HSA domain III are of surface accessible residues. In certain embodiments, at least one of said amino acid substitutions in HSA domain III is of a residue that is both surface accessible and conserved across multiple species. In certain embodiments, all of said amino acid substitutions in HSA domain III are of residues that are both surface accessible and conserved across multiple species. In certain embodiments, at least one amino acid substitutions in HSA domain III are at any of the following positions, numbered relative to the position in full length mature HSA: residue 383, residue 389, residue 391, residue 410, residue 417, residue 425, residue 442, residue 465, residue 467, residue 468, residue 486, residue 499, residue 502, residue 520, residue 532, residue 536, residue 543, and residue 571. In certain embodiments, at least one amino acid substitutions in HSA domain III are at any of the following positions, numbered relative to the position in full length mature HSA: residue 417, residue 442, residue 499, and residue 502. In certain embodiments, at least one amino acid substitutions in HSA domain III are at any of the following positions, numbered relative to the position in full length mature HSA: residue 383, residue 391, and residue 442. In certain embodiments, more than one amino acid substitution (e.g., 2, 3, 4, 5, 6, 7, 8, 9, 10, 11, 12, 13, 14, 15, 16, 17, 18) or even all of the amino acid substitutions in domain III are in the foregoing residues. Polypeptides (e.g., HSA variants and chimeric polypeptides) comprising any combination of the foregoing categories of amino acid substitutions are specifically contemplated. In certain embodiments, at least one of the amino acid substitutions in HSA domain III are selected from the group consisting of: E383A, E383G, E383I, E383L, E383V, N391A, N391G, N391I, N391L, N391V, E442K, E442R. In certain embodiments, more than one amino acid substitution (e.g., 2, 3, 4, 5 . . . ) or even all of the amino acid substitutions in domain III are selected from the foregoing substitutions.

In certain embodiments, the at least one amino acid substitution in HSA domain III is not solely a substitution of R410c; K466E; E479K; D494N; E501K; E505K; V533M; K536E536; K541E; D550A or D550G; K560E; D563N; E565K; E570K; K573E; or K574E.

In certain embodiments, polypeptides (e.g., HSA variants and chimeric polypeptides with an HSA portion) comprise an HSA domain III which comprises an amino acid sequence at least 80%, 85%, or at least 90% identical to SEQ ID NO: 1. In certain embodiments, the HSA domain III comprises an amino acid sequence at least 95% identical to SEQ ID NO: 1. In certain embodiments, the HSA domain III comprises an amino acid sequence at least 98% identical to SEQ ID NO: 1. In certain embodiments, the HSA portion comprises an amino acid sequence at least 80%, 85%, or at least 90% identical to the corresponding portion of SEQ ID NO: 2. In certain embodiments, the HSA portion comprises an amino acid sequence at least 95% identical to the corresponding portion of SEQ ID NO: 2. In certain embodiments, the HSA portion comprises an amino acid sequence at least 98% identical to the corresponding portion of SEQ ID NO: 2.

In certain embodiments, the disclosure contemplates that, in addition to one or more amino acid substitutions in HSA domain III, a polypeptide (e.g., HSA variants and chimeric polypeptides with an HSA portion) may include one or more amino acid substitutions in the HSA portion outside of domain III.

In certain embodiments, the disclosure contemplates that polypeptides (e.g., HSA variants and chimeric polypeptides with an HSA portion), in addition to one or more amino acid substitutions in HSA domain III, may also include one or more amino acid deletions and/or insertions (e.g., 1, 2, 3, 4, 5, 6, 7, 8) in domain III. Note that when an HSA portion contains one or more amino acid deletions and/or insertions, such inserted or deleted residues can be denoted using letters so as not to disrupt the numbering of residue, relative to that of native HSA. For example, if an amino acid residue was inserted between residues 414 and 415, such a residue could be denoted as 414a. In certain embodiments, the inserted amino acid residues are inserted into a surface accessible loop to increase the size of such a loop. In certain embodiments, the inserted amino acid residues are inserted into a helix to increase the size and/or alter the structure of such a helix.

In certain embodiments, at least one of said amino acid substitutions in HSA domain III is in loop 2 of HSA domain III. In certain embodiments, all of said amino acid substitutions in HSA domain III are in loop 2 of HSA domain III. In certain embodiments, the HSA domain III comprises one to five (1, 2, 3, 4, 5) amino acid substitutions, wherein said one to five amino acid substitutions are in loop 2 of HSA domain III. In certain embodiments, the HSA domain III comprises one to five (1, 2, 3, 4, or 5) amino acid substitutions in loop 2 of HSA domain III, and further includes one or more additional amino acid substitutions in HSA domain III that are not in loop 2. In certain embodiments, at least one of said amino acid substitutions in HSA domain III is in loop 3 of HSA domain III. In certain embodiments, all of said amino acid substitutions in HSA domain III are in loop 3 of HSA domain III. In certain embodiments, the HSA domain III comprises one to five (1, 2, 3, 4, 5) amino acid substitutions, wherein said one to five amino acid substitutions are in loop 3 of HSA domain III. In certain embodiments, the HSA domain III comprises one to five (1, 2, 3, 4, or 5) amino acid substitutions in loop 3 of HSA domain III, and further includes one or more additional amino acid substitutions in HSA domain III that are not in loop 3. In certain embodiments, at least one of said amino acid substitutions in HSA domain III is in loop 6 of HSA domain III. In certain embodiments, all of said amino acid substitutions in HSA domain III are in loop 6 of HSA domain III. In certain embodiments, the HSA domain III comprises one to eighteen (1, 2, 3, 4, 5, 6, etc.) amino acid substitutions, wherein said one to eighteen amino acid substitutions are in loop 6 of HSA domain III. In certain embodiments, the HSA domain III comprises one to eighteen (1, 2, 3, 4, 5, 6, etc.) amino acid substitutions in loop 6 of HSA domain III, and further includes one or more additional amino acid substitutions in HSA domain III that are not in loop 6. In certain embodiments, at least one of said amino acid substitutions in HSA domain III is in helix 7 of HSA domain III. In certain embodiments, all of said amino acid substitutions in HSA domain III are in helix 7 of HSA domain III. In certain embodiments, the HSA domain III comprises one to six (1, 2, 3, 4, 5, or 6) amino acid substitutions, wherein said one to six amino acid substitutions are in helix 7 of HSA domain III. In certain embodiments, the HSA domain III comprises one to six (1, 2, 3, 4, 5, or 6) amino acid substitutions in helix 7 of HSA domain III, and further includes one or more additional amino acid substitutions in HSA domain III that are not in helix 7. In certain embodiments, at least one of said amino acid substitutions in HSA domain III is in loop 7 of HSA domain III. In certain embodiments, all of said amino acid substitutions in HSA domain III are in loop 7 of HSA domain III. In certain embodiments, the HSA domain III comprises one to three (1, 2, or 3) amino acid substitutions, wherein said one to three amino acid substitutions are in loop 7 of HSA domain III. In certain embodiments, the HSA domain III comprises one to three (1, 2, or 3) amino acid substitutions in loop 7 of HSA domain III, and further includes one or more additional amino acid substitutions in HSA domain III that are not in loop 7. In certain embodiments, at least one of said amino acid substitutions in HSA domain III is in helix 8 of HSA domain III. In certain embodiments, all of said amino acid substitutions in HSA domain III are in helix 8 of HSA domain III. In certain embodiments, the HSA domain III comprises one to eighteen (1, 2, 3, 4, 5, 6, etc.) amino acid substitutions, wherein said one to eighteen amino acid substitutions are in helix 8 of HSA domain III. In certain embodiments, the HSA domain III comprises one to six (1, 2, 3, 4, 5, 6, etc.) amino acid substitutions in helix 8 of HSA domain III, and further includes one or more additional amino acid substitutions in HSA domain III that are not in helix 8. In certain embodiments, at least one of said amino acid substitutions in HSA domain III is in loop 8 of HSA domain III. In certain embodiments, all of said amino acid substitutions in HSA domain III are in loop 8 of HSA domain III. In certain embodiments, the HSA domain III comprises one to five (1, 2, 3, 4, 5) amino acid substitutions, wherein said one to five amino acid substitutions are in loop 8 of HSA domain III. In certain embodiments, the HSA domain III comprises one to five (1, 2, 3, 4, or 5) amino acid substitutions in loop 8 of HSA domain III, and further includes one or more additional amino acid substitutions in HSA domain III that are not in loop 8. In certain embodiments, at least one of said amino acid substitutions in HSA domain III is in loop 9 of HSA domain III. In certain embodiments, all of said amino acid substitutions in HSA domain III are in loop 9 of HSA domain III. In certain embodiments, the HSA domain III comprises one to four amino acid substitutions in, wherein said one to four (1, 2, 3, 4) amino acid substitutions are in loop 9 of HSA domain III. In certain embodiments, the HSA domain III comprises one to five (1, 2, 3, 4) amino acid substitutions in loop 9 of HSA domain III, and further includes one or more additional amino acid substitutions in HSA domain III that are not in loop 9. As detailed above, potential amino acid substitutions, independently at each position, are selected from any of the classes of substitution detailed above (e.g., alanine, conservative substitution, etc.). Polypeptides (e.g., HSA variants and chimeric polypeptides) comprising any combination of the foregoing categories of amino acid substitutions are also contemplated.

In certain embodiments, said amino acid substitutions in HSA domain III are not in loop 2 of HSA domain III. In certain embodiments, said amino acid substitutions in HSA domain III are not in loop 3 of HSA domain III. In certain embodiments, said amino acid substitutions in HSA domain III are not in loop 6 of HSA domain III. In certain embodiments, said amino acid substitutions are not in helix 7 of HSA domain III. In certain embodiments, said amino acid substitutions are not in loop 7 of HSA domain III. In certain embodiments, said amino acid substitutions are not in helix 8 of HSA domain III. In certain embodiments, said amino acid substitutions in HSA domain III are not in loop 8 of HSA domain III. In certain embodiments, said amino acid substitutions in HSA domain III are not in loop 9 of HSA domain III.

In certain embodiments, said amino acid substitutions in HSA domain III are not in at least two loops of HSA domain III selected from the group consisting of loops 2, 3, 6, 7, 8 and 9. In certain embodiments, said amino acid substitutions in HSA domain III are not in at least three loops of HSA domain III selected from the group consisting of loops 2, 3, 6, 7, 8 and 9. In certain embodiments, said amino acid substitutions in HSA domain III are not in at least four loops of HSA domain III selected from the group consisting of loops 2, 3, 6, 7, 8 and 9. In certain embodiments, said amino acid substitutions in HSA domain III are not in helices 7 or 8.

In certain embodiments, domain III comprises at least two amino acid substitutions and said amino acid substitutions are in at least two of the loops and/or helices of HSA domain III selected from the group consisting of loops 2, 3, 6, 7, 8 and 9 and helices 7 and 8. In certain embodiments, domain III comprises at least three amino acid substitutions and said amino acid substitutions are in at least three of the loops and/or helices of HSA domain III selected from the group consisting of loops 2, 3, 6, 7, 8 and 9 and helices 7 and 8. In certain embodiments, domain III comprises at least four amino acid substitutions and said amino acid substitutions are in at least four of the loops and or helices of HSA domain III selected from the group consisting of loops 2, 3, 6, 7, 8 and 9 and helices 7 and 8. In certain embodiments, domain III comprises at least five amino acid substitutions and said amino acid substitutions are in at least five of the loops and or helices of HSA domain III selected from the group consisting of loops 2, 3, 6, 7, 8 and 9 and helices 7 and 8. In certain embodiments, domain III comprises at least six amino acid substitutions and said amino acid substitutions are in at least six of the loops and or helices of HSA domain III selected from the group consisting of loops 2, 3, 6, 7, 8 and 9 and helices 7 and 8. In certain embodiments, domain III comprises at least five amino acid substitutions and said amino acid substitutions are in each of loops 2, 3, 6, 7, 8 and 9 of HSA domain III. In certain embodiments, domain III comprises at least six amino acid substitutions and said amino acid substitutions are in each of loops 2, 3, 6, 7, 8 and 9 of HSA domain III. In certain embodiments, domain III comprises at least two amino acid substitutions and said amino acid substitutions are in each of helices 7 and 8 of HSA domain III.

In certain embodiments, at least one of said amino acid substitutions in HSA domain III is in loop 2 and is selected from: residue 415, residue 416, residue 417, residue 418, and residue 419. In certain embodiments, more than one (2, 3, 4, 5) amino acid substitution is in loop 2 and is selected from: residue 415, residue 416, residue 417, residue 418, and residue 419. In certain embodiments, at least one of said amino acid substitutions in HSA domain III loop 2 is selected from: V415C, V415S, V415T, Q416H, and Q416P. In certain embodiments, at least one of said amino acid substitutions in HSA domain III is in loop 3 and is selected from: residue 439, residue 440, residue 441, residue 442, and residue 443. In certain embodiments, more than one (2, 3, 4, 5) amino acid substitution is in loop 3 and is selected from: residue 439, residue 440, residue 441, residue 442, and residue 443. In certain embodiments, at least one of said amino acid substitutions in HSA domain III loop 3 is selected from: E442K, and E442R. In certain embodiments, at least one of said amino acid substitutions in HSA domain III is in loop 6 and is selected from: residue 492, residue 493, residue 494, residue 495, residue 496, residue 497, residue 498, residue 499, residue 500, residue 501, residue 502, residue 503, residue 504, residue 505, residue 506, residue 507, residue 508, and residue 509. In certain embodiments, more than one (2, 3, 4, 5, 6, 7, 8, 9, 10, etc.) amino acid substitution is in loop 6 and is selected from: residue 492, residue 493, residue 494, residue 495, residue 496, residue 497, residue 498, residue 499, residue 500, residue 501, residue 502, residue 503, residue 504, residue 505, residue 506, residue 507, residue 508, and residue 509. In certain embodiments, at least one of said amino acid substitutions in HSA domain III loop 6 is selected from: T506F, T506W, T506Y, T508K, T508R, T508S, F509C, F509I, F509L, F509M, F509V, F509W and F509Y. In certain embodiments, at least one of said amino acid substitutions in HSA domain III is in helix 7 and is selected from: residue 510, residue 511, residue 512, residue 513, residue 514, and residue 515. In certain embodiments, more than one (2, 3, 4, 5, 6) amino acid substitution is in helix 7 and is selected from: residue 510, residue 511, residue 512, residue 513, residue 514, and residue 515. In certain embodiments, at least one of said amino acid substitutions in HSA domain III loop 7 is selected from: A511F, A511W, A511Y, D512F, D512W, D512Y, T515C, T515H, T515N, T515P, T515Q, and T515S. In certain embodiments, at least one of said amino acid substitutions in HSA domain III is in loop 7 and is selected from: residue 516, residue 517, and residue 518. In certain embodiments, more than one (2, 3) amino acid substitution is in loop 7 and is selected from: residue 516, residue 517, and residue 518. In certain embodiments, at least one of said amino acid substitutions in HSA domain III loop 7 is selected from: L516F, L516S, L516T, L516W, L516Y, S517C, S517F, S517M, S517T, S517W, and S517Y. In certain embodiments, at least one of said amino acid substitutions in HSA domain III is in helix 8 and is selected from: residue 519, residue 518, residue 519, residue 520, residue 521, residue 522, residue 523, residue 524, residue 525, residue 526, residue 527, residue 528, residue 529, residue 530, residue 531, residue 532, residue 533, residue 534, residue 535, and residue 536. In certain embodiments, more than one (2, 3, 4, 5, 6, 7, 8, 9, 10, etc.) amino acid substitution is in helix 8 and is selected from: residue 519, residue 518, residue 519, residue 520, residue 521, residue 522, residue 523, residue 524, residue 525, residue 526, residue 527, residue 528, residue 529, residue 530, residue 531, residue 532, residue 533, residue 534, residue 535, and residue 536. In certain embodiments, at least one of said amino acid substitutions in HSA domain III helix 8 is selected from: K519A, K519G, K519I, K519L, K519V, R521F, R521W, R521Y, I523A, I523D, I523E, I523F, I523G, I523I, I523K, I523L, I523N, I523Q, I523R, I523V, I523W, I523Y, K524A, K524G, K524I, K524L, K524V, K525A, K525G, K525I, K525L, K525V, Q526C, Q526M, Q526S, Q526T, Q526Y, T527F, T527W, T527Y, E531A, E531G, E531I, E531L, E531V, H535D, H535E, and H535P. In certain embodiments, at least one of said amino acid substitutions in HSA domain III is in loop 8 and is selected from: residue 537, residue 538, residue 539, residue 540, and residue 541. In certain embodiments, more than one (2, 3, 4, 5) amino acid substitution is in loop 8 and is selected from: residue 537, residue 538, residue 539, residue 540, residue 541. In certain embodiments, at least one of said amino acid substitutions in HSA domain III is in loop 9 and is selected from: residue 561, residue 562, residue 563, residue 564. In certain embodiments, at least one of said amino acid substitutions in HSA domain III loop 8 is selected from: K538F, K538W, K538Y, A539I, A539L, A539V, K541F, K541W, K541Y, In certain embodiments, more than one (2, 3, 4) amino acid substitution is in loop 9 and is selected from: residue 561, residue 562, residue 563, residue 564. In certain embodiments, at least one of said amino acid substitutions in HSA domain III loop 9 is selected from: A561F, A561W, and A561Y.

Additionally contemplated are insertions or deletions in domain III that, for example, increase or decrease the length of a HSA domain III loop. In certain embodiments, said insertion or deletion in HSA domain III alters the length of loop 2. In certain embodiments, said insertion or deletion in HSA domain III alters the length of loop 3. In certain embodiments, said insertion or deletion in HSA domain III alters the length of loop 6. In certain embodiments, said insertion or deletion in HSA domain III alters the length of helix 7. In certain embodiments, said insertion or deletion in HSA domain III alters the length of loop 7. In certain embodiments, said insertion or deletion in HSA domain III alters the length of helix 8. In certain embodiments, said insertion or deletion in HSA domain III alters the length of loop 8. In certain embodiments, said insertion or deletion in HSA domain III alters the length of loop 9. In certain embodiments, said insertion or deletion in domain III alters the length of at least two loops and/or helices selected from the group consisting of loops 2, 3, 6, 7, 8 and 9 and helices 7 and 8. In certain embodiments, said insertion or deletion in domain III alters the length of at least three loops and/or helices selected from the group consisting of loops 2, 3, 6, 7, 8 and 9 and helices 7 and 8. In certain embodiments, said insertion or deletion in domain III alters the length of at least four loops and/or helices of selected from the group consisting of loops 2, 3, 6, 7, 8 and 9 and helices 7 and 8. In certain embodiments, said insertion or deletion in domain III alters the length of at least five loops and/or helices selected from the group consisting of loops 2, 3, 6, 7, 8 and 9 and helices 7 and 8. In certain embodiments, said insertion or deletion in HSA domain III alters the length of each of loops 2, 3, 6, 7, 8 and 9 of HSA domain III. Note that when multiple loops and/or helices are altered, the disclosure contemplates that the loops and/or helices are independently altered, such that one or more loops/helices may be increased by insertion and one or more loops/helices may be decreased by deletion.

For embodiments in which domain III includes an insertion or deletion of amino acids, the disclosure contemplates insertions or deletions of one amino acid. Also contemplated, are insertions or deletions of greater than one amino acid, such as, 2, 3, 4, 5, 6, 7, 8, 9, 10 amino acids. In certain embodiments, the disclosure contemplates insertions of more than 10 amino acid residues, such as 10-20, 20-40, 40-50, 50-100 amino acids. Consistent with the chimeric polypeptides and HSA variant polypeptides of the disclosure, compositions that include insertions or deletions are tested to confirm that they retain FcRn binding activity. Preferred compositions are compositions that provide improved FcRn binding and/or serum half life relative to controls.

For the purpose of clarity, the disclosure specifically contemplates combinations of any of the foregoing or following aspects and embodiments. In the context of a chimeric polypeptide comprising an HSA portion, as well as in the context of a variant HSA polypeptide comprising an HSA portion, such an HSA portion comprises domain III, or an FcRn binding portion thereof. Further, as described herein, domain III of the HSA portion includes one to eighteen amino acid substitutions. In certain embodiments, domain III of the HSA portion includes 1, 2, 3, 4, 5, 6, 7, 8, 9, 10, 11, 12, 13, 14, 15, 16, 17, or 18 amino acid substitutions. Exemplary amino acid substitutions include: (i) replacement with alanine; (ii) conservative amino acid substitution; (iii) non-conservative amino acid substitution. The disclosure contemplates that all of the amino acid substitutions in domain III of a given polypeptide may be a member of one of these categories of amino acid substitution, and also contemplates that each amino acid substitution in domain III of a given polypeptide may be individually and independently selected from these categories. In certain embodiments, native cysteine residues in domain III are maintained and are not substituted. In certain embodiments, native proline residues in domain III are maintained and are not substituted. In certain embodiments, native cysteine residues and native proline residues in domain III are maintained and are not substituted. In certain embodiments, a cysteine residue is not substituted (e.g., a cysteine is not used to replace a native residue). In certain embodiments, a proline residue is not substituted (e.g., a proline is not used to replace a native residue). In other embodiments, any one of the twenty amino acids is used to substitute for a given native residue.

HSA variants and chimeric polypeptides comprising any combination of the foregoing classes of amino acid substitutions are also contemplated.

The present invention encompasses variants and chimeric polypeptides with an HSA portion comprising amino acids in a sequence that is substantially the same as an amino acid sequence described herein. Amino acid sequences that are substantially the same as the sequences described herein include sequences comprising conservative amino acid substitutions, as well as amino acid deletions and/or insertions. A conservative amino acid substitution refers to the replacement of a first amino acid by a second amino acid that has chemical and/or physical properties (e.g., charge, structure, polarity, hydrophobicity/hydrophilicity) that are similar to those of the first amino acid. Conservative amino acid substitutions include replacement of one amino acid by another within the following groups: lysine (K), arginine (R) and histidine (H); aspartate (D) and glutamate (E); asparagine (N), glutamine (Q), serine (S), threonine (T), tyrosine (Y), K, R, H, D and E; alanine (A), valine (V), leucine (L), isoleucine (I), proline (P), phenylalanine (F), tryptophan (W), methionine (M), cysteine (C) and glycine (G); F, W and Y; C, S and T.

In certain embodiments, said HSA variant polypeptide is substantially purified. In certain embodiments, said chimeric polypeptide is substantially purified. In certain aspects, the disclosure provides a composition comprising the HSA variant or the chimeric polypeptide of the disclosure, and a pharmaceutically acceptable carrier. In certain embodiments, the composition is a sterile composition. In certain embodiments, the composition is non-pyrogenic.

6.4 Combinatorial Domain III Mutants

This invention further contemplates generating sets of combinatorial mutants of an HSA portion comprising domain III, as well as truncation mutants, and is especially useful for identifying bioactive variant sequences. Combinatorially-derived variants can be generated which have a selective potency relative to a naturally occurring HSA polypeptide. Likewise, mutagenesis can give rise to variants which have intracellular half-lives dramatically different than the corresponding wild-type HSA polypeptide. For example, the altered protein can be rendered either more stable or less stable to proteolytic degradation or other cellular process which result in destruction of, or otherwise inactivation of the protein of interest. Such variants can be utilized to alter the HSA polypeptide level by modulating their half-life. There are many ways by which the library of potential HSA variants sequences can be generated, for example, from a degenerate oligonucleotide sequence. Chemical synthesis of a degenerate gene sequence can be carried out in an automatic DNA synthesizer, and the synthetic genes then be ligated into an appropriate gene for expression. The purpose of a degenerate set of genes is to provide, in one mixture, all of the sequences encoding the desired set of potential polypeptide sequences. The synthesis of degenerate oligonucleotides is well known in the art (see for example, Narang, S A (1983) Tetrahedron 39:3; Itakura et al., (1981) Recombinant DNA, Proc. 3rd Cleveland Sympos. Macromolecules, ed. A G Walton, Amsterdam: Elsevier pp 273-289; Itakura et al., (1984) Annu Rev. Biochem. 53:323; Itakura et al., (1984) Science 198: 1056; Ike et al., (1983) Nucleic Acid Res. 11:477). Such techniques have been employed in the directed evolution of other proteins (see, for example, Scott et al., (1990) Science 249:386-390; Roberts et al., (1992) PNAS USA 89:2429-2433; Devlin et al., (1990) Science 249: 404-406; Cwirla et al., (1990) PNAS USA 87: 6378-6382; as well as U.S. Pat. Nos. 5,223,409, 5,198,346, and 5,096,815).

Alternatively, other forms of mutagenesis can be utilized to generate a combinatorial library. For example, HSA polypeptide variants can be generated and isolated from a library by screening using, for example, alanine scanning mutagenesis and the like (Ruf et al., (1994) Biochemistry 33:1565-1572; Wang et al., (1994) J. Biol. Chem. 269:3095-3099; Balint et al., (1993) Gene 137:109-118; Grodberg et al., (1993) Eur. J. Biochem. 218:597-601; Nagashima et al., (1993) J. Biol. Chem. 268:2888-2892; Lowman et al., (1991) Biochemistry 30:10832-10838; and Cunningham et al., (1989) Science 244:1081-1085), by linker scanning mutagenesis (Gustin et al., (1993) Virology 193:653-660; Brown et al., (1992) Mol. Cell. Biol. 12:2644-2652; McKnight et al., (1982) Science 232:316); by saturation mutagenesis (Meyers et al., (1986) Science 232:613); by PCR mutagenesis (Leung et al., (1989) Method Cell Mol Biol 1:11-19); or by random mutagenesis, including chemical mutagenesis, etc. (Miller et al., (1992) A Short Course in Bacterial Genetics, CSHL Press, Cold Spring Harbor, N.Y.; and Greener et al., (1994) Strategies in Mol Biol 7:32-34). Linker scanning mutagenesis, particularly in a combinatorial setting, is an attractive method for identifying truncated (bioactive) forms of the HSA polypeptide. Additional methods for generating and screening libraries of HSA polypeptide variants are provided herein, see for e.g., Section 8 entitled "Exemplifications". In particular Sections 8.10 and 8.11 for specific methods useful for the generation and screening of a combinatorial HSA domain III mutant library.

Any of the embodiments described above for amino acid substitutions in the polypeptides of the disclosure may be used to create libraries of peptides. In certain embodiments, combinatorially-derived variants are generated in residues in HSA domain III. In certain embodiments, the domain III mutations are introduced and screened in the context of on or more of the following: (i) variant domain III constructs alone; (ii) variant domain III constructs presented in the context of full length HSA; or (iii) in the context of truncated HSA or a chimeric polypeptide comprising at least domain III. In certain embodiments, the libraries of peptides are screened for variants which have one or both of increased affinity for FcRn and increased serum half-life relative to a the starting polypeptide. In certain embodiments, variants are evaluated using standard in vitro assays described in the application (e.g., flow cytometry). In certain embodiments, variant(s) that display improved affinity for FcRn are identified. In other embodiments, variant are screened to determine whether the improved affinity for FcRn occurs only at acidic pH (e.g., pH of approx. 5.5), but not a neutral pH (e.g., pH of approx. 7.4).

In certain embodiments, combinatorially-derived variants comprise at least two amino acid substitutions at any of the following positions, numbered relative to the position in full length mature HSA: residue 407, residue 415, residue 463, residue 495, residue 508, residue 509, residue 511, residue 512, residue 515, residue 516, residue 517, residue 521, residue 523, residue 524, residue 526, residue 527 and residue 557.

In certain embodiments, combinatorially-derived variants comprise at least two amino acid substitutions selected from the group consisting of: L407N, L407Y, V415T, L463N, L463F, E495D, T508R, T508S, F509M, F509W, F509I, A511F, D512Y, D512M, T515Q, L516T, L516W, S517W, R521W, I523D, I523E, I523F, I523G, I523K, I523R, K524L, Q526A, Q526M, Q526Y, T527Y, and T557G.

In certain embodiments, combinatorially-derived variants comprise amino acid substitutions in HSA domain III at positions, numbered relative to the position in full length mature HSA, selected from the group consisting of: (a) residues 383 and 413; (b) residues 401 and 523; (c) residues 407 and 447; (d) residues 407 and 447 and 539; (e) residues 407 and 509; (f) residues 407 and 526; (g) residues 411 and 535; (h) residues 414 and 456; (i) residues 415 and 569; (j) residues 426 and 526; (k) residues 442 and 450 and 459; (l) residues 463 and 508; (m) residues 508 and 519 and 525; (n) residues 509 and 527; (o) residues 523 and 538; (p) residues 526 and 557; and (q) residues 541 and 561.

In certain embodiments, combinatorially-derived variants are generated in residues that are conserved across multiple species. In certain embodiments, combinatorially-derived variants are generated in surface accessible residues. In certain embodiments, combinatorially-derived variants are generated in residues that are both surface accessible and conserved across multiple species. In certain embodiments, combinatorially-derived variants are generated in residues that are conserved across multiple species, but are not conserved in chicken HSA.

In certain aspects, the disclosure provides a library comprising a plurality of polypeptides, wherein each of said plurality of polypeptides comprises HSA domain III, or an FcRn binding fragment thereof, and wherein each of said plurality of polypeptides independently comprises at least one amino acid substitution of a residue in said HSA domain III that is conserved among serum albumin proteins from human, pig, rat, mouse, dog, rabbit, cow, chicken, donkey, Mongolian gerbil, sheep, cat, and horse.

In certain aspects, the disclosure provides a library comprising a plurality of polypeptides, wherein each of said plurality of polypeptides comprises HSA domain III, or an FcRn binding fragment thereof, and wherein each of said plurality of polypeptides independently comprises at least one amino acid substitution of a residue in said HSA domain III that is conserved among serum albumin proteins from human, pig, rat, mouse, dog, rabbit, cow, donkey, Mongolian gerbil, sheep, cat, and horse and which is not conserved in serum albumin from chicken.

In certain aspects, the disclosure provides a library comprising a plurality of polypeptides, wherein each of said plurality of polypeptides comprises HSA domain III, or an FcRn binding fragment thereof, and wherein each of said plurality of polypeptides independently comprises at least one amino acid substitution of a residue in said HSA domain III that is a surface accessible residue.

In certain aspects, the disclosure provides a library comprising a plurality of polypeptides, wherein each of said plurality of polypeptides comprises HSA domain III, or an FcRn binding fragment thereof, and wherein each of said plurality of polypeptides independently comprises at least one amino acid substitution of a residue in said HSA domain III that is both (i) a surface accessible residue and (ii) conserved among serum albumin proteins from human, pig, rat, mouse, dog, rabbit, cow, chicken, donkey, Mongolian gerbil, sheep, cat, and horse.

In certain embodiments, said surface accessible residue is in loop 2 of HSA domain III. In certain embodiments, said surface accessible residue is in loop 3 of HSA domain III. In certain embodiments, said surface accessible residue is in loop 6 of HSA domain III. In certain embodiments, said surface accessible residue is in helix 7 of HSA domain III. In certain embodiments, said surface accessible residue is in loop 7 of HSA domain III. In certain embodiments, said surface accessible residue is in helix 8 of HSA domain III. In certain embodiments, said surface accessible residue is in loop 8 of HSA domain III. In certain embodiments, said surface accessible residue is in loop 9 of HSA domain III.

In certain embodiments, at least one amino acid substitutions in HSA domain III are at any of the following positions, numbered relative to the position in full length mature HSA: residue 383, residue 389, residue 391, residue 410, residue 417, residue 425, residue 442, residue 465, residue 467, residue 468, residue 486, residue 499, residue 502, residue 520, residue 532, residue 536, residue 543, and residue 571. In certain embodiments, at least one amino acid substitutions in HSA domain III are at any of the following positions, numbered relative to the position in full length mature HSA: residue 417, residue 442, residue 499, and residue 502.

In certain embodiments, at least one amino acid substitutions in HSA domain III are at any of the following positions, numbered relative to the position in full length mature HSA: residue 392, residue 399, residue 403, residue 411, residue 412, residue 414, residue 416, residue 418, residue 420, residue 423, residue 434, residue 437, residue 438, residue 445, residue 448, residue 450, residue 453, residue 461, residue 476, residue 477, residue 484, residue 485, residue 487, residue 488, residue 494, residue 497, residue 507, residue 509, residue 514, residue 529, residue 534, residue 537, residue 540, residue 551, residue 558, residue 559, residue 567, residue 568, residue 572. In certain embodiments, at least one of the amino acid substitutions in HSA domain III are at any of the following positions, numbered related to the position in full length mature HSA domain III: residue 380, residue 381, residue 384, residue 387, residue 396, residue 401, residue 404, residue 405, residue 406, residue 409, residue 419, residue 421, residue 422, residue 424, residue 428, residue 430, residue 431, residue 433, residue 441, residue 457, residue 458, residue 463, residue 464, residue 466, residue 469, residue 470, residue 474, residue 475, residue 480, residue 481, residue 489, residue 491, residue 495, residue 500, residue 508, residue 510, residue 515, residue 516, residue 524, residue 525, residue 526, residue 528, residue 531, residue 535, residue 539, residue 544, residue 547, residue 576.

In certain embodiments, at least one of said amino acid substitutions in HSA domain III is in loop 2 of HSA domain III. In certain embodiments, all of said amino acid substitutions in HSA domain III are in loop 2 of HSA domain III. In certain embodiments, the HAS domain III comprises at least one of said amino acid substitutions in HSA domain III is in loop 2 of HSA domain III, and further includes one or more additional amino acid substitutions in HSA domain III are not in loop 2. In certain embodiments, at least one of said amino acid substitutions in HSA domain III is in loop 3 of HSA domain III. In certain embodiments, all of said amino acid substitutions in HSA domain III are in loop 3 of HSA domain III. In certain embodiments, the HSA domain III comprises at least one amino acid substitution in loop 3 of HSA domain III, and further includes one or more additional substitutions in HSA domain III that are not in loop 3. In certain embodiments, at least one of said amino acid substitutions in HSA domain III is in loop 6 of HSA domain III. In certain embodiments, all of said amino acid substitutions in HSA domain III are in loop 6 of HSA domain III. In certain embodiments, the HSA domain comprises at least one amino acid substitutions in loop 6 of HSA domain III, and further includes one or more additional amino acid substitutions in HSA domain III that are not in loop 6. In certain embodiments, at least one of said amino acid substitutions in HSA domain III is in helix 7 of HSA domain III. In certain embodiments, all of said amino acid substitutions in HSA domain III are in helix 7 of HSA domain III. In certain embodiments, the HSA domain comprises at least one amino acid substitutions in helix 7 of HSA domain III, and further includes one or more additional amino acid substitutions in HSA domain III that are not in helix 7. In certain embodiments, at least one of said amino acid substitutions in HSA domain III is in loop 7 of HSA domain III. In certain embodiments, all of said amino acid substitutions in HSA domain III are in loop 7 of HSA domain III. In certain embodiments, the HSA domain comprises at least one amino acid substitutions in loop 7 of HSA domain III, and further includes one or more additional amino acid substitutions in HSA domain III that are not in loop 7. In certain embodiments, at least one of said amino acid substitutions in HSA domain III is in helix 8 of HSA domain III. In certain embodiments, all of said amino acid substitutions in HSA domain III are in helix 8 of HSA domain III. In certain embodiments, the HSA domain comprises at least one amino acid substitutions in helix 8 of HSA domain III, and further includes one or more additional amino acid substitutions in HSA domain III that are not in helix 8. In certain embodiments, at least one of said amino acid substitutions in HSA domain III is in loop 8 of HSA domain III. In certain embodiments, all of said amino acid substitutions in HSA domain III are in loop 8 of HSA domain III. In certain embodiments, the HSA domain III comprises at least one amino acid substitution in loop 8 of HSA domain III, and further includes one or more additional amino acid substitutions in HSA domain III that are not in loop 8. In certain embodiments, at least one of said amino acid substitutions in HSA domain III is in loop 9 of HSA domain III. In certain embodiments, all of said amino acid substitutions in HSA domain III are in loop 9 of HSA domain III. In certain embodiments, the HSA domain III comprises at least one amino acid substitution in HSA domain III, and further includes one or more additional amino acid substitutions in HSA domain III that are not in loop 9.

In certain embodiments of any of the foregoing or following aspects or embodiments, an amino acid substitution may be an alteration of a residue to an alanine. In certain embodiments of any of the foregoing or following aspects or embodiments, an amino acid substitution may be a conservative amino acid substitution wherein a residue is replaced with a residue with similar charge and other properties. In certain embodiments of any of the foregoing or following aspects or embodiments, an amino acid substitution may be a non-conservative amino acid substitution wherein a residue is replaced with a residue that does not have similar charge or other properties. In certain embodiments of any of the foregoing or following aspects or embodiments, an amino acid substitution may be an alteration of a residue to any other residue. When an HSA portion includes more than one amino acid residue, it is contemplated that the substitutions may fall into any one or any combination of the foregoing categories of amino acid substitutions. For example, all of the substitutions may be changes to alanine or may be conservative amino acid substitutions or may be non-conservative amino acid substitutions. Alternatively, the amino acid substitutions may include any combination, such as, for example, one change to an alanine, one conservative amino acid substitution, and one non-conservative amino acid substitution.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of the HSA polypeptides. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate sequences created by combinatorial mutagenesis techniques.

In certain embodiments, an HSA polypeptide may include a peptide and a peptidomimetic. As used herein, the term "peptidomimetic" includes chemically modified peptides and peptide-like molecules that contain non-naturally occurring amino acids, peptoids, and the like. Peptidomimetics provide various advantages over a peptide, including enhanced stability when administered to a subject. Methods for identifying a peptidomimetic are well known in the art and include the screening of databases that contain libraries of potential peptidomimetics. For example, the Cambridge Structural Database contains a collection of greater than 300,000 compounds that have known crystal structures (Allen et al., Acta Crystallogr. Section B, 35:2331 (1979)). Where no crystal structure of a target molecule is available, a structure can be generated using, for example, the program CONCORD (Rusinko et al., J. Chem. Inf. Comput. Sci. 29:251 (1989)). Another database, the Available Chemicals Directory (Molecular Design Limited, Informations Systems; San Leandro Calif.), contains about 100,000 compounds that are commercially available and also can be searched to identify potential peptidomimetics of the HSA polypeptides.

In certain embodiments, an HSA polypeptide may further comprise post-translational modifications. Exemplary post-translational protein modification include phosphorylation, acetylation, methylation, ADP-ribosylation, ubiquitination, glycosylation, carbonylation, sumoylation, biotinylation or addition of a polypeptide side chain or of a hydrophobic group. As a result, the modified HSA polypeptides may contain non-amino acid elements, such as lipids, poly- or mono-saccharide, and phosphates. Effects of such non-amino acid elements on the functionality of an HSA polypeptide may be tested for its biological activity, for example, its ability to bind FcRn. Given that the native HSA polypeptide can be glycosylated, in certain embodiments an HSA polypeptide used in a chimeric polypeptide according to the present disclosure is glycosylated. In certain embodiments, the level and pattern of glycosylation is the same as or substantially the same as that of the native HSA polypeptide. In other embodiments, the level and/or pattern of glycosylation differs from that of the native HSA polypeptide (e.g., underglycosylated, overglycosylated, not glycosylated).

In certain embodiments of the present invention, a polypeptide comprising a HSA portion (e.g., HSA variant or chimeric polypeptide) may be conjugated to a non-protein agent. Such non-protein agents include, but are not limited to, nucleic acid molecules, chemical agents, organic molecules, etc., each which may be derived from natural sources, such as for example natural product screening, or may be chemically synthesized. In certain embodiments, the HSA portion is chemically conjugated to the non-protein agent.

In one specific embodiment of the present invention, an HSA polypeptide may be modified with nonproteinaceous polymers. In one specific embodiment, the polymer is polyethylene glycol ("PEG"), polypropylene glycol, or polyoxyalkylenes, in the manner as set forth in U.S. Pat. No. 4,640,835; 4,496,689; 4,301,144; 4,670,417; 4,791,192 or 4,179,337. PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161).

In certain embodiments, fragments or variants of the HSA polypeptide will preferably retain at least 50%, 60%, 70%, 80%, 85%, 90%, 95% or 100% of the biological activity associated with the native HSA polypeptide. In certain embodiments, fragments or variants of the HSA polypeptide have a half-life ($t_{1/2}$) which is enhanced relative to the half-life of the native protein. For embodiments in which the half-life is enhanced, the half-life of HSA fragments or variants is enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of the native HSA protein. In some embodiments, the protein half-life is determined in vitro, such as in a buffered saline solution or in serum. In other embodiments, the protein half-life is an in vivo half-life, such as the half-life of the protein in the serum or other bodily fluid of an animal.

In certain aspects, a polypeptide comprising an HSA portion may be a fusion protein which further comprises one or more fusion domains. Well known examples of such fusion domains include, but are not limited to, polyhistidine, Glu-Glu, glutathione S transferase (GST), thioredoxin, protein A, protein G, and an immunoglobulin heavy chain constant region (Fc), maltose binding protein (MBP), which are particularly useful for isolation of the fusion proteins by affinity chromatography. For the purpose of affinity purification, relevant matrices for affinity chromatography, such as glutathione-, amylase-, and nickel- or cobalt-conjugated resins are used. Fusion domains also include "epitope tags," which are usually short peptide sequences for which a specific antibody is available. Well known epitope tags for which specific monoclonal antibodies are readily available include FLAG, influenza virus haemagglutinin (HA), and c-myc tags. In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation. In certain embodiments, the HSA polypeptides may contain one or more modifications that are capable of stabilizing the polypeptides. For example, such modifications enhance the in vitro half-life of the polypeptides, enhance circulatory half-life of the polypeptides or reducing proteolytic degradation of the polypeptides. Similarly, in the context of chimeric polypeptides, the foregoing types of modifications may be additionally or alternatively appended to the heterologous protein portion of the chimeric polypeptide.

In some embodiments, a polypeptide comprising an HSA portion may be a fusion protein with all or a portion of an Fc region of an immunoglobulin. In certain embodiments, the fusion protein comprises the FcRn binding domain of IgG or a fragment thereof. Similarly, in certain embodiment, all or a portion of an Fc region of an immunoglobulin can be used as a linker to link an HSA portion to a heterologous protein. As is known, each immunoglobulin heavy chain constant region comprises four or five domains. The domains are named sequentially as follows: CH1-hinge-CH2-CH3(-CH4). The DNA sequences of the heavy chain domains have cross-homology among the immunoglobulin classes, e.g., the CH2 domain of IgG is homologous to the CH2 domain of IgA and IgD, and to the CH3 domain of IgM and IgE. As used herein, the term, "immunoglobulin Fc region" is understood to mean the carboxyl-terminal portion of an immunoglobulin chain constant region, preferably an immunoglobulin heavy chain constant region, or a portion thereof. For example, an immunoglobulin Fc region may comprise 1) a CH1 domain, a CH2 domain, and a CH3 domain, 2) a CH1 domain and a CH2 domain, 3) a CH1 domain and a CH3 domain, 4) a CH2 domain and a CH3 domain, or 5) a combination of two or more domains and an immunoglobulin hinge region. In a preferred embodiment the immunoglobulin Fc region comprises at least an immunoglobulin hinge region a CH2 domain and a CH3 domain, and preferably lacks the CH1 domain. In one embodiment, the class of immunoglobulin from which the heavy chain constant region is derived is IgG (Igγ) (γ subclasses 1, 2, 3, or 4). Other classes of immunoglobulin, IgA (Igα), IgD (Igδ), IgE (Igε) and IgM (Igμ), may be used. The choice of appropriate immunoglobulin heavy chain constant regions is discussed in detail in U.S. Pat. Nos. 5,541,087, and 5,726,044. The choice of particular immunoglobulin heavy chain constant region sequences from certain immunoglobulin classes and subclasses to achieve a particular result is considered to be within the level of skill in the art. The portion of the DNA construct encoding the immunoglobulin Fc region preferably comprises at least a portion of a hinge domain, and preferably at least a portion of a $CH_3$ domain of Fc γ or the homologous domains in any of IgA, IgD, IgE, or IgM. Furthermore, it is contemplated that substitution or deletion of amino acids within the immunoglobulin heavy chain constant regions may be useful in the practice of the invention. One example would be to introduce amino acid substitutions in the upper CH2 region to create a Fc variant with reduced affinity for Fc receptors (Cole et al. (1997) J. IMMUNOL. 159:3613). One of ordinary skill in the art can prepare such constructs using well known molecular biology techniques. Similarly, in the context of chimeric polypeptides, the foregoing types of modifications may be additionally or alternatively appended to the heterologous protein portion of the chimeric polypeptide.

In certain aspects, an HSA polypeptide may be a scaffold. In certain embodiments, a protein is used to select or design a protein framework which can specifically bind to a target. When designing proteins from the scaffold, amino acid residues that are important for the framework's favorable properties are retained, while others residues may be varied. In certain embodiments, a scaffold may have less than or equal to 50% of the amino acid residues that vary between protein derivatives having different properties and greater than or equal to 50% of the residues that are constant between such derivatives. In certain embodiments, a scaffold may have less than or equal to 45%, 40%, 35, 30%, 25%, 20%, 15%, 10%, or 5% of the amino acid residues that vary between protein derivatives having different properties and greater than or equal to 55%, 60%, 65%, 70%, 75%, 80%, 85%, 90% or 95% of the residues that are constant between such derivatives. In certain embodiments, a scaffold may have greater than or equal to 55%, 60%, 65%, 70%, 75%, 80%, 85%, 90% or 95% of the amino acid residues that vary between protein derivatives having different properties and less than or equal to 45%, 40%, 35, 30%, 25%, 20%, 15%, 10%, or 5% of the residues that are constant between such derivatives. In certain embodiments, these constant residues confer the same overall three-dimensional fold to all the variant domains, regardless of their properties. In certain embodiments, the HSA polypeptide scaffold may be modified or substituted as discussed in other aspects and embodiments of the disclosure. In certain embodiments, the HSA polypeptide scaffold may be a therapeutic. In certain embodiments, the HSA polypeptide scaffold may be agonistic to the target. In certain embodiments, the HSA polypeptide scaffold may be antagonistic to the target.

6.5 Chimeric Polypeptides

Polypeptides comprising an HSA portion, including HSA variant polypeptides, of the disclosure may be conjugated to any heterologous protein. In certain embodiments, the heterologous protein is a therapeutic. In certain embodiments, the therapeutic is an antibody or peptide. In certain embodiments, the heterologous protein portion of the chimeric polypeptide comprises an antibody or an antigen-binding fragment thereof. In certain embodiments, the chimeric polypeptide further comprises a constant region of an IgG immunoglobulin. In certain embodiments, the heterologous protein comprises a non-antibody therapeutic protein. In certain embodiments, the heterologous protein portion of a chimeric polypeptide comprises a growth factor or a cytokine. In certain embodiments, the chimeric polypeptide further comprises an epitope. For example, an epitope useful for detection and/or purification (e.g., His tag, FLAG tag, etc.).

In certain embodiments, the HSA portion is chemically conjugated to the heterologous protein. In certain embodiments, the HSA portion is recombinantly conjugated to the heterologous protein. In certain embodiments, the chimeric polypeptide is produced using a recombinant vector encoding both the HSA portion and the heterologous protein.

In certain embodiments, the HSA variant is produced in a prokaryotic or eukaryotic cell. In certain embodiments, the chimeric polypeptide is produced in a prokaryotic or eukaryotic cell. In certain embodiments, the eukaryotic cell is selected from a yeast cell, an avian cell, an insect cell, or a mammalian cell.

Chimeric polypeptides of the present invention can be made in various manners. In certain embodiments, the C-terminus of an HSA portion can be linked to the N-terminus of a heterologous protein (e.g., an antibody or a therapeutic peptide). Alternatively, the C-terminus of a heterologous protein (e.g., an antibody or a therapeutic peptide) can be linked to the N-terminus of an HSA portion. In certain embodiments, the HSA portion is conjugated to an internal amino acid of the heterologous protein. In certain embodiments, potential configurations include the use of truncated portions of an antibody's heavy and light chain sequences as needed to maintain the functional integrity of the attached HSA portion and/or the attached heterologous protein. In certain other embodiments, the HSA portion comprises HSA domain III, or a neonatal Fc receptor (FcRn) binding fragment thereof, and at least a portion of HSA domain I, or HSA domain II, or HSA domains I and II. Further still, the heterologous protein can be linked to an exposed internal (non-terminus) residue of the HSA portion or a variant thereof. In further embodiments, any combination of the HSA-heterologous protein configurations can be employed, thereby resulting in an HSA:heterologous protein ratio that is greater than 1:1 (e.g., two HSA molecules to one heterologous protein).

The HSA portion and the heterologous protein may be conjugated directly to each other. Alternatively, they may be linked to each other via a linker sequence, which separates the HSA portion and the heterologous protein by a distance sufficient to ensure that each domain properly folds into its secondary and tertiary structures. In certain embodiments, the linker is a cleavable linker. Preferred linkers (1) should adopt a flexible extended conformation, (2) should not exhibit a propensity for developing an ordered secondary structure which could interact with the functional domains of the HSA polypeptide or the heterologous protein, and (3) should have minimal hydrophobic or charged character, which could promote interaction with the functional protein domains.

In certain embodiments, the linker length is at least 80 angstroms (Å), or at least 100 Å, or at least 120 Å, or at least 140 Å, or at least 160 Å, or at least 180 Å, or at least 200 Å. In certain embodiments, the linker length is between about 80 Å to about 200 Å, or between about 100 Å to about 180 Å, or between about 120 Å to about 160 Å.

In certain embodiments, the linker is a peptide linker. In certain embodiments, the linker is a peptide linker and the peptide linker has one or more of the following characteristics: a) it allows for the rotation of the heterologous protein sequence and the HSA portion relative to each other; b) it is resistant to digestion by proteases; and c) it does not interact with the of the heterologous protein sequence or the HSA portion. Typical surface amino acids in flexible protein regions include Gly, Asn and Ser. Permutations of amino acid sequences containing Gly, Asn and Ser would be expected to satisfy the above criteria for a linker sequence. Other near neutral amino acids, such as Thr and Ala, can also be used in the linker sequence. In certain embodiments, each of the amino acids in the peptide linker is selected from the group consisting of Gly, Ser, Asn, Thr and Ala. In certain embodiments the peptide linker includes a Gly-Ser element. In a specific embodiments, the peptide linker comprises one or more Gly-Gly-Gly-Gly-Ser repeats. In specific embodiments, the linker includes 1, 2, 3, 4, 5, 6 or 7 Gly-Gly-Gly-Gly-Ser repeats. In a specific embodiment, a linker sequence length of about 20 amino acids can be used to provide a suitable separation of functional protein domains, although longer or shorter linker sequences may also be used. The length of the linker sequence separating the HSA polypeptide and the heterologous protein can be from 5 to 500 amino acids in length, or more preferably from 5 to 100 amino acids in length. In some embodiments, the linker sequence is from about 5-60 or from about 5-30 amino acids in length. In certain embodiments, the linker sequence is from about 5 to about 20 amino acids, and is advantageously from about 10 to about 30 amino acids. In other embodiments, the linker joining the HSA portion to a heterologous protein can be a constant domain of an antibody (e.g., all or a portion of an Fc region of an antibody). In certain embodiments, the linker is a cleavable linker.

In certain embodiments, the chimeric polypeptides of the present invention can be generated using well-known cross-linking reagents and protocols. For example, there are a large number of chemical cross-linking agents that are known to those skilled in the art and useful for cross-linking the HSA polypeptide with a heterologous protein (e.g., an antibody). For example, the cross-linking agents are heterobifunctional cross-linkers, which can be used to link molecules in a step-wise manner. Heterobifunctional cross-linkers provide the ability to design more specific coupling methods for conjugating proteins, thereby reducing the occurrences of unwanted side reactions such as homo-protein polymers. A wide variety of heterobifunctional cross-linkers are known in the art, including succinimidyl 4-(N-maleimidomethyl)cyclohexane-1-carboxylate (SMCC), m-Maleimidobenzoyl-N-hydroxysuccinimide ester (MBS); N-succinimidyl (4-iodoacetyl) aminobenzoate (SIAB), succinimidyl 4-(p-maleimidophenyl)butyrate (SMPB), 1-ethyl-3-(3-dimethylaminopropyl)carbodiimide hydrochloride (EDC); 4-succinimidyloxycarbonyl-a-methyl-a-(2-pyridyldithio)-toluene (SMPT), N-succinimidyl 3-(2-pyridyldithio)propionate (SPDP), succinimidyl 6-[3-(2-pyridyldithio)propionate]hexanoate (LC-SPDP). Those cross-linking agents having N-hydroxysuccinimide moieties can be obtained as the N-hydroxysulfosuccinimide analogs, which generally have greater water solubility. In addition, those cross-linking agents having disulfide bridges within the linking chain can be synthesized instead as the alkyl derivatives so as to reduce the amount of linker cleavage in vivo. In addition to the heterobifunctional cross-linkers, there exists a number of other cross-linking agents including homobifunctional and photoreactive cross-linkers. Disuccinimidyl subcrate (DSS), bismaleimidohexane (BMH) and dimethylpimelimidate.2HCl (DMP) are examples of useful homobifunctional cross-linking agents, and bis-[B-(4-azidosalicylamido)ethyl]disulfide (BASED) and N-succinimidyl-6(4'-azido-2'-nitrophenylamino)hexanoate (SANPAH) are examples of useful photoreactive cross-linkers for use in this invention. For a recent review of protein coupling techniques, see Means et al. (1990) Bioconjugate Chemistry. 1:2-12, incorporated by reference herein.

One particularly useful class of heterobifunctional cross-linkers, included above, contain the primary amine reactive group, N-hydroxysuccinimide (NHS), or its water soluble analog N-hydroxysulfosuccinimide (sulfo-NHS). Primary amines (lysine epsilon groups) at alkaline pH's are unprotonated and react by nucleophilic attack on NHS or sulfo-NHS esters. This reaction results in the formation of an amide bond, and release of NHS or sulfo-NHS as a by-product. Another reactive group useful as part of a heterobifunctional cross-linker is a thiol reactive group. Common thiol reactive groups include maleimides, halogens, and pyridyl disulfides. Maleimides react specifically with free sulfhydryls (cysteine residues) in minutes, under slightly acidic to neutral (pH 6.5-7.5) conditions. Halogens (iodoacetyl functions) react with —SH groups at physiological pH's. Both of these reactive groups result in the formation of stable thioether bonds. The third component of the heterobifunctional cross-linker is the spacer arm or bridge. The bridge is the structure that connects the two reactive ends. The most apparent attribute of the bridge is its effect on steric hindrance. In some instances, a longer bridge can more easily span the distance necessary to link two complex biomolecules.

Preparing protein-conjugates using heterobifunctional reagents is a two-step process involving the amine reaction and the sulfhydryl reaction. For the first step, the amine reaction, the protein chosen should contain a primary amine. This can be lysine epsilon amines or a primary alpha amine found at the N-terminus of most proteins. The protein should not contain free sulfhydryl groups. In cases where both proteins to be conjugated contain free sulfhydryl groups, one protein can be modified so that all sulfhydryls are blocked using for instance, N-ethylmaleimide (see Partis et al. (1983) J. Pro. Chem. 2:263, incorporated by reference herein). Ellman's Reagent can be used to calculate the quantity of sulfhydryls in a particular protein (see for example Ellman et al. (1958) Arch. Biochem. Biophys. 74:443 and Riddles et al. (1979) Anal. Biochem. 94:75, incorporated by reference herein).

In certain embodiments, chimeric polypeptides of the invention can be produced by using standard protein chemistry techniques such as those described in Bodansky, M. Principles of Peptide Synthesis, Springer Verlag, Berlin (1993) and Grant G. A. (ed.), Synthetic Peptides: A User's Guide, W. H. Freeman and Company, New York (1992). In addition, automated peptide synthesizers are commercially available (e.g., Advanced ChemTech Model 396; Milligen/Biosearch 9600). In any of the foregoing methods of cross-linking for chemical conjugation of HSA to a heterologous protein, a cleavable domain or cleavable linker can be used. Cleavage will allow separation of the heterologous protein and the HSA polypeptide. For example, following penetration of a cell by a chimeric polypeptide, cleavage of the cleavable linker would allow separation of HSA from the heterologous protein.

In certain embodiments, the chimeric polypeptides of the present invention can be generated as a fusion protein containing an HSA portion and a heterologous protein (e.g., an antibody or a therapeutic peptide), expressed as one contiguous polypeptide chain. Such chimeric polypeptides are referred to herein as recombinantly conjugated. In preparing such fusion proteins, a fusion gene is constructed comprising nucleic acids which encode an HSA portion and a heterologous protein, and optionally, a peptide linker sequence to span the HSA portion and the heterologous protein. The use of recombinant DNA techniques to create a fusion gene, with the translational product being the desired fusion protein, is well known in the art. Both the coding sequence of a gene and its regulatory regions can be redesigned to change the functional properties of the protein product, the amount of protein made, or the cell type in which the protein is produced. The coding sequence of a gene can be extensively altered—for example, by fusing part of it to the coding sequence of a different gene to produce a novel hybrid gene that encodes a fusion protein. Examples of methods for producing fusion proteins are described in PCT applications PCT/US87/02968, PCT/US89/03587 and PCT/US90/07335, as well as Traunecker et al. (1989) Nature 339:68, incorporated by reference herein. Essentially, the joining of various DNA fragments coding for different polypeptide sequences is performed in accordance with conventional techniques, employing blunt-ended or stagger-ended termini for ligation, restriction enzyme digestion to provide for appropriate termini, filling in of cohesive ends as appropriate, alkaline phosphatase treatment to avoid undesirable joining, and enzymatic ligation. Alternatively, the fusion gene can be synthesized by conventional techniques including automated DNA synthesizers. In another method, PCR amplification of gene fragments can be carried out using anchor primers which give rise to complementary overhangs between two consecutive gene fragments which can subsequently be annealed to generate a chimeric gene sequence (see, for example, Current Protocols in Molecular Biology, Eds. Ausubel et al. John Wiley & Sons: 1992). The chimeric polypeptides encoded by the fusion gene may be recombinantly produced using various expression systems as is well known in the art (also see below).

Recombinantly conjugated chimeric polypeptides include embodiments in which the HSA portion is conjugated to the N-terminus or C-terminus of the heterologous protein.

In some embodiments, the immunogenicity of the chimeric polypeptide may be reduced by identifying a candidate T-cell epitope within a junction region spanning the chimeric polypeptide and changing an amino acid within the junction region as described in U.S. Patent Publication No. 2003/0166877.

The term chimeric protein will be used to refer to proteins comprising an HSA portion (such as an HSA variant polypeptide) and a heterologous protein, regardless of how these portions are interconnected (e.g., chemically conjugated, recombinantly conjugated). As such, the terms chimeric protein, fusion protein, and conjugated protein will be used interchangeably.

Exemplary categories of heterologous proteins include, but are not limited to, enzymes, growth factors, and cytokines. In certain embodiments, the heterologous protein is an antibody.

Heterologous proteins for use in a chimeric polypeptide comprising an HSA portion may be a therapeutic protein, or fragments thereof, such as growth factors, enzymes, bone morphogenetic proteins and soluble receptor fragments.

Exemplary heterologous polypeptides include growth factors, such as hepatocyte growth factor (HGF), nerve growth factors (NGF), epidermal growth factors (EGF; a member of the EGF family of growth factors), fibroblast growth factors (FGF; a member of the FGF family of growth factors), transforming growth factors (e.g., TGF-alpha, TGF-beta, TGF-beta2, TGF-beta3), vascular endothelial growth factors (VEGF; e.g., VEGF-2), interferons (e.g., INF-alpha, INF-beta), interleukins (e.g., IL-1, IL-2), cytokines, and insulin. Other exemplary heterologous proteins include enzymes. Other exemplary heterologous polypeptides include bone morphogenetic proteins (BMP; a member of the BMP family of proteins), erythropoietins (EPO), myostatin, and tumor necrosis factors (e.g., TNF-α). Other exemplary heterologous polypeptides include extracellular domains of transmembrane receptors, including any naturally occurring extracellular domain of a cellular receptor as well as any variants thereof (including mutants, fragments and peptidomimetic forms).

Heterologous proteins for use in a chimeric polypeptide comprising an HSA portion may be a therapeutic protein, or fragments thereof, including an antibody or antigen binding portion thereof. Exemplary antibodies and antibody fragments include, but are not limited to, Humira®, Remicade®, Simponi®, Rituxan®, Herceptin®, Avastin®, Erbitux®; Synagis®, Mylotarg®, Campath®, TheraCIM®, Vectibix®, Tysabri®, ReoPro®, Lucentis®, Cimzia®, and the like.

6.6 HSA-Related Nucleic Acids and Expression

In certain aspects, the disclosure provides a nucleic acid construct comprising a nucleotide sequence that encodes any of the polypeptides (e.g., HSA variants and chimeric polypeptides with an HSA portion) of the disclosure. Further, the present invention makes use of such nucleic acids for producing a chimeric polypeptide or HSA variant polypeptide (e.g., HSA portion—including bioactive fragments, variants, and fusions thereof). In certain specific embodiments, the nucleic acids may further comprise DNA which encodes a heterologous protein (e.g., an antibody or a therapeutic peptide) for making a recombinant chimeric protein of the invention. All these nucleic acids are collectively referred to as HSA nucleic acids.

In certain aspects, the disclosure provides a nucleic acid construct, comprising (i) a nucleotide sequence that encodes a human serum albumin (HSA) portion, which HSA portion comprises HSA domain III, or an FcRn binding fragment thereof, which HSA domain III comprises one to eighteen amino acid substitutions, operably linked to (ii) a nucleotide sequence that encodes a heterologous protein, wherein the nucleic acid construct encodes a chimeric polypeptide that retains a functional activity of the heterologous protein and can bind to an FcRn, and wherein said chimeric polypeptide has an increased serum half-life and/or affinity for FcRn relative to a control chimeric polypeptide in which the HSA portion does not include said amino acid substitutions.

In certain embodiments, the chimeric polypeptide encoded by the nucleic acid construct binds to FcRn with a higher affinity then said control chimeric polypeptide. In certain embodiments, the chimeric polypeptide encoded by the nucleic acid construct has an increased serum half-life relative to said control chimeric polypeptide. In certain embodiments, the chimeric polypeptide encoded by the nucleic acid construct has both of these properties.

In certain embodiments, (i) comprises a nucleotide sequence that encodes a human serum albumin (HSA) portion, which HSA portion comprises HSA domain III, or an FcRn binding fragment thereof, which HSA domain III comprises one to eighteen (1, 2, 3, 4, 5, 6, 7, 8, 9, 10, 11, 12, 13, 14, 15, 16, 17, or 18) amino acid substitutions.

In certain embodiments, at least one of said amino acid substitutions in HSA domain III encoded by the nucleic acid construct is of a residue that is conserved across multiple species. In certain embodiments, all of said amino acid substitutions in HSA domain III are of residues that are conserved across multiple species. In certain embodiments, at least one of said amino acid substitutions in HSA domain III is of a residue that is conserved among serum albumin proteins from human, pig, rat, mouse, dog, rabbit, cow, chicken, donkey, Mongolian gerbil, sheep, cat, and horse. In certain embodiments, all of said amino acid substitutions in HSA domain III are of residues that are conserved among serum albumin proteins from human, pig, rat, mouse, dog, rabbit, cow, chicken, donkey, Mongolian gerbil, sheep, cat, and horse. In certain embodiments, at least one of said amino acid substitutions in HSA domain III is of a surface accessible residue. In certain embodiments, all of said amino acid substitutions in HSA domain III are of surface accessible residues. In certain embodiments, at least one of said amino acid substitutions in HSA domain III is of a residue that is both surface accessible and conserved across multiple species. In certain embodiments, all of said amino acid substitutions in HSA domain III are of residues that are both surface accessible and conserved across multiple species.

In certain embodiments, (i) comprises a nucleotide sequence that encodes an HSA domain III at least 90% identical to SEQ ID NO: 1. In certain embodiments, (i) comprises a nucleotide sequence that encodes an HSA domain III at least 95% identical to SEQ ID NO: 1. In certain embodiments, (i) comprises a nucleotide sequence that encodes an HSA domain III at least 98% identical to SEQ ID NO: 1.

In certain embodiments, at least one of said amino acid substitutions is in loop 2 of HSA domain III. In certain embodiments, at least one of said amino acid substitutions is in loop 3 of HSA domain III. In certain embodiments, at least one of said amino acid substitutions is in loop 6 of HSA domain III. In certain embodiments, at least one of said amino acid substitutions is in helix 7 of HSA domain III. In certain embodiments, at least one of said amino acid substitutions is in loop 7 of HSA domain III. In certain embodiments, at least one of said amino acid substitutions is in helix 8 of HSA domain III. In certain embodiments, at least one of said amino acid substitutions is in loop 8 of HSA domain III. In certain embodiments, at least one of said amino acid substitutions is in loop 9 of HSA domain III.

In certain embodiments, (ii) comprises a nucleotide sequence that encodes a heterologous protein, which heterologous protein comprises an antibody or an antigen-binding fragment thereof. In certain embodiments, (ii) comprises a nucleotide sequence that encodes a heterologous protein, which heterologous protein comprises a therapeutic protein.

In certain embodiments, the nucleotide sequence further encodes a constant region of an IgG immunoglobulin.

In certain embodiments, (ii) comprises a nucleotide sequence that encodes a heterologous protein, which heterologous protein comprises a growth factor or a cytokine. In certain embodiments, the nucleic acid construct further comprises a nucleotide sequence that encodes a linker.

The nucleic acids may be single-stranded or double-stranded, DNA or RNA molecules. In certain embodiments, the disclosure relates to isolated or recombinant nucleic acid sequences that encode an HSA portion that is at least 80%, 85%, 90%, 95%, 97%, 98%, 99% or 100% identical to the same region of an HSA sequence (e.g., SEQ ID NOs: 1 and 2).

In further embodiments, the HSA nucleic acid sequences can be isolated, recombinant, and/or fused with a heterologous nucleotide sequence, or in a DNA library.

In certain embodiments, HSA nucleic acids also include nucleotide sequences that hybridize under highly stringent conditions to any of the above-mentioned native HSA nucleotide sequence, or complement sequences thereof. One of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the invention provides nucleic acids which hybridize under low stringency conditions of 6×SSC at room temperature followed by a wash at 2×SSC at room temperature.

Isolated nucleic acids which differ from the native HSA nucleic acids due to degeneracy in the genetic code are also within the scope of the invention. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this invention.

In certain embodiments, the recombinant HSA nucleic acids may be operably linked to one or more regulatory nucleotide sequences in an expression construct. Regulatory nucleotide sequences will generally be appropriate for a host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the invention. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used. In certain aspects, this invention relates to an expression vector comprising a nucleotide sequence encoding an HSA polypeptide and operably linked to at least one regulatory sequence. Regulatory sequences are art-recognized and are selected to direct expression of the encoded polypeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, Calif. (1990). It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

This invention also pertains to a host cell transfected with a recombinant gene which encodes an HSA polypeptide or a chimeric polypeptide of the invention. The host cell may be any prokaryotic or eukaryotic cell. For example, an HSA polypeptide or a chimeric polypeptide may be expressed in bacterial cells such as *E. coli*, insect cells (e.g., using a baculovirus expression system), yeast, or mammalian cells. Other suitable host cells are known to those skilled in the art.

The present invention further pertains to methods of producing an HSA polypeptide, a heterologous protein, and/or a chimeric polypeptide of the invention. For example, a host cell transfected with an expression vector encoding an HSA polypeptide or a chimeric polypeptide can be cultured under appropriate conditions to allow expression of the polypeptide to occur. The polypeptide may be secreted and isolated from a mixture of cells and medium containing the polypeptides. Alternatively, the polypeptides may be retained in the cytoplasm or in a membrane fraction and the cells harvested, lysed and the protein isolated. A cell culture includes host cells, media and other byproducts. Suitable media for cell culture are well known in the art. The polypeptides can be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of the polypeptides (e.g., an HSA polypeptide). In a preferred embodiment, the polypeptide is a fusion protein containing a domain which facilitates its purification.

A recombinant HSA nucleic acid can be produced by ligating the cloned gene, or a portion thereof, into a vector suitable for expression in either prokaryotic cells, eukaryotic cells (yeast, avian, insect or mammalian), or both. Expression vehicles for production of a recombinant polypeptide include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as *E. coli*. The preferred mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual,* 2nd Ed., ed. by Sambrook, Fritsch and Maniatis (Cold Spring Harbor Laboratory Press, 1989) Chapters 16 and 17. In some instances, it may be desirable to express the recombinant polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the —-gal containing pBlueBac III).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology,* eds. Ausubel et al., John Wiley & Sons: 1992).

6.7 Methods of Treatment

In certain embodiments, the present disclosure provides methods of treating conditions treatable using the heterologous protein of the chimeric fusions of the disclosure. In certain embodiments, the present disclosure provides methods of increasing serum half-life and/or increasing the binding affinity to FcRn of a protein in a subject comprising conjugating to said protein an HSA portion, which HSA portion comprises domain III, or a neonatal Fc receptor (FcRn) binding fragment thereof. In certain embodiments the HSA domain III comprises one to eighteen amino acid substitutions to increase one or both of affinity for FcRn and serum half-life of the relative chimeric polypeptide relative to a control polypeptide resulting. These methods involve administering to an individual in need thereof a therapeutically effective amount of a chimeric or HSA variant polypeptide as described above. In certain embodiments, the method comprises administering a chimeric polypeptide comprising (a) an HSA portion or bioactive fragment thereof and (b) a heterologous protein. These methods are particularly aimed at therapeutic and prophylactic treatments of animals, and more particularly, humans.

Note that the particular diseases and conditions that can be treated depend on the heterologous protein portion of the chimeric protein. Further, the disclosure contemplates that chimeric polypeptides that include a heterologous protein appropriate for treating a particular disease or condition can be administered as part of a therapeutic regimen along with one or more other compounds or other therapeutic modalities appropriate to treat a particular disease or condition. Further, the disclosure contemplates that the chimeric polypeptide is administered is a manner consistent with medically appropriate treatment given the patient's age, weight, health, severity of illness, etc.

By way of example, if the heterologous protein is Humira, the chimeric polypeptide may be used in, for example, the treatment of rheumatoid arthritis, psoriasis, juvenile arthritis, and Crohn's disease. If the heterologous protein is insulin, the chimeric polypeptide may be used in, for example, the treatment of insulin.

The terms "treatment", "treating", and the like are used herein to generally mean obtaining a desired pharmacologic and/or physiologic effect. The effect may be prophylactic in terms of completely or partially preventing a disease, condition, or symptoms thereof, and/or may be therapeutic in terms of a partial or complete cure for a disease or condition and/or adverse effect attributable to the disease or condition. "Treatment" as used herein covers any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition (e.g., arresting its development); or (c) relieving the disease or condition (e.g., causing regression of the disease or condition, providing improvement in one or more symptoms). Improvements in any conditions can be readily assessed according to standard methods and techniques known in the art. The population of subjects treated by the method of the disease includes subjects suffering from the undesirable condition or disease, as well as subjects at risk for development of the condition or disease.

By the term "therapeutically effective dose" or "effective amount" is meant a dose that produces the desired effect for which it is administered. The exact dose will depend on the purpose of the treatment, and will be ascertainable by one skilled in the art using known techniques (see, e.g., Lloyd (1999) The Art, Science and Technology of Pharmaceutical Compounding).

In certain embodiments, one or more chimeric or HSA variant polypeptides of the present invention can be administered, together (simultaneously) or at different times (sequentially). In addition, chimeric or HSA variant polypeptides of the present invention can be administered in combination with one or more additional compounds or therapies for treating the same disease or symptom. For example, one or more chimeric or HSA variant polypeptides can be co-administered in conjunction with one or more therapeutic compounds. The combination therapy may encompass simultaneous or alternating administration. In addition, the combination may encompass acute or chronic administration. Optionally, the chimeric or HSA variant polypeptide of the present invention and additional compounds act in an additive or synergistic manner for treating the disease or symptom. Additional compounds to be used in combination therapies include, but are not limited to, small molecules, polypeptides, antibodies, antisense oligonucleotides, and siRNA molecules. Further, combination therapy also includes the methods disclosed herein together with other non-medicament therapies. Depending on the nature of the combinatory therapy, administration of the chimeric or HSA variant polypeptides of the invention may be continued while the other therapy is being administered and/or thereafter. Administration of the chimeric or HSA variant polypeptides may be made in a single dose, or in multiple doses. In some instances, administration of the chimeric or HSA variant polypeptides is commenced at least several days prior to the other therapy, while in other instances, administration is begun either immediately before or at the time of the administration of the other therapy.

6.8 Methods of Administration

In certain embodiments, administering to said subject comprises administering the HSA variant or the chimeric polypeptide systemically. In certain embodiments, administering to said subject comprises administering the HSA variant or the chimeric polypeptide orally. In certain embodiments, administering to said subject comprises administering said HSA variant or the chimeric polypeptide intravenously.

In certain aspects, the disclosure provides a composition comprising the HSA variant or the chimeric polypeptide of the disclosure, and a pharmaceutically acceptable carrier. In certain embodiments, the composition is a sterile composition. In certain embodiments, the composition is non-pyrogenic.

Various delivery systems are known and can be used to administer the chimeric or HSA variant polypeptides of the disclosure, e.g., encapsulation in liposomes, microparticles, microcapsules, recombinant cells capable of expressing the compound, receptor-mediated endocytosis (see, e.g., Wu and Wu, 1987, J. Biol. Chem. 262:4429-4432). Methods of introduction can be enteral or parenteral, including but not limited to, intradermal, transdermal, intramuscular, intraperitoneal, intravenous, subcutaneous, pulmonary, intranasal, intraocular, epidural, topical and oral routes. In particular embodiments, parenteral introduction includes intramuscular, subcutaneous, intravenous, intravascular, and intrapericardial administration.

The chimeric or HSA variant polypeptides may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local. Pulmonary administration can also be employed, e.g., by use of an inhaler or nebulizer, and formulation with an aerosolizing agent.

In certain embodiments, it may be desirable to administer the chimeric or HSA variant polypeptides of the invention locally to the area in need of treatment (e.g., muscle); this may be achieved, for example, and not by way of limitation, by local infusion during surgery, topical application, e.g., by injection, by means of a catheter, or by means of an implant, the implant being of a porous, non-porous, or gelatinous material, including membranes, such as sialastic membranes, fibers, or commercial skin substitutes.

In other embodiments, the chimeric or HSA variant polypeptides of the disclosure can be delivered in a vesicle, in particular, a liposome (see Langer, 1990, Science 249:1527-1533). In yet another embodiment, the chimeric or HSA variant polypeptides of the disclosure can be delivered in a controlled release system. In another embodiment, a pump may be used (see Langer, 1990, supra). In another embodiment, polymeric materials can be used (see Howard et al., 1989, J. Neurosurg. 71:105). In certain specific embodiments, the chimeric or variant polypeptides of the disclosure can be delivered intravenously.

In certain embodiments, the chimeric or HSA variant polypeptides are administered by intravenous infusion. In certain embodiments, the chimeric or HSA variant polypeptides are infused over a period of at least 10, at least 15, at least 20, or at least 30 minutes. In other embodiments, the chimeric or HSA variant polypeptides are infused over a period of at least 60, 90, or 120 minutes. Regardless of the infusion period, the disclosure contemplates that each infusion is part of an overall treatment plan where chimeric or HSA variant polypeptide is administered according to a regular schedule (e.g., weekly, monthly, etc.).

6.9 Methods of Evaluating

The chimeric polypeptides of the disclosure are characterized based on (i) substantially retaining a function of the heterologous protein and (ii) having increased affinity for FcRn and/or increased serum half-life relative to a chimeric polypeptide conjugated to a non-modified HSA portion or relative to another appropriate control. The HSA variant polypeptides of the disclosure are characterized based on having increased affinity for FcRn and/or increased serum half-life relative to a native HSA portion or relative to another appropriate control. The properties of a chimeric polypeptide or HSA variant polypeptide may be evaluated in any one or more suitable assays, in vitro or in vivo.

By way of example, affinity (Ka and/or Kd) for FcRn may be evaluated in vitro using, for example, any one or more of the assays described in the examples or other binding assays. Similarly, $k_{off}$ and/or $k_{on}$ may be evaluated in vitro using, for example, any one or more of the assays described in the examples or other binding assays.

Measurement of the affinity constant and specificity of binding between antigen and antibody is a pivotal element in determining the efficacy of therapeutic, diagnostic and research methods using the anti-HSA antibodies. "Binding affinity" generally refers to the strength of the sum total of the noncovalent interactions between a single binding site of a molecule (e.g., an antibody, an HSA portion) and its binding partner (e.g., an antigen, an FcRn). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the equilibrium dissociation constant (Kd or $K_D$), which is calculated as the ratio $k_{off}/k_{on}$. See, e.g., Chen, Y., et al., (1999) J. Mol. Biol 293:865-881. Affinity can be measured by common methods known in the art, including those described and exemplified herein, such as BIAcore. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention.

In certain embodiments, the chimeric polypeptide or variant HSA polypeptide has an affinity for FcRn that is improved by approximately 1.5, 2, 2.5, 3, 4, or approximately 5 fold relative to that of the control. In certain embodiments, the chimeric polypeptide has an affinity that is improved by greater than 5, or event greater than 10 fold relative to that of the control. In certain embodiments, the chimeric polypeptide or HSA variant polypeptide has an affinity that is improved by greater than 20, 25, 40, or greater than 50 fold relative to that of the control. In certain embodiments, the chimeric polypeptide or HSA variant polypeptide has an affinity that is improved by approximately 5-10 fold, approximately 10-20 fold, approximately 25-40 fold, approximately 40-50 fold, approximately 50-75, or approximately 75-100 fold relative to that of the control. When affinity is evaluated by calculating Ka, these improvements of affinity translate to an increase in Ka (e.g., 2 fold, 5 fold, 10, fold, etc, as outlined above). When affinity is evaluated by calculating Kd, these improvements of affinity translate to a decrease in Kd (e.g., 2 fold, 5 fold, 10, fold, etc, as outlined above).

In certain embodiments, the affinity for FcRn at low pH (e.g., pH ~5.5) is improved. In certain other embodiments, the affinity for FcRn at low pH is improved and the affinity at neutral pH (e.g., pH ~7.2) is unchanged.

By way of further example, serum half-life may be measured in a human or animal model. An increase in serum half-life in any animal model (including, but not limited to, a transgenic animal having a human FcRn) is sufficient to characterize a chimeric or HSA variant polypeptide as having an increase in serum half-life relative to a control.

In one embodiment, the chimeric polypeptide or HSA variant polypeptide has a half-life in the blood no less than 10 days, preferably no less than about 14 days, and most preferably no less than 50% of the half-life of the native serum albumin protein or homolog thereof. In another embodiment, the half-life of the chimeric polypeptide or HSA variant polypeptide is increased by approximately 1.5, 2, 2.5, 3, 4, or approximately 5 fold relative to that of the control polypeptide. In certain embodiments, the half-life of the chimeric polypeptide or HSA variant polypeptide is increased by greater than 5, or event greater than 10 fold relative to that of the control polypeptide. In certain embodiments, the half-life of the chimeric polypeptide or HSA variant polypeptide is increased by greater than 20, 25, 40, or greater than 50 fold relative to that of the control polypeptide. In certain embodiments, the half-life of the chimeric polypeptide or HSA variant polypeptide is increased by approximately 5-10 fold, approximately 10-20 fold, approximately 25-40 fold, approximately 40-50 fold, approximately 50-75, or approximately 75-100 fold relative to that of the control polypeptide.

Suitable assays for evaluating whether a chimeric polypeptide substantially retains a function of the heterologous protein will depend on the heterologous protein and its native function. However, function may be evaluated in any appropriate in vitro or in vivo assay, including in animal models. Exemplary functions include, but are not limited to, (i) the ability to bind to a particular receptor; (ii) the ability to induce or inhibit signaling via a particular signal transduction pathway; (iii) the ability to induce or inhibit apoptosis; (iv) the ability to induce or inhibit angiogenesis; (v) the ability to stimulate or inhibit cell proliferation; (vi) the ability to promote or inhibit cell differentiation; (vii) the ability to promote cell survival; and (viii) the ability to promote or inhibit secretion of a another protein factor.

In certain embodiments, a chimeric polypeptide of the present disclosure comprising a biologically active heterologous protein is more potent than the biologically active heterologous protein itself, e.g., not fused to a HSA portion. For example, a chimeric polypeptide may be 2 times, 4 times, 5 times, 10 times, 25 times, 50 times, 100 times, or even 1000 times more active than the biologically active protein sequence alone, e.g., 1, 2, or even 3 orders of magnitude more active. Thus, in embodiments wherein the biologically active peptide sequence inhibits a biological activity, the $IC_{50}$ of the chimeric polypeptide may be 10 times lower, 100 times lower, or even 1000 times lower than the $IC_{50}$ of the biologically active protein alone, and in embodiments wherein the biologically active protein sequence induces or promotes a biological activity, the $EC_{50}$ of the chimeric polypeptide may be 10 times lower, 100 times lower, or even 1000 times lower than the $EC_{50}$ of the biologically active peptide alone. In embodiments wherein the biologically active protein sequence binds to a biological molecule, such as a nucleic acid, peptide, or carbohydrate, the dissociation constant $K_d$ of the chimeric polypeptide and the biological molecule to which it binds may be 10 times lower, 100 times lower, or even 1000 times lower than the $K_d$ of the biological molecule and the biologically active protein alone, e.g., binding of the two entities is increasingly favored over their dissociation.

6.10 Pharmaceutical Compositions

In certain embodiments, the subject chimeric or HSA variant polypeptides of the present disclosure are formulated with a pharmaceutically acceptable carrier. One or more chimeric or HSA variant polypeptides can be administered alone or as a component of a pharmaceutical formulation (composition). The chimeric or HSA variant polypeptides may be formulated for administration in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the subject chimeric or HSA variant polypeptides include those suitable for oral, nasal, topical, parenteral, rectal, and/or intravaginal administration. The formulations may conveniently be presented in unit dosage form and may be prepared by any methods well known in the art of pharmacy. The amount of active ingredient which can be combined with a carrier material to produce a single dosage form will vary depending upon the host being treated and the particular mode of administration. The amount of active ingredient which can be combined with a carrier material to produce a single dosage form will generally be that amount of the compound which produces a therapeutic effect.

In certain embodiments, methods of preparing these formulations or compositions include combining another type of therapeutic agents and a carrier and, optionally, one or more accessory ingredients. In general, the formulations can be prepared with a liquid carrier, or a finely divided solid carrier, or both, and then, if necessary, shaping the product.

Formulations for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a subject polypeptide therapeutic agent as an active ingredient. Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

In solid dosage forms for oral administration (capsules, tablets, pills, dragees, powders, granules, and the like), one or more polypeptide therapeutic agents of the present invention may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like. Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Pharmaceutical compositions suitable for parenteral administration may comprise one or more chimeric or HSA variant polypeptides in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

In certain embodiments, compositions of the disclosure, including pharmaceutical compositions, are non-pyrogenic. In other words, in certain embodiments, the compositions are substantially pyrogen free. In one embodiment the formulations of the invention are pyrogen-free formulations which are substantially free of endotoxins and/or related pyrogenic substances. Endotoxins include toxins that are confined inside a microorganism and are released only when the microorganisms are broken down or die. Pyrogenic substances also include fever-inducing, thermostable substances (glycoproteins) from the outer membrane of bacteria and other microorganisms. Both of these substances can cause fever, hypotension and shock if administered to humans. Due to the potential harmful effects, even low amounts of endotoxins must be removed from intravenously administered pharmaceutical drug solutions. The Food & Drug Administration ("FDA") has set an upper limit of 5 endotoxin units (EU) per dose per kilogram body weight in a single one hour period for intravenous drug applications (The United States Pharmacopeial Convention, Pharmacopeial Forum 26 (1):223 (2000)). When therapeutic proteins are administered in amounts of several hundred or thousand milligrams per kilogram body weight, as can be the case with antibodies, even trace amounts of harmful and dangerous endotoxin must be removed. In certain specific embodiments, the endotoxin and pyrogen levels in the composition are less then 10 EU/mg, or less then 5 EU/mg, or less then 1 EU/mg, or less then 0.1 EU/mg, or less then 0.01 EU/mg, or less then 0.001 EU/mg.

Injectable depot forms are made by forming microencapsule matrices of one or more polypeptide therapeutic agents in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

In certain embodiments, the chimeric or HSA variant polypeptides of the present disclosure are formulated in accordance with routine procedures as a pharmaceutical composition adapted for intravenous administration to human beings. Where necessary, the composition may also include a solubilizing agent and a local anesthetic such as lidocaine to ease pain at the site of the injection. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The amount of the chimeric or HSA variant polypeptides of the disclosure which will be effective in the treatment of a tissue-related condition or disease can be determined by standard clinical techniques. In addition, in vitro assays may optionally be employed to help identify optimal dosage ranges. The precise dose to be employed in the formulation will also depend on the route of administration, and the seriousness of the condition, and should be decided according to the judgment of the practitioner and each subject's circumstances. However, suitable dosage ranges for intravenous administration are generally about 20-5000 micrograms of the active chimeric or HSA variant polypeptide per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

6.11 Articles of Manufacture and Kits

In certain embodiments, the disclosure also provides a pharmaceutical package or kit comprising one or more containers filled with at least one chimeric or HSA variant polypeptide of the disclosure. In a specific embodiment, the formulations of the disclosure comprise chimeric or HSA variant polypeptides recombinantly fused or chemically conjugated to another moiety, including but not limited to, a heterologous protein, a heterologous polypeptide, a heterologous peptide, a large molecule, a small molecule, a marker sequence, a diagnostic or detectable agent, a therapeutic moiety, a drug moiety, a radioactive metal ion, a second antibody, and a solid support. In a specific embodiment, the formulations of the disclosure are formulated in single dose vials as a sterile liquid. The formulations of the disclosure may be supplied in 3 cc USP Type I borosilicate amber vials (West Pharmaceutical Serices—Part No. 6800-0675) with a target volume of 1.2 mL. Exemplary containers include, but are not limited to, vials, bottles, pre-filled syringes, IV bags, blister packs (comprising one or more pills). Optionally associated with such container(s) can be a notice in the form prescribed by a governmental agency regulating the manufacture, use or sale of pharmaceuticals or biological products, which notice reflects approval by the agency of manufacture, use or sale for human diagnosis and/or administration.

In certain embodiments, kits comprising chimeric or HSA variant polypeptides are also provided that are useful for various purposes, e.g., increasing serum half-life or increasing FcRn binding affinity of a therapeutic. For isolation and purification of a reagent, the kit may contain polypeptides coupled to beads (e.g., sepharose beads). Kits may be provided which contain the polypeptides for detection and quantitation of a target in vitro, e.g. in an ELISA or a Western blot. As with the article of manufacture, the kit comprises a container and a label or package insert on or associated with the container. The container holds a composition comprising at least one chimeric or HSA variant polypeptide of the disclosure. Additional containers may be included that contain, e.g., diluents and buffers, control diagnostic reagents. The label or package insert may provide a description of the composition as well as instructions for the intended in vitro or diagnostic use.

6.12 Adenovirus Vectors and Methods

DNA vectors useful for the generation of recombinant adenovirus particles from host cells are well known in the art and commercial reagents are readily available (see for example Catalog Nos. V493-20 and V494-20 from Invitrogen). The instant disclosure provides a method for enhancing the generation of recombinant adenovirus by incorporating an OriP sequence into a DNA vector useful for the generation of adenovirus particles (also referred to here as adenovirus vectors). The OriP containing adenovirus vectors may further comprise sequences for the expression of the EBNA-1 protein or alternatively host cells expressing the EBNA-1 protein are used for the generation of recombinant adenovirus particles. The OriP containing adenovirus vectors are particularly useful for the generation of populations of recombinant adenovirus comprising a diverse/complex library of DNA sequences of interest (e.g., DNA sequences encoding HSA domain III variants).

An OriP sequence can readily be engineered into any known adenovirus vector using numerous techniques know in the art. For example, if a Gateway recombination system is utilized the OriP sequence should be located between the att recombination sites of the entry vector or the adenoviral destination vector. When adding sequences to an adenoviral vector care should be taken to avoid inserting them into a site that would interfere with the replication or assembly of adenoviral DNA. Alternatively, or optionally the adenovirus vector containing the OriP sequence may be engineered to also express the EBNA-1 protein (see FIG. 10). By expressing the EBNA-1 protein directly from the adenovirus vector the host cell does not need to express the EBNA-1 gene.

Adenovirus vectors of the invention comprise an OriP sequence and adenovirus genome sequences. The adenovirus vectors of the invention may further comprise one or more of the following elements:
(i) Recombination site(s) (e.g., attR1 and attR2) for recombination cloning with another vector, such site are useful to effect the cloning of DNA sequences of interest for expression in a recombinant Adenovirus generated from the instant vector;
(ii) Antibiotic/drug (e.g., Chloramphenicol) resistance gene(s) and/or a toxin expressing gene (e.g. ccdB gene) useful for selection and/or counter selection;
(iii) Cloning site (may be a multicloning site) useful for subcloning a DNA sequence of interest;
(iv) DNA of interest which may comprise one or more genes of interest encoding one or more proteins of interest;
(v) Promoter for expression of a gene of interest in a wide range of mammalian cells (e.g., Human Cytomegalovirus (CMV) immediate early promoter), the promoter may be constitutive or may be inducible;
(vi) Epitope tag (e.g., His6X epitope) for detection and/or purification of the protein of interest. The epitope tag may be present at either the 5' or 3' end of the recombinant protein of interest;
(vii) Polyadenylation (polyA) sequence (e.g., a Simian 40 Virus polyA sequence) for efficient transcription termination and polyadenylation of mRNA;
(viii) Origin of replication for high-copy replication and maintenance of the plasmid in E. coli;
(ix) Antibiotic resistance gene for selection in E. coli;
(x) Restriction enzyme site(s) (e.g., PacI) for linearizing the vector, restriction enzyme sites may flank elements (viii) and (ix); and
(xi) DNA sequence encoding EBNA-1 protein.

The Epstein-Barr Viral (EBV) origin of plasmid DNA synthesis, oriP, efficiently supports DNA synthesis in a variety of higher eukaryotic cells. A representative OriP sequence is provided in FIG. 9C. This origin uses only one viral protein, EBNA-1, while all other factors are provided by the cell. In certain embodiments the EBNA-1 protein is provided by the host cell (e.g., 293E cells). In other embodiments, the adenovirus vectors of the invention further comprise element (xi) DNA sequence encoding EBNA-1 protein. Representative EBNA-1 protein and DNA sequences are provided in FIGS. 9A and 9B, respectively.

It is specifically contemplated that the adenovirus genome sequences (e.g., Human adenovirus type 5 sequences will encode genes and other elements (e.g. Left and Right Inverted Terminal Repeats (ITRs), encapsidation signal sequence, late genes) required for proper packaging and production of adenovirus (Hitt et al., 1999, The Development of Human Gene Therapy, T. Friedmann, ed. (Cold Spring Harbor, N.Y.: Cold Spring Harbor Laboratory Press), pp. 61-86; Russell, 2000, J. Gen. Virol. 81, 2573-2604). The adenovirus genome sequences may encode a complete adenoviral genome. Alternatively the adenovirus genome sequences may encode all proteins and other regulatory elements except one or more protein and/or regulatory element, which is provided in trans, to produce replication-incompetent adenovirus. For example the E1 region encoding the E1 proteins (E1a and E1b) may be excluded from the adenovirus vectors of the invention (Russell, 2000, J. Gen. Virol. 81, 2573-2604). The missing proteins and/or other elements will then be provided in trans, generally by the host used to generate adenoviruses, for example 293 cell lines contain a genomic copy of the E1 region. In a specific embodiment the adenovirus genome sequences comprise, or consist essentially of human adenovirus type 5 sequences corresponding to the wild-type sequences 1-458 and 3513-35935.

It will be understood by one of skill in the art that certain elements will be provided in combination and/or may incorporate other elements, for example, element (iv) may incorporate elements (v)-(vii). It will further be understood certain elements will be provided 5' and/or 3' to other elements, for example element (x) may be useful for linearization of the adenovirus vector, element (x), when incorporated for linearization, should be provided 5' to the 5'ITR and/or 3' to the 3'ITR. Similarly, Element (viii) and (ix), when present, are generally located such that they will not be incorporated into rescued adenovirus, for example these elements may be located 5' to the 5'ITR and 3' to the 3'ITR. The OriP and elements (i)-(vii) if present are flanked on one side by an adenovirus genome sequences which include the 3' ITR and by a 5' ITR sequence on the other side (e.g., FIG. 10).

A representative adenovirus vector of the invention incorporating elements (i), (ii), (iv), (viii)-(x) and optionally (xi) is provided in FIG. 10.

7 EMBODIMENTS

1. A chimeric polypeptide comprising: (a) a human serum albumin (HSA) portion, which HSA portion comprises HSA domain III, or a neonatal Fc receptor (FcRn) binding fragment thereof, and (b) a heterologous protein, wherein the chimeric polypeptide retains a functional activity of the heterologous protein and can bind to an FcRn, and wherein said HSA domain III comprises one to eighteen amino acid substitutions to increase one or both of affinity for FcRn and serum half-life of the chimeric polypeptide relative to a control chimeric polypeptide in which the HSA portion does not include said amino acid substitutions.

2. The chimeric polypeptide of embodiment 1, wherein the chimeric polypeptide binds to FcRn with a higher affinity than said control chimeric polypeptide.

3. The chimeric polypeptide of embodiment 1 or 2, wherein the chimeric polypeptide binds to FcRn with a higher affinity than said control chimeric polypeptide, and wherein said affinity is measured at acidic pH.

4. The chimeric polypeptide of embodiment 3, where the acidic pH is between 5.0 and 6.0.

5. The chimeric polypeptide of embodiment 4, wherein the acidic pH is 5.5±0.2.

6. The chimeric polypeptide of any one of embodiments 1-3, wherein the chimeric polypeptide binds to FcRn with a higher affinity than said control chimeric polypeptide at acidic pH, but which chimeric polypeptide does not bind to FcRn with higher affinity than said control chimeric polypeptide at neutral pH.

7. The chimeric polypeptide of embodiment 6, wherein the neutral pH is between 6.9 and 7.9.

8. The chimeric polypeptide of embodiment 7, wherein the neutral pH is 7.4±0.2.

9. The chimeric polypeptide of any of embodiments 1-6, wherein the chimeric polypeptide binds to FcRn and has an off rate or on rate that differs from that of said control chimeric polypeptide.

10. The chimeric polypeptide of embodiment 9, wherein the chimeric polypeptide binds to FcRn and has, relative to said control polypeptide, an increased on rate and/or a decreased off rate.

11. The chimeric polypeptide of embodiment 9, wherein the chimeric polypeptide binds to FcRn and has, relative to said control polypeptide, an increased off rate.

12. The chimeric polypeptide of any of embodiments 1-11, wherein the HSA domain III comprises one to ten amino acid substitutions to increase serum half-life of the chimeric polypeptide relative to a control chimeric polypeptide in which the HSA portion does not include said amino acid substitutions.

13. The chimeric polypeptide of any of embodiments 1-12, wherein at least one of said amino acid substitutions in HSA domain III is of a residue that is conserved across multiple species.

14. The chimeric polypeptide of embodiment 13, wherein all of said amino acid substitutions in HSA domain III are of residues that are conserved across multiple species.

15. The chimeric polypeptide of any of embodiments 1-13, wherein at least one of said amino acid substitutions in HSA domain III is of a residue that is conserved among serum albumin proteins from human, pig, rat, mouse, dog, rabbit, cow, chicken, donkey, Mongolian gerbil, sheep, cat, and horse.

16. The chimeric polypeptide of embodiment 15, wherein all of said amino acid substitutions in HSA domain III are of residues that are conserved among serum albumin proteins from human, pig, rat, mouse, dog, rabbit, cow, chicken, donkey, Mongolian gerbil, sheep, cat, and horse.

17. The chimeric polypeptide of any of embodiments 1-15, wherein at least one of said amino acid substitutions in HSA domain III are selected from those listed in Table 5.

18. The chimeric polypeptide of any of embodiments 1-15, wherein at least one of said amino acid substitutions in HSA domain III are at any of the following positions, numbered relative to the position in full length mature HSA (SEQ ID NO: 2): residue 381, residue 383, residue 391, residue 401, residue 402, residue 407, residue 411, residue 413, residue 414, residue 415, residue 416, residue 424, residue 426, residue 434, residue 442, residue 445, residue 447, residue 450, residue 454, residue 455, residue 456, residue 457, residue 459, residue 463, residue 495, residue 506, residue 508, residue 509, residue 511, residue 512, residue 515, residue 516, residue 517, residue 519, residue 521, residue 523, residue 524, residue 525, residue 526, residue 527, residue 531, residue 535, residue 538, residue 539, residue 541, residue 557, residue 561, residue 566, residue 569.

19. The chimeric polypeptide of any of embodiments 1-15, wherein the chimeric polypeptide comprises amino acid substitutions in HSA domain III at positions, numbered relative to the position in full length mature HSA, selected from the group consisting of: (a) residues 383 and 413; (b) residues 401 and 523; (c) residues 407 and 447; (d) residues 407 and 447 and 539; (e) residues 407 and 509; (f) residues 407 and 526; (g) residues 411 and 535; (h) residues 414 and 456; (i) residues 415 and 569; (j) residues 426 and 526; (k) residues 442 and 450 and 459; (l) residues 463 and 508; (m) residues 508 and 519 and 525; (n) residues 509 and 527; (o) residues 523 and 538; (p) residues 526 and 557; and (q) residues 541 and 561.

20. The chimeric polypeptide of any of embodiments 1-15, or 18, wherein at least one of said amino acid substitutions in HSA domain III are selected from the group consisting of: V381N, V381Q, E383A, E383G, E383I, E383L, E383V, N391A, N391G, N391I, N391L, N391V, Y401D, Y401E, K402A, K402G, K402I, K402L, K402V, L407F, L407N, L407Q, L407W, L407Y, Y411Q, Y411N, K413C, K413S, K413T, K414S, K414T, V415C, V415S, V415T, Q416H, Q416P, V424A, V424G, V424I, V424L, V424N, V424Q, V426D, V426E, V426H, V426P, G434C, G434S, G434T, E442K, E442R, R445F, R445W, R445Y, P447S, P447T, E450D, E450E, S454C, S454M, S454T, V455N, V455Q, V456N, V456Q, L457F, L457W, L457Y, Q459K, Q459R, L463N, L463Q, E495D, T506F, T506W, T506Y, T508K, T508R, T508S, F509C, F509I, F509L, F509M, F509V, F509W, F509Y, A511F, A511W, A511Y, D512F, D512W, D512Y, T515C, T515H, T515N, T515P, T515Q, T515S, L516F, L516S, L516T, L516W, L516Y, S517C, S517F, S517M, S517T, S517W, S517Y, K519A, K519G, K519I, K519L, K519V, R521F, R521W, R521Y, I523A, I523D, I523E, I523F, I523G, I523I, I523K, I523L, I523N, I523Q, I523R, I523V, I523W, I523Y, K524A, K524G, K524I, K524L, K524V, K525A, K525G, K525I, K525L, K525V, Q526C, Q526M, Q526S, Q526T, Q526Y, T527F, T527W, T527Y, E531A, E531G, E531I, E531L, E531V, H535D, H535E, H535P, K538F, K538W, K538Y, A539I, A539L, A539V, K541F, K541W, K541Y, K557A, K557G, K557I, K557L, K557V, A561F, A561W, A561Y, T566F, T566W, T566Y, A569H, and A569P.

21. The chimeric polypeptide of any of embodiments 1-15, 18, or 20, wherein at least one of said amino acid substitutions in HSA domain III are selected from the group consisting of: V381N, E383G, N391V, Y401E, K402A, L407N, L407Y, Y411Q, K414S, K413S, V415T, V415C, Q416P, V424I, V424Q, V426E, V426H, G434C, E442K, R445W, P447S, E450D, S454C, V455N, V456N, L457F, Q459R, L463N, E495D, T506Y, T508R, T508S, F509I, F509M, F509W, A511F, D512Y, T515P, T515Q, T515S, L516T, L516W, S517C, S517W, K519I, R521W, I523D, I523E, I523Q, I523K, I523G, I523R, I523Y, K524L, K524V, K525V, Q526T, Q526M, Q526Y, T527Y, E531I, H535N, H535P, K538Y, A539I, K541F, K557G, A561F, T566W, and A569P.

22. The chimeric polypeptide of any of embodiments 1-15, or 18, wherein the chimeric polypeptide comprises one amino acid substitution in HSA domain III selected from the group consisting of: V381N, E383G, N391V, Y401E, K402A, L407N, L407Y, Y411Q, K414S, K413S, V415T, V415C, Q416P, V424I, V424Q, V426E, V426H, G434C, E442K, R445W, P447S, E450D, S454C, V455N, V456N, L457F, Q459R, L463N, E495D, T506Y, T508R, T508S, F509I, F509M, F509W, A511F, D512Y, T515P, T515Q, T515S, L516T, L516W, S517C, S517W, K519I, R521W, I523D, I523E, I523Q, I523K, I523G, I523R, I523Y, K524L, K524V, K525V, Q526T, Q526M, Q526Y, T527Y, E531I, H535N, H535P, K538Y, A539I, K541F, K557G, A561F, T566W, and A569P.

23. The chimeric polypeptide of embodiment 21, wherein at least one of said amino acid substitutions in HSA domain III are selected from the group consisting of: L407N, L407Y, V415T, V424I, V424Q, V426E, V426H, P447S, V455N, V456N, L463N, E495D, T506Y, T508R, F509M, F509W, A511F, D512Y, T515Q, L516T, L516W, S517W, R521W, I523D, I523E, I523G, I523K, I523R, K524L, Q526M, T527Y, H535P and K557G.

24. The chimeric polypeptide of embodiment 22, wherein the chimeric polypeptide comprises one amino acid substitution in HSA domain III selected from the group consisting of: L407N, L407Y, V415T, V424I, V424Q, V426E, V426H, P447S, V455N, V456N, L463N, E495D, T506Y, T508R, F509M, F509W, A511F, D512Y, T515Q, L516T, L516W, S517W, R521W, I523D, I523E, I523G, I523K, I523R, K524L, Q526M, T527Y, H535P and K557G.

25. The chimeric polypeptide of any of embodiments 1-14, or 18, wherein the chimeric polypeptide comprises amino acid substitutions in HSA domain III selected from the group consisting of: (a) E383G/K413S; (b) Y401E/I523G, (c) L407N/P447S; (d) L407N/P447S/A5391; (e) L407N/F509M; (f) L407Y/Q526T; (g) Y411Q/H535N; (h) K414S/V456N; (i) V415T/A569P; (j) V426H/Q526Y; (k) E442K/E450D/Q459R; (l) L463N/T508R; (m) T508R/K519I/K525V; (n) F509I/T527Y; (o) I523Q/K538Y; (p) Q526M/K557G; and (q) K541F/A561F.

26. The chimeric polypeptide of embodiment 25, wherein the chimeric polypeptide comprises amino acid substitutions in HSA domain III selected from the group consisting of: (a) L407N/P447S; (b) L407N/P447S/A5391; (c) L407N/F509M; (d) Y411Q/H535N; (e) K414S/V456N; (f) V426H/Q526Y; (g) L463N/T508R; (h) F509I/T527Y; (i) I523Q/K538Y; (j) Q526M/K557G; and (k) K541F/A561F.

27. The chimeric polypeptide of any of embodiments 1-15, wherein at least one of said amino acid substitutions in HSA domain III is of a residue that is conserved among serum albumin proteins from human, pig, rat, mouse, dog, rabbit, cow, chicken, donkey, Mongolian gerbil, sheep, cat, and horse, but which is not conserved in chicken serum albumin.

28. The chimeric polypeptide of embodiment 27, wherein all of said amino acid substitutions in HSA domain III are of residues that are conserved among serum albumin proteins from human, pig, rat, mouse, dog, rabbit, cow, chicken, donkey, Mongolian gerbil, sheep, cat, and horse, but which are not conserved in chicken serum albumin.

29. The chimeric polypeptide of embodiment 15, wherein said at least one amino acid substitutions in HSA domain III are at any of the following positions, numbered relative to the position in full length mature HSA (SEQ ID NO: 2): residue 383, residue 389, residue 391, residue 410, residue 417, residue 425, residue 442, residue 465, residue 467, residue 468, residue 486, residue 499, residue 502, residue 520, residue 532, residue 536, residue 543, and residue 571.

30. The chimeric polypeptide of embodiment 29, wherein said at least one amino acid substitutions in HSA domain III are at any of the following positions, numbered relative to the position in full length mature HSA: residue 383, residue 391, residue 434, residue 442, residue 445, and residue 450.

31. The chimeric polypeptide of embodiment 30, wherein at least one of said amino acid substitutions in HSA domain III are selected from the group consisting of: V381N, E383A, E383G, E383I, E383L, E383V, N391A, N391G, N391I, N391L, N391V, G434C, G434S, G434T, E442K, E442R, R445F, R445W, R445Y, E450D, and E450E.

32. The chimeric polypeptide of embodiment 29, wherein said at least one amino acid substitutions in HSA domain III are at any of the following positions, numbered relative to the position in full length mature HSA: residue 417, residue 442, residue 499, and residue 502.

33. The chimeric polypeptide of embodiment 27, wherein said at least one amino acid substitutions in HSA domain III are at any of the following positions, numbered relative to the position in full length mature HSA: residue 380, residue 381, residue 384, residue 387, residue 396, residue 401, residue 404, residue 405, residue 406, residue 409, residue 419, residue 421, residue 422, residue 424, residue 428, residue 430, residue 431, residue 433, residue 441, residue 457, residue 458, residue 463, residue 464, residue 466, residue 469, residue 470, residue 474, residue 475, residue 480, residue 481, residue 489, residue 491, residue 495, residue 500, residue 508, residue 510, residue 515, residue 516, residue 524, residue 525, residue 526, residue 528, residue 531, residue 535, residue 539, residue 544, residue 547, and residue 576.

34. The chimeric polypeptide of embodiment 33, wherein said at least one amino acid substitutions in HSA domain III are at any of the following positions, numbered relative to the position in full length mature HSA: residue 381, residue 401, residue 424, residue 457, residue 463, residue 495, residue 508, residue 515, residue 516, residue 524, residue 525, residue 526, residue 531, residue 535, and residue 539.

35. The chimeric polypeptide of embodiment 34, wherein at least one of said amino acid substitutions in HSA domain III are selected from the group consisting of: V381N, V381Q, Y401D, Y401E, V424N, V424Q, L457F, L457W, L457Y, L463N, L463Q, E495D, T508K, T508R, T508S, T515C, T515H, T515N, T515P, T515Q, T515S, L516F, L516S, L516T, L516W, L516Y, K524A, K524G, K524I, K524L, K524V, K525A, K525G, K525I, K525L, K525V, Q526C, Q526M, Q526S, Q526T, Q526Y, E531A, E531G, E531I, E531L, E531V, H535D, H535E, H535P, A539I, and A539L, A539V.

36. The chimeric polypeptide of embodiment 29, wherein all of said amino acid substitutions are selected from among the members of the group consisting of: residue 383, residue 389, residue 391, residue 410, residue 417, residue 425, residue 442, residue 465, residue 467, residue 468, residue 486, residue 499, residue 502, residue 520, residue 532, residue 536, residue 543, and residue 571.

37. The chimeric polypeptide of embodiment 33, wherein all of said amino acid substitutions are selected from among the members of the group consisting of: residue 380, residue 381, residue 384, residue 387, residue 396, residue 401, residue 404, residue 405, residue 406, residue 409, residue 419, residue 421, residue 422, residue 424, residue 428, residue 430, residue 431, residue 433, residue 441, residue 457, residue 458, residue 463, residue 464, residue 466, residue 469, residue 470, residue 474, residue 475, residue 480, residue 481, residue 489, residue 491, residue 495, residue 500, residue 508, residue 510, residue 515, residue 516, residue 524, residue 525, residue 526, residue 528, residue 531, residue 535, residue 539, residue 544, residue 547, and residue 576.

38. The chimeric polypeptide of embodiment 29 or 33, wherein all of said amino acid substitutions are selected from among the members of the group consisting of: residue 380, residue 381, residue 384, residue 383, residue 387, residue 389, residue 391, residue 396, residue 401, residue 404, residue 405, residue 406, residue 409, residue 410, residue 417, residue 419, residue 421, residue 422, residue 424, residue 425, residue 428, residue 430, residue 431, residue 433, residue 441, residue 442, residue 457, residue 458, residue 463, residue 464, residue 465, residue 466, residue 467, residue 468, residue 469, residue 470, residue 474, residue 475, residue 480, residue 481, residue 486, residue 489, residue 491, residue 495, residue 499, residue 500, residue 502, residue 508, residue 510, residue 515, residue 516, residue 520, residue 524, residue 525, residue 526, residue 528, residue 531, residue 532, residue 535, residue 536, residue 539, residue 543, residue 544, residue 547, residue 571, and residue 576.

39. The chimeric polypeptide of embodiment 38, wherein all of said amino acid substitutions are selected from among the members of the group consisting of: residue 381, residue 383, residue 391, residue 401, residue 424, residue 442, residue 463, residue 495, residue 506, residue 508, residue 515, residue 516, residue 524, residue 525, residue 526, residue 531, residue 535, and residue 539.

40. The chimeric polypeptide of embodiment 39, wherein at least one of said amino acid substitutions in HSA domain III are selected from the group consisting of: V381N, V381Q, E383A, E383G, E383I, E383L, E383V, N391A, N391G, N391I, N391L, N391V, Y401D, Y401E, V424A, V424G, V424I, V424L, V424N, V424Q, E442K, E442R, L463N, L463Q, E495D, T506F, T506W, T506Y, T508K, T508R, T508S, T515C, T515H, T515N, T515P, T515Q, T515S, L516S, L516T, L516W, L516Y, K524A, K524G, K524I, K524L, K524V, K525A, K525G, K525I, K525L, K525V, Q526C, Q526M, Q526S, Q526T, Q526Y, E531A, E531G, E531I, E531L, E531V, H535D, H535E, H535P, A539I, A539L, and A539V.

41. The chimeric polypeptide of any of embodiments 1-40, wherein at least one of said amino acid substitutions in HSA domain III is of a surface accessible residue.

42. The chimeric polypeptide of embodiment 41, wherein all of said amino acid substitutions in HSA domain III are of surface accessible residues.

43. The chimeric polypeptide of any of embodiments 1-12, wherein at least one of said amino acid substitutions in HSA domain III is of a residue that is both surface accessible and conserved across multiple species.

44. The chimeric polypeptide of embodiment 43, wherein all of said amino acid substitutions in HSA domain III are of residues that are both surface accessible and conserved across multiple species.

45. The chimeric polypeptide of embodiment 43 or 44, wherein said at least one amino acid substitutions in HSA domain III are at any of the following positions, numbered relative to the position in full length mature HSA: residue 383, residue 389, residue 391, residue 410, residue 417, residue 425, residue 442, residue 465, residue 467, residue 468, residue 486, residue 499, residue 502, residue 520, residue 532, residue 536, residue 543, and residue 571.

46. The chimeric polypeptide of embodiment 45, wherein said at least one amino acid substitutions in HSA domain III are at any of the following positions, numbered relative to the position in full length mature HSA: residue 383, residue 391, and residue 442.

47. The chimeric polypeptide of embodiment 45, wherein at least one of said amino acid substitutions in HSA domain III are selected from the group consisting of: E383A, E383G, E383I, E383L, E383V, N391A, N391G, N391I, N391L, N391V, and E442K, E442R.

48. The chimeric polypeptide of embodiment 45, wherein said at least one amino acid substitutions in HSA domain III are at any of the following positions, numbered relative to the position in full length mature HSA: residue 417, residue 442, residue 499, and residue 502.

49. The chimeric polypeptide of any of embodiments 1-48, wherein the HSA domain III comprises an amino acid sequence at least 90% identical to SEQ ID NO: 1.

50. The chimeric polypeptide of embodiment 49, wherein the HSA domain III comprises an amino acid sequence at least 95% identical to SEQ ID NO: 1.

51. The chimeric polypeptide of embodiment 49, wherein the HSA domain III comprises an amino acid sequence at least 98% identical to SEQ ID NO: 1.

52. The chimeric polypeptide of any of embodiments 1-48, wherein the HSA portion comprises an amino acid sequence at least 90% identical to SEQ ID NO: 2.

53. The chimeric polypeptide of embodiment 52, wherein the HSA portion comprises an amino acid sequence at least 95% identical to SEQ ID NO: 2.

54. The chimeric polypeptide of embodiment 52, wherein the HSA portion comprises an amino acid sequence at least 98% identical to SEQ ID NO: 2.

55. The chimeric polypeptide of any of embodiments 1-54, wherein at least one of said amino acid substitutions in HSA domain III is in loop 2 of HSA domain III.

56. The chimeric polypeptide of any of embodiments 1-22, 27-29, 32, 33, 36-38, 41-45, or 48-55, wherein all of said amino acid substitutions in HSA domain III are in loop 2 of HSA domain III.

57. The chimeric polypeptide of embodiment 55 or 56, comprising one to five amino acid substitutions in HSA domain III, wherein said one to five amino acid substitutions are in loop 2 of HSA domain III.

58. The chimeric polypeptide of any of embodiments 1-55, wherein at least one of said amino acid substitutions in HSA domain III is in loop 3 of HSA domain III.

59. The chimeric polypeptide of any of embodiments 1-22, 27-33, 36-54, or 58, wherein all of said amino acid substitutions in HSA domain III are in loop 3 of HSA domain III.

60. The chimeric polypeptide of embodiment 58 or 59, comprising one to five amino acid substitutions in HSA domain III, wherein said one to five amino acid substitutions are in loop 3 of HSA domain III.

61. The chimeric polypeptide of any of embodiments 1-55 or 58, wherein at least one of said amino acid substitutions in HSA domain III is in loop 6 of HSA domain III.

62. The chimeric polypeptide of any of embodiments 1-22, 27-29, 32, 33-45, 48-54 or 61, wherein all of said amino acid substitutions in HSA domain III are in loop 6 of HSA domain III.

63. The chimeric polypeptide of embodiment 61 or 62, comprising one to eighteen amino acid substitutions in HSA domain III, wherein said one to eighteen amino acid substitutions are in loop 6 of HSA domain III.

64. The chimeric polypeptide of any of embodiments 1-55, 58, or 61, wherein at least one of said amino acid substitutions in HSA domain III is in helix 7 of HSA domain III.

65. The chimeric polypeptide of any of embodiments 1-22, 27-29, 32, 33-45, 48-54 or 64, wherein all of said amino acid substitutions in HSA domain III are in helix 7 of HSA domain III.

66. The chimeric polypeptide of embodiment 67 or 68, comprising one to three amino acid substitutions in HSA domain III, wherein said one to six amino acid substitutions are in helix 7 of HSA domain III.

67. The chimeric polypeptide of any of embodiments 1-55, 58, 61, 64, wherein at least one of said amino acid substitutions in HSA domain III is in loop 7 of HSA domain III.

68. The chimeric polypeptide of any of embodiments 1-22, 27-29, 32, 33-45, 48-54 or 67, wherein all of said amino acid substitutions in HSA domain III are in loop 7 of HSA domain III.

69. The chimeric polypeptide of embodiment 67 or 68, comprising one to three amino acid substitutions in HSA domain III, wherein said one to three amino acid substitutions are in loop 7 of HSA domain III.

70. The chimeric polypeptide of any of embodiments 1-55, 58, 61, 64, or 67, wherein at least one of said amino acid substitutions in HSA domain III is in helix 8 of HSA domain III.

71. The chimeric polypeptide of any of embodiments 1-22, 27-28, 37, 38, 41-44, 49-54 or 70, wherein all of said amino acid substitutions in HSA domain III are in helix 8 of HSA domain III.

72. The chimeric polypeptide of embodiment 70 or 71, comprising one to five amino acid substitutions in HSA domain III, wherein said one to eighteen amino acid substitutions are in helix 8 of HSA domain III.

73. The chimeric polypeptide of any of embodiments 1-55, 58, 61, 64, 67, or 70, wherein at least one of said amino acid substitutions in HSA domain III is in loop 8 of HSA domain III.

74. The chimeric polypeptide of any of embodiments 1-22, 27-28, 37, 38, 41-44, 49-54 or 73, wherein all of said amino acid substitutions in HSA domain III are in loop 8 of HSA domain III.

75. The chimeric polypeptide of embodiment 73 or 74, comprising one to five amino acid substitutions in HSA domain III, wherein said one to five amino acid substitutions are in loop 8 of HSA domain III.

76. The chimeric polypeptide of any of embodiments 1-55, 58, 61, 64, 67, 70, or 73, wherein at least one of said amino acid substitutions in HSA domain III is in loop 9 of HSA domain III.

77. The chimeric polypeptide of any of embodiments 1-22, 27-28, 41-44, 49-54 or 76, wherein all of said amino acid substitutions in HSA domain III are in loop 9 of HSA domain III.

78. The chimeric polypeptide of embodiment 76 or 77, comprising one to four amino acid substitutions in HSA domain III, wherein said one to four amino acid substitutions are in loop 9 of HSA domain III.

79. The chimeric polypeptide of any of embodiments 1-78, wherein at least one of said amino acid substitutions comprises a replacement of an amino acid residue with an alanine.

80. The chimeric polypeptide of any of embodiments 1-79, wherein at least one of said amino acid substitutions comprises a conservative amino acid substitution.

81. The chimeric polypeptide of any of embodiments 1-80, wherein at least one of said amino acid substitutions comprises a replacement of a basic amino acid with another basic amino acid.

82. The chimeric polypeptide of any of embodiments 1-81, wherein at least one of said amino acid substitutions comprises a replacement of an acidic amino acid with another acidic amino acid.

83. The chimeric polypeptide of any of embodiments 1-83, wherein at least one of said amino acid substitutions comprises a replacement of a neutral amino acid with another neutral amino acid.

84. The chimeric polypeptide of any of embodiments 1-83, wherein at least one of said amino acid substitutions comprises a replacement of one amino acid with another within the following group: lysine, arginine, and histidine.

85. The chimeric polypeptide of any of embodiments 1-84, wherein at least one of said amino acid substitutions comprises a replacement of one amino acid with another within the following group: aspartate and glutamate.

86. The chimeric polypeptide of any of embodiments 1-85, wherein at least one of said amino acid substitutions comprises a replacement of one amino acid with another within the following group: asparagine, glutamine, serine, threonine, and tyrosine.

87. The chimeric polypeptide of any of embodiments 1-86, wherein at least one of said amino acid substitutions comprises a replacement of one amino acid with another within the following group: alanine, valine, isoleucine, leucine, proline, phenylalanine, tryptophan, methionine, cysteine and glycine.

88. The chimeric polypeptide of any of embodiments 1-87, wherein at least one of said amino acid substitutions comprises a replacement of one amino acid with another within the following group: phenylalanine, tryptophan and tyrosine.

89. The chimeric polypeptide of any of embodiments 1-88, wherein at least one of said amino acid substitutions comprises a replacement of one amino acid with another within the following group: cysteine, serine, and threonine.

90. The chimeric polypeptide of any of embodiments 1-89, wherein at least one of said amino acid substitutions comprises a replacement of one amino acid with another within the following group: asparagine, glutamine, serine, threonine, tyrosine, lysine, arginine, histidine, aspartate, glutamate.

91. The chimeric polypeptide of any of embodiments 1-90, wherein at least one of said amino acid substitutions comprises a replacement of one amino acid with another within the following group: glycine, serine, threonine, alanine, valine, leucine, and isoleucine.

92. The chimeric polypeptide of any of embodiments 1-91, wherein at least one of said amino acid substitutions comprises a non-conservative substitution.

93. The chimeric polypeptide of embodiment 79, wherein all of said amino acid substitutions comprise a replacement of an amino acid residue with an alanine.

94. The chimeric polypeptide of embodiment 80, wherein all of said amino acid substitutions comprise, independently at each position, conservative amino acid substitutions.

95. The chimeric polypeptide of embodiment 81, wherein all of said amino acid substitutions comprise, independently at each position, replacement of a basic amino acid with another basic amino acid.

96. The chimeric polypeptide of embodiment 83, wherein all of said amino acid substitutions comprise, independently at each position, replacement of an acidic amino acid with another acidic amino acid.

97. The chimeric polypeptide of embodiment 83, wherein all of said amino acid substitutions comprise, independently at each position, replacement of a neutral amino acid with another neutral amino acid.

98. The chimeric polypeptide of embodiment 84, wherein all of said amino acid substitutions comprise, independently at each position, replacement of one amino acid with another within the following group: lysine, arginine, and histidine.

99. The chimeric polypeptide of embodiment 85, wherein all of said amino acid substitutions comprise, independently at each position, replacement of one amino acid with another within the following group: aspartate and glutamate.

100. The chimeric polypeptide of embodiment 86, wherein all of said amino acid substitutions comprise, independently at each position, replacement of one amino acid with another within the following group: asparagine, glutamine, serine, threonine, and tyrosine.

101. The chimeric polypeptide of embodiment 87, wherein all of said amino acid substitutions comprise, independently at each position, replacement of one amino acid with another within the following group: alanine, valine, isoleucine, leucine, proline, phenylalanine, tryptophan, methionine, cysteine and glycine.

102. The chimeric polypeptide of embodiment 88, wherein all of said amino acid substitutions comprise, independently at each position, replacement of one amino acid with another within the following group: phenylalanine, tryptophan and tyrosine.

103. The chimeric polypeptide of embodiment 89, wherein all of said amino acid substitutions comprise, independently at each position, replacement of one amino acid with another within the following group: cysteine, serine, and threonine.

104. The chimeric polypeptide of embodiment 90, wherein all of said amino acid substitutions comprise, independently at each position, replacement of one amino acid with another within the following group: asparagine, glutamine, serine, threonine, tyrosine, lysine, arginine, histidine, aspartate, glutamate.

105. The chimeric polypeptide of embodiment 91, wherein all of said amino acid substitutions comprise, independently at each position, replacement of one amino acid with another within the following group: glycine, serine, threonine, alanine, valine, leucine, and isoleucine.

106. The chimeric polypeptide of embodiment 92, wherein all of said amino acid substitutions comprise, independently at each position, non-conservative substitutions.

107. The chimeric polypeptide of any of embodiments 1-106, wherein the heterologous protein comprises an antibody or an antigen-binding fragment thereof.

108. The chimeric polypeptide of any of embodiments 1-107, wherein the heterologous protein comprises a therapeutic protein.

109. The chimeric polypeptide of any of embodiments 1-108, further comprising a constant region of an IgG immunoglobulin.

110. The chimeric polypeptide of any of embodiments 1-109, wherein the HSA portion is chemically conjugated to the heterologous protein.

111. The chimeric polypeptide of any of embodiments 1-109, wherein the HSA portion is recombinantly conjugated to the heterologous protein.

112. The chimeric polypeptide of embodiment 111, wherein the chimeric polypeptide is produced using a recombinant vector encoding both the HSA portion and the heterologous protein.

113. The chimeric polypeptide of embodiment 111 or 112, wherein the chimeric polypeptide is produced in a prokaryotic or eukaryotic cell.

114. The chimeric polypeptide of embodiment 113, wherein the eukaryotic cell is selected from a yeast cell, an avian cell, an insect cell, or a mammalian cell.

115. The chimeric polypeptide of any of embodiments 110-114, wherein the HSA portion and the heterologous protein are directly conjugated to each other.

116. The chimeric polypeptide of any of embodiments 110-114, wherein the HSA portion and the heterologous protein are conjugated via a linker.

117. The chimeric polypeptide of embodiment 116, wherein the linker comprises one or more Gly-Gly-Gly-Gly-Ser repeats.

118. The chimeric polypeptide of any of embodiments 1-117, wherein the HSA portion is conjugated to the N-terminal amino acid of the heterologous protein.

119. The chimeric polypeptide of any of embodiments 1-117, wherein the HSA portion is conjugated to the C-terminal amino acid of the heterologous protein.

120. The chimeric polypeptide of any of embodiments 1-117, wherein the HSA portion is conjugated to an internal amino acid of the heterologous protein.

121. The chimeric polypeptide of any of embodiments 1-120, wherein the HSA portion further comprises at least a portion of HSA domain I; or at least a portion of HSA domain II; or at least a portion of HSA domain I and at least a portion of HSA domain II.

122. The chimeric polypeptide of any of embodiments 1-121, wherein said chimeric polypeptide is substantially purified.

123. A composition comprising the chimeric polypeptide of any of embodiments 1-122, and a pharmaceutically acceptable carrier.

124. The composition of embodiment 123, wherein said composition is a sterile composition.

125. The composition of embodiment 123 or 124, wherein said composition is non-pyrogenic.

126. A method of treating a subject in need thereof, comprising administering to said subject a chimeric polypeptide according to any of embodiments 1-122 or a composition according to any of embodiments 123-125.

127. A method of increasing serum half-life of a protein in a subject in need thereof, comprising administering to said subject a chimeric polypeptide according to any of embodiments 1-122.

128. The method of embodiment 126 or 127, wherein administering to said subject comprises administering said chimeric polypeptide systemically.

129. The method of embodiment 126 or 127, wherein administering to said subject comprises administering said chimeric polypeptide by a route selected from the group consisting of: intradermal, transdermal, intramuscular, intraperitoneal, intravenous, intravascular, intrapericardial, subcutaneous, pulmonary, intranasal, intraocular, epidural, topical and oral.

130. The method of embodiment 126 or 127, wherein administering to said subject comprises administering said chimeric polypeptide intravenously.

131. A nucleic acid construct comprising a nucleotide sequence that encodes the chimeric polypeptide of any of embodiments 1-121.

132. A human serum albumin (HSA) variant polypeptide, comprising HSA domain III, or a neonatal Fc receptor (FcRn) binding fragment thereof, wherein said variant polypeptide can bind to an FcRn, and wherein said HSA domain III comprises one to eighteen amino acid substitutions to increase affinity of said variant polypeptide for FcRn relative to a control HSA polypeptide lacking said substitutions.

133. The variant polypeptide of embodiment 132, wherein the variant polypeptide binds to FcRn with a higher affinity than said control polypeptide, and wherein said affinity is measured at acidic pH.

134. The variant polypeptide of embodiment 132 or 133, where the acidic pH is between 5.0 and 6.0.

135. The variant polypeptide of embodiment 134, wherein the acidic pH is 5.5±0.2.

136. The variant polypeptide of any of embodiments 132, wherein the variant polypeptide binds to FcRn with a higher affinity than said control polypeptide at acidic pH, but which variant polypeptide does not bind to FcRn with higher affinity than said control polypeptide at neutral pH.

137. The variant polypeptide of embodiment 136, wherein the neutral pH is between 6.9 and 7.9.

138. The variant polypeptide of embodiment 137, wherein the neutral pH is 7.4±0.2

139. The variant polypeptide of any of embodiments 132, wherein the variant polypeptide has a longer serum half-life than said control HSA polypeptide.

140. The variant polypeptide of any of embodiments 132-139, wherein the HSA domain III comprises one to ten amino acid substitutions.

141. The variant polypeptide of any of embodiments 132-140, wherein at least one of said amino acid substitutions in HSA domain III is of a residue that is conserved across multiple species.

142. The variant polypeptide of embodiment 141, wherein all of said amino acid substitutions in HSA domain III are of residues that are conserved across multiple species.

143. The variant polypeptide of any of embodiments 132-140, wherein at least one of said amino acid substitutions in HSA domain III is of a residue that is conserved among serum albumin proteins from human, pig, rat, mouse, dog, rabbit, cow, chicken, donkey, Mongolian gerbil, sheep, cat, and horse.

144. The variant polypeptide of embodiment 143, wherein all of said amino acid substitutions in HSA domain III are of residues that are conserved among serum albumin proteins from human, pig, rat, mouse, dog, rabbit, cow, chicken, donkey, Mongolian gerbil, sheep, cat, and horse.

145. The variant polypeptide of any of embodiments 132-143, wherein at least one of said amino acid substitutions in HSA domain III are selected from those listed in Table 5.

146. The variant polypeptide of any of embodiments 132-143, wherein at least one of said amino acid substitutions in HSA domain III are at any of the following positions, numbered relative to the position in full length mature HSA: residue 381, residue 383, residue 391, residue 401, residue 402, residue 407, residue 411, residue 413, residue 414, residue 415, residue 416, residue 424, residue 426, residue 434, residue 442, residue 445, residue 447, residue 450, residue 454, residue 455, residue 456, residue 457, residue 459, residue 463, residue 495, residue 506, residue 508, residue 509, residue 511, residue 512, residue 515, residue 516, residue 517, residue 519, residue 521, residue 523, residue 524, residue 525, residue 526, residue 527, residue 531, residue 535, residue 538, residue 539, residue 541, residue 557, residue 561, residue 566, residue 569.

147. The variant polypeptide of any of embodiments 132-143, wherein the variant polypeptide comprises amino acid substitutions in HSA domain III at positions, numbered relative to the position in full length mature HSA, selected from the group consisting of: (a) residues 383 and 413; (b) residues 401 and 523; (c) residues 407 and 447; (d) residues 407 and 447 and 539; (e) residues 407 and 509; (f) residues 407 and 526; (g) residues 411 and 535; (h) residues 414 and 456; (i) residues 415 and 569; (j) residues 426 and 526; (k) residues 442 and 450 and 459; (l) residues 463 and 508; (m) residues 508 and 519 and 525; (n) residues 509 and 527; (o) residues 523 and 538; (p) residues 526 and 557; and (q) residues 541 and 561.

148. The variant polypeptide of any of embodiments 132-143, or 146, wherein at least one of said amino acid substitutions in HSA domain III are selected from the group consisting of: V381N, V381Q, E383A, E383G, E383I, E383L, E383V, N391A, N391G, N391I, N391L, N391V, Y401D, Y401E, K402A, K402G, K402I, K402L, K402V, L407F, L407N, L407Q, L407W, L407Y, Y411Q, Y411N, K413C, K413S, K413T, K414S, K414T, V415C, V415S, V415T, Q416H, Q416P, V424A, V424G, V424I, V424L, V424N, V424Q, V426D, V426E, V426H, V426P, G434C, G434S, G434T, E442K, E442R, R445F, R445W, R445Y, P447S, P447T, E450D, E450E, S454C, S454M, S454T, V455N, V455Q, V456N, V456Q, L457F, L457W, L457Y, Q459K, Q459R, L463N, L463Q, E495D, T506F, T506W, T506Y, T508K, T508R, T508S, F509C, F509I, F509L, F509M, F509V, F509W, F509Y, A511F, A511W, A511Y, D512F, D512W, D512Y, T515C, T515H, T515N, T515P, T515Q, T515S, L516F, L516S, L516T, L516W, L516Y, S517C, S517M, S517T, S517W, S517Y, K519A, K519G, K519I, K519L, K519V, R521F, R521W, R521Y, I523A, I523D, I523E, I523F, I523G, I523I, I523K, I523L, I523N, I523Q, I523R, I523V, I523W, I523Y, K524A, K524G, K524I, K524L, K524V, K525A, K525G, K525I, K525L, K525V, Q526C, Q526M, Q526S, Q526T, Q526Y, T527F, T527W, T527Y, E531A, E531G, E531I, E531L, E531V, H535D, H535E, H535P, K538F, K538W, K538Y, A539I, A539L, A539V, K541F, K541W, K541Y, K557A, K557G, K557I, K557L, K557V, A561F, A561W, A561Y, T566F, T566W, T566Y, A569H, and A569P.

149. The variant polypeptide of any of embodiments 132-143, 146, or 148, wherein at least one of said amino acid substitutions in HSA domain III are selected from the group consisting of: V381N, E383G, N391V, Y401E, K402A, L407N, L407Y, Y411Q, K414S, K413S, V415T, V415C, Q416P, V424I, V424Q, V426E, V426H, G434C, E442K, R445W, P447S, E450D, S454C, V455N, V456N, L457F, Q459R, L463N, E495D, T506Y, T508R, T508S, F509I, F509M, F509W, A511F, D512Y, T515P, T515Q, T515S, L516T, L516W, S517C, S517W, K519I, R521W, I523D, I523E, I523Q, I523K, I523G, I523R, I523Y, K524L, K524V, K525V, Q526T, Q526M, Q526Y, T527Y, E531I, H535N, H535P, K538Y, A539I, K541F, K557G, A561F, T566W, and A569P.

150. The variant polypeptide of any of embodiments 132-143, or 146, wherein the variant polypeptide comprises one amino acid substitution in HSA domain III selected from the group consisting of: V381N, E383G, N391V, Y401E, K402A, L409N, L407Y, Y411Q, K414S, K413S, V415T, V415C, Q416P, V424I, V424Q, V426E, V426H, G434C, E442K, R445W, P447S, E450D, S454C, V455N, V456N, L457F, Q459R, L463N, E495D, T506Y, T508R, T508S, F509I, F509M, F509W, A511F, D512Y, T515P, T515Q, T515S, L516T, L516W, S517C, S517W, K519I, R521W, I523D, I523E, I523Q, I523K, I523G, I523R, I523Y, K524L, K524V, K525V, Q526T, Q526M, Q526Y, T527Y, E531I, H535N, H535P, K538Y, A539I, K541F, K557G, A561F, T566W, and A569P.

151. The variant polypeptide of embodiment 149, wherein at least one of said amino acid substitutions in HSA domain III are selected from the group consisting of: L407N, L407Y, V415T, V424I, V424Q, V426E, V426H, P447S, V455N, V456N, L463N, E495D, T506Y, T508R, F509M, F509W, A511F, D512Y, T515Q, L516T, L516W, S517W, R521W, I523D, I523E, I523Q, I523G, I523R, K524L, Q526M, T527Y, H535P and K557G.

152. The variant polypeptide of embodiment 150, wherein the variant polypeptide comprises one amino acid substitution in HSA domain III selected from the group consisting of: L407N, L407Y, V415T, V424I, V424Q, V426E, V426H, P447S, V455N, V456N, L463N, E495D, T506Y, T508R, F509M, F509W, A511F, D512Y, T515Q, L516T, L516W, S517W, R521W, I523D, I523E, I523G, I523K, I523R, K524L, Q526M, T527Y, H535P and K557G.

153. The variant polypeptide of any of embodiments 132-143, or 146, wherein the variant polypeptide comprises amino acid substitutions in HSA domain III selected from the group consisting of: (a) E383G/K413S; (b) Y401E/I523G; (c) L407N/P447S; (d) L407N/P447S/A539I; (e) L407N/F509M; (f) L407Y/Q526T; (g) Y411Q/H535N; (h) K414S/V456N; (i) V415T/A569P; (j) V426H/Q526Y; (k) E442K/E450D/Q459R; (l) L463N/T508R; (m) T508R/K519I/K525V; (n) F509I/T527Y; (o) I523Q/K538Y; (p) Q526M/K557G; and (q) K541F/A561F.

154. The variant polypeptide of any of embodiments 132-143, or 146, wherein the variant polypeptide comprises amino acid substitutions in HSA domain III selected from the group consisting of: (a) L407N/P447S; (b) L407N/P447S/A539I; (c) L407N/F509M; (d) Y411Q/H535N; (e) K414S/V456N; (f) V426H/Q526Y; (g) L463N/T508R; (h) F509I/T527Y; (i) I523Q/K538Y; (j) Q526M/K557G; and (k) K541F/A561F.

155. The variant polypeptide of any of embodiments 132-143, wherein at least one of said amino acid substitutions in HSA domain III is of a residue that is conserved among serum albumin proteins from human, pig, rat, mouse, dog, rabbit, cow, chicken, donkey, Mongolian gerbil, sheep, cat, and horse, but which is not conserved in chicken serum albumin.

156. The variant polypeptide of embodiment 155, wherein all of said amino acid substitutions in HSA domain III are of residues that are conserved among serum albumin proteins from human, pig, rat, mouse, dog, rabbit, cow, chicken, donkey, Mongolian gerbil, sheep, cat, and horse, but which are not conserved in chicken serum albumin.

157. The variant polypeptide of embodiment 143, wherein said at least one amino acid substitutions in HSA domain III are at any of the following positions, numbered relative to the position in full length mature HSA (SEQ ID NO: 2): residue 383, residue 389, residue 391, residue 410, residue 417, residue 425, residue 442, residue 465, residue 467, residue 468, residue 486, residue 499, residue 502, residue 520, residue 532, residue 536, residue 543, and residue 571.

158. The variant polypeptide of embodiment 157, wherein said at least one amino acid substitutions in HSA domain III are at any of the following positions, numbered relative to the position in full length mature HSA: residue 383, residue 391, residue 434, residue 442, residue 445, and residue 450.

159. The variant polypeptide of embodiment 158, wherein at least one of said amino acid substitutions in HSA domain III are selected from the group consisting of: V381N, E383A, E383G, E383I, E383L, E383V, N391A, N391G, N391I, N391L, N391V, G434C, G434S, G434T, E442K, E442R, R445F, R445W, R445Y, E450D, and E450E.

160. The variant polypeptide of embodiment 157, wherein said at least one amino acid substitutions in HSA domain III are at any of the following positions, numbered relative to the position in full length mature HSA: residue 417, residue 442, residue 499, and residue 502.

161. The variant polypeptide of embodiment 155, wherein said at least one amino acid substitutions in HSA domain III are at any of the following positions, numbered relative to the position in full length mature HSA: residue 380, residue 381, residue 384, residue 387, residue 396, residue 401, residue 404, residue 405, residue 406, residue 409, residue 419, residue 421, residue 422, residue 424, residue 428, residue 430, residue 431, residue 433, residue 441, residue 457, residue 458, residue 463, residue 464, residue 466, residue 469, residue 470, residue 474, residue 475, residue 480, residue 481, residue 489, residue 491, residue 495, residue 500, residue 508, residue 510, residue 515, residue 516, residue 524, residue 525, residue 526, residue 528, residue 531, residue 535, residue 539, residue 544, residue 547, and residue 576.

162. The variant polypeptide of embodiment 161, wherein said at least one amino acid substitutions in HSA domain III are at any of the following positions, numbered relative to the position in full length mature HSA: residue 381, residue 401, residue 424, residue 457, residue 463, residue 495, residue 508, residue 515, residue 516, residue 524, residue 525, residue 526, residue 531, residue 535, and residue 539.

163. The variant polypeptide of embodiment 162, wherein at least one of said amino acid substitutions in HSA domain III are selected from the group consisting of: V381N, V381Q, Y401D, Y401E, V424N, V424Q, L457F, L457W, L457Y, L463N, L463Q, E495D, T508K, T508R, T508S, T515C, T515H, T515N, T515P, T515Q, T515S, L516F, L516S, L516T, L516W, L516Y, K524A, K524G, K524I, K524L, K524V, K525A, K525G, K525I, K525L, K525V, Q526C, Q526M, Q526S, Q526T, Q526Y, E531A, E531G, E531I, E531L, E531V, H535D, H535E, H535P, A539I, and A539L, A539V.

164. The variant polypeptide of embodiment 157, wherein all of said amino acid substitutions are selected from among the members of the group consisting of: residue 383, residue 389, residue 391, residue 410, residue 417, residue 425, residue 442, residue 465, residue 467, residue 468, residue 486, residue 499, residue 502, residue 520, residue 532, residue 536, residue 543, and residue 571.

165. The variant polypeptide of embodiment 161, wherein all of said amino acid substitutions are selected from among the members of the group consisting of: residue 380, residue 381, residue 384, residue 387, residue 396, residue 401, residue 404, residue 405, residue 406, residue 409, residue 419, residue 421, residue 422, residue 424, residue 428, residue 430, residue 431, residue 433, residue 441, residue 457, residue 458, residue 463, residue 464, residue 466, residue 469, residue 470, residue 474, residue 475, residue 480, residue 481, residue 489, residue 491, residue 495, residue 500, residue 508, residue 510, residue 515, residue 516, residue 524, residue 525, residue 526, residue 528, residue 531, residue 535, residue 539, residue 544, residue 547, and residue 576.

166. The variant polypeptide of embodiment 157 or 161, wherein all of said amino acid substitutions are selected from among the members of the group consisting of: residue 380, residue 381, residue 384, residue 383, residue 387, residue 389, residue 391, residue 396, residue 401, residue 404, residue 405, residue 406, residue 409, residue 410, residue 417, residue 419, residue 421, residue 422, residue 424, residue 425, residue 428, residue 430, residue 431, residue 433, residue 441, residue 442, residue 457, residue 458, residue 463, residue 464, residue 465, residue 466, residue 467, residue 468, residue 469, residue 470, residue 474, residue 475, residue 480, residue 481, residue 486, residue 489, residue 491, residue 495, residue 499, residue 500, residue 502, residue 508, residue 510, residue 515, residue 516, residue 520, residue 524, residue 525, residue 526, residue 528, residue 531, residue 532, residue 535, residue 536, residue 539, residue 543, residue 544, residue 547, residue 571, and residue 576.

167. The variant polypeptide of embodiment 166, wherein all of said amino acid substitutions are selected from among the members of the group consisting of: residue 381, residue 383, residue 391, residue 401, residue 424, residue 442, residue 463, residue 495, residue 508, residue 515, residue 516, residue 524, residue 525, residue 526, residue 531, residue 535, and residue 539.

168. The variant polypeptide of embodiment 167, wherein at least one of said amino acid substitutions in HSA domain III are selected from the group consisting of: V381N, V381Q, E383A, E383G, E383I, E383L, E383V, N391A, N391G, N391I, N391L, N391V, Y401D, Y401E, V424A, V424G, V424I, V424L, V424N, V424Q, E442K, E442R, L463N, L463Q, E495D, T506F, T506W, T506Y, T508K, T508R, T508S, T515C, T515H, T515N, T515P, T515Q, T515S, L516S, L516T, L516W, L516Y, K524A, K524G, K524I, K524L, K524V, K525A, K525G, K525I, K525L, K525V, Q526C, Q526M, Q526S, Q526T, Q526Y, E531A, E531G, E531I, E531L, E531V, H535D, H535E, H535P, A539I, A539L, and A539V.

169. The variant polypeptide of any of embodiments 132-166, wherein at least one of said amino acid substitutions in HSA domain III is of a surface accessible residue.

170. The variant polypeptide of embodiment 169, wherein all of said amino acid substitutions in HSA domain III are of surface accessible residues.

171. The variant polypeptide of any of embodiments 132-166, wherein at least one of said amino acid substitutions in HSA domain III is of a residue that is both surface accessible and conserved across multiple species.

172. The variant polypeptide of embodiment 171, wherein all of said amino acid substitutions in HSA domain III are of residues that are both surface accessible and conserved across multiple species.

173. The variant polypeptide of embodiment 171 or 172, wherein said at least one amino acid substitutions in HSA domain III are at any of the following positions, numbered relative to the position in full length mature HSA: residue 383, residue 389, residue 391, residue 410, residue 417, residue 425, residue 442, residue 465, residue 467, residue 468, residue 486, residue 499, residue 502, residue 520, residue 532, residue 536, residue 543, and residue 571.

174. The variant polypeptide of embodiment 173, wherein said at least one amino acid substitutions in HSA domain III are at any of the following positions, numbered relative to the position in full length mature HSA: residue 383, residue 391, and residue 442.

175. The variant polypeptide of embodiment 174, wherein at least one of said amino acid substitutions in HSA domain III are selected from the group consisting of: E383A, E383G, E383I, E383L, E383V, N391A, N391G, N391I, N391L, N391V, and E442K, E442R.

176. The variant polypeptide of any of embodiments 132-172, wherein the HSA domain III comprises an amino acid sequence at least 90% identical to SEQ ID NO: 1.

177. The variant polypeptide of embodiment 176, wherein the HSA domain III comprises an amino acid sequence at least 95% identical to SEQ ID NO: 1.

178. The variant polypeptide of embodiment 169177, wherein the HSA domain III comprises an amino acid sequence at least 98% identical to SEQ ID NO: 1.

179. The variant polypeptide of any of embodiments 132-178, wherein at least one of said amino acid substitutions in HSA domain III is in loop 2 of HSA domain III.

180. The variant polypeptide of any of embodiments 132-150, 155-157, 161, 164-166, 169-173, 176-179, wherein all of said amino acid substitutions in HSA domain III are in loop 2 of HSA domain III.

181. The variant polypeptide of embodiment 179 or 180, comprising one to five amino acid substitutions in HSA domain III, wherein said one to five amino acid substitutions are in loop 2 of HSA domain III.

182. The variant polypeptide of any of embodiments 132-179, wherein at least one of said amino acid substitutions in HSA domain III is in loop 3 of HSA domain III.

183. The variant polypeptide of any of embodiments 132-150, 155-161, 164-166-178, or 182, wherein all of said amino acid substitutions in HSA domain III are in loop 3 of HSA domain III.

184. The variant polypeptide of embodiment 182 or 183, comprising one to five amino acid substitutions in HSA domain III, wherein said one to five amino acid substitutions are in loop 3 of HSA domain III.

185. The variant polypeptide of any of embodiments 132-173 or 182, wherein at least one of said amino acid substitutions in HSA domain III is in loop 6 of HSA domain III.

186. The variant polypeptide of embodiment 132-150, 155-157, 160-173, 176-178, or 185, wherein all of said amino acid substitutions in HSA domain III are in loop 6 of HSA domain III.

187. The variant polypeptide of embodiment 185 or 186, comprising one to five amino acid substitutions in HSA domain III, wherein said one to five amino acid substitutions are in loop 6 of HSA domain III.

188. The variant polypeptide of any of embodiments 132-173, 182 or 185, wherein at least one of said amino acid substitutions in HSA domain III is in helix 7 of HSA domain III.

189. The variant polypeptide of embodiment 132-150, 155-157, 160-173, 176-178, or 188, wherein all of said amino acid substitutions in HSA domain III are in helix 7 of HSA domain III.

190. The variant polypeptide of embodiment 188 or 192, comprising one to three amino acid substitutions in HSA domain III, wherein said one to six amino acid substitutions are in helix 7 of HSA domain III.

191. The variant polypeptide of any of embodiments 132-173, 182, 185, or 188, wherein at least one of said amino acid substitutions in HSA domain III is in loop 7 of HSA domain III.

192. The variant polypeptide of embodiment 132-150, 155-157, 160-173, 176-178, or 191, wherein all of said amino acid substitutions in HSA domain III are in loop 7 of HSA domain III.

193. The variant polypeptide of embodiment 191 or 192, comprising one to three amino acid substitutions in HSA domain III, wherein said one to three amino acid substitutions are in loop 7 of HSA domain III.

194. The variant polypeptide of any of embodiments 132-173, 182, 185, 188, or 191, wherein at least one of said amino acid substitutions in HSA domain III is in helix 8 of HSA domain III.

195. The variant polypeptide of embodiment 132-150, 155-157, 165-166, 169-173, 176-178, or 194, wherein all of said amino acid substitutions in HSA domain III are in helix 8 of HSA domain III.

196. The variant polypeptide of embodiment 194 or 195, comprising one to five amino acid substitutions in HSA domain III, wherein said one to eighteen amino acid substitutions are in helix 8 of HSA domain III.

197. The variant polypeptide of any of embodiments 132-173, 182, 185, 188, 191 or 194, wherein at least one of said amino acid substitutions in HSA domain III is in loop 8 of HSA domain III.

198. The variant polypeptide of embodiment 132-150, 155-157, 165-166, 169-173, 176-178, or 197, wherein all of said amino acid substitutions in HSA domain III are in loop 8 of HSA domain III.

199. The variant polypeptide of embodiment 197 or 198, comprising one to five amino acid substitutions in HSA domain III, wherein said one to five amino acid substitutions are in loop 8 of HSA domain III.

200. The variant polypeptide of any of embodiments 132-173, 182, 185 or 197, wherein at least one of said amino acid substitutions in HSA domain III is in loop 9 of HSA domain III.

201. The variant polypeptide of embodiment 132-150, 155, 156, 169-172, 176-178, or 200, wherein all of said amino acid substitutions in HSA domain III are in loop 9 of HSA domain III.

202. The variant polypeptide of embodiment 200 or 201, comprising one to four amino acid substitutions in HSA domain III, wherein said one to four amino acid substitutions are in loop 9 of HSA domain III.

203. The variant polypeptide of any of embodiments 132-202, wherein at least one of said amino acid substitutions comprises a replacement of an amino acid residue with an alanine.

204. The variant polypeptide of any of embodiments 132-203, wherein at least one of said amino acid substitutions comprises a conservative amino acid substitution.

205. The variant polypeptide of any of embodiments 132-204, wherein at least one of said amino acid substitutions comprises a replacement of a basic amino acid with another basic amino acid.

206. The variant polypeptide of any of embodiments 132-205, wherein at least one of said amino acid substitutions comprises a replacement of an acidic amino acid with another acidic amino acid.

207. The variant polypeptide of any of embodiments 132-206, wherein at least one of said amino acid substitutions comprises a replacement of a neutral amino acid with another neutral amino acid.

208. The variant polypeptide of any of embodiments 132-207, wherein at least one of said amino acid substitutions comprises a replacement of one amino acid with another within the following group: lysine, arginine, and histidine.

209. The variant polypeptide of any of embodiments 132-208, wherein at least one of said amino acid substitutions comprises a replacement of one amino acid with another within the following group: aspartate and glutamate.

210. The variant polypeptide of any of embodiments 132-209, wherein at least one of said amino acid substitutions comprises a replacement of one amino acid with another within the following group: asparagine, glutamine, serine, threonine, and tyrosine.

211. The variant polypeptide of any of embodiments 132-210, wherein at least one of said amino acid substitutions comprises a replacement of one amino acid with another within the following group: alanine, valine, isoleucine, leucine, proline, phenylalanine, tryptophan, methionine, cysteine and glycine.

212. The variant polypeptide of any of embodiments 132-211, wherein at least one of said amino acid substitutions comprises a replacement of one amino acid with another within the following group: phenylalanine, tryptophan and tyrosine.

213. The variant polypeptide of any of embodiments 132-212, wherein at least one of said amino acid substitutions comprises a replacement of one amino acid with another within the following group: cysteine, serine, and threonine.

214. The variant polypeptide of any of embodiments 132-213, wherein at least one of said amino acid substitutions comprises a replacement of one amino acid with another within the following group: asparagine, glutamine, serine, threonine, tyrosine, lysine, arginine, histidine, aspartate, glutamate.

215. The variant polypeptide of any of embodiments 132-214, wherein at least one of said amino acid substitutions comprises a replacement of one amino acid with another within the following group: glycine, serine, threonine, alanine, valine, leucine, and isoleucine.

216. The variant polypeptide of any of embodiments 132-215, wherein at least one of said amino acid substitutions comprises a non-conservative substitution.

217. The variant polypeptide of embodiment 203, wherein all of said amino acid substitutions comprise replacement of an amino acid residue with an alanine.

218. The variant polypeptide of embodiment 204, wherein all of said amino acid substitutions comprise, independently at each position, conservative amino acid substitutions.

219. The variant polypeptide of embodiment 205, wherein all of said amino acid substitutions comprise, independently at each position, replacement of a basic amino acid with another basic amino acid.

220. The variant polypeptide of embodiment 206, wherein all of said amino acid substitutions comprise, independently at each position, replacement of an acidic amino acid with another acidic amino acid.

221. The variant polypeptide of embodiment 207, wherein all of said amino acid substitutions comprise, independently at each position, replacement of a neutral amino acid with another neutral amino acid.

222. The variant polypeptide of embodiment 208, wherein all of said amino acid substitutions comprise, independently at each position, replacement of one amino acid with another within the following group: lysine, arginine, and histidine.

223. The variant polypeptide of embodiment 209, wherein all of said amino acid substitutions comprise, independently at each position, replacement of one amino acid with another within the following group: aspartate and glutamate.

224. The variant polypeptide of embodiment 210, wherein all of said amino acid substitutions comprise, independently at each position, replacement of one amino acid with another within the following group: asparagine, glutamine, serine, threonine, and tyrosine.

225. The variant polypeptide of embodiment 211, wherein all of said amino acid substitutions comprise, independently at each position, replacement of one amino acid with another within the following group: alanine, valine, isoleucine, leucine, proline, phenylalanine, tryptophan, methionine, cysteine and glycine.

226. The variant polypeptide of embodiment 212, wherein all of said amino acid substitutions comprise, independently at each position, replacement of one amino acid with another within the following group: phenylalanine, tryptophan and tyrosine.

227. The variant polypeptide of embodiment 213, wherein all of said amino acid substitutions comprise, independently at each position, replacement of one amino acid with another within the following group: cysteine, serine, and threonine.

228. The variant polypeptide of embodiment 214, wherein all of said amino acid substitutions comprise, independently at each position, replacement of one amino acid with another within the following group: asparagine, glutamine, serine, threonine, tyrosine, lysine, arginine, histidine, aspartate, glutamate.

229. The variant polypeptide of embodiment 215, wherein all of said amino acid substitutions comprise, independently at each position, replacement of one amino acid with another within the following group: glycine, serine, threonine, alanine, valine, leucine, and isoleucine.

230. The variant polypeptide of embodiment 216, wherein all of said amino acid substitutions comprise, independently at each position, non-conservative substitutions.

231. The variant polypeptide of any of embodiments 132-230, wherein the HSA portion further comprises at least a portion of HSA domain I; or at least a portion of HSA domain II; or at least a portion of HSA domain I and at least a portion of HSA domain II.

232. The variant polypeptide of any of embodiments 132-231, wherein said variant polypeptide is substantially purified.

233. The variant polypeptide of any of embodiments 132-232, wherein said variant polypeptide further comprises a binding site for an epitope on a target.

234. The variant polypeptide of embodiment 233, wherein the binding site antagonizes said target.

235. The variant polypeptide of embodiment 233, wherein the binding site agonizes said target.

236. A composition comprising the variant polypeptide of any of embodiments 132-235, and a pharmaceutically acceptable carrier.

237. The composition of embodiment 236, wherein said composition is a sterile composition.

238. The composition of embodiment 236 or 237, wherein said composition is non-pyrogenic.

239. A method of increasing serum half-life of a protein, comprising conjugating to said protein a variant polypeptide according to any of embodiments 132-235.

240. A method of treating a subject in need thereof, comprising administering to said subject a variant polypeptide according to any of embodiments 233-235.

241. A nucleic acid construct comprising a nucleotide sequence that encodes the variant polypeptide of any of embodiments 132-231.

242. A nucleic acid construct, comprising (a) a nucleotide sequence that encodes a human serum albumin (HSA) portion, which HSA portion comprises HSA domain III, or an FcRn binding fragment thereof, which HSA domain III comprises one to eighteen amino acid substitutions, operably linked to (b) a nucleotide sequence that encodes a heterologous protein, wherein the nucleic acid construct encodes a chimeric polypeptide that retains a functional activity of the heterologous protein and can bind to an FcRn, and wherein said chimeric polypeptide has an increased serum half-life and/or an increased affinity for FcRn relative to a control chimeric polypeptide in which the HSA portion does not include said amino acid substitutions.

243. The nucleic acid construct of embodiment 242, wherein the chimeric polypeptide binds to FcRn with a higher affinity then said control chimeric polypeptide.

244. The nucleic acid construct of embodiment 242 or 243, wherein the chimeric polypeptide binds to FcRn with a higher affinity than said control chimeric polypeptide, and wherein said affinity is measured at acidic pH.

245. The nucleic acid construct of embodiment 244, where the acidic pH is between 5.0 and 6.0.

246. The nucleic acid construct of embodiment 245, wherein the acidic pH is 5.5±0.2.

247. The nucleic acid construct of any of embodiments 242-247, wherein the chimeric polypeptide binds to FcRn with a higher affinity than said control chimeric polypeptide at acidic pH, but which chimeric polypeptide does not bind to FcRn with higher affinity than said control chimeric polypeptide at neutral pH.

248. The nucleic acid construct of embodiment 247, wherein the neutral pH is between 6.9 and 7.9.

249. The nucleic acid construct of embodiment 248, wherein the neutral pH is 7.4±0.2.

250. The nucleic acid construct of any of embodiments 242, wherein (i) comprises a nucleotide sequence that encodes a human serum albumin (HSA) portion, which HSA portion comprises HSA domain III, or an FcRn binding fragment thereof, which HSA domain III comprises one to ten amino acid substitutions.

251. The nucleic acid construct of any of embodiments 242-250, wherein at least one of said amino acid substitutions in HSA domain III is of a residue that is conserved across multiple species.

252. The nucleic acid construct of embodiment 251, wherein all of said amino acid substitutions in HSA domain III are of residues that are conserved across multiple species.

253. The nucleic acid construct of any of embodiments 242-250, wherein at least one of said amino acid substitutions in HSA domain III is of a residue that is conserved among serum albumin proteins from human, pig, rat, mouse, dog, rabbit, cow, chicken, donkey, Mongolian gerbil, sheep, cat, and horse.

254. The nucleic acid construct of embodiment 253, wherein all of said amino acid substitutions in HSA domain III are of residues that are conserved among serum albumin proteins from human, pig, rat, mouse, dog, rabbit, cow, chicken, donkey, Mongolian gerbil, sheep, cat, and horse.

255. The nucleic acid construct of any of embodiments 242-254, wherein at least one of said amino acid substitutions in HSA domain III are selected from those listed in Table 5.

256. The nucleic acid construct of any of embodiments 242-254, wherein at least one of said amino acid substitutions in HSA domain III are at any of the following positions, numbered relative to the position in full length mature HSA: residue 381, residue 383, residue 391, residue 401, residue 402, residue 407, residue 411, residue 413, residue 414, residue 415, residue 416, residue 424, residue 426, residue 434, residue 442, residue 445, residue 447, residue 450, residue 454, residue 455, residue 456, residue 457, residue 459, residue 463, residue 495, residue 506, residue 508, residue 509, residue 511, residue 512, residue 515, residue 516, residue 517, residue 519, residue 521, residue 523, residue 524, residue 525, residue 526, residue 527, residue 531, residue 535, residue 538, residue 539, residue 541, residue 557, residue 561, residue 566, residue 569.

257. The nucleic acid construct of any of embodiments 242-254, wherein the nucleic acid construct comprises amino acid substitutions in HSA domain III at positions, numbered relative to the position in full length mature HSA, selected from the group consisting of: (a) residues 383 and 413; (b) residues 401 and 523; (c) residues 407 and 447; (d) residues 407 and 447 and 539; (e) residues 407 and 509; (f) residues 407 and 526; (g) residues 411 and 535; (h) residues 414 and 456; (i) residues 415 and 569; (j) residues 426 and 526; (k) residues 442 and 450 and 459; (l) residues 463 and 508; (m) residues 508 and 519 and 525; (n) residues 509 and 527; (o) residues 523 and 538; (p) residues 526 and 557; and (q) residues 541 and 561.

258. The nucleic acid construct of any of embodiments 242-254 or 256, wherein at least one of said amino acid substitutions in HSA domain III are selected from the group consisting of: V381N, V381Q, E383A, E383G, E383I, E383L, E383V, N391A, N391G, N391I, N391L, N391V, Y401D, Y401E, K402A, K402G, K402I, K402L, K402V, L407F, L407N, L407Q, L407W, L407Y, Y411Q, Y411N, K413C, K413S, K413T, K414S, K414T, V415C, V415S, V415T, Q416H, Q416P, V424A, V424G, V424I, V424L, V424N, V424Q, V426D, V426E, V426H, V426P, G434C, G434S, G434T, E442K, E442R, R445F, R445W, R445Y, P447S, P447T, E450D, E450E, S454C, S454M, S454T, V455N, V455Q, V456N, V456Q, L457F, L457W, L457Y, Q459K, Q459R, L463N, L463Q, E495D, T506F, T506W, T506Y, T508K, T508R, T508S, F509C, F509I, F509L, F509M, F509V, F509W, F509Y, A511F, A511W, A511Y, D512F, D512W, D512Y, T515C, T515H, T515N, T515P, T515Q, T515S, L516F, L516S, L516T, L516W, L516Y, S517C, S517F, S517M, S517T, S517W, S517Y, K519A, K519G, K519I, K519L, K519V, R521F, R521W, R521Y, I523A, I523D, I523E, I523F, I523G, I523I, I523K, I523L, I523N, I523Q, I523R, I523V, I523W, I523Y, K524A, K524G, K524I, K524L, K524V, K525A, K525G, K525I, K525L, K525V, Q526C, Q526M, Q526S, Q526T, Q526Y, T527F, T527W, T527Y, E531A, E531G, E531I, E531L, E531V, H535D, H535E, H535P, K538F, K538W, K538Y, A539I, A539L, A539V, K541F, K541W, K541Y, K557A, K557G, K557I, K557L, K557V, A561F, A561W, A561Y, T566F, T566W, T566Y, A569H, and A569P.

259. The nucleic acid construct of any of embodiments 242-254, or 256, wherein at least one of said amino acid substitutions in HSA domain III are selected from the group consisting of: V381N, E383G, N391V, Y401E, K402A, L407N, L407Y, Y411Q, K414S, K413S, V415T, V415C, Q416P, V424I, V424Q, V426E, V426H, G434C, E442K, R445W, P447S, E450D, S454C, V455N, V456N, L457F, Q459R, L463N, E495D, T506Y, T508R, T508S, F509I, F509M, F509W, A511F, D512Y, T515P, T515Q, T515S, L516T, L516W, S517C, S517W, K519I, R521W, I523D, I523E, I523Q, I523K, I523G, I523R, I523Y, K524L, K524V, K525V, Q526T, Q526M, Q526Y, T527Y, E531I, H535N, H535P, K538Y, A539I, K541F, K557G, A561F, T566W, and A569P.

260. The nucleic acid construct of embodiment 259, wherein at least one of said amino acid substitutions in HSA domain III are selected from the group consisting of: L407N, L407Y, V415T, V424I, V424Q, V426E, V426H, P447S, V455N, V456N, L463N, E495D, T506Y, T508R, F509M, F509W, A511F, D512Y, T515Q, L516T, L516W, S517W, R521W, I523D, I523E, I523G, I523K, I523R, K524L, Q526M, T527Y, H535P and K557G.

261. The nucleic acid construct of any of embodiments 242-254, or 256, wherein the chimeric polypeptide comprises amino acid substitutions in HSA domain III selected from the group consisting of: (a) E383G/K413S; (b) Y401E/I523G; (c) L407N/P447S; (d) L407N/P447S/A539I; (e) L407N/F509M; (f) L407Y/Q526T; (g) Y411Q/H535N; (h) K414S/V456N; (i) V415T/A569P; (j) V426H/Q526Y; (k) E442K/E450D/Q459R; (l) L463N/T508R; (m) T508R/K519I/K525V; (n) F509I/T527Y; (o) I523Q/K538Y; (p) Q526M/K557G; and (q) K541F/A561F.

262. The nucleic acid construct of 261, wherein the chimeric polypeptide comprises amino acid substitutions in HSA domain III selected from the group consisting of: (a) L407N/P447S; (b) L407N/P447S/A539I; (c) L407N/F509M; (d) Y411Q/H535N; (e) K414S/V456N; (f) V426H/Q526Y; (g) L463N/T508R; (h) F509I/T527Y; (i) I523Q/K538Y; (j) Q526M/K557G; and (k) K541F/A561F.

263. The nucleic acid construct of any of embodiments 242-254, wherein at least one of said amino acid substitutions in HSA domain III is of a surface accessible residue.

264. The nucleic acid construct of embodiment 263, wherein all of said amino acid substitutions in HSA domain III are of surface accessible residues.

265. The nucleic acid construct of any of embodiments 242-250, wherein at least one of said amino acid substitutions in HSA domain III is of a residue that is both surface accessible and conserved across multiple species.

266. The nucleic acid construct of embodiment 265, wherein all of said amino acid substitutions in HSA domain III are of residues that are both surface accessible and conserved across multiple species.

267. The nucleic acid construct of any of embodiments 242-266, wherein (i) comprises a nucleotide sequence that encodes an HSA domain III at least 90% identical to SEQ ID NO: 1.

268. The nucleic acid construct of embodiment 267, wherein (i) comprises a nucleotide sequence that encodes an HSA domain III at least 95% identical to SEQ ID NO: 1.

269. The nucleic acid construct of embodiment 268, wherein (i) comprises a nucleotide sequence that encodes an HSA domain III at least 98% identical to SEQ ID NO: 1.

270. The nucleic acid construct of any of embodiments 242-269, wherein at least one of said amino acid substitutions in HSA domain III is in loop 2 of HSA domain III.

271. The nucleic acid construct of any of embodiments 242-270, wherein at least one of said amino acid substitutions in HSA domain III is in loop 3 of HSA domain III.

272. The nucleic acid construct of any of embodiments 242-271, wherein at least one of said amino acid substitutions in HSA domain III is in loop 6 of HSA domain III.

273. The nucleic acid construct of any of embodiments 242-272, wherein at least one of said amino acid substitutions in HSA domain III is in helix 7 of HSA domain III 274. The nucleic acid construct of any of embodiments 242-273, wherein at least one of said amino acid substitutions in HSA domain III is in loop 7 of HSA domain III.

275. The nucleic acid construct of any of embodiments 242-274272, wherein at least one of said amino acid substitutions in HSA domain III is in helix 8 of HSA domain III.

276. The nucleic acid construct of any of embodiments 242-275, wherein at least one of said amino acid substitutions in HSA domain III is in loop 8 of HSA domain III.

277. The nucleic acid construct of any of embodiments 242-276, wherein at least one of said amino acid substitutions in HSA domain III is in loop 9 of HSA domain III.

278. The nucleic acid construct of any of embodiments 242-277, wherein (ii) comprises a nucleotide sequence that encodes a heterologous protein, which heterologous protein comprises an antibody or an antigen-binding fragment thereof.

279. The nucleic acid construct of any of embodiments 242-278, further comprising a nucleotide sequence that encodes a linker.

280. The nucleic acid construct of embodiment 279, wherein the nucleotide sequence encodes a linker comprising one or more Gly-Gly-Gly-Gly-Ser repeats.

281. The nucleic acid construct of any of embodiments 242-280, wherein the HSA portion further comprises at least a portion of HSA domain I; or at least a portion of HSA domain II; or at least a portion of HSA domain I and at least a portion of HSA domain II.

282. A library comprising a plurality of polypeptides, wherein each of said plurality of polypeptides comprises HSA domain III, or an FcRn binding fragment thereof, and wherein each of said plurality of polypeptides independently comprises at least one amino acid substitution of a residue in said HSA domain III that is conserved among serum albumin proteins from human, pig, rat, mouse, dog, rabbit, cow, chicken, donkey, Mongolian gerbil, sheep, cat, and horse.

283. A library comprising a plurality of polypeptides, wherein each of said plurality of polypeptides comprises HSA domain III, or an FcRn binding fragment thereof, and wherein each of said plurality of polypeptides independently comprises at least one amino acid substitution of a residue in said HSA domain III that is conserved among serum albumin proteins from human, pig, rat, mouse, dog, rabbit, cow, donkey, Mongolian gerbil, sheep, cat, and horse, and which is not conserved in serum albumin from chicken.

284. A library comprising a plurality of polypeptides, wherein each of said plurality of polypeptides comprises HSA domain III, or an FcRn binding fragment thereof, and wherein each of said plurality of polypeptides independently comprises at least one amino acid substitution of a residue in said HSA domain III that is a surface accessible residue.

285. The library of embodiment 284, wherein said surface accessible residue is in loop 2 of HSA domain III.

286. The library of embodiment 284 or 285, wherein said surface accessible residue is in loop 3 of HSA domain III.

287. The library of any of embodiments 284-286, wherein said surface accessible residue is in loop 6 of HSA domain III.

288. The library of any of embodiments 284-273, wherein said surface accessible residue is in loop 7 of HSA domain III.

289. The library of any of embodiments 284-288, wherein said surface accessible residue is in loop 8 of HSA domain III.

290. The library of any of embodiments 284-289, wherein said surface accessible residue is in loop 9 of HSA domain III.

291. A library comprising a plurality of polypeptides, wherein each of said plurality of polypeptides comprises HSA domain III, or an FcRn binding fragment thereof, and wherein each of said plurality of polypeptides independently comprises at least one amino acid substitution of a residue in said HSA domain III that is both (i) a surface accessible residue and (ii) conserved among serum albumin proteins from human, pig, rat, mouse, dog, rabbit, cow, chicken, donkey, Mongolian gerbil, sheep, cat, and horse.

292. A library comprising a plurality of polypeptides, wherein each of said plurality of polypeptides comprises HSA domain III, or an FcRn binding fragment thereof, and wherein each of said plurality of polypeptides independently comprises at least one amino acid substitution of a residue in said HSA domain III to an amino acid that is conserved among serum albumin proteins from two or more species other than human selected from the group consisting of pig, rat, mouse, dog, rabbit, cow, chicken, donkey, Mongolian gerbil, sheep, cat, and horse.

293. The library of embodiment 291 or 292, wherein said at least one amino acid substitution is in loop 2 of HSA domain III.

294. The library of any of embodiments 291-293, wherein said at least one amino acid substitution is in loop 3 of HSA domain III.

295. The library of any of embodiments 291-294, wherein said at least one amino acid substitution is in loop 6 of HSA domain III.

296. The library of any of embodiments 291-295, wherein said at least one amino acid substitution is in helix 7 of HSA domain III.

297. The library of any of embodiments 291-296, wherein said at least one amino acid substitution is in loop 7 of HSA domain III.

298. The library of any of embodiments 291-297, wherein said at least one amino acid substitution is in helix 8 of HSA domain III 299. The library of any of embodiments 291-298, wherein said at least one amino acid substitution is in loop 8 of HSA domain III.

300. The library of any of embodiments 291-299, wherein said at least one amino acid substitution is in loop 9 of HSA domain III.

301. The library of any of embodiments 282-300, where each of said plurality of polypeptide further comprises at least a portion of HSA domain I; or at least a portion of HSA domain II; or at least a portion of HSA domain I and at least a portion of HSA domain II.

302. The library of any of embodiments 282-301, wherein the library is a display library.

303. The library of embodiment 302, wherein the type of display library is selected from the group consisting of yeast, phage, and mammalian.

304. A method of screening the library of any of embodiments 282-303, said method comprising: (a) selecting a plurality of polypeptides for screening; (b) screening for polypeptides with increased binding affinity to FcRn or increased serum half-life; and (c) determining the sequence of the polypeptides with increased binding affinity to FcRn or increased serum half-life.

8 EXEMPLIFICATIONS

The invention now being generally described, it will be more readily understood by reference to the following examples, which are included merely for purposes of illustration of certain aspects and embodiments of the present invention, and are not intended to limit the invention. For example, the particular constructs and experimental design disclosed herein represent exemplary tools and methods for validating proper function. As such, it will be readily apparent that any of the disclosed specific constructs and experimental plan can be substituted within the scope of the present disclosure. Furthermore, it will be appreciated that specific listing or description of particular equipment and reagents used, sizes, manufacturer, etc., is not to be considered limiting on the current invention unless specifically stated to be so. It with be further appreciated that other equipment and reagents which perform similarly may be readily substituted.

8.1 Example 1

Kinetic and Affinity Analysis of Human FcRn Binding to Domain III of Human Serum Albumin (HSA)

This example measures the association, dissociation and equilibrium affinity constants of domain III of HSA for human FcRn using surface Plasmon resonance (SPR). Domain III (also abbreviated as "DIII") is a fragment of the human serum albumin protein spanning amino acid residues 381-585. The amino acid sequence of domain III is set forth in SEQ ID NO: 1. The amino acid sequence of full length mature HSA is set forth in SEQ ID NO: 2. For use in these experiments, domain III was expressed and purified from *Pichia Patoris*.

8.1.1 Recombinant Protein Expression and Purification

The recombinant plasmid encoding the domain III gene was obtained from Geneart AG, Regensburg, Germany. The domain III gene was excised from the supplier provided vector using restriction enzymes EcoRI and NotI and cloned into the pPICZ-alpha-A *Pichia* expression vector (Invitrogen, Catalog no. V195-20). Recombinant domain III protein was expressed, in the manner outlined in the manufacturer's instructions. The recombinant domain III protein was secreted into the media, and was purified by hydrophobic interaction chromatography on a Hi Trap Butyl-Sepharose Fast Flow column from GE Healthcare (Catalog. no. 17 5197 01). Briefly, the salinity and pH of the culture media was first adjusted to 1.5M ammonium sulfate and 50 mM sodium phosphate, pH 7.0. The culture media was filtered and passed over the butyl sepharose column and the bound domain III was eluted by using a low salt pH 7.0 sodium phosphate buffer. A fraction of the purified protein was delipidated by passing over a Hydroxyaloxypsopyl Dextran (Sigma-Aldrich, Catalog no. H6258) column with a circulating water jacket maintained at 50° C. The purity of both delipidated and nondelipidated forms was 99%, as visualized by 4-12% SDS PAGE by Coomassie blue staining (FIG. 1A). The protein concentration was determined by A280. The proper folding of the purified domain III was confirmed by near-UV-CD and far-UV-CD measurements which correlated closely with previously published measurements (see, e.g., Giancola et al. International Journal of Biological Macromolecules 20 (1997) 193-204).

8.1.2 Kinetic Measurement

The equilibrium, association, and dissociation rate constants were measured at 25° C. on a BIAcore T100 instrument (Uppsala, Sweden) and the data analyzed using BIAcore T100 evaluation software, v. 1.1 (BIAcore, Inc, Uppsala, Sweden). Both non-delipidated and delipidated forms of domain III were covalently immobilized at coupling densities 1016 and 1184 RUs respectively on CM4 (catalog no. BR-1005-39) or CM5 chip (catalog no. BR-1000-14) by standard amine coupling (BIAcore Handbook, 2002). One of the flow cells was mock coupled using the identical immobilization protocol without protein to serve as a blank. All of the injections were made in pH 5.5, 50 mM phosphate and 150 mM NaCl buffer, and the chip surface was regenerated between injections with pH 7.4 phosphate buffered saline (PBS). To measure association constant ($k_{on}$), dissociation constant ($k_{off}$) and equilibrium dissociation constants ($K_D$) in a single experiment, increasing concentrations of human FcRn (39 nM-40 µM) were injected at 50 µL/min over immobilized domain III protein (FIG. 1B). The binding was allowed to reach equilibrium, and the kinetic constants $k_{on}$ and $k_{off}$ were derived by simultaneously fitting both the association (4 min) and dissociation phase (1 min) of the curves to 1:1 langmuir model. The $K_D$ was derived by fitting the plot of the binding response at equilibrium (Req) versus analyte concentration to a steady-state affinity model using nonlinear regression analysis (FIG. 1C). Both delipidated and non-delipidated forms of domain III showed similar binding sensorgrams and Req vs Ligand conc plots.

The interaction of FcRn with domain III shows rapid association ($k_{on} \approx 7e^3$) and dissociation ($k_{off} \approx 4e^{-2}$) kinetics (Table 1). The $K_D$ of FcRn for domain III is between 5-8 µM which is approximately 7 fold greater (e.g., a larger dissociation constant) than that of the full length HSA for FcRn (Table 1). This difference in $K_D$ is largely due to a faster $k_{off}$ for domain III relative to HSA while the $k_{on}$ for both molecules is comparable. The $K_D$ derived from the $k_{on}$ and $k_{off}$ are in close agreement with the experimentally obtained values thereby corroborating the kinetic measurements. Moreover, two different kinds of sensor chips (CM4 and CM5) with variable carboxy moieties gave similar affinities. The kinetic and equilibrium constants are comparable between the delipidated and non-delipidated forms of domain III suggesting that lipid molecules do not mediate or facilitate FcRn binding to domain III.

TABLE 1

The table provides SPR-derived kinetic and equilibrium constants for human FcRn binding to domain III of human serum albumin (HSA) and comparison with published kinetic constants for the full length HSA (lower panel).

| Immobilized DIII | Sensor Chip | Kinetic Analysis | | | Steady-State Analysis |
|---|---|---|---|---|---|
| | | $k_{on}$ (M$^{-1}$s$^{-1}$) | $k_{off}$(s$^{-1}$) | $k_D$ (µM) | $k_D$ (µM) |
| Delipidated | CM4 | 7.7e3 | 6.5e-2 | 8.5 | 7.9 |
| | CM5 | 7.2e3 | 5.1e-2 | 7.1 | 6.0 |
| | CM5 | 7.4e3 | 4.7e-2 | 6.3 | 5.5 |
| Non-delipidated | CM4 | 7.3e3 | 6.6e-2 | 9.1 | 8.4 |
| | CM5 | 7.8e3 | 6.5e-2 | 6.3 | 6.6 |
| | CM5 | 7.9e3 | 4.9e-2 | 5.7 | 6.2 |
| Immobilized HSA | CM5 | 9.3e3 | 4.5e-3 | 0.74 | 1.2 |

8.2 Example 2

Fusion with Full Length HSA or Domain III Alone Enhances the Affinity of Human IgG for FcRn This experiment demonstrated that fusion of domain III of HSA to a therapeutic protein or antibody, or a variant thereof, enhanced the affinity of the therapeutic protein/antibody for FcRn at acidic pH without influencing the pH dependence of the interaction. This increase in affinity for FcRn at pH 5.5 likely translates into an increased serum half-life (e.g., an enhanced lifespan in vivo or in an appropriate model system). Pharmacokinetic half-life measurements of an HSA portion comprising domain III fused to a therapeutic protein may be performed in, for example, transgenic mice expressing a single copy of human FcRn gene (but lacking murine FcRn) to evaluate the effects on half-life of fusion with a portion comprising wild type or variant domain III.

8.2.1 Construct Design

As a representative protein, human IgG1 was used to compare FcRn affinity between IgG alone and IgG fused with HSA or domain III. HSA or domain III was fused to the C-terminus of human IgG1 heavy chain via a linker comprising 4 repeating units of Gly-Gly-Gly-Gly-Ser (FIG. 2A). The length of the linker was designed based on the distance between the IgG binding site and HSA binding site on FcRn to allow both ligands to simultaneously bind their respective binding sites. An HSA and domain III fusion version of a previously described high affinity variant of IgG (IgG-YTE, see Dall'Acqua, et al., 2002, J. Immunol., 169:5171-5180) which shows 10-fold improved affinity for FcRn, relative to native IgG, was also created in a similar manner. Accordingly, the following constructs were made and used:

IgG
IgG(YTE)
IgG-$(G_4S)_4$-HSA
IgG-$(G_4S)_4$-Domain III
IgG(YTE)-$(G_4S)_4$-HSA
IgG(YTE)-$(G_4S)_4$-Domain III 8.2.2 Purification and Characterization Briefly, all 6 constructs were cloned into an expression vector and the proteins purified by transient expression in 293F cells (GIBCO Cat. No. R79007). The IgG1 and the fusion proteins secreted into the culture media were purified using a HiTrap™ Protein A affinity column (catalog no. 17-0403-03) from GE Healthcare. The purified proteins were resolved by SDS PAGE under both reducing and non-reducing conditions, and 99% purity was observed, as visualized by coomassie staining (FIG. 2B).

The estimated molecular weights of the IgG-$(G_4S)_4$-HSA fusion protein is 284 kilodaltons (KDa) while that of IgG-$(G_4S)_4$-Domain III is 196 KDa. The observed molecular weights correlated very well with these estimates. To evaluate whether these fusion proteins form aggregates due to their larger size or altered physicochemical properties, the fusion proteins were analyzed by size exclusion chromatography (SEC) using Agilent Technologies 1200 series SEC (FIG. 2C). Both IgG-$(G_4S)_4$-HSA and IgG-$(G_4S)_4$-Domain III show a single peak on an A280 vs retention time (min) plot corresponding to a monomer indicating that the fusion proteins do not aggregate to any measurable extent. The SEC profiles of the fusion proteins for the IgG-YTE variant were indistinguishable from the IgG-$(G_4S)_4$-HSA or IgG-$(G_4S)_4$-HSA chimeric proteins.

8.2.3 Measurement of Equilibrium Binding Constants ($K_D$)

The affinity ($K_D$) of human FcRn for the fusion proteins was measured on a BIAcore T100 instrument (Uppsala, Sweden). Briefly, human IgG, IgG-$(G_4S)_4$-Domain III, IgG-$(G_4S)_4$-HSA, IgG-YTE, IgG-YTE-$(G_4S)_4$-Domain III and IgG-YTE-$(G_4S)_4$-HSA were immobilized at high density onto separate flow cells on two Series 5 sensor chips (GE Healthcare), using standard amino coupling chemistry as outlined by the instrument manufacturer. Final surface IgG densities were 5116, 5258, 6097, 5256, 5561 and 5531 RUs, respectively. A reference flow cell was also prepared on each sensor chip without any protein using the identical immobilization protocol. Two-fold serial dilutions of human FcRn, ranging from 5.86 nM to 3000 nM, in 50 mM $PO_4$, 150 mM NaCl buffer at pH5.5 were injected over both the protein coupled and reference cell surfaces at a flow rate of 5 µL/min. Binding data was collected for 50 minutes, followed by regeneration with multiple 60 second injections of pH 7.4 Phosphate Buffered Saline containing 0.05% Tween20. The binding response at equilibrium (Req) for each injection was plotted against concentration and fit to a steady state affinity model (FIG. 3), using BIAcore T100 evaluation software, v. 1.1 (BIAcore, Inc, Uppsala, Sweden) to derive the equilibrium binding constant $K_D$. The inset represents the binding of a range of concentrations of FcRn to the immobilized ligands. The $K_D$ for the IgG-YTE variant and corresponding fusion proteins were also derived in identical manner (data not shown).

The $K_D$ of IgG-$(G_4S)_4$-HSA is 183 nM and that of IgG-$(G_4S)_4$-Domain III is 305 nM compared to 1.51 µM for IgG alone demonstrating that fusing HSA or Domain III to IgG improves FcRn affinity by 10 and 5 fold respectively (Table 2). A similar yet less pronounced trend is also observed for the YTE variants where the IgG-YTE-$(G_4S)_4$-HSA displays 3.8 fold (42.5 nM) and IgG-YTE-$(G_4S)_4$-Domain III shows 2.5 fold (65.1 nM) improvement in affinity relative to IgG-YTE (Table 2).

TABLE 2

The table provides SPR-derived equilibrium constants for human FcRn binding to IgG fused with HSA or IgG fused with domain III, as well as their YTE variant analogues at pH5.5.

| Construct | $K_D$ (nM) |
| --- | --- |
| IgG | 1510 |
| IgG-(G4S)4-HSA | 183 |
| IgG-(G4S)4-DIII | 305 |
| IgG-YTE | 161 |
| IgG-YTE-(G4S)4-HSA | 42.5 |
| IgG-YTE-(G4S)4-DIII | 65.1 |

The improvement in affinity at pH 5.5 however, does not influence FcRn binding at neutral pH. This was tested by injecting 1 µM FcRn at pH 7.2 over the same immobilized surface. No measurable difference in FcRn binding to any of the fusion protein coupled surfaces was detected (data not shown) as compared to the IgG/IgG-YTE controls.

Binding of the HSA-fusions to FcRn at acidic pH (~5.5-6.0), and release at neutral pH (~7.4) correlates with in vivo efficacy as such characteristics mimic in vivo binding. Accordingly, preferred HSA variants are (i) variants with improved affinity relative to native HSA or conjugates that include native HSA and (ii) variants for which the improved affinity is observed at acidic pH. Moreover, variants with increased binding affinity for FcRn at neutral pH may compromise efficacy and decrease the beneficial effects of increased affinity at acidic pH.

8.3 Example 3

Fusion with Full Length HSA Enhances the Serum Persistence of Human IgG

This experiment demonstrated that fusion of HSA to an antibody increased the serum half-life of an antibody. As shown in FIG. 7, the serum persistence of the IgG-HSA fusion described in Example 1 was increased as compared to IgG alone. The increase in serum half-life was comparable to that seen for the IgG-YTE variant. However, the addition of HSA to the IgG-YTE variant did not appear to result in a significant enhancement over YTE alone in this study.

The PK study was performed using 4-5 month old human FcRnC57BL/6 transgenic mice (JAX laboratories) that have the mouse neonatal Fc receptors (mFcRn) replaced with a single copy of human FcRn (huFcRn). The mice are injected via the tail vein with 15 mg/kg dose of the appropriate protein diluted in phosphate buffered saline pH 7.2. All animals are bled from the retro-orbital plexus to collect (75 µl) serum 1 hour post injection to determine the actual amount injected in circulation. Serum samples are then collected at 24, 72, 168 and 240 hours post injection and stored at −80° C. The amount of the indicated protein remaining in serum is analyzed by ELISA. Briefly, anti HSA coated plates are used to capture the various IgG fusion constructs and detected using anti-Kappa detection antibody. For IgG and YTE constructs, antigen coated plates are used to capture the IgG and detected using an anti-heavy chain detection antibody. The % of protein remaining in the serum is plotted as a fraction of amount injected (1 hour sample) versus time.

8.4 Example 4

The Epitope on HSA for FcRn is Conformational

Human FcRn was observed to bind native HSA well, in a concentration dependent fashion, as visualized by immunoblotting with anti-β-2 microglobulin antibody. However, similar results were not observed using denatured HSA tested under similar experimental conditions.

Human serum albumin (HSA; catalog no. A-8763), human IgG (hIgG; catalog no. I-4506) from Sigma-Aldrich, Tris buffer, were immobilized on CNBr-activated Sepharose 4B (GE HealthCare) at 10 mg protein/ml Sepharose. Sepharose-Tris was prepared by blocking the reactive groups of CNBr-activated Sepharose 4B with 0.1 M Trizma base, 0.5 M NaCl, pH 8. Sepharose beads linked to HSA, hIgG or Tris (20 µl beads equivalent to ~180 µg linked protein) were boiled for 10 minutes in the presence of SDS containing sample buffer (60 mM Tris, pH 6.8, 2.3% SDS, 10% glycerol, 0.01% bromophenol blue) under reducing (1% 2-mercaptoethanol) or non reducing conditions or left untreated. Protein or Tris coupled beads thus treated were washed with 50 mM Sodium phosphate, 150 mM NaCl buffer containing 0.1% fish gelatin (BIOFX Laboratories Inc, catalog no. PFGP-1000-01) at pH 5.5 and then incubated for 2 hours at room temperature with 200 µl of varying concentrations of human FcRn (0-20 µg) in pH 5.5 buffer. Unbound protein was washed away using pH 5.5 buffer. Bound protein was eluted by boiling with SDS-containing sample buffer containing 1% 2-mercaptoethanol, and was analyzed on a SDS polyacrylamide gel followed by immunoblotting with anti-132 microglobulin antibody (Abcam catalog no. Ab6608).

Binding of human FcRn to Sepharose-HSA was maximal for the native HSA for the entire FcRn concentration range. However, the binding was drastically diminished when HSA was denatured under both reducing and non-reducing conditions, suggesting that the epitope on HSA for FcRn is most likely a conformational epitope. (FIG. 4). As expected, Sepharose-IgG bound human FcRn while Tris blocked beads did not bind FcRn under any conditions.

8.5 Example 5

HSA and Domain III Can be Displayed on the Surface of Yeast Cells and the Displayed Proteins Retain FcRn Binding Capacity This example demonstrates that HSA and Domain III can both be successfully expressed on the surface of yeast cells and that these displayed proteins bind FcRn in a pH dependent manner, as assessed by modified flow cytometry performed at acidic pH. Thus, expression on yeast cells provides one method for screening constructs (e.g., domain III alone, full length HSA, truncated HSA or chimeric polypeptide comprising at least domain III) containing variation in Domain III to assess the ability of such constructs (i) to bind FcRn and (ii) to bind FcRn with increased affinity relative to, for example, non-variant constructs.

8.5.1 Yeast Cell Surface Display

HSA, Domain III or a single chain Fv fragment (scfv), were cloned into the pYD1 Yeast Display Vector (Invitrogen Catalog no. V835-01) and transformed into *S. cerevisiae* for presentation on the yeast cell surface. pYD1 displays the protein of interest as a C-terminus fusion with the *S. cerevisiae* protein Aga2p under the control of a galactose inducible promoter. All experimental procedures were performed as described in the supplier's manual. The transformed cells were selected using auxotrophic selection markers uracil and tryptophan, and were cultured in appropriate selection media (Teknova Inc., Catalog no. C8140). The cultures were induced with galactose for up to 48 hours to allow expression of Aga2p fusion proteins. Cells were sampled at 0, 24 and 48 hours. The cell samples were washed and blocked with pH 7.2 PBS containing 0.1% fish gelatin, stained with a FITC conjugated rabbit polyclonal anti-HSA antibody (Abcam Inc., Catalog no. AB34669), and analyzed by flow cytometry.

No cell surface expression of HSA or Domain III was observed at 0 hours, while expression of both proteins on the yeast cells was observed at 24 hours. Such expression was maintained at 48 hours post induction. Expression was visualized by positive FITC staining FIG. 5A shows that both HSA and Domain III can be successfully expressed on the surface of yeast cells. The scfv transformed cells did not stain (e.g., were negative) with anti-HSA, as expected. Thus, the scfv transformed cells served as a negative control.

8.5.2 FcRn Binding Capacity of Surface Expressed HSA or Domain III

Yeast cells expressing HSA, Domain III or scfv and induced with galactose for 48 hours were blocked with pH 5.5, 50 mM Sodium Phosphate, 150 mM NaCl buffer (also referred to as FACS buffer) containing 0.1% Fish Gelatin for 1 hour. The cells were then incubated with biotinylated FcRn (70 µM) in pH 5.5 phosphate buffer and the bound FcRn visualized using Streptavidin phycoerythrin (PE) (Invitrogen Inc.). The cells so stained were analyzed by flow cytometry with a pH 5.5 50 mM Sodium Phosphate, 150 mM NaCl buffer instead of the routinely used PBS.

Both HSA and Domain III expressing cells stained positive for PE, while negative control scfv expressing cells did not, as seen from the shift in the histogram compared to that for scfv (FIG. 5B), demonstrating that HSA and Domain III expressed on yeast cell surfaces retain FcRn binding capacity and are therefore functional. In a separate experiment, the cells were treated similarly as the low pH flow cytometry for FcRn binding and assayed using a high throughput sampling technique, HyperCyt® System (IntelliCyt Corporation) with similar results.

8.6 Example 6

Figure 8A:
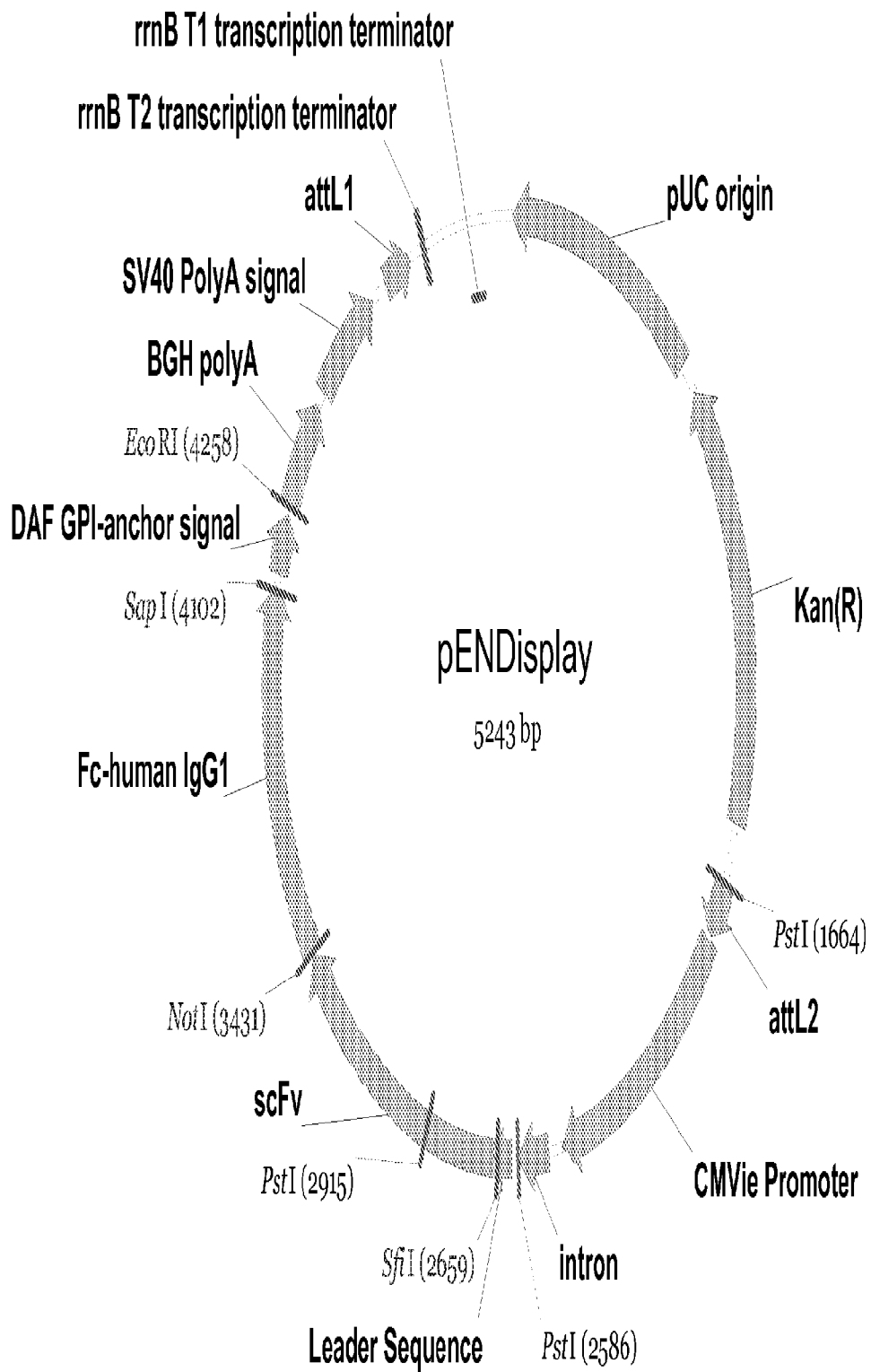

Adenovirus Mammalian Cell Surface Display Vectors Comprising OriP for Generating Libraries with High Diversity A mammalian surface display library using a Glycosylphosphatidylinositol (GPI)-anchor for surface display of scFv-Fc proteins was constructed in a Gateway® entry vector that was engineered to contain an scFv-Fc expression cassette designated pENDisplay (see FIG. 8A). The library of different scFv sequences is readily inserted into the Sfi/NotI sites. The library in the pENDisplay vector was combined with the pAd/PL-DEST™ vector (Invitrogen Cat. No. V494-20) vector as per the manufacturer to generate an adenovirus expression library, a total of ~5×10$^6$ colony forming units (cfu) were obtained. To generate adenovirus, 293A cells (Invitrogen Cat. No. R70507), which contain a stably integrated copy of the E1 gene that supplies the E1 proteins (E1a and E1b) required to generate recombinant adenovirus in trans, are transfected with adenovirus expression library that has been linearized to expose the left and right Inverted Terminal Repeats (ITRs). At least 50% of 293A cells transfected directly with the linearized adenovirus library were found to display antibody on their surface by FACS analysis. However, when linearized adenovirus library was transfected into 293A cells for production of adenovirus fewer than 50 plaques per 110 mm (diameter) dish were obtained. The adenovirus were harvested at day 10 and the viral DNA was isolated, PCR was used to amplify the scFv coding region which was re-cloned back into the pENDisplay vector, 96 colonies were picked and sequenced. Only 14 unique VH sequence were identified from the 96 clones analyzed. The low efficiency of plaque recovery may be due to degradation of the linearized adenovirus vector and results in a significant reduction in the complexity of the adenovirus library.

Figure 8B:
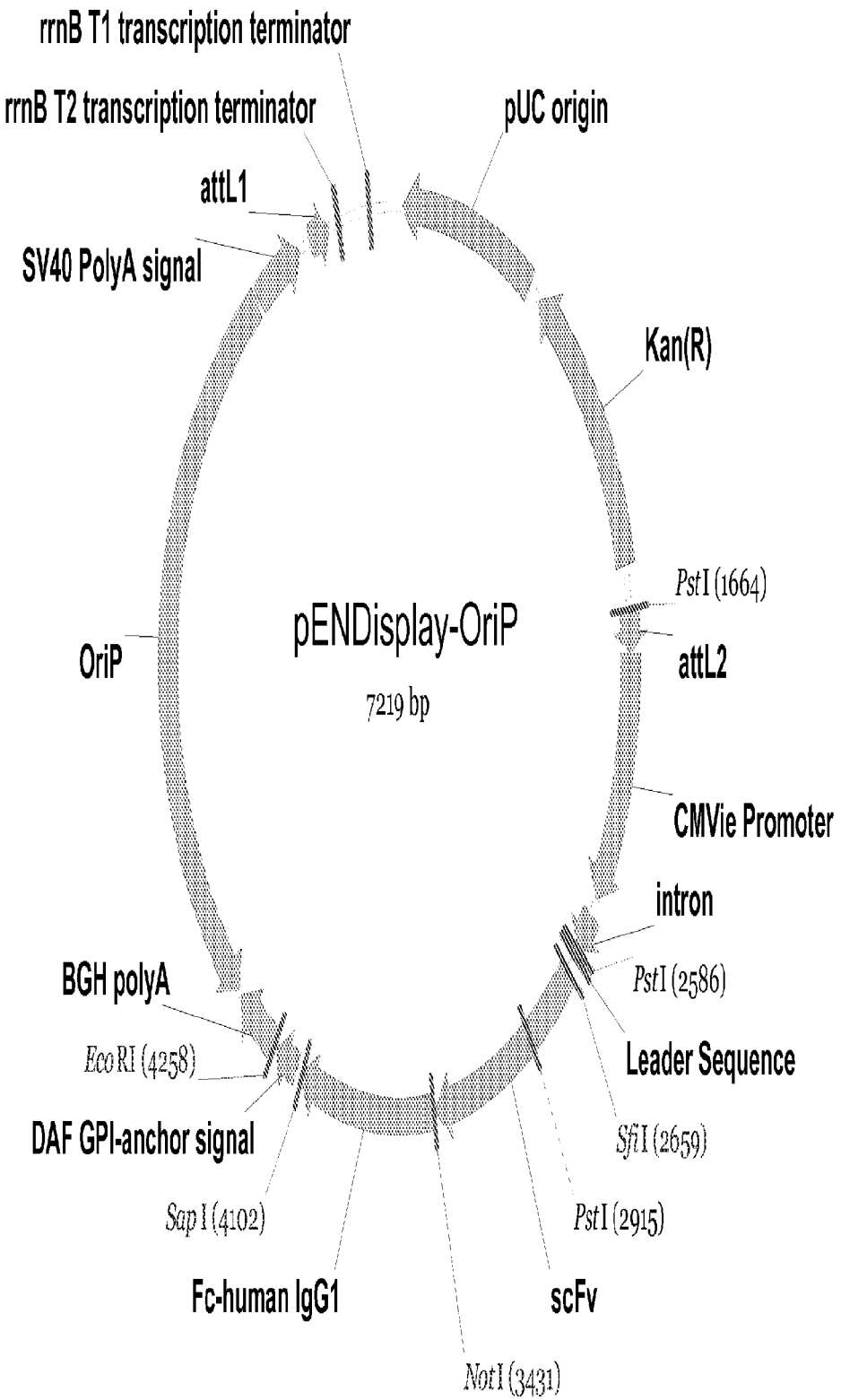

The Epstein-Barr nuclear antigen 1 (EBNA-1) contains a nuclear localization signal (NLS) and binds to OriP containing nucleic acids such as plasmids. EBNA-1 protein (see FIG. 9A) may help to translocate OriP containing nucleic acids to the nucleus via the NLS and enhance episomal maintenance. Although episomal maintained is not thought to be required for adenovirus rescue an OriP sequence (see FIG. 9C) was introduced after the polyA sequence of the scFv-Fc cassette between the attL1 and attL2 sequences, of the pENDisplay vector. The new vector designated pENDisplay-OriP is depicted in FIG. 8B. The library in the pENDisplay-OriP was combined with the pAd/PL-DEST™ vector (Invitrogen Cat. No. V494-20) vector to generate a second adenovirus expression library also having ~5×10$^6$ cfu. The library generated from the pENDisplay-OriP vector was linearized and transfected into 293E cells (Invitrogen Cat. No. R620-07), which stably expresses the Epstein-Barr virus nuclear antigen (EBNA-1) and the adenovirus E1a protein, resulting in well over 10,000 plaques per 110 mm (diameter) dish. The virus were harvested at day 7 and 96 clones were analyzed as described above. In contrast to the low number of unique clones isolated from the first library, without an OriP site, all 96 VH sequences analyzed were unique. Together these results demonstrate that the addition of the OriP sequence to the adenovirus expression library vector greatly enhanced both the rescue of adenovirus from cells expressing EBNA-1 and the diversity of the adenovirus library.

The addition of the OriP sequence (e.g. FIG. 9C) to an adenovirus vector enhances the efficiency of generation of recombinant adenovirus particles from host cells in the presence of EBNA-1 protein. When constructing adenovirus expression libraries the enhanced efficiency of virus generation maintains the diversity/complexity of the library by reducing the number of clones lost. Example 7, below, details the construction and screening of a mammalian surface display library expressing HSA Domain III variants that incorporates the OriP sequence into an adenovirus expression vector essentially as described above.

FIG. 10 provides a schematic of a representative generic adenovirus expression vector for expression of protein(s) of interest. In this example a mutant adenovirus genome is provided in which the E1 and/or E3 portions are deleted. The missing viral genes are provided in trans by the host cell used for viral rescue. The deletions prevent replication of the adenovirus in the host cell used for expression of the protein(s) of interest. The DNA of interest will include all the components required for expression of the protein(s) including, but not limited to, the coding sequence(s), promoter sequence(s), termination signal(s), polyA sequence(s), etc. The protein(s) of interest may be soluble or may include a sequence that will anchor the protein(s) to the cell surface, such as a transmembrane domain or a GPI-anchor signal. As exemplified herein, adenovirus vectors may be engineered to express a library of variant proteins. The adenovirus expression vector depicted in FIG. 10 provides the location of att recombination sites that would result from using Gateway™ entry and destination plasmids for construction. Also depicted is one possible location where an EBNA-1 DNA sequence could be located. Other locations and orientations for the vector components are contemplated. It will be understood by one of skill in the art that the orientation and/or relative position of the vector regions may be varied.

8.7 Example 7

Use of Other Display Platforms for HSA and Domain III

Phage display and mammalian cell surface display technologies were also evaluated as potential display platforms for HSA and Domain III. A phage display platform did not express either HSA and Domain III on the surface of the bacterial cells, presumably due to the abundance of disulfide bonds in these molecules (data not shown). However, the mammalian cell display system using transient surface expression in 293-F cells mediated via Glycosylphosphatidylinisotol (GPI)-anchor signal from Decay Accelerating Factor (e.g. the mutated DAF as described in US 2007/0111260) was successful for displaying HSA and Domain III. The displayed proteins retained FcRn binding capacity (data not shown).

Figure 11A:
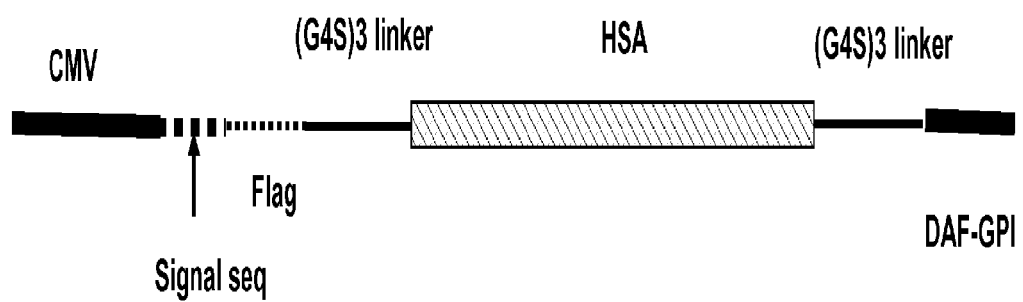
Figure 11B:
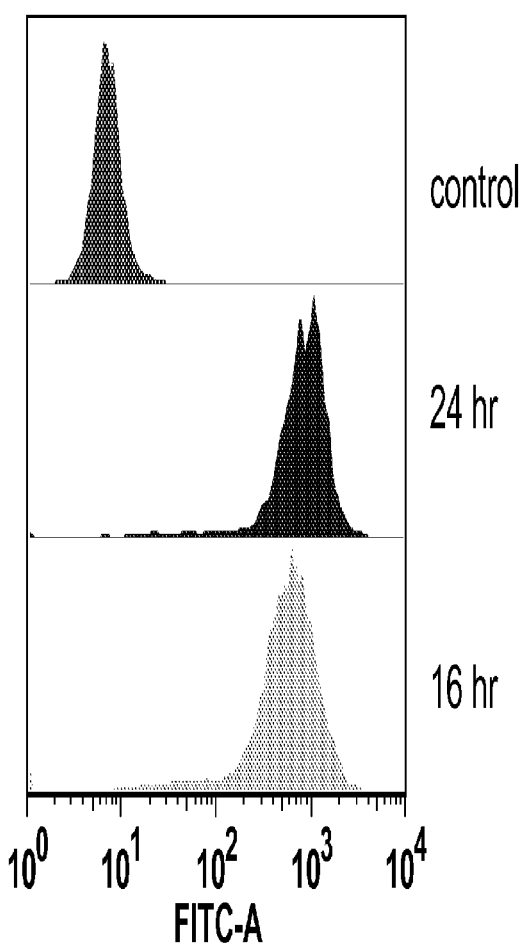
Figure 11C:
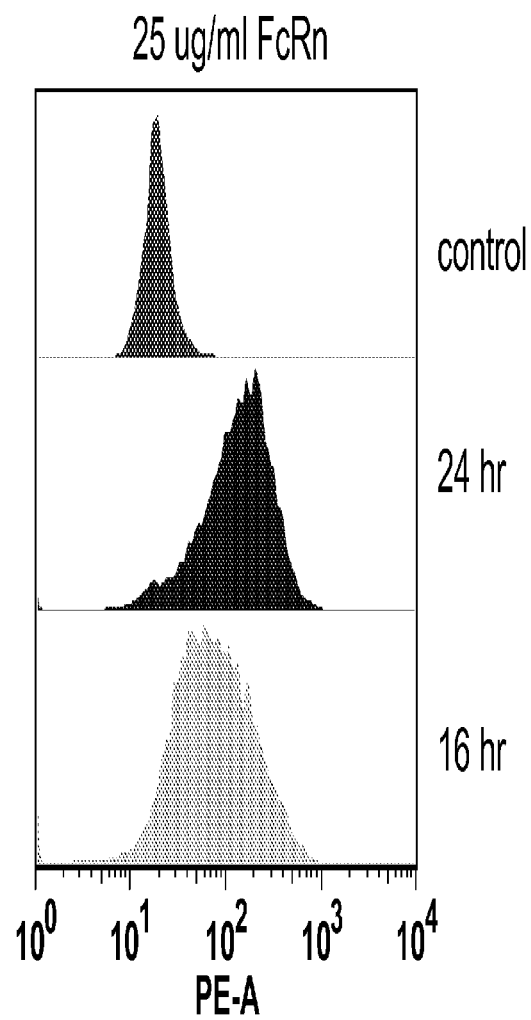
Figure 11D:
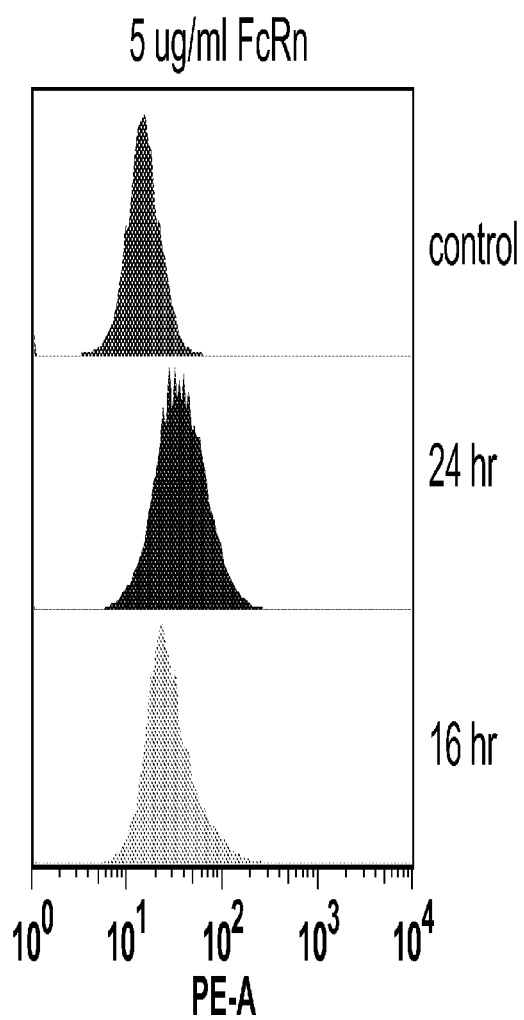

An additional mammalian expression construct, designated pEN-HSA-GPI, was generated in which an epitope tag (e.g., Flag tag) was added for double staining and linkers were added both 5' and 3' of the HSA to increase the flexibility of the fusion protein and facilitate HSA binding to FcRn (FIG. 11A), this construct was used directly for transient transfection or was used to generate an adenoviral expression vector that also incorporates the OriP sequence, designated pAd-HSA-GPI. Functional HSA was expressed on the surface of mammalian cells (e.g. 293F cells) from this construct in both transient transfection assays (data not shown) and using the adenoviral expression system. FIG. 11 shows the resulting shift in the histogram of cells stained with anti-HSA (FIG. 11B) or FcRn at 25 µg/ml and 5 µl/ml (FIGS. 11C and 11D, respectively). Thus, several potential systems exist for expressing HSA and Domain III variants, and for screening such variants for (i) binding to FcRn and (ii) ability to bind FcRn with increased affinity relative to, for example, non-variant constructs.

Transfection of 293F Cells to Display HSA on Cell Surface:

1.5 µg of plasmid and 2.25 µl of 293 fectin were added to 100 µl of Optimem medium (Invitrogen) in a separate tube, incubated at RT for 5 min, and then the two components combined together. After incubation at room temperature for additional 20 min, the mixture was added in to 2 ml of 293F cells at the density of 1×10$^6$ cells/ml in 24 deep well plate. The transfected cells were grown for 24 hours at 250 rpm in the presence of 8% $CO_2$.

Generation and Use of Adenovirus Expression Vector:

Gateway® technology (Invitrogen) was used to recombine HSA in entry vector (pEN-HSA-GPI) to Invitrogen destination vector to generate adenoviral expression vector. Briefly, 150 ng of pEN-HSA-GPI vector, 300 ng of pAd/PL-DEST (Invitrogen), 2 μl of LR Clonase II (Invitrogen), and TE buffer were added to a total of 10 μl reaction mixtures. After incubation at 25° C. for overnight, 2 μl of the reaction mixture was used to transform One-shot Top 10 competent cells (Invitrogen) following manufacturer's protocol. The transformed TOP 10 cells were plated on Ampicillin plate and incubated at 37° C. over night. Single colonies were picked into LB medium to prepare plasmid. HSA gene containing adenoviral expression vector was linearized with Pac I before transfection to generate adenovirus. 2 μg of linearized adenoviral vector and 6 μl of lipofecatine-2000 were used to transfect 293E cells to produce adenovirus. 7 days post transfection, the adenovirus was released from the transfected cells by alternately freezing (at −80° C.) and thawing (at 37° C.) 2-3 times. The cell debris were removed by centrifugation at 3000 rpm for 10 minutes and the adenovirus containing supernatant was aliquotted into the new tubes and stored at −80 C. The viral titer was determined using Adeno-XTM rapid titer kit (Clontech:PT3651-2) according to manufacturer's instructions. The adenovirus was used at an MOI of 1 for expression of HSA constructs.

8.8 Example 8

Alanine Scanning Mutagenesis of Surface Exposed Loops on DIII to Identify the FcRn Binding Epitope This example delineates the role of surface exposed loops on Domain III in mediating FcRn binding to HSA.

Domain III is composed of 205 amino acid residues and encodes 10 helices linked via 9 loops and stabilized through 6 disulfide bonds (Sugio et al. 1999, Protein Eng. 12:439-46 and PDB: 1BM0). The positions of the amino acid residues that comprise these loops, as well as the length of each loop are listed below. Amino acid numbering is relative to the position of these loops in the full length mature HSA protein (SEQ ID NO: 2).

Loop 1: residues 398-400=3 amino acids
Loop 2: residues 415-419=5 amino acids
Loop 3: residues 439-443=5 amino acids
Loop 4: residues 468-470=3 amino acids
Loop 5: residues 480-482=3 amino acids
Loop 6: residues 492-509=18 amino acids
Loop 7: residues 516-517=2 amino acids
Loop 8: residues 537-541=5 amino acids
Loop 9: residues 561-564=4 amino acids Loops numbered 2, 3, 6, 8 and 9 are solvent accessible and exposed on the surface of the molecule (Sugio et al. ibid, and PDB: 1BM0).

In certain examples, alternate amino acids in each individual surface accessible loop are mutated to alanine (except prolines and cysteines, which are not mutated) with odd numbered residues mutated in one set and even numbered residues mutated in another set. Two such mutant sets per loop are created with the exception of loop 9 where only one construct is needed to fit the experimental design. A total of 9 such constructs are created in a vector for cell surface display (e.g., the pYD1 yeast display vector) and evaluated for FcRn binding capacity. Variants may be evaluated using standard in vitro assays described in the application (e.g., flow cytometry). Variant(s) that display improved affinity for FcRn are identified. Each variant may also screened to determine whether the improved affinity for FcRn occurs only at acidic pH, but not a neutral pH. Improved affinity for FcRn at acidic pH but not neutral pH may be tested for (i) variant domain III constructs alone; (ii) variant domain III constructs presented in the context of full length HSA; or (iii) in the context of truncated HSA or a chimeric polypeptide comprising at least domain III. The foregoing are compared to wildtype domain III, a wildtype full length HSA, or chimeric polypeptide without the mutations.

In certain examples, the information obtained from the foregoing screen identifies residues in the surface accessible loops that are amenable to variation while maintaining (or even improving) FcRn binding capacity. A series of variants in which such identified positions are mutated to each of the other 20 amino acids are constructed, and such variant are also screened. Further variants that include mutations at more than one position are subsequently constructed and screened.

In certain examples, a library of variants is created and evaluated.

8.9 Example 9

Alanine Scanning Mutagenesis of Conserved, Surface Exposed Residues

The surface accessible amino acid residues conserved in Domain III amongst 13 different animal species were identified by amino acid sequence alignment. Such conserved residues are singly mutated to alanine to determine their role in FcRn binding.

The Domain III amino acid sequence of HSA was compared with serum albumin Domain III sequences from 12 different species including rat, mouse, bovine, dog, rabbit, pig, chicken, donkey, Mongolian gerbil, sheep, cat and horse and the residues that are conserved amongst all these species were identified (FIG. 6A-D). As chicken HSA is distinct from mammalian HSA proteins a second alignment is provided of just the mammalian species (FIG. 6E-H). Serum albumin from pig, rat, mouse, dog, sheep, rabbit and bovine have already been shown to bind human FcRn by ELISA, Immunoblotting and SPR (data not shown). In a separate analysis, the surface exposed residues in Domain III were identified using GETAREA 1.0 beta software available on the internet (http://curie.utmb.edu/getarea.html). This software calculates accessible surface areas of individual atoms and their gradients and scores each amino acid residue for likelihood of surface accessibility expressed as "i" or "o", indicating inaccessible and accessible respectively (Table 3). The amino acids that are both conserved amongst all of these different species and surface exposed, as computed by the software and confirmed by manual inspection of the HSA crystal structure, were identified (Boxed in Table 3).

All 18 amino acid residues thus identified are singly mutated to alanine and evaluated for impact on FcRn binding using cell surface display (e.g., the pYD1 yeast display system). The domain III mutations are introduced and screened in the context of on or more of the following: domain III alone, the full HSA protein, truncated HSA or a chimeric polypeptide comprising at least domain III. The conserved, surface exposed cysteine and prolines are not included in the analysis.

In another example, all 18 amino acid residues (or fewer that all 18 if the alanine experiment indicates that particular positions cannot tolerate substitution) are singly mutated to each of the other 19 amino acid residues and evaluated for impact on FcRn binding using the pYD1 yeast display system (or another display system).

In another example, variants that include combinations of mutations are constructed and evaluated. Variants may be evaluated using standard in vitro assays described in the application (e.g., flow cytometry). Variant(s) that display improved affinity for FcRn are identified. Each variant may also screened to determine whether the improved affinity for FcRn occurs only at acidic pH, but not a neutral pH. Improved affinity for FcRn at acidic pH but not neutral pH is tested for one or more of the following (i) variant domain III constructs alone; (ii) variant domain III constructs in the context of full length HSA, or (iii) in the context of truncated HSA or a chimeric polypeptide comprising at least domain III. The foregoing are compared to wildtype domain III, wildtype full length HSA, or chimeric polypeptide without the mutations.

TABLE 3

| | Residue | | Total | Apolar | Back-bone | Side-chain | Ratio (%) | In/Out |
|---|---|---|---|---|---|---|---|---|
| @@ | LEU | 380 | 56.42 | 56.02 | 0.75 | 55.67 | 38.1 | |
| @@ | VAL | 381 | 19.57 | 19.57 | 0.00 | 19.57 | 16.0 | i |
| | GLU | 382 | 99.24 | 31.30 | 0.67 | 98.57 | 69.8 | o |
| | GLU | 383 | 69.94 | 52.61 | 5.53 | 64.41 | 45.6 | |
| @@ | PRO | 384 | 0.05 | 0.05 | 0.00 | 0.05 | 0.1 | i |
| | GLN | 385 | 82.77 | 29.45 | 6.62 | 76.15 | 53.0 | o |
| | ASN | 386 | 78.25 | 23.65 | 1.24 | 77.01 | 67.4 | o |
| @@ | LEU | 387 | 32.41 | 32.41 | 3.66 | 28.75 | 19.7 | i |
| | ILE | 388 | 11.04 | 11.04 | 2.42 | 8.62 | 5.9 | i |
| | LYS | 389 | 98.41 | 0.70 | 0.70 | 97.71 | 59.4 | o |
| | GLN | 390 | 119.91 | 30.84 | 1.91 | 117.99 | 82.1 | o |
| | ASN | 391 | 24.47 | 5.20 | 0.08 | 24.39 | 21.3 | |
| ## | CYS | 392 | 5.45 | 2.53 | 0.11 | 5.34 | 5.2 | i |
| | GLU | 393 | 99.50 | 48.97 | 2.36 | 97.14 | 68.8 | o |
| | LEU | 394 | 63.00 | 63.00 | 0.87 | 62.13 | 42.5 | |
| | PHE | 395 | 31.26 | 30.80 | 0.46 | 30.80 | 17.1 | i |
| @@ | GLU | 396 | 114.69 | 53.25 | 27.05 | 87.64 | 62.1 | o |
| | GLN | 397 | 140.39 | 48.20 | 36.11 | 104.28 | 72.6 | o |
| | LEU | 398 | 37.07 | 28.66 | 11.72 | 25.35 | 17.3 | i |
| ## | GLY | 399 | 38.33 | 37.17 | 38.33 | 0.00 | 44.0 | |
| | GLU | 400 | 67.29 | 26.00 | 3.58 | 63.71 | 45.1 | |
| @@ | TYR | 401 | 45.66 | 45.21 | 0.90 | 44.76 | 23.2 | |
| | LYS | 402 | 110.95 | 67.17 | 1.41 | 109.53 | 66.6 | o |
| ## | PHE | 403 | 0.77 | 0.77 | 0.00 | 0.77 | 0.4 | i |
| @@ | GLN | 404 | 2.71 | 0.00 | 0.00 | 2.71 | 1.9 | i |
| @@ | ASN | 405 | 11.20 | 10.68 | 0.03 | 11.17 | 9.8 | i |
| @@ | ALA | 406 | 27.44 | 24.63 | 11.95 | 15.49 | 23.9 | |
| | LEU | 407 | 4.22 | 4.22 | 0.00 | 4.22 | 2.9 | i |
| | LEU | 408 | 0.25 | 0.25 | 0.00 | 0.25 | 0.2 | i |
| @@ | VAL | 409 | 21.68 | 21.68 | 0.09 | 21.59 | 17.7 | i |
| | ARG | 410 | 71.52 | 60.94 | 5.56 | 65.95 | 33.7 | |
| ## | TYR | 411 | 7.20 | 1.62 | 0.00 | 7.20 | 3.7 | i |
| ## | THR | 412 | 0.05 | 0.05 | 0.00 | 0.05 | 0.1 | i |
| | LYS 413 | | 25.26 | 23.68 | 3.75 | 21.51 | 13.1 | i |
| ## | LYS | 414 | 11.99 | 7.84 | 0.02 | 11.97 | 7.3 | i |
| | VAL | 415 | 0.20 | 0.20 | 0.04 | 0.16 | 0.1 | i |
| ## | PRO | 416 | 3.69 | 2.47 | 1.22 | 2.47 | 2.3 | i |
| | GLN | 417 | 52.78 | 30.06 | 14.94 | 37.84 | 26.3 | |
| ## | VAL | 418 | 3.63 | 3.62 | 1.19 | 2.44 | 2.0 | i |
| @@ | SER | 419 | 54.77 | 51.36 | 9.44 | 45.33 | 58.6 | o |
| ## | THR | 420 | 9.84 | 7.74 | 0.88 | 8.96 | 8.4 | i |
| @@ | PRO | 421 | 101.86 | 100.54 | 10.53 | 91.33 | 86.8 | o |
| @@ | THR | 422 | 11.77 | 1.22 | 0.72 | 11.04 | 10.4 | |
| ## | LEU | 423 | 1.05 | 1.05 | 0.00 | 1.05 | 0.7 | i |
| | VAL | 424 | 5.56 | 5.56 | 0.00 | 5.56 | 4.5 | i |
| | GLU | 425 | 66.36 | 34.10 | 4.64 | 61.72 | 43.7 | |
| | VAL | 426 | 0.54 | 0.54 | 0.00 | 0.54 | 0.4 | i |
| | SER | 427 | 0.00 | 0.00 | 0.00 | 0.00 | 0.0 | i |
| @@ | ARG | 428 | 28.01 | 6.40 | 0.00 | 28.01 | 14.3 | i |

TABLE 3-continued

| | Residue | | Total | Apolar | Back-bone | Side-chain | Ratio (%) | In/Out |
|---|---|---|---|---|---|---|---|---|
| | ASN | 429 | 27.74 | 1.54 | 0.00 | 27.74 | 24.3 | |
| @@ | LEU | 430 | 7.30 | 7.09 | 0.21 | 7.09 | 4.9 | i |
| @@ | GLY | 431 | 0.00 | 0.00 | 0.00 | 0.00 | 0.0 | i |
| | LYS | 432 | 80.30 | 40.11 | 0.01 | 80.29 | 48.8 | |
| @@ | VAL | 433 | 11.51 | 11.51 | 0.00 | 11.51 | 9.4 | i |
| ## | GLY | 434 | 0.14 | 0.02 | 0.14 | 0.00 | 0.2 | i |
| | SER | 435 | 57.78 | 16.10 | 14.45 | 43.33 | 56.0 | o |
| | LYS | 436 | 85.65 | 58.15 | 10.32 | 75.33 | 45.8 | |
| ## | CYS | 437 | 0.35 | 0.35 | 0.00 | 0.35 | 0.3 | i |
| ## | CYS | 438 | 8.30 | 1.53 | 6.41 | 1.89 | 1.8 | i |
| | LYS | 439 | 162.28 | 116.42 | 39.17 | 123.11 | 74.8 | o |
| | HIS | 440 | 38.03 | 24.38 | 3.93 | 34.10 | 22.1 | |
| @@ | PRO | 441 | 89.28 | 89.28 | 13.53 | 75.75 | 72.0 | o |
| | GLU | 442 | 121.29 | 28.48 | 25.71 | 95.58 | 67.7 | o |
| | ALA | 443 | 63.34 | 57.69 | 17.11 | 46.23 | 71.2 | o |
| | LYS | 444 | 132.96 | 87.59 | 1.81 | 131.15 | 79.7 | o |
| ## | ARG | 445 | 25.14 | 7.16 | 0.00 | 25.14 | 12.9 | i |
| | MET | 446 | 10.99 | 10.94 | 0.05 | 10.94 | 6.9 | i |
| | PRO | 447 | 29.51 | 28.45 | 1.15 | 28.37 | 27.0 | |
| ## | CYS | 448 | 28.63 | 21.61 | 16.45 | 12.17 | 11.9 | i |
| | ALA | 449 | 2.04 | 2.04 | 0.00 | 2.04 | 3.1 | i |
| ## | GLU | 450 | 0.00 | 0.00 | 0.00 | 0.00 | 0.0 | i |
| | ASP | 451 | 36.51 | 31.08 | 1.41 | 35.10 | 31.1 | |
| | TYR | 452 | 40.33 | 35.83 | 5.38 | 34.95 | 18.1 | i |
| ## | LEU | 453 | 14.95 | 14.95 | 0.00 | 14.95 | 10.2 | i |
| | SER | 454 | 11.34 | 10.42 | 2.62 | 8.72 | 11.3 | i |
| | VAL | 455 | 15.44 | 14.89 | 0.55 | 14.89 | 12.2 | i |
| | VAL | 456 | 4.31 | 4.31 | 0.71 | 3.60 | 2.9 | i |
| @@ | LEU | 457 | 0.66 | 0.66 | 0.00 | 0.66 | 0.4 | i |
| @@ | ASN | 458 | 0.55 | 0.01 | 0.00 | 0.55 | 0.5 | i |
| | GLN | 459 | 30.73 | 11.43 | 0.96 | 29.78 | 20.7 | |
| | LEU | 460 | 0.81 | 0.81 | 0.00 | 0.81 | 0.6 | i |
| ## | CYS | 461 | 5.78 | 5.21 | 0.59 | 5.19 | 5.1 | i |
| | VAL | 462 | 12.56 | 11.51 | 1.05 | 11.51 | 9.4 | i |
| @@ | LEU | 463 | 11.00 | 11.00 | 0.00 | 10.99 | 7.5 | |
| @@ | HIS | 464 | 8.67 | 7.03 | 4.93 | 3.74 | 2.4 | i |
| | GLU | 465 | 81.88 | 39.50 | 12.23 | 69.65 | 49.3 | |
| @@ | LYS | 466 | 123.40 | 80.33 | 29.10 | 94.30 | 57.3 | o |
| | THR | 467 | 66.67 | 56.99 | 5.55 | 61.12 | 57.6 | o |
| | PRO | 468 | 92.50 | 70.96 | 21.54 | 70.96 | 67.5 | o |
| @@ | VAL | 469 | 90.51 | 73.61 | 23.88 | 66.63 | 54.5 | o |
| @@ | SER | 470 | 5.53 | 4.62 | 5.14 | 0.39 | 0.5 | i |
| | ASP | 471 | 122.67 | 42.14 | 3.75 | 118.92 | 100.0 | o |
| | ARG | 472 | 92.31 | 48.09 | 3.99 | 88.32 | 45.2 | |
| | VAL | 473 | 0.00 | 0.00 | 0.00 | 0.00 | 0.0 | i |
| @@ | THR | 474 | 57.41 | 55.78 | 2.30 | 55.11 | 51.9 | o |
| @@ | LYS | 475 | 131.17 | 87.36 | 4.11 | 127.07 | 77.2 | o |
| ## | CYS | 476 | 0.27 | 0.00 | 0.00 | 0.27 | 0.3 | i |
| ## | CYS | 477 | 14.41 | 11.81 | 2.60 | 11.81 | 11.5 | i |
| | THR | 478 | 89.89 | 62.73 | 11.19 | 78.69 | 74.1 | o |
| | GLU | 479 | 98.03 | 36.44 | 36.37 | 61.66 | 43.7 | |
| @@ | SER | 480 | 18.58 | 18.58 | 4.99 | 13.59 | 17.6 | i |
| @@ | LEU | 481 | 19.63 | 15.94 | 3.69 | 15.94 | 10.9 | i |
| | VAL | 482 | 11.85 | 10.99 | 0.87 | 10.99 | 9.0 | i |
| | ASN | 483 | 39.73 | 8.35 | 0.00 | 39.73 | 34.8 | |
| ## | ARG | 484 | 11.05 | 4.76 | 0.00 | 11.05 | 5.7 | i |
| ## | ARG | 485 | 5.72 | 5.41 | 0.30 | 5.41 | 2.8 | i |
| | PRO | 486 | 23.90 | 21.92 | 2.55 | 21.35 | 20.3 | |
| ## | CYS | 487 | 20.34 | 9.90 | 8.30 | 12.03 | 11.8 | i |
| ## | PHE | 488 | 0.15 | 0.15 | 0.00 | 0.15 | 0.1 | i |
| @@ | SER | 489 | 28.76 | 10.00 | 17.50 | 11.26 | 14.5 | i |
| | ALA | 490 | 84.33 | 64.50 | 32.36 | 51.97 | 80.1 | o |
| @@ | LEU | 491 | 25.03 | 17.27 | 8.78 | 16.25 | 11.1 | i |
| | GLU | 492 | 127.22 | 68.17 | 2.88 | 124.34 | 88.1 | o |

TABLE 3-continued

| | Residue | | Total | Apolar | Back-bone | Side-chain | Ratio (%) | In/Out |
|---|---|---|---|---|---|---|---|---|
| | VAL | 493 | 59.47 | 50.11 | 9.36 | 50.11 | 41.0 | |
| ## | ASP | 494 | 23.97 | 5.10 | 11.99 | 11.99 | 10.6 | i |
| @@ | GLU | 495 | 151.35 | 58.71 | 32.51 | 118.84 | 84.2 | o |
| | THR | 496 | 128.82 | 92.46 | 28.49 | 100.33 | 94.5 | o |
| ## | TYR | 497 | 39.86 | 23.56 | 15.79 | 24.07 | 12.5 | i |
| | VAL | 498 | 127.91 | 120.24 | 7.78 | 120.14 | 98.2 | o |
| | PRO | 499 | 48.26 | 38.96 | 9.29 | 38.96 | 37.0 | |
| @@ | LYS | 500 | 148.50 | 107.74 | 5.26 | 143.24 | 87.1 | o |
| | GLU | 501 | 137.88 | 67.19 | 7.44 | 130.44 | 92.4 | o |
| | PHE | 502 | 145.85 | 127.83 | 18.01 | 127.83 | 71.0 | o |
| | ASN | 503 | 79.74 | 11.97 | 2.89 | 76.85 | 67.2 | o |
| | ALA | 504 | 67.05 | 47.09 | 20.71 | 46.34 | 71.4 | o |
| | GLU | 505 | 112.60 | 25.86 | 4.28 | 108.31 | 76.7 | o |
| | THR | 506 | 61.97 | 54.22 | 17.79 | 44.18 | 41.6 | |
| ## | PHE | 507 | 39.42 | 28.99 | 10.43 | 28.99 | 16.1 | i |
| @@ | THR | 508 | 34.75 | 25.10 | 10.55 | 24.20 | 22.8 | |
| ## | PHE | 509 | 7.64 | 6.14 | 3.09 | 4.55 | 2.5 | i |
| @@ | HIS | 510 | 92.59 | 80.12 | 2.75 | 89.84 | 58.1 | o |
| | ALA | 511 | 33.98 | 30.78 | 3.23 | 30.75 | 47.4 | |
| | ASP | 512 | 79.47 | 46.67 | 5.24 | 74.23 | 65.7 | o |
| | ILE | 513 | 0.51 | 0.51 | 0.00 | 0.51 | 0.3 | i |
| ## | CYS | 514 | 42.31 | 19.66 | 23.41 | 18.90 | 18.5 | i |
| @@ | THR | 515 | 123.18 | 80.99 | 37.55 | 85.63 | 80.6 | o |
| @@ | LEU | 516 | 48.28 | 43.20 | 7.83 | 40.45 | 27.7 | |
| | SER | 517 | 54.47 | 51.13 | 20.10 | 34.38 | 44.4 | |
| | GLU | 518 | 100.49 | 23.48 | 2.18 | 98.32 | 69.6 | o |
| | LYS | 519 | 138.34 | 93.44 | 0.25 | 138.09 | 83.9 | o |
| | GLU | 520 | 74.95 | 33.52 | 2.44 | 72.51 | 51.3 | o |
| | ARG | 521 | 42.31 | 11.10 | 0.00 | 42.31 | 21.6 | |
| | GLN | 522 | 24.47 | 0.98 | 0.00 | 24.47 | 17.0 | i |
| | ILE | 523 | 63.17 | 63.17 | 0.00 | 63.17 | 42.9 | |
| @@ | LYS | 524 | 86.04 | 57.44 | 1.03 | 85.01 | 51.7 | o |
| @@ | LYS | 525 | 8.72 | 0.27 | 0.00 | 8.72 | 5.3 | i |
| @@ | GLN | 526 | 0.00 | 0.00 | 0.00 | 0.00 | 0.0 | i |
| | THR | 527 | 44.15 | 37.83 | 0.00 | 44.15 | 41.6 | |
| @@ | ALA | 528 | 2.30 | 2.30 | 0.31 | 2.00 | 3.1 | i |
| ## | LEU | 529 | 1.24 | 1.24 | 0.00 | 1.24 | 0.8 | i |
| | VAL | 530 | 0.18 | 0.18 | 0.17 | 0.02 | 0.0 | i |
| @@ | GLU | 531 | 33.31 | 0.91 | 0.00 | 33.31 | 23.6 | |
| | LEU | 532 | 40.59 | 40.59 | 0.00 | 40.59 | 27.8 | |
| | VAL | 533 | 0.62 | 0.62 | 0.02 | 0.60 | 0.5 | i |
| ## | LYS | 534 | 22.23 | 12.56 | 0.05 | 22.18 | 13.5 | i |
| @@ | HIS | 535 | 16.21 | 12.70 | 3.51 | 12.70 | 8.2 | i |
| | LYS | 536 | 125.97 | 80.88 | 1.15 | 124.82 | 75.9 | o |
| ## | PRO | 537 | 27.87 | 20.96 | 6.91 | 20.96 | 19.9 | i |
| | LYS | 538 | 175.55 | 132.98 | 24.90 | 150.65 | 91.6 | o |
| @@ | ALA | 539 | 56.44 | 54.45 | 12.79 | 43.65 | 67.3 | o |
| ## | THR | 540 | 13.80 | 0.29 | 13.29 | 0.51 | 0.5 | i |
| | LYS | 541 | 151.76 | 134.73 | 10.81 | 140.96 | 85.7 | o |
| | GLU | 542 | 143.28 | 57.29 | 0.82 | 142.46 | 100.0 | o |
| | GLN | 543 | 94.49 | 50.37 | 5.53 | 88.96 | 61.9 | o |
| @@ | LEU | 544 | 7.38 | 7.00 | 0.39 | 6.99 | 4.8 | i |
| | LYS | 545 | 122.91 | 82.05 | 5.96 | 116.95 | 71.1 | o |
| | ALA | 546 | 52.65 | 52.51 | 2.40 | 50.25 | 77.4 | o |
| @@ | VAL | 547 | 37.83 | 37.83 | 0.46 | 37.37 | 30.6 | |
| | MET | 548 | 7.10 | 7.09 | 0.01 | 7.09 | 4.5 | i |
| | ASP | 549 | 79.72 | 33.37 | 9.30 | 70.42 | 62.3 | o |
| | ASP | 550 | 81.72 | 24.24 | 6.19 | 75.53 | 66.8 | o |
| ## | PHE | 551 | 16.40 | 16.40 | 0.00 | 16.40 | 9.1 | i |
| | ALA | 552 | 26.97 | 15.46 | 11.51 | 15.46 | 23.8 | |
| | ALA | 553 | 46.71 | 43.76 | 6.20 | 40.51 | 62.4 | o |
| | PHE | 554 | 31.60 | 31.60 | 0.92 | 30.68 | 17.0 | i |
| | VAL | 555 | 1.51 | 1.51 | 0.00 | 1.51 | 1.2 | i |
| | GLU | 556 | 87.68 | 24.41 | 9.37 | 78.31 | 55.5 | o |
| | LYS | 557 | 108.24 | 67.45 | 6.00 | 102.25 | 62.2 | o |
| ## | CYS | 558 | 0.47 | 0.00 | 0.47 | 0.00 | 0.0 | i |
| ## | CYS | 559 | 40.50 | 20.21 | 20.91 | 19.58 | 19.1 | i |
| | LYS | 560 | 171.40 | 121.84 | 23.55 | 147.84 | 89.9 | o |
| | ALA | 561 | 40.51 | 22.45 | 32.45 | 8.06 | 12.4 | i |
| | ASP | 562 | 140.81 | 38.02 | 34.22 | 106.59 | 94.3 | o |
| | ASP | 563 | 89.28 | 21.77 | 5.33 | 83.95 | 74.3 | o |
| | LYS | 564 | 179.18 | 123.99 | 17.96 | 161.22 | 98.0 | o |
| | GLU | 565 | 81.62 | 24.70 | 3.45 | 78.18 | 55.4 | o |
| | THR | 566 | 65.21 | 52.57 | 9.24 | 55.97 | 52.7 | o |
| ## | CYS | 567 | 18.00 | 6.61 | 2.26 | 15.75 | 15.4 | i |
| ## | PHE | 568 | 7.30 | 5.31 | 1.99 | 5.31 | 2.9 | i |
| | ALA | 569 | 69.77 | 60.43 | 19.45 | 50.32 | 77.5 | o |
| | GLU | 570 | 122.28 | 62.01 | 33.64 | 88.64 | 62.8 | o |
| | GLU | 571 | 91.89 | 17.51 | 27.02 | 64.87 | 45.9 | |
| ## | GLY | 572 | 80.42 | 41.46 | 80.42 | 0.00 | 92.2 | o |

The table depicts the solvent accessibility parameter for all the amino acids in Domain III. The residues (numbered with respect to the mature full length HSA sequence presented in SEQ ID NO: 2) that are conserved amongst all of the species aligned FIG. 6A-D are shown in bold and marked (##) and residues that are both surface accessible and conserved amongst all of the aligned species are boxed.
http://curie.utmb.edu/getarea.html.
Moreover, residues that are conserved in all of the species aligned in FIG. 6E-H, except chicken, are marked (@@).
The residues are annotated as (i) and (o) indicating surface inaccessible and accessible respectively.

8.10 Example 10

Mutagenesis of Each Residue on Domain III to all Possible Amino Acids to Create a Library of Single Amino Acid Mutants Every amino acid in Domain III, with the exception of cysteines and proline, is mutated to all the 20 amino acids (i.e. the wild type amino acid and all 19 non-wild type amino acids) to create a library of mutants such that each individual mutant has a single mutation at only one position. The entire length of 205 amino acids is covered in the library construction; accordingly 184 residues are mutated individually resulting in a total library diversity of 3496. The domain III mutations are introduced and screened in the context of one or more of the following: domain III alone, full HSA protein, truncated HSA or a chimeric protein comprising at least domain III. Standard mutagenesis methods can be utilized to generate a library of domain III mutants. Optionally or alternatively the library of domain III mutants is made by a commercial facility such as Geneart AG, Germany. The library of mutants is cloned into a display vector such as the pYD1 yeast display vector or the mammalian display vector pEN-HSA-GPI described above that comprises an OriP sequence for enhanced generation of recombinant adenovirus (see, FIG. 10 for a schematic of a generic entry vector comprising an OriP), and screened for FcRn binding capacity using standard in vitro assays described in the application (e.g., flow cytometry). Variant(s) that display improved affinity for FcRn are identified. Each variant may also be screened to determine whether the improved affinity for FcRn occurs only at acidic pH, but not a neutral pH. Improved affinity for FcRn at acidic pH but not neutral pH is tested for (i) variant domain III constructs alone; (ii) variant domain III constructs presented in the contest of full length HSA; or (iii) in the context of a chimeric polypeptide. The foregoing are compared to wild-type domain III, wildtype full length HSA, or the chimeric polypeptide without the mutations. The experimental design allows for identifying the binding epitope, along with mutation(s) that improve affinity for FcRn.

A synthetic Domain III (DIII) library was generated as described above having 6×10e4 independent transformants. Although, the library was designed such that each individual mutant would have a single mutation at only one position, a number of double and even triple mutations were generated. The synthetic DIII library was PCR amplified and assembled with DI and DII to form full length HSA libraries by overlapping PCR. The PCR was digested with Sfi I and EcoR I and cloned into the similarly digested vector pEN-HSA-GPI, an enhanced mammalian display Gateway™ entry vector comprising an OriP sequence as described above (see, e.g., FIGS. 8B and 10). The primers used to amplify the DIII library have six (6) wild type amino acid residues at the N and C terminal ends, accordingly, diversity at these 12 amino acids of Domain III was removed. Two libraries were generated in the pEN-HSA-GPI vector and corresponding adenoviral libraries were generated essentially as described above except 12 μg of PAC I linearized adenoviral expression vector was used for library generation. The size of each library is shown in (Table 4). The diversity of the pEN-HSA-GPI libraries was examined, in library 1: ~50% of the clones were wild type, while in library 2: ~30% of the clones were wild type.

TABLE 4

| DIII library size | | |
|---|---|---|
| | pEN-HSA | pAd-HSA |
| library 1 | $1.3 \times 10^6$ | $5.4 \times 10^6$ |
| library 2 | $6.4 \times 10^6$ | $1.7 \times 10^7$ |

Cells infected with adenovirus expressing wild type HSA, HSA-DIII library 1 or HSA-DIII library 2 were stained with anti-HSA-FITC antibody and FcRn-biotin (detected with SA-PE) essentially as described in Example 5 above and analyzed/screened by FACS as described below. The expression levels of the wild type HSA and the two libraries were comparable (FIG. 12A). Only the cell population expressing the HSA-DIII libraries showed a shift in the histogram when stained with 10 μg/ml FcRn (FIG. 12B). FIG. 13 shows the corresponding double staining FACS profiles. Enriched cell populations recovered from the sorting, amplified and were either subjected to a second round of enrichment by sorting or were used to isolate individual clones as described below. As can been seen from the histograms in FIG. 14A, the expression levels of wild type HSA, the starting library and the sorted libraries are comparable. However, staining with FcRn shows that the round 1 and 2 sorted libraries have been enriched for cells expressing HSA-DIII mutants that can bind to FcRn present at low concentrations, 1 μg/ml and even 0.1 μg/ml (FIGS. 14B and C).

A number of individual clones were isolated (as described below) and screened for pH dependent FcRn binding essentially as described in Example 2 above except the experiment was performed at pH 7.2. FIG. 15 shows representative histograms for control cells, wild type HSA and several representative clones at pH 5.5 (panel A) and pH 7.2 (panel B). Expression levels between these HSA mutants and wild type HSA are comparable (FIG. 15C). As shown in FIG. 16 clones identified as retaining pH dependent binding (i.e., preferential binding at low pH) are sequenced and may be subjected to addition FACS analysis using several FcRn concentrations (e.g., 0.1 μg/ml, 1 μg/ml, and 10 μg/ml of FcRn-biotin) along with wild type HSA and control cells to analyze the relative affinity of the mutations for FcRn. An additional ~1100 clones from the enriched population were sequenced prior to any other characterization. Table 5 provides a summary of the amino acid substitutions identified in the clones isolated and/or sequenced from the libraries. Bolded positions indicate that substitutions were found at that position in between about 1-5% of the clones and may be referred to as "preferred spots". Bolded and underlined positions indicate that substitutions were found at that position in over 5% of the clones and may be referred to as "hot spots". Amino acid substitutions (Substituted AA column) listed in italics were identified only in the context of a double/triple mutation. Amino acids substitutions (Substituted AA column) found in 5 or more clones are shown in bold. Combinations found in three or more clones are also shown in bold with the number of clones identified shown in parenthesis. Amino acid numbering is in respect to the mature full length HSA provided in SEQ ID NO: 2. Multiple clones containing the same amino acid substitution at the same position and/or different amino acid substitutions at the same position were isolated (see Table 5) indicating that these positions may represent mutational hot spots.

The location of several of the preferred and/or hot spots on the solved structure of HSA are indicated on FIG. 17. The majority of the hotspots and preferred spots, except amino acids 407, 415 and 463, are found in the loops 6 and 7 (encompassing residues 492-509 and 516-518, respectively) and helicies 7 and (encompassing residues 510-515 and 519-536, respectively), circled in FIG. 16.

TABLE 5

| Summary of DIII Mutations Identified | | |
|---|---|---|
| Position* | Substituted AA* | Combinations* |
| V381 | D2; N1 | V381D/T506R/Q522R |
| E382 | none | |
| E383 | A1; *G1* | E383G/K413S |
| P384 | *A1*; S2 | P384A/L463N; P384S/Q459A |
| Q385 | *E1*; *L4* | Q385E/Q526H; Q385L/R472W; Q385L/T412G; Q385L/S454C; Q385L/L463N |
| N386 | *S1* | N386S/I523T |
| L387 | none | |
| I388 | none | |
| K389 | G1; *M1* | K389M/406P/408E |
| Q390 | none | |
| N391 | E2; L1; *T1*; V2 | N391T/D549L |
| C392 | none | |
| E393 | C2; *V2* | E393V/K524L; E393V/Q522H |
| L394 | none | |
| F395 | *K1* | F395K/K414N |
| E396 | *K1* | E396K/I523H |

TABLE 5-continued Summary of DIII Mutations Identified

| Position* | Substituted AA* | Combinations* |
|---|---|---|
| Q397 | *G1* | Q397G/L463N |
| L398 | K3 | L398K/L463F/K524H; L398K/K524H |
| G399 | none | |
| E400 | *I1* | E400I/I523T |
| Y401 | *E1; K1;* Q2; *V1* | Y401E/I523G; Y401K/F488Y/L516F; Y401V/F509G |
| K402 | A1; D1; W2 | |
| F403 | *L1; N1; V1;* W1 | F403L/V426N/T515G; F403N/I523G; F403V/A443P |
| Q404 | H1; *N1; M1;* T1; W2 | Q404N/K524L; Q404M/K525E |
| N405 | E1; *T5* | N405T/T508R; N405T/E495D/H510P; N405T/K524L; N405T/E495D; N405T/L516C |
| A406 | K1; *M1*; P1 | K389M/406P/408E |
| L407 | H2; M1; *N6; Y6; R1* | L407N/P447S (3 Ω); L407N/P447S/A539I (3); L407Y/F509M (5); L407Y/Q526T; L407R/V555P |
| L408 | E2; F1; R1 | K389M/406P/408E |
| V409 | P1; W1 | |
| R410 | K1; L2 | R410L/E495D |
| Y411 | *A1*; F1; *H1; L3; Q3; R1* | Y411A/455E; Y411H/I523L; Y411L/L463N/T508R; Y411L/I523Q (2); Y411Q/H535N (3); Y411R/I523M |
| T412 | *G1*; L1; *R1*; S1; W1 | Q385L/T412G; T412R/K534G; T412L/E479Q/I523A |
| K413 | *S1* | E383G/K413S |
| K414 | *N1; Q1; S3; Y1* | K414S/V456N (3); K414Y/E465W; F395K/K414N |
| V415 | C1; *L1;* T11 | V415L/T467N; V415T/A569P; V415T/571K |
| P416 | P1 | |
| Q417 | *P1* | Q417P/I523D |
| V418 | K1; L1 | |
| S419 | *M1*; P1 | S419M/K524L |
| T420 | K1; S1 | |
| P421 | none | |
| T422 | none | |
| L423 | H1; *N1*; R2; Y1 | L423N/I523D; L423R/A443D (2) |
| V424 | *D1;* I5; M2; Q4; W1 | V424D/E505H; V424I/L463F; V424M/E531I |
| E425 | K3 | |
| V426 | E4; F1; H3; *L1; N2; Q1* | F403L/V426N/T515G; V426E/K524L; V426H/Q526Y (2); V426L/E495D/Q526Y; V426N/T515G; V426Q/D512M/E520N |
| S427 | none | |
| R428 | *E1*; F2 | R428E/T506M/L516I |
| N429 | W1 | |
| L430 | none | |
| G431 | *F1*; M2 | G431F/L516T/E520Y |
| K432 | C1 | |
| V433 | G1; *T2* | V433T/L463N/T508R; V433T/T508R |
| G434 | C1; K1 | |
| S435 | none | |
| K436 | *P2* | K436P/I523G |
| C437 | none | |
| C438 | none | |
| K439 | none | |
| H440 | *F1*; R2 | H440F/F488G |
| P441 | none | |
| E442 | *K1* | E442K/E450D/Q459R |
| A443 | P2; D2 | F403V/A443P; L423R/A443D (2) |
| K444 | *S1; Q1* | K444S/D549L; K444Q/E465G |
| R445 | D2; W1; *Y1* | R445D/I523C; R445D/N503T; R445Y/K519I/K525V |
| M446 | *T1*; W3 | M446W/H535P; M446T/T515Y |
| P447 | *S7* | L407N/P447S (3Ω); L407N/P447S/A539I (3); P447S/A539V; |
| C448 | none | |
| A449 | none | |
| E450 | *D1* | E442K/E450D/Q459R |
| D451 | none | |
| Y452 | R1 | |
| L453 | none | |
| S454 | C4; E2; K1 | Q385L/S454C; S454C/A539R |
| V455 | D1; *E1*; G1; I1; N6 | Y411A/455E; 455N/K524L |
| V456 | *A1*; E3; F1; L2; N5; | K414S/V456N (3); V456A/E518Y; V456E/L516W; V456E/R521W; V456N/R472S/F509M (2) |
| L457 | F1; I1; | |
| N458 | none | |
| Q459 | *A1*; P1; *R1* | P384S/Q459A; E442K/E450D/Q459R |
| L460 | N1 | L460N/K524L |

TABLE 5-continued

Summary of DIII Mutations Identified

| Position* | Substituted AA* | Combinations* |
|---|---|---|
| C461 | none | |
| V462 | none | |
| L463 | F3; G1; I1; N~230†; S2 | P384A/L463N; Q385L/L463N; Q397G/L463N; L398K/L463F/K524H; V424I/L463F; L463F/E505I; L463N/T506N; L463N/T506Y; L463N/T508S (2); L463N/T508R₡ (~190¥); L463G/D512Y; L463N/D512Y; L463I/S517W; L463N/Q526M (2); L463N/K534M; |
| H464 | E2; V1 | H464V/T474N |
| E465 | G1; W2 | K414Y/E465W; K444Q/E465G |
| K466 | W3 | K466W/S517W; |
| T467 | N1; P1; W1 | V415L/T467N; |
| P468 | none | |
| V469 | none | |
| S470 | none | |
| D471 | N1 | D471N/R521Q |
| R472 | D1; R1; S2; W1 | Q385L/R472W; V456N/R472S/F509M (2); R472D/I523G; R472R/Q522D |
| V473 | E1; L2 | V473L/S517W (2) |
| T474 | N2; Q1 | H464V/T474N |
| K475 | F1; Y1 | |
| C476 | none | |
| C477 | none | |
| T478 | none | |
| E479 | Q1 | T412L/E479Q/I523A |
| S480 | none | |
| L481 | none | |
| V482 | E1; I1 | V482E/I523R; V482I/I523K |
| N483 | K1 | N483K/K524L |
| R484 | none | |
| R485 | P1 | R485P/N503V |
| P486 | none | |
| C487 | none | |
| F488 | G1; Y1 | Y401K/F488Y/L516F; H440F/F488G |
| S489 | none | |
| A490 | none | |
| L491 | none | |
| E492 | none | |
| V493 | none | |
| D494 | none | |
| E495 | D9 | N405T/E495D/H510P; N405T/E495D; R410L/E495D; V426L/E495D/Q526Y; L463N/E495D/T508R (2); E495D/Q526Y |
| T496 | none | |
| Y497 | none | |
| V498 | M1 | |
| P499 | none | |
| K500 | none | |
| E501 | none | |
| F502 | none | |
| N503 | T1; V2 | R445D/N503T; R485P/N503V; N503V/A539R |
| A504 | none | |
| E505 | H1; I5 | V424D/E505H; L463F/E505I |
| T506 | M1; N1; R2; W1; Y6 | V381D/T506R/Q522R; R428E/T506M/L516I; L463N/T506N; L463N/T506Y; T506R/Q522C; T506Y/C559R |
| F507 | V1; W1 | F507W/I523F |
| T508 | R~200; S3 | N405T/T508R; V433T/T508R; L463N/T508R₡ (~190¥); L463N/T508S (2); |
| F509 | D2; G1; I4; M12; P1; W6 | Y401V/F509G; L407Y/F509M (5); F509W/K557G; 456N/R472S/F509M (2); F509I/T527Y (4); |
| H510 | C5; P3; Q2; R1 | N405T/E495D/H510P; H510C/H535L; H510R/K557G |
| A511 | D1; F9; I1; R1; T1; V1; Y1 | A511F/Q526P; A511I/K538W; A511V/H535S/K541T; A511Y/V555E; |
| D512 | F1; M2‡; Q1; Y13 | V426Q/D512M/E520N; L463G/D512Y; L463N/D512Y; D512M/E520N |
| I513 | T1; Q1; | I513Q/I523Y |
| C514 | Y1 | |
| T515 | C3; D2; E2; G1; H2; L2; N1; P2; Q11; S4; W2; Y2 | 326N/T515G; F403L/V426N/T515G; M446T/T515Y; T515W/Q522K; T515P/I523R; T515L/M548F; T515N/D549S; |
| L516 | C2; F3; G1;I1; T6; W6; Y1 | Y401K/F488Y/L516F; N405T/L516C; R428E/T506M/L516I; G431F/L516T/E520Y; V456E/L516W; L516W/A539V; L516W/Q543W; |
| S517 | C1, W7 | L463I/S517W; K466W/S517W; V473L/S517W (2) |
| E518 | A2; V1; Y1 | V456A/E518Y; |

TABLE 5-continued

Summary of DIII Mutations Identified

| Position* | Substituted AA* | Combinations* |
|---|---|---|
| K519 | C3; D2; E1; I3 | R445Y/K519I/K525V; T508R/K519I/K525V |
| E520 | C1; *N2*; V1; W2; *Y1* | V426Q/D512M/E520N; G431F/L516T/E520Y; D512M/E520N |
| R521 | H1; *M1; Q1*; T1; W18; Y1 | V456E/R521W; D471N/R521Q; R521M/D563F |
| Q522 | *C1; D1; H1; K1*; R2; W1; Y2 | V381D/T506R/Q522R; E393V/Q522H; R472R/Q522D; T506R/Q522C; T515W/Q522K; |
| I523 | A2; *C1*; D13; E8; F4; G31; H3; K13; *L1; M1*; P1; Q4; R11; S2; T3; W2; Y2£ | N386S/I523T; E396K/I523H; E400I/I523T; F403N/I523G; Y411H/I523L; Y411L/I523Q (2); Y411R/I523M; T412L/E479Q/I523A; 416P/I523D; Q417P/I523D; L423N/I523D; K436P/I523G; R445D/I523C; R472D/I523G; V482E/I523R; V482I/I523K; F507W/I523F; I513Q/I523Y; T515P/I523R; I523Q/K538Y |
| K524 | H3; I2; L68; M2; Q3; V4 | E393V/K524L; L398K/L463F/K524H; L398K/K524H; Q404N/K524L; N405T/K524L; S419M/K524L; V426E/K524L; 455N/K524L; L460N/K524L; N483K/K524L; K524L/T540I/571K; K524Q/K545M; |
| K525 | *E1*; V3 | Q404M/K525E; R445Y/K519I/K525V; T508R/K519I/K525V |
| Q526 | A4; F1; *H1*; L1; M10; *P1;T1*; V1; Y4 | Q385E/Q526H; V426H/Q526Y (2); V426L/E495D/Q526Y; L407Y/Q526T; L463N/Q526M (2); E495D/Q526Y; A511F/Q526P; Q526M/K557G |
| T527 | E1; V1; Y7 | F509I/T527Y (4); |
| A528 | G1; N1; | |
| L529 | F1 | |
| V530 | E1; I1; | |
| E531 | G1; I2; P1; | V424M/E531I; |
| L532 | V2; | |
| V533 | S1 | |
| K534 | *G1; M1* | T412R/K534G; L463N/K534M |
| H535 | D1; K1; *L1; N3*; P5; S2 | Y411Q/H535N (3); M446W/H535P; H510C/H535L; A511V/H535S/K541T; |
| K536 | L1; R1; T1 | |
| P537 | none | |
| K538 | C1; D2; *W1; Y1* | A511I/K538W; I523Q/K538Y |
| A539 | I3; N1; R1; V2 | L407N/P447S/A539I (3); P447S/A539V; P447S/A539I (3); S454C/A539R; N503V/A539R; L516W/A539V |
| T540 | I1; K1 | K524L/T540I/E571K; |
| K541 | P1; T2; F2 | A511V/H535S/K541T; K541F/A561F |
| E542 | W1 | |
| Q543 | P1; *W1* | L516W/Q543W |
| L544 | M1 | |
| K545 | *M1*; N1 | K524Q/K545M; |
| A546 | I1; D1 | |
| V547 | none | |
| M548 | F2 | T515L/M548F; |
| D549 | A1; L3; S2 | N391T/D549L; K444S/D549L; T515N/D549S |
| D550 | none | |
| F551 | none | |
| A552 | P2 | |
| A553 | none | |
| F554 | P2 | |
| V555 | D1; *E1*; P2 | L407R/V555P; A511Y/V555E |
| E556 | none | |
| K557 | G11; N1; S1 | F509W/K557G; H510R/K557G; Q526M/K557G |
| C558 | none | |
| C559 | *R1* | T506Y/C559R |
| K560 | Q1 | |
| A561 | F2; T1 | K541F/A561F |
| D562 | V1; S1 | |
| D563 | A1; Y1; M1; *F1* | R521M/D563F |
| K564 | I1; R2 | |
| E565 | K1; Y5; W1 | L463N/T508R/E565Y; |
| T566 | K1; W1 | |
| C567 | none | |
| F568 | I3; T1 | |
| A569 | H2; P2; Y1 | V415T/A569P |
| E570 | none | |
| E571 | K5; D1 | V415T/571K; K524L/T540I/E571K |
| G572 | E1; R2; Y1 | |
| K573 | A1 | |
| K574 | none | |
| L575 | M1; Y1 | |
| V576 | D2 | |
| A577 | none | |

TABLE 5-continued

Summary of DIII Mutations Identified

| Position* | Substituted AA* | Combinations* |
|---|---|---|
| A578 | T1; V2 | |
| S579 | none | |
| Q580 | none | |
| A581 | none | |
| A582 | D2; T2 | |
| L583 | none | |
| G584 | none | |
| L585 | none | |

*Numbered with respect to mature full length HSA (SEQ ID NO: 2); the substituted amino acid residue is followed by a number indicating the number of times that residue was found; the combinations are generally listed in the row for each position found in the combination Ω sequence not definitive at position 407 for two of the three clones
†L463N first identified as clone 12
€ L463N/T508R first identified as clone 45
¥occasionally w/a third substitutions (e.g., Y411L, V433T, E495D, A504G, E531G, 571K)
‡these clones may also have a deletion at 523
£I523Y first identified as clone 46

Several mutants thus identified were generated as soluble protein by site directed mutagenesis and purified as described below for further analysis. The binding affinity ($K_D$ at pH 5.5) and pH dependence (7.2 vs. 5.5) were determined by ProteOn (as described below) and/or BIAcore (essentially as described above). Table 6 provides a summary of the binding studies and includes the protein densities for these studies. A number of mutants were found to have enhanced binding at pH 5.5, including L407Y/Q526T; L463N/T508R; I523G; V424Q; L83N/I28R/I143G; and K144, bolded in Table 6. Of those tested all that showed enhance binding at pH 5.5 were also found to maintain pH dependent binding (see last column in Table 6). Several mutants assayed were found to have unchanged or even increased $K_D$ (i.e. unchanged or worse binding) at pH 5.5. There are several possible reasons why such clones may have been identified, for example, these mutations may enhance protein expression or stability in the display system. It is also possible that the GPI anchor used for display may have some impact on binding which these mutants can compensate for that is not duplicated when the mutant HSA is expressed as a soluble molecule. Furthermore, the design of the screening methodology optimized for capturing off rate stabilized mutants which may or may not translate to an overall affinity improvement. It may also reflect that these mutations provide enhancement when in combination with one or more other mutations. A number of mutations were found in combinations (see Table 5).

TABLE 6

| Summary of Binding Studies | | | |
|---|---|---|---|
| huFcRn vs. | | Surface Density (RU) | pH dependence |
| | $K_D$(μM)-ProteOn | | |
| WT | 2.83 | 1880 | Y |
| L407Y/Q526T | 0.191 | 3940 | Y |
| L463N/T508R | 0.105 | 3950 | Y |
| F509W | nb | 4920 | |
| A511I | nb | 3720 | |
| K519E | nb | 3260 | |
| R521W | 3.13 | 3940 | |
| I523G | 0.074 | 3740 | Y |
| | $K_D$ (μM)-BIAcore | | |
| WT | 0.91 | 2952 | Y |

TABLE 6-continued

| Summary of Binding Studies | | | |
|---|---|---|---|
| huFcRn vs. | | Surface Density (RU) | pH dependence |
| V424Q | 0.46 | 3441 | Y |
| V426E | 2.50 | 7279 | Y |
| V426H | 3.59 | 6665 | |
| L463N/T508R/I523G | ~0.184** | 6427 | |
| F509M | ~27.4* | 7337 | |
| A511F | 1.48 | 3395 | Y |
| D512Y | 1.00 | 3355 | Y |
| T515S | 2.88 | 3522 | N |
| L516T | 5.02 | 6780 | |
| S517W | 0.69 | 3144 | |
| K524L | ~0.360** | 6388 | |

Blank indicates not tested;
nb indicates no binding under the conditions used
*Estimate - weak affinity + top conc. at 10uM resulted in only marginal curvature to the Req vs. Conc. isotherm
**Estimate - strong affinity-binding of lower conc. curves did not reach "true" steady-state Cell Staining and FACS Analysis and Sorting:

30 million 293F cell at a density $1\times10^6$/ml were infected with HSA adenoviral library at MOI=1. The cells were harvested 16 hours post transduction by centrifugation, washed with cold FACS buffer, and resuspended at $\sim1\times10^7$ cells/ml. Biotinylated FcRn was added at 10 μg/ml (212 nM) for the 1$^{st}$ round of sorting. After incubation at 4° C. for 60 min, the cells were washed twice with FACS buffer and resuspended in Streptavidin-PE at 1:500 dilutions. Following incubation at 4° C. for 30 min and washed once with FACS buffer and sorted for FcRn binding, this enriches for those cells that bind FcRn at pH 5.5. Sorted cells were amplified for additional screening. For 2$^{nd}$ round sorting the enriched cell population was sorted essentially as described above except biotinylated FcRn was used at 1 μg/ml (21.2 nM) to further enrich for high affinity HSA mutants. Additional analysis of the enriched libraries was also performed at 0.1 μg/ml (2.12 nM), see for example FIG. 14. In some screens a "deselection" step was incorporated into the 1$^{st}$ or 2$^{nd}$ round of screening in which the enriched population of cells was sorted to remove those which bound FnRc at neutral pH (pH 7.4). To identify individual clones, viral DNA is extracted from the enriched cell population and the DIII HSA variants cloned into a mammalian expression vector for transient transfection of 293F cells. Individual clones are screened for pH dependent binding by flow cytometry at pH 5.5 and pH 7.4 essentially as described above.

Generation and Expression of HSA-DIII Mutants:

Wild type HSA is mutated to generate several DIII mutants using standard protocols (QuikChange® II XL Site-Directed Mutagenesis Kit, Agilent Catalog #200521) in a mammalian expression vector using specific mutagenic primers. The mutants are expressed in 293F cells by transient transfection with 293Fectin™ Transfection Reagent (Invitrogen, Catalog #Sku12347-019) as per manufacturer's protocol and the mutants purified on ANTI-FLAG M2 Affinity Gel (Sigma-Aldrich Catalog #A2220) using standard procedures. All the mutants thus purified were analyzed by SDS PAGE and size exclusion to chromatography to assess purity and aggregation. All the mutants were judged to be ~99% pure with no significant aggregation (more than 95% monomeric) (data not shown).

ProteOn Analysis:

The affinity (KD) of human FcRn for the HSA variants was measured on a ProteOn XPR36 Protein Interaction Array System (BioRad). Briefly, HSA variants were immobilized at high density onto separate flow surfaces on a ProteOn GLM Sensor Chip, using ProteOn Amine Coupling Kit as outlined by the manufacturer. Final surface HSA densities were between 3740-3950 RUs. A reference flow surface was also prepared on the chip without any protein using the identical immobilization protocol. Two-fold serial dilutions of human FcRn, ranging from 5.86 nM to 10000 nM, in 50 mM P04, 150 mM NaCl buffer at pH5.5 were injected over both the protein coupled and reference cell surfaces at a flow rate of 25 L/min. Binding data was collected for 8 min, followed by regeneration with multiple 60 sec. injections of pH 7.4 Phosphate Buffered Saline containing 0.05% Tween20. The binding response at equilibrium (Req) for each injection was plotted against concentration and fit to a steady state affinity model, using ProteOn Manager Software to derive the equilibrium binding constant KD.

Based on this analysis, further analysis of identified combination mutations is performed to assess the activity of each individual mutation. Additionally, further screening to identify whether different combinations of mutations (e.g., constructs having mutations at more than one position which were not directly identified in the screen) provide improved affinity for FcRn is conducted.

8.11 Example 11

Combinatorial Mutagenesis of Selected Residues on Domain III

To examine combinations of the most frequent mutations identified in Example 10 (above) a synthetic Domain III library is generated such that residues: 407; 415; 463; 495; 508; 509; 511; 512; 515; 516; 517; 521; 523; 524; 526; 527; and 557, are mutated to the residues indicated in Table 7 to create a library of mutants such that each individual mutant has a 2-4 mutations. Alternatively, the library may be generated such that each of the listed residues are mutated to all the 20 amino acids (i.e. the wild type amino acid and all 19 non-wild type amino acids) to examine a more extensive set of combinations.

The domain III combinatorial mutations are introduced and screened in the context of one or more of the following: domain III alone, full HSA protein, truncated HSA or a chimeric protein comprising at least domain III. Standard mutagenesis methods can be utilized to generate a library of domain III mutants. Optionally or alternatively the library of domain III mutants is made by a commercial facility such as Geneart AG, Germany.

The library of combinatorial mutants is cloned into a display vector such as the pYD1 yeast display vector or the mammalian display vector pEN-HSA-GPI described above and screened for FcRn binding capacity using standard in vitro assays described in the application (e.g., flow cytometry). Positive and/or negative selection methods, such as those described in Example 10 may be employed. Combinatorial variant(s) that display improved affinity for FcRn are identified. Each combinatorial variant may also be screened to determine whether the improved affinity for FcRn occurs only at acidic pH, but not a neutral pH. Improved affinity for FcRn at acidic pH but not neutral pH is tested for (i) variant domain III constructs alone; (ii) variant domain III constructs presented in the contest of full length HSA; or (iii) in the context of a chimeric polypeptide. The foregoing may be compared to wildtype domain III, wildtype full length HSA, or a chimeric polypeptide without the mutations. Alternatively, or optionally, the combinatorial mutations may be compared to domain III, full length HSA, or a chimeric polypeptide comprising each mutation singly to determine if the combination further enhances affinity for FcRn and/or serum half-life. The experimental design allows for the identification combinatorial mutations that improve affinity for FcRn and/or improved serum half-life.

TABLE 7

Mutations For Combinatorial Library

| Position | Mutation |
|---|---|
| 407 | N, Y |
| 415 | T |
| 463 | F, N |
| 495 | D |
| 508 | R, S |
| 509 | I, M, W |
| 511 | F |
| 512 | M, Y |
| 515 | Q |
| 516 | T, W |
| 517 | W |
| 521 | W |
| 523 | D, E, F, G, K, R |
| 524 | L |
| 526 | A, M, Y |
| 527 | Y |
| 557 | G |

8.12 Example 12

Mutagenesis of Residues on Domain III to Create Single Amino Acid Mutants to be Screened for Improved FcRn Affinity Eighteen single amino acids are selected from conserved amino acids in Domain III and are singly mutated to alanine so that each variant has a single mutation at only one position using standard methods described in the application. The eighteen variants are introduced and screened in the context of the full HSA protein, or alternatively in a truncated HSA or chimeric protein comprising at least domain III. The eighteen variants are screened for FcRn binding capacity using standard in vitro assays described in the application. Variant(s) that display improved affinity for FcRn are identified. Each variant is also screened to determine whether the improved affinity for FcRn occurs only at acidic pH, but not a neutral pH. Improved affinity for FcRn at acidic pH but not neutral pH is tested for (i) variant domain III constructs alone; (ii) variant domain III constructs presented in the context of full length HSA; or in the context of a chimeric polypeptide. The foregoing are compared to wildtype domain III, wildtype full length HSA, or chimeric polypeptide without mutations.

Based on this analysis, further screening to identify whether combinations of mutations (e.g., constructs having mutations at more than one position) provide improved affinity for FcRn is conducted.

9 SEQUENCES human HSA DIII protein sequence
SEQ ID NO: 1
VEEPQNLIKQNCELFEQLGEYKFQNALLVRYTKKVPQVSTPTLVEVSR

NLGKVGSKCCKHPEAKRMPCAEDYLSVVLNQLCVLHEKTPVSDRVTKC

CTESLVNRRPCFSALEVDETYVPKEFNAETFTFHADICTLSEKERQIK

KQTALVELVKHKPKATKEQLKAVMDDFAAFVEKCCKADDKETCFAEEG

KKLVAASQAALGL human full-length HSA protein sequence
SEQ ID NO: 2
DAHKSEVAHRFKDLGEENFKALVLIAFAQYLQQCPFEDHVKLVNEVTE

FAKTCVADESAENCDKSLHTLFGDKLCTVATLRETYGEMADCCAKQEP

ERNECFLQHKDDNPNLPRLVRPEVDVMCTAFHDNEETFLKKYLYEIAR

RHPYFYAPELLFFAKRYKAAFTECCQAADKAACLLPKLDELRDEGKAS

SAKQRLKCASLQKFGERAFKAWAVARLSQRFPKAEFAEVSKLVTDLTK

VHTECCHGDLLECADDRADLAKYICENQDSISSKLKECCEKPLLEKSH

CIAEVENDEMPADLPSLAADFVESKDVCKNYAEAKDVFLGMFLYEYAR

RHPDYSVVLLLRLAKTYETTLEKCCAAADPHECYAKVFDEFKPLVEEP

QNLIKQNCELFEQLGEYKFQNALLVRYTKKVPQVSTPTLVEVSRNLGK

VGSKCCKHPEAKRMPCAEDYLSVVLNQLCVLHEKTPVSDRVTKCCTES

LVNRRPCFSALEVDETYVPKEFNAETFTFHADICTLSEKERQIKKQTA

LVELVKHKPKATKEQLKAVMDDFAAFVEKCCKADDKETCFAEEGKKLV

AASQAALGL

FIG. 6 provides an alignment of domain III of serum albumin proteins from various species.

The wild type amino acid sequence for domain III of rat serum albumin is set forth in FIG. 6 as SEQ ID NO: 3. The wild type amino acid sequence for domain III of mouse serum albumin is set forth in FIG. 6 as SEQ ID NO: 4. The wild type amino acid sequence for domain III of bovine serum albumin is set forth in FIG. 6 as SEQ ID NO: 5. The wild type amino acid sequence for domain III of human serum albumin is set forth in FIG. 6 as SEQ ID NO: 2. The wild type amino acid sequence for domain III of dog serum albumin is set forth in FIG. 6 as SEQ ID NO: 6. The wild type amino acid sequence for domain III of rabbit serum albumin is set forth in FIG. 6 as SEQ ID NO: 7. The wild type amino acid sequence for domain III of pig serum albumin is set forth in FIG. 6 as SEQ ID NO: 8. The wild type amino acid sequence for domain III of chicken serum albumin is set forth in FIG. 6 as SEQ ID NO: 9. The wild type amino acid sequence for domain III of donkey serum albumin is set forth in FIG. 6 as SEQ ID NO: 10. The wild type amino acid sequence for domain III of Mongolian gerbil serum albumin is set forth in FIG. 6 as SEQ ID NO: 11. The wild type amino acid sequence for domain III of ovine serum albumin is set forth in FIG. 6 as SEQ ID NO: 12. The wild type amino acid sequence for domain III of cat serum albumin is set forth in FIG. 6 as SEQ ID NO: 13. The wild type amino acid sequence for domain III of horse serum albumin is set forth in FIG. 6 as SEQ ID NO: 14.

All publications and patents mentioned herein are hereby incorporated by reference in their entirety as if each individual publication or patent was specifically and individually indicated to be incorporated by reference. In addition, U.S. Provisional Patent Application Nos. 61/304,954 filed Feb. 16, 2010; and 61/364,503 filed Jul. 15, 2010, are incorporated by reference in their entirety for all purposes.

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. A polypeptide comprising a human serum albumin (HSA) portion, which HSA portion comprises HSA domain III, or a neonatal Fc receptor (FcRn) binding fragment thereof, wherein:
the HSA portion comprises one or more amino acid substitutions at positions chosen from positions 463, 508, 523 and 524, which positions are numbered relative to positions in full length mature HSA (SEQ ID NO: 2);
the one or more amino acid substitutions increase one or both of affinity for FcRn and serum half-life of the polypeptide relative to a control polypeptide in which the HSA portion does not include the one or more amino acid substitutions; and
an amino acid substitution at position 508, if present in the HSA portion, is chosen from lysine, arginine and serine.

2. The polypeptide of claim 1, wherein an amino acid substitution at position 463, if present in the HSA portion, is chosen from asparagine and glutamine.

3. The polypeptide of claim 1, wherein an amino acid substitution at position 523, if present in the HSA portion, is chosen from alanine, aspartate, glutamate, phenylalanine, glycine, lysine, leucine, asparagine, glutamine, arginine, valine, tryptophan and tyrosine.

4. The polypeptide of claim 1, wherein an amino acid substitution at position 524, if present in the HSA portion, is chosen from alanine, glycine, isoleucine, leucine and valine.

5. The polypeptide of claim 1, wherein an amino acid substitution at position 463, if present in the HSA portion, is asparagine.

6. The polypeptide of claim 1, wherein an amino acid substitution at position 508, if present in the HSA portion, is arginine.

7. The polypeptide of claim 1, wherein an amino acid substitution at position 523, if present in the HSA portion, is glycine.

8. The polypeptide of claim 1, wherein an amino acid substitution at position 524, if present in the HSA portion, is leucine.

9. The polypeptide of claim 1, wherein the HSA portion comprises amino acid substitutions at positions 463 and 508.

10. The polypeptide of claim 9, wherein the amino acid substitutions are asparagine at position 463 and arginine at position 508.

11. The polypeptide of claim 1, wherein the HSA portion comprises amino acid substitutions at positions 463, 508 and 523.

12. The polypeptide of claim 11, wherein the amino acid substitutions are asparagine at position 463, arginine at position 508 and glycine at position 523.

13. The polypeptide of claim 1, wherein the HSA portion comprises one or more amino acid substitutions at positions chosen from positions 463, 523 and 524, and not position 508.

14. The polypeptide of claim 1, which binds to a FcRn with a higher affinity than the control polypeptide at acidic pH.

15. The polypeptide of claim 1, comprising a heterologous protein or a non-protein agent, wherein functional activity of the heterologous protein or non-protein agent is retained and the polypeptide can bind to a FcRn.

16. The polypeptide of claim 15, wherein the heterologous protein is chosen from an enzyme, growth factor, cytokine and a bioactive peptide thereof.

17. The polypeptide of claim 15, wherein the non-protein agent is chosen from a nucleic acid molecule, chemical agent and organic molecule.

18. The polypeptide of claim 15, wherein the heterologous protein or the non-protein agent is conjugated to: the N-terminal amino acid of the HSA portion, the C-terminal amino acid of the HSA portion, or a side chain of an internal amino acid of the HSA portion.

19. A composition comprising the polypeptide of claim 1 and a pharmaceutically acceptable carrier.

20. A composition comprising the polypeptide of claim 15 and a pharmaceutically acceptable carrier.

21. A polypeptide comprising a human serum albumin (HSA) portion, which HSA portion comprises HSA domain III, or a neonatal Fc receptor (FcRn) binding fragment thereof, wherein:

the HSA portion comprises an amino acid substitution at position 524 to leucine, which position is numbered relative to positions in full length mature HSA (SEQ ID NO: 2); and the polypeptide comprises a heterologous protein or a non-protein agent, wherein functional activity of the heterologous protein or non-protein agent is retained and the polypeptide can bind to a FcRn.

22. The polypeptide of claim 21, wherein the heterologous protein is chosen from an enzyme, growth factor, cytokine and a bioactive peptide thereof.

23. The polypeptide of claim 21, wherein the non-protein agent is chosen from a nucleic acid molecule, chemical agent and organic molecule.

24. The polypeptide of claim 21, wherein the heterologous protein or the non-protein agent is conjugated to: the N-terminal amino acid of the HSA portion, the C-terminal amino acid of the HSA portion, or a side chain of an internal amino acid of the HSA portion.

25. A composition comprising the polypeptide of claim 21 and a pharmaceutically acceptable carrier.

26. A polypeptide comprising a human serum albumin (HSA) portion, which HSA portion comprises HSA domain III, or a neonatal Fc receptor (FcRn) binding fragment thereof, wherein:

the HSA portion comprises an amino acid substitution at position 508 to arginine and an amino acid substitution at position 463 to asparagine, which positions are numbered relative to positions in full length mature HSA (SEQ ID NO: 2); and the polypeptide comprises a heterologous protein or a non-protein agent, wherein functional activity of the heterologous protein or non-protein agent is retained and the polypeptide can bind to a FcRn.

27. The polypeptide of claim 26, wherein the heterologous protein is chosen from an enzyme, growth factor, cytokine and a bioactive peptide thereof.

28. The polypeptide of claim 26, wherein the non-protein agent is chosen from a nucleic acid molecule, chemical agent and organic molecule.

29. The polypeptide of claim 26, wherein the heterologous protein or the non-protein agent is conjugated to: the N-terminal amino acid of the HSA portion, the C-terminal amino acid of the HSA portion, or a side chain of an internal amino acid of the HSA portion.

30. A composition comprising the polypeptide of claim 26 and a pharmaceutically acceptable carrier.

* * * * *

SEQUENCE LISTING

<160> NUMBER OF SEQ ID NOS: 17

<210> SEQ ID NO 1
<211> LENGTH: 205
<212> TYPE: PRT
<213> ORGANISM: Homo sapiens

<400> SEQUENCE: 1

Val Glu Glu Pro Gln Asn Leu Ile Lys Gln Asn Cys Glu Leu Phe Glu
1               5                   10                  15

Gln Leu Gly Glu Tyr Lys Phe Gln Asn Ala Leu Leu Val Arg Tyr Thr
            20                  25                  30

Lys Lys Val Pro Gln Val Ser Thr Pro Thr Leu Val Glu Val Ser Arg
        35                  40                  45

Asn Leu Gly Lys Val Gly Ser Lys Cys Cys Lys His Pro Glu Ala Lys
    50                  55                  60

```
Arg Met Pro Cys Ala Glu Asp Tyr Leu Ser Val Val Leu Asn Gln Leu
 65                  70                  75                  80

Cys Val Leu His Glu Lys Thr Pro Val Ser Asp Arg Val Thr Lys Cys
                 85                  90                  95

Cys Thr Glu Ser Leu Val Asn Arg Arg Pro Cys Phe Ser Ala Leu Glu
                100                 105                 110

Val Asp Glu Thr Tyr Val Pro Lys Glu Phe Asn Ala Glu Thr Phe Thr
                115                 120                 125

Phe His Ala Asp Ile Cys Thr Leu Ser Glu Lys Glu Arg Gln Ile Lys
                130                 135                 140

Lys Gln Thr Ala Leu Val Glu Leu Val Lys His Lys Pro Lys Ala Thr
145                 150                 155                 160

Lys Glu Gln Leu Lys Ala Val Met Asp Asp Phe Ala Ala Phe Val Glu
                165                 170                 175

Lys Cys Cys Lys Ala Asp Asp Lys Glu Thr Cys Phe Ala Glu Glu Gly
                180                 185                 190

Lys Lys Leu Val Ala Ala Ser Gln Ala Ala Leu Gly Leu
                195                 200                 205

<210> SEQ ID NO 2
<211> LENGTH: 585
<212> TYPE: PRT
<213> ORGANISM: Homo sapiens

<400> SEQUENCE: 2

Asp Ala His Lys Ser Glu Val Ala His Arg Phe Lys Asp Leu Gly Glu
  1               5                  10                  15

Glu Asn Phe Lys Ala Leu Val Leu Ile Ala Phe Ala Gln Tyr Leu Gln
                 20                  25                  30

Gln Cys Pro Phe Glu Asp His Val Lys Leu Val Asn Glu Val Thr Glu
                 35                  40                  45

Phe Ala Lys Thr Cys Val Ala Asp Glu Ser Ala Glu Asn Cys Asp Lys
             50                  55                  60

Ser Leu His Thr Leu Phe Gly Asp Lys Leu Cys Thr Val Ala Thr Leu
 65                  70                  75                  80

Arg Glu Thr Tyr Gly Glu Met Ala Asp Cys Cys Ala Lys Gln Glu Pro
                 85                  90                  95

Glu Arg Asn Glu Cys Phe Leu Gln His Lys Asp Asp Asn Pro Asn Leu
                100                 105                 110

Pro Arg Leu Val Arg Pro Glu Val Asp Val Met Cys Thr Ala Phe His
                115                 120                 125

Asp Asn Glu Glu Thr Phe Leu Lys Lys Tyr Leu Tyr Glu Ile Ala Arg
                130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
                180                 185                 190

Ser Ala Lys Gln Arg Leu Lys Cys Ala Ser Leu Gln Lys Phe Gly Glu
                195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240
```

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
                260                 265                 270

Ser Lys Leu Lys Glu Cys Cys Glu Lys Pro Leu Leu Glu Lys Ser His
                275                 280                 285

Cys Ile Ala Glu Val Glu Asn Asp Glu Met Pro Ala Asp Leu Pro Ser
            290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
                340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
            370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
                420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
            450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
                500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
            530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Gly Lys Lys Leu Val
                565                 570                 575

Ala Ala Ser Gln Ala Ala Leu Gly Leu
            580                 585

<210> SEQ ID NO 3
<211> LENGTH: 205
<212> TYPE: PRT
<213> ORGANISM: Rattus norvegicus

<400> SEQUENCE: 3

Leu Val Glu Glu Pro Lys Asn Leu Val Lys Thr Asn Cys Glu Leu Tyr
1               5                   10                  15

Glu Lys Leu Gly Glu Tyr Gly Phe Gln Asn Ala Val Leu Val Arg Tyr
                20                  25                  30

```
Thr Gln Lys Ala Pro Gln Val Ser Thr Pro Thr Leu Val Glu Ala Ala
        35                  40                  45

Arg Asn Leu Gly Arg Val Gly Thr Lys Cys Cys Thr Leu Pro Glu Ala
 50                  55                  60

Gln Arg Leu Pro Cys Val Glu Asp Tyr Leu Ser Ala Ile Leu Asn Arg
 65                  70                  75                  80

Leu Cys Val Leu His Glu Lys Thr Pro Val Ser Glu Lys Val Thr Lys
                 85                  90                  95

Cys Cys Ser Gly Ser Leu Val Glu Arg Arg Pro Cys Phe Ser Ala Leu
                100                 105                 110

Thr Val Asp Glu Thr Tyr Val Pro Lys Glu Phe Lys Ala Glu Thr Phe
            115                 120                 125

Thr Phe His Ser Asp Ile Cys Thr Leu Pro Asp Lys Glu Lys Gln Ile
        130                 135                 140

Lys Lys Gln Thr Ala Leu Ala Glu Leu Val Lys His Lys Pro Lys Ala
145                 150                 155                 160

Thr Glu Asp Gln Leu Lys Thr Val Met Gly Asp Phe Ala Gln Phe Val
                165                 170                 175

Asp Lys Cys Cys Lys Ala Ala Asp Lys Asp Asn Cys Phe Ala Thr Glu
                180                 185                 190

Gly Pro Asn Leu Val Ala Arg Ser Lys Glu Ala Leu Ala
            195                 200                 205

<210> SEQ ID NO 4
<211> LENGTH: 205
<212> TYPE: PRT
<213> ORGANISM: Mus musculus

<400> SEQUENCE: 4

Leu Val Glu Glu Pro Lys Asn Leu Val Lys Thr Asn Cys Asp Leu Tyr
 1               5                  10                  15

Glu Lys Leu Gly Glu Tyr Gly Phe Gln Asn Ala Ile Leu Val Arg Tyr
                20                  25                  30

Thr Gln Lys Ala Pro Gln Val Ser Thr Pro Thr Leu Val Glu Ala Ala
        35                  40                  45

Arg Asn Leu Gly Arg Val Gly Thr Lys Cys Cys Thr Leu Pro Glu Asp
 50                  55                  60

Gln Arg Leu Pro Cys Val Glu Asp Tyr Leu Ser Ala Ile Leu Asn Arg
 65                  70                  75                  80

Val Cys Leu Leu His Glu Lys Thr Pro Val Ser Glu His Val Thr Lys
                 85                  90                  95

Cys Cys Ser Gly Ser Leu Val Glu Arg Arg Pro Cys Phe Ser Ala Leu
                100                 105                 110

Thr Val Asp Glu Thr Tyr Val Pro Lys Glu Phe Lys Ala Glu Thr Phe
            115                 120                 125

Thr Phe His Ser Asp Ile Cys Thr Leu Pro Glu Lys Glu Lys Gln Ile
        130                 135                 140

Lys Lys Gln Thr Ala Leu Ala Glu Leu Val Lys His Lys Pro Lys Ala
145                 150                 155                 160

Thr Ala Glu Gln Leu Lys Thr Val Met Asp Asp Phe Ala Gln Phe Leu
                165                 170                 175

Asp Thr Cys Cys Lys Ala Ala Asp Lys Asp Thr Cys Phe Ser Thr Glu
                180                 185                 190

Gly Pro Asn Leu Val Thr Arg Cys Lys Asp Ala Leu Ala
            195                 200                 205
```

<210> SEQ ID NO 5
<211> LENGTH: 205
<212> TYPE: PRT
<213> ORGANISM: Bos taurus

<400> SEQUENCE: 5

```
Leu Val Asp Glu Pro Gln Asn Leu Ile Lys Gln Asn Cys Asp Gln Phe
1               5                   10                  15

Glu Lys Leu Gly Glu Tyr Gly Phe Gln Asn Ala Leu Ile Val Arg Tyr
            20                  25                  30

Thr Arg Lys Val Pro Gln Val Ser Thr Pro Thr Leu Val Glu Val Ser
        35                  40                  45

Arg Ser Leu Gly Lys Val Gly Thr Arg Cys Cys Thr Lys Pro Glu Ser
    50                  55                  60

Glu Arg Met Pro Cys Thr Glu Asp Tyr Leu Ser Leu Ile Leu Asn Arg
65                  70                  75                  80

Leu Cys Val Leu His Glu Lys Thr Pro Val Ser Glu Lys Val Thr Lys
                85                  90                  95

Cys Cys Thr Glu Ser Leu Val Asn Arg Arg Pro Cys Phe Ser Ala Leu
            100                 105                 110

Thr Pro Asp Glu Thr Tyr Val Pro Lys Ala Phe Asp Glu Lys Leu Phe
        115                 120                 125

Thr Phe His Ala Asp Ile Cys Thr Leu Pro Asp Thr Glu Lys Gln Ile
    130                 135                 140

Lys Lys Gln Thr Ala Leu Val Glu Leu Leu Lys His Lys Pro Lys Ala
145                 150                 155                 160

Thr Glu Glu Gln Leu Lys Thr Val Met Glu Asn Phe Val Ala Phe Val
                165                 170                 175

Asp Lys Cys Cys Ala Ala Asp Asp Lys Glu Ala Cys Phe Ala Val Glu
            180                 185                 190

Gly Pro Lys Leu Val Val Ser Thr Gln Thr Ala Leu Ala
        195                 200                 205
```

<210> SEQ ID NO 6
<211> LENGTH: 205
<212> TYPE: PRT
<213> ORGANISM: Canis familiaris

<400> SEQUENCE: 6

```
Leu Val Asp Glu Pro Gln Asn Leu Val Lys Thr Asn Cys Glu Leu Phe
1               5                   10                  15

Glu Lys Leu Gly Glu Tyr Gly Phe Gln Asn Ala Leu Leu Val Arg Tyr
            20                  25                  30

Thr Lys Lys Ala Pro Gln Val Ser Thr Pro Thr Leu Val Glu Val Ser
        35                  40                  45

Arg Lys Leu Gly Lys Val Gly Thr Lys Cys Cys Lys Lys Pro Glu Ser
    50                  55                  60

Glu Arg Met Ser Cys Ala Glu Asp Phe Leu Ser Val Val Leu Asn Arg
65                  70                  75                  80

Leu Cys Val Leu His Glu Lys Thr Pro Val Ser Glu Arg Val Thr Lys
                85                  90                  95

Cys Cys Ser Glu Ser Leu Val Asn Arg Arg Pro Cys Phe Ser Gly Leu
            100                 105                 110

Glu Val Asp Glu Thr Tyr Val Pro Lys Glu Phe Asn Ala Glu Thr Phe
        115                 120                 125
```

```
Thr Phe His Ala Asp Leu Cys Thr Leu Pro Glu Ala Glu Lys Gln Val
        130                 135                 140

Lys Lys Gln Thr Ala Leu Val Glu Leu Leu Lys His Lys Pro Lys Ala
145                 150                 155                 160

Thr Asp Glu Gln Leu Lys Thr Val Met Gly Asp Phe Gly Ala Phe Val
                165                 170                 175

Glu Lys Cys Cys Ala Ala Glu Asn Lys Glu Gly Cys Phe Ser Glu Glu
            180                 185                 190

Gly Pro Lys Leu Val Ala Ala Gln Ala Ala Leu Val
        195                 200                 205

<210> SEQ ID NO 7
<211> LENGTH: 205
<212> TYPE: PRT
<213> ORGANISM: Oryctolagus cuniculus

<400> SEQUENCE: 7

Leu Val Asp Glu Pro Lys Asn Leu Val Lys Gln Asn Cys Glu Leu Tyr
1               5                   10                  15

Glu Gln Leu Gly Asp Tyr Asn Phe Gln Asn Ala Leu Leu Val Arg Tyr
                20                  25                  30

Thr Lys Lys Val Pro Gln Val Ser Thr Pro Thr Leu Val Glu Ile Ser
            35                  40                  45

Arg Ser Leu Gly Lys Val Gly Ser Lys Cys Cys Lys His Pro Glu Ala
    50                  55                  60

Glu Arg Leu Pro Cys Val Glu Asp Tyr Leu Ser Val Val Leu Asn Arg
65                  70                  75                  80

Leu Cys Val Leu His Glu Lys Thr Pro Val Ser Glu Lys Val Thr Lys
                85                  90                  95

Cys Cys Ser Glu Ser Leu Val Asp Arg Arg Pro Cys Phe Ser Ala Leu
            100                 105                 110

Gly Pro Asp Glu Thr Tyr Val Pro Lys Glu Phe Asn Ala Glu Thr Phe
        115                 120                 125

Thr Phe His Ala Asp Ile Cys Thr Leu Pro Glu Thr Glu Arg Lys Ile
        130                 135                 140

Lys Lys Gln Thr Ala Leu Val Glu Leu Val Lys His Lys Pro His Ala
145                 150                 155                 160

Thr Asn Asp Gln Leu Lys Thr Val Val Gly Glu Phe Thr Ala Leu Leu
                165                 170                 175

Asp Lys Cys Cys Ser Ala Glu Asp Lys Glu Ala Cys Phe Ala Val Glu
            180                 185                 190

Gly Pro Lys Leu Val Glu Ser Ser Lys Ala Thr Leu Gly
        195                 200                 205

<210> SEQ ID NO 8
<211> LENGTH: 205
<212> TYPE: PRT
<213> ORGANISM: Sus scrofa

<400> SEQUENCE: 8

Leu Val Asp Glu Pro Lys Asn Leu Ile Lys Gln Asn Cys Glu Leu Phe
1               5                   10                  15

Glu Lys Leu Gly Glu Tyr Gly Phe Gln Asn Ala Leu Ile Val Arg Tyr
                20                  25                  30

Thr Lys Lys Val Pro Gln Val Ser Thr Pro Thr Leu Val Glu Val Ala
            35                  40                  45

Arg Lys Leu Gly Leu Val Gly Ser Arg Cys Cys Lys Arg Pro Glu Glu
```

```
                50                  55                  60
Glu Arg Leu Ser Cys Ala Glu Asp Tyr Leu Ser Leu Val Leu Asn Arg
 65                  70                  75                  80

Leu Cys Val Leu His Glu Lys Thr Pro Val Ser Glu Lys Val Thr Lys
                 85                  90                  95

Cys Cys Thr Glu Ser Leu Val Asn Arg Arg Pro Cys Phe Ser Ala Leu
                100                 105                 110

Thr Pro Asp Glu Thr Tyr Lys Pro Lys Glu Phe Val Glu Gly Thr Phe
                115                 120                 125

Thr Phe His Ala Asp Leu Cys Thr Leu Pro Glu Asp Glu Lys Gln Ile
                130                 135                 140

Lys Lys Gln Thr Ala Leu Val Glu Leu Leu Lys His Lys Pro His Ala
145                 150                 155                 160

Thr Glu Glu Gln Leu Arg Thr Val Leu Gly Asn Phe Ala Ala Phe Val
                165                 170                 175

Gln Lys Cys Cys Ala Ala Pro Asp His Glu Ala Cys Phe Ala Val Glu
                180                 185                 190

Gly Pro Lys Phe Val Ile Glu Ile Arg Gly Ile Leu Ala
                195                 200                 205

<210> SEQ ID NO 9
<211> LENGTH: 198
<212> TYPE: PRT
<213> ORGANISM: Gallus gallus

<400> SEQUENCE: 9

His Ile Lys Glu Thr Gln Asp Val Val Lys Thr Asn Cys Asp Leu Leu
 1               5                  10                  15

His Asp His Gly Glu Ala Asp Phe Leu Lys Ser Ile Leu Ile Arg Tyr
                20                  25                  30

Thr Lys Lys Met Pro Gln Val Pro Thr Asp Leu Leu Leu Glu Thr Gly
                35                  40                  45

Lys Lys Met Thr Thr Ile Gly Thr Lys Cys Cys Gln Leu Gly Glu Asp
 50                  55                  60

Arg Arg Met Ala Cys Ser Glu Gly Tyr Leu Ser Ile Val Ile His Asp
 65                  70                  75                  80

Thr Cys Arg Lys Gln Glu Thr Thr Pro Ile Asn Asp Asn Val Ser Gln
                 85                  90                  95

Cys Cys Ser Gln Leu Tyr Ala Asn Arg Arg Pro Cys Phe Thr Ala Met
                100                 105                 110

Gly Val Asp Thr Lys Tyr Val Pro Pro Pro Phe Asn Pro Asp Met Phe
                115                 120                 125

Ser Phe Asp Glu Lys Leu Cys Ser Ala Pro Ala Glu Glu Arg Glu Val
                130                 135                 140

Gly Gln Met Lys Leu Leu Ile Asn Leu Ile Lys Arg Lys Pro Gln Met
145                 150                 155                 160

Thr Glu Glu Gln Ile Lys Thr Ile Ala Asp Gly Phe Thr Ala Met Val
                165                 170                 175

Asp Lys Cys Cys Lys Gln Ser Asp Ile Asn Thr Cys Phe Gly Glu Glu
                180                 185                 190

Gly Ala Asn Leu Ile Val
                195

<210> SEQ ID NO 10
<211> LENGTH: 205
<212> TYPE: PRT
```

<213> ORGANISM: Equus asinus

<400> SEQUENCE: 10

Leu Val Glu Glu Pro Lys Ser Leu Val Lys Lys Asn Cys Asp Leu Phe
1               5                   10                  15

Glu Glu Val Gly Glu Tyr Asp Phe Gln Asn Ala Leu Ile Val Arg Tyr
            20                  25                  30

Thr Lys Lys Ala Pro Gln Val Ser Thr Pro Thr Leu Val Glu Ile Gly
        35                  40                  45

Arg Thr Leu Gly Lys Val Gly Ser Arg Cys Cys Lys Leu Pro Glu Ser
    50                  55                  60

Glu Arg Leu Pro Cys Ser Glu Asn His Leu Ala Leu Ala Leu Asn Arg
65                  70                  75                  80

Leu Cys Val Leu His Glu Lys Thr Pro Val Ser Glu Lys Ile Thr Lys
                85                  90                  95

Cys Cys Thr Asp Ser Leu Ala Glu Arg Arg Pro Cys Phe Ser Ala Leu
            100                 105                 110

Glu Leu Asp Glu Gly Tyr Ile Pro Lys Glu Phe Lys Ala Glu Thr Phe
        115                 120                 125

Thr Phe His Ala Asp Ile Cys Thr Leu Pro Glu Asp Glu Lys Gln Ile
    130                 135                 140

Lys Lys Gln Ser Ala Leu Ala Glu Leu Val Lys His Lys Pro Lys Ala
145                 150                 155                 160

Thr Lys Glu Gln Leu Lys Thr Val Leu Gly Asn Phe Ser Ala Phe Val
                165                 170                 175

Ala Lys Cys Cys Gly Ala Glu Asp Lys Glu Ala Cys Phe Ala Glu Glu
            180                 185                 190

Gly Pro Lys Leu Val Ala Ser Ser Gln Leu Ala Leu Ala
        195                 200                 205

<210> SEQ ID NO 11
<211> LENGTH: 198
<212> TYPE: PRT
<213> ORGANISM: Meriones unguiculatus

<400> SEQUENCE: 11

Leu Val Glu Glu Pro Gln Asn Leu Val Lys Ser Asn Cys Glu Leu Tyr
1               5                   10                  15

Glu Lys Leu Gly Glu Tyr Gly Phe Gln Asn Ala Val Leu Val Arg Tyr
            20                  25                  30

Thr Lys Lys Ala Pro Gln Val Ser Thr Pro Thr Leu Val Glu Ala Ala
        35                  40                  45

Arg Ser Leu Gly Arg Val Gly Thr His Cys Cys Ala Leu Pro Glu Lys
    50                  55                  60

Lys Arg Leu Pro Cys Val Glu Asp Tyr Leu Ser Ala Ile Leu Asn Arg
65                  70                  75                  80

Val Cys Leu Leu His Glu Lys Thr Pro Val Ser Glu Gln Val Thr Lys
                85                  90                  95

Cys Cys Ser Gly Ser Leu Val Glu Arg Arg Pro Cys Phe Ser Ala Leu
            100                 105                 110

Pro Val Asp Glu Thr Tyr Val Pro Lys Glu Phe Lys Ala Glu Thr Phe
        115                 120                 125

Thr Phe His Ala Asn Ile Cys Thr Leu Pro Glu Lys Glu Lys Gln Met
    130                 135                 140

Glu Lys Gln Thr Ala Leu Ala Glu Leu Val Lys His Lys Pro Gln Ala
145                 150                 155                 160

```
Thr Glu Glu Gln Leu Lys Lys Val Met Gly Asp Phe Ala Glu Phe Leu
                165                 170                 175

Glu Lys Cys Cys Lys Gln Asp Lys Glu Ala Cys Phe Ser Thr Glu
        180                 185                 190

Gly Pro Lys Leu Val Ala
        195

<210> SEQ ID NO 12
<211> LENGTH: 198
<212> TYPE: PRT
<213> ORGANISM: Ovis aries

<400> SEQUENCE: 12

Leu Val Asp Glu Pro Gln Asn Leu Ile Lys Lys Asn Cys Glu Leu Phe
1               5                   10                  15

Glu Lys His Gly Glu Tyr Gly Phe Gln Asn Ala Leu Ile Val Arg Tyr
                20                  25                  30

Thr Arg Lys Ala Pro Gln Val Ser Thr Pro Thr Leu Val Glu Ile Ser
            35                  40                  45

Arg Ser Leu Gly Lys Val Gly Thr Lys Cys Cys Ala Lys Pro Glu Ser
        50                  55                  60

Glu Arg Met Pro Cys Thr Glu Asp Tyr Leu Ser Leu Ile Leu Asn Arg
65                  70                  75                  80

Leu Cys Val Leu His Glu Lys Thr Pro Val Ser Glu Lys Val Thr Lys
                85                  90                  95

Cys Cys Thr Glu Ser Leu Val Asn Arg Arg Pro Cys Phe Ser Asp Leu
            100                 105                 110

Thr Leu Asp Glu Thr Tyr Val Pro Lys Pro Phe Asp Glu Lys Phe Phe
        115                 120                 125

Thr Phe His Ala Asp Ile Cys Thr Leu Pro Asp Thr Glu Lys Gln Ile
    130                 135                 140

Lys Lys Gln Thr Ala Leu Val Glu Leu Leu Lys His Lys Pro Lys Ala
145                 150                 155                 160

Thr Asp Glu Gln Leu Lys Thr Val Met Glu Asn Phe Val Ala Phe Val
                165                 170                 175

Asp Lys Cys Cys Ala Ala Asp Asp Lys Glu Gly Cys Phe Val Leu Glu
            180                 185                 190

Gly Pro Lys Leu Val Ala
        195

<210> SEQ ID NO 13
<211> LENGTH: 198
<212> TYPE: PRT
<213> ORGANISM: Felis catus

<400> SEQUENCE: 13

Leu Val Glu Glu Pro His Asn Leu Val Lys Thr Asn Cys Glu Leu Phe
1               5                   10                  15

Glu Lys Leu Gly Glu Tyr Gly Phe Gln Asn Ala Leu Leu Val Arg Tyr
                20                  25                  30

Thr Lys Lys Val Pro Gln Val Ser Thr Pro Thr Leu Val Glu Val Ser
            35                  40                  45

Arg Ser Leu Gly Lys Val Gly Ser Lys Cys Cys Thr His Pro Glu Ala
        50                  55                  60

Glu Arg Leu Ser Cys Ala Glu Asp Tyr Leu Ser Val Val Leu Asn Arg
65                  70                  75                  80
```

```
Leu Cys Val Leu His Glu Lys Thr Pro Val Ser Glu Arg Val Thr Lys
                85                  90                  95

Cys Cys Thr Glu Ser Leu Val Asn Arg Arg Pro Cys Phe Ser Ala Leu
                100                 105                 110

Gln Val Asp Glu Thr Tyr Val Pro Lys Glu Phe Ser Ala Glu Thr Phe
            115                 120                 125

Thr Phe His Ala Asp Leu Cys Thr Leu Pro Glu Ala Glu Lys Gln Ile
        130                 135                 140

Lys Lys Gln Ser Ala Leu Val Glu Leu Leu Lys His Lys Pro Lys Ala
145                 150                 155                 160

Thr Glu Glu Gln Leu Lys Thr Val Met Gly Asp Phe Gly Ser Phe Val
                165                 170                 175

Asp Lys Cys Cys Ala Ala Glu Asp Lys Glu Ala Cys Phe Ala Glu Glu
            180                 185                 190

Gly Pro Lys Leu Val Ala
        195

<210> SEQ ID NO 14
<211> LENGTH: 198
<212> TYPE: PRT
<213> ORGANISM: Equus caballus

<400> SEQUENCE: 14

Leu Val Glu Glu Pro Lys Ser Leu Val Lys Lys Asn Cys Asp Leu Phe
1               5                   10                  15

Glu Glu Val Gly Glu Tyr Asp Phe Gln Asn Ala Leu Ile Val Arg Tyr
                20                  25                  30

Thr Lys Lys Ala Pro Gln Val Ser Thr Pro Thr Leu Val Glu Ile Gly
            35                  40                  45

Arg Thr Leu Gly Lys Val Gly Ser Arg Cys Cys Lys Leu Pro Glu Ser
    50                  55                  60

Glu Arg Leu Pro Cys Ser Glu Asn His Leu Ala Leu Ala Leu Asn Arg
65                  70                  75                  80

Leu Cys Val Leu His Glu Lys Thr Pro Val Ser Glu Lys Ile Thr Lys
                85                  90                  95

Cys Cys Thr Asp Ser Leu Ala Glu Arg Arg Pro Cys Phe Ser Ala Leu
                100                 105                 110

Glu Leu Asp Glu Gly Tyr Val Pro Lys Glu Phe Lys Ala Glu Thr Phe
            115                 120                 125

Thr Phe His Ala Asp Ile Cys Thr Leu Pro Glu Asp Glu Lys Gln Ile
        130                 135                 140

Lys Lys Gln Ser Ala Leu Ala Glu Leu Val Lys His Lys Pro Lys Ala
145                 150                 155                 160

Thr Lys Glu Gln Leu Lys Thr Val Leu Gly Asn Phe Ser Ala Phe Val
                165                 170                 175

Ala Lys Cys Cys Gly Arg Glu Asp Lys Glu Ala Cys Phe Ala Glu Glu
            180                 185                 190

Gly Pro Lys Leu Val Ala
        195

<210> SEQ ID NO 15
<211> LENGTH: 641
<212> TYPE: PRT
<213> ORGANISM: Human herpesvirus 4

<400> SEQUENCE: 15

Met Ser Asp Glu Gly Pro Gly Thr Gly Pro Gly Asn Gly Leu Gly Glu
```

-continued

```
1               5                   10                  15
Lys Gly Asp Thr Ser Gly Pro Glu Gly Ser Gly Gly Ser Gly Pro Gln
                20                  25                  30

Arg Arg Gly Gly Asp Asn His Gly Arg Gly Arg Gly Arg Gly Arg Gly
                35                  40                  45

Arg Gly Gly Gly Arg Pro Gly Ala Pro Gly Gly Ser Gly Ser Gly Pro
            50                  55                  60

Arg His Arg Asp Gly Val Arg Arg Pro Gln Lys Arg Pro Ser Cys Ile
65                  70                  75                  80

Gly Cys Lys Gly Thr His Gly Gly Thr Gly Ala Gly Ala Gly Ala Gly
                85                  90                  95

Gly Ala Gly Ala Gly Gly Ala Gly Ala Gly Gly Ala Gly Ala Gly Ala
                100                 105                 110

Gly Gly Ala Gly Gly Ala Gly Gly Ala Gly Gly Ala Gly Ala Gly Gly
            115                 120                 125

Gly Ala Gly Ala Gly Gly Ala Gly Gly Ala Gly Gly Ala Gly Gly Ala
        130                 135                 140

Gly Gly Gly Ala Gly Ala Gly Gly Ala Gly Gly Ala Gly Ala Gly Gly
145                 150                 155                 160

Gly Gly Ala Gly Gly Ala Gly Gly Ala Gly Gly Ala Gly Gly Ala Gly
                165                 170                 175

Ala Gly Gly Gly Ala Gly Gly Ala Gly Gly Ala Gly Gly Ala Gly Gly
                180                 185                 190

Ala Gly Gly Ala Gly Ala Gly Gly Ala Gly Ala Gly Gly Ala Gly Gly
            195                 200                 205

Gly Ala Gly Gly Ala Gly Ala Gly Gly Ala Gly Ala Gly Gly Gly Ala
        210                 215                 220

Gly Gly Ala Gly Gly Ala Gly Ala Gly Gly Ala Gly Ala Gly Gly Ala
225                 230                 235                 240

Gly Ala Gly Gly Ala Gly Ala Gly Gly Ala Gly Ala Gly Ala Gly Gly
                245                 250                 255

Gly Ala Gly Gly Ala Gly Ala Gly Gly Ala Gly Ala Gly Ala Gly Gly
                260                 265                 270

Gly Gly Ala Gly Gly Ala Gly Ala Gly Gly Gly Ala Gly Gly Ala Gly
            275                 280                 285

Ala Gly Gly Ala Gly Gly Ala Gly Gly Ala Gly Gly Gly Ala Gly Gly
        290                 295                 300

Ala Gly Gly Ala Gly Gly Ala Gly Ala Gly Gly Ala Gly Gly Ala Gly
305                 310                 315                 320

Gly Ala Gly Ala Gly Gly Gly Gly Arg Gly Arg Gly Gly Ser Gly Gly
                325                 330                 335

Arg Gly Arg Gly Gly Ser Gly Gly Arg Gly Arg Gly Gly Ser Gly Gly
                340                 345                 350

Arg Arg Gly Arg Gly Arg Glu Arg Ala Arg Gly Gly Ser Arg Glu Arg
            355                 360                 365

Ala Arg Gly Arg Gly Arg Gly Arg Gly Glu Lys Arg Pro Arg Ser Pro
        370                 375                 380

Ser Ser Gln Ser Ser Ser Gly Ser Pro Pro Arg Arg Pro Pro Pro Gly
385                 390                 395                 400

Gly Arg Arg Pro Phe Phe His Pro Val Gly Glu Ala Asp Tyr Phe Glu
                405                 410                 415

Tyr His Gln Glu Gly Gly Pro Asp Gly Glu Pro Asp Val Pro Pro Gly
                420                 425                 430
```

```
Ala Ile Glu Gln Gly Pro Ala Asp Asp Pro Gly Glu Gly Pro Ser Thr
            435                 440                 445
Gly Pro Arg Gly Gln Gly Asp Gly Gly Arg Arg Lys Lys Gly Gly Trp
        450                 455                 460
Phe Gly Lys His Arg Gly Gln Gly Gly Ser Asn Pro Lys Phe Glu Asn
465                 470                 475                 480
Ile Ala Glu Gly Leu Arg Ala Leu Leu Ala Arg Ser His Val Glu Arg
                485                 490                 495
Thr Thr Asp Glu Gly Thr Trp Val Ala Gly Val Phe Val Tyr Gly Gly
            500                 505                 510
Ser Lys Thr Ser Leu Tyr Asn Leu Arg Arg Gly Thr Ala Leu Ala Ile
        515                 520                 525
Pro Gln Cys Arg Leu Thr Pro Leu Ser Arg Leu Pro Phe Gly Met Ala
    530                 535                 540
Pro Gly Pro Gly Pro Gln Pro Gly Pro Leu Arg Glu Ser Ile Val Cys
545                 550                 555                 560
Tyr Phe Met Val Phe Leu Gln Thr His Ile Phe Ala Glu Val Leu Lys
                565                 570                 575
Asp Ala Ile Lys Asp Leu Val Met Thr Lys Pro Ala Pro Thr Cys Asn
            580                 585                 590
Ile Arg Val Thr Val Cys Ser Phe Asp Asp Gly Val Asp Leu Pro Pro
        595                 600                 605
Trp Phe Pro Pro Met Val Glu Gly Ala Ala Ala Glu Gly Asp Asp Gly
    610                 615                 620
Asp Asp Gly Asp Glu Gly Gly Asp Gly Asp Glu Gly Glu Glu Gly Gln
625                 630                 635                 640
Glu

<210> SEQ ID NO 16
<211> LENGTH: 1926
<212> TYPE: DNA
<213> ORGANISM: Human herpesvirus 4

<400> SEQUENCE: 16
atgtctgacg aggggccagg tacaggacct ggaaatggcc taggagagaa gggagacaca      60
tctggaccag aaggctccgg cggcagtgga cctcaaagaa gagggggtga taaccatgga     120
cgaggacggg gaagaggacg aggacgagga ggcggaagac caggagcccc gggcggctca     180
ggatcagggc caagacatag agatggtgtc cggagacccc aaaaacgtcc aagttgcatt     240
ggctgcaaag ggacccacgg tggaacagga gcaggagcag gagcgggagg ggcaggagca     300 ggagggcag gagcaggagg aggggcagga gcaggaggag gggcaggagg ggcaggaggg     360
gcaggagggg caggagcagg aggaggggca ggagcaggag gaggggcagg aggggcagga     420
ggggcaggag caggaggagg ggcaggagca ggaggagggg caggagggc aggagcagga     480 ggaggggcag gaggggcagg aggggcagga gcaggaggag gggcaggagc aggaggaggg     540
gcaggagggg caggagcagg aggaggggca ggaggggcag gaggggcagg agcaggagga     600
ggggcaggag caggaggggc aggaggggca ggaggggcag gagcaggagg ggcaggagca     660
ggaggagggg caggaggggc aggaggggca ggagcaggag gggcaggagc aggaggggca     720
ggagcaggag ggcaggagc aggaggggca ggaggggcag gagcaggagg ggcaggaggg     780
gcaggagcag gaggggcagg aggggcagga gcaggaggag gggcaggagg ggcaggagca     840
ggaggagggg caggaggggc aggagcagga ggggcaggag ggcaggagc aggaggggca     900 ggaggggcag gagcaggagg ggcaggaggg gcaggagcag gaggagggc aggagcagga     960
```

| | |
|---|---:|
| ggggcaggag caggaggtgg aggccggggt cgaggaggca gtggaggccg gggtcgagga | 1020 |
| ggtagtggag gccggggtcg aggaggtagt ggaggccgcc ggggtagagg acgtgaaaga | 1080 |
| gccagggggg gaagtcgtga aagagccagg gggagaggtc gtggacgtgg agaaaagagg | 1140 |
| cccaggagtc ccagtagtca gtcatcatca tccgggtctc caccgcgcag gcccccctcca | 1200 |
| ggtagaaggc cattttttcca ccctgtaggg gaagccgatt attttgaata ccaccaagaa | 1260 |
| ggtggcccag atggtgagcc tgacgtgccc ccgggagcga tagagcaggg ccccgcagat | 1320 |
| gacccaggag aaggcccaag cactggaccc cggggtcagg gtgatggagg caggcgcaaa | 1380 |
| aaaggagggt ggtttggaaa gcatcgtggt caaggaggtt ccaacccgaa atttgagaac | 1440 |
| attgcagaag gtttaagagc tctcctggct aggagtcacg tagaaaggac taccgacgaa | 1500 |
| ggaacttggg tcgccggtgt gttcgtatat ggaggtagta agacctccct ttacaaccta | 1560 |
| aggcgaggaa ctgcccttgc tattccacaa tgtcgtctta caccattgag tcgtctcccc | 1620 |
| tttggaatgg cccctggacc cggccacaa cctggcccgc taagggagtc cattgtctgt | 1680 |
| tatttcatgg tcttttttaca aactcatata tttgctgagg ttttgaagga tgcgattaag | 1740 |
| gaccttgtta tgacaaagcc cgctcctacc tgcaatatca gggtgactgt gtgcagcttt | 1800 |
| gacgatggag tagatttgcc tccctggttt ccacctatgg tggaagggc tgccgcggag | 1860 |
| ggtgatgacg gagatgacgg agatgaagga ggtgatggag atgagggtga ggaagggcag | 1920 |
| gagtga | 1926 |

```
<210> SEQ ID NO 17
<211> LENGTH: 1976
<212> TYPE: DNA
<213> ORGANISM: Human herpesvirus 4

<400> SEQUENCE: 17
```

| | |
|---|---:|
| cctttatgtg taactcttgg ctgaagctct tacaccaatg ctgggggaca tgtacctccc | 60 |
| aggggcccag gaagactacg ggaggctaca ccaacgtcaa tcagaggggc ctgtgtagct | 120 |
| accgataagc ggaccctcaa gagggcatta gcaatagtgt ttataaggcc cccttgttaa | 180 |
| ccctaaacgg gtagcatatg cttcccgggt agtagtatat actatccaga ctaaccctaa | 240 |
| ttcaatagca tatgttaccc aacgggaagc atatgctatc gaattagggt tagtaaaagg | 300 |
| gtcctaagga acagcgatat ctcccacccc atgagctgtc acggttttat ttacatgggg | 360 |
| tcaggattcc acgagggtag tgaaccattt tagtcacaag ggcagtggct gaagatcaag | 420 |
| gagcgggcag tgaactctcc tgaatcttcg cctgcttctt cattctcctt cgtttagcta | 480 |
| atagaataac tgctgagttg tgaacagtaa ggtgtatgtg aggtgctcga aaacaaggtt | 540 |
| tcaggtgacg ccccagaat aaaatttgga cgggggttc agtggtggca ttgtgctatg | 600 |
| acaccaatat aaccctcaca aaccccttgg gcaataaata ctagtgtagg aatgaaacat | 660 |
| tctgaatatc tttaacaata gaaatccatg gggtggggac aagccgtaaa gactggatgt | 720 |
| ccatctcaca cgaatttatg ctatgggca acacataatc ctagtgcaat atgatactgg | 780 |
| ggttattaag atgtgtccca ggcagggacc aagacaggtg aaccatgttg ttacactcta | 840 |
| tttgtaacaa ggggaaagag agtggacgcc gacagcagcg gactccactg gttgtctcta | 900 |
| acaccccga aaattaaacg gggctccacg ccaatgggc cataaacaa agacaagtgg | 960 |
| ccactctttt ttttgaaatt gtggagtggg ggcacgcgtc agcccccaca cgccgccctg | 1020 |
| cggttttgga ctgtaaaata aggggtgtaat aacttggctg attgtaaccc cgctaaccac | 1080 |
| tgcggtcaaa ccacttgccc acaaaaccac taatggcacc ccggggaata cctgcataag | 1140 |

-continued

```
taggtgggcg ggccaagata ggggcgcgat tgctgcgatc tggaggacaa attacacaca      1200
cttgcgcctg agcgccaagc acagggttgt tggtcctcat attcacgagg tcgctgagag      1260
cacggtgggc taatgttgcc atgggtagca tatactaccc aaatatctgg atagcatatg      1320
ctatcctaat ctatatctgg gtagcatagg ctatcctaat ctatatctgg gtagcatatg      1380
ctatcctaat ctatatctgg gtagtatatg ctatcctaat ttatatctgg gtagcatagg      1440
ctatcctaat ctatatctgg gtagcatatg ctatcctaat ctatatctgg gtagtatatg      1500
ctatcctaat ctgtatccgg gtagcatatg ctatcctaat agagattagg gtagtatatg      1560
ctatcctaat ttatatctgg gtagcatata ctacccaaat atctggatag catatgctat      1620
cctaatctat atctgggtag catatgctat cctaatctat atctgggtag cataggctat      1680
cctaatctat atctgggtag catatgctat cctaatctat atctgggtag tatatgctat      1740
cctaatttat atctgggtag cataggctat cctaatctat atctgggtag catatgctat      1800
cctaatctat atctgggtag tatatgctat cctaatctgt atccgggtag catatgctat      1860
cctcatgcat atacagtcag catatgatac ccagtagtag agtgggagtg ctatcctttg      1920
catatgccgc cacctcccaa ggggcgtga attttcgctg cttgtcctttt tcctgc         1976
```